(12) United States Patent
Gritzan et al.

(10) Patent No.: US 9,914,764 B2
(45) Date of Patent: Mar. 13, 2018

(54) VARIANT FACTOR VIII POLYPEPTIDES AND METHODS OF THEIR PRODUCTION AND USE

(71) Applicant: BAYER HEALTHCARE LLC, Whippany, NJ (US)

(72) Inventors: Uwe Gritzan, Cologne (DE); Peter Kretschmer, San Francisco, CA (US); Lilley Leong, Hercules, CA (US); Chandra Patel, Foster City, CA (US)

(73) Assignee: BAYER HEALTHCARE, LLC, Whippany, NJ (US)

( * ) Notice: Subject to any disclaimer, the term of this patent is extended or adjusted under 35 U.S.C. 154(b) by 37 days.

(21) Appl. No.: 14/773,702

(22) PCT Filed: Mar. 14, 2014

(86) PCT No.: PCT/US2014/027443
§ 371 (c)(1),
(2) Date: Sep. 8, 2015

(87) PCT Pub. No.: WO2014/152530
PCT Pub. Date: Sep. 25, 2014

(65) Prior Publication Data
US 2016/0031968 A1    Feb. 4, 2016

Related U.S. Application Data

(60) Provisional application No. 61/789,112, filed on Mar. 15, 2013.

(51) Int. Cl.
*C07K 14/755*    (2006.01)
*A61K 38/37*    (2006.01)

(52) U.S. Cl.
CPC ............ *C07K 14/755* (2013.01); *A61K 38/37* (2013.01)

(58) Field of Classification Search
None
See application file for complete search history.

(56) References Cited

U.S. PATENT DOCUMENTS

| | | | |
|---|---|---|---|
| 8,338,571 B2 | 12/2012 | Fay et al. | |
| 2008/0227691 A1* | 9/2008 | Ostergaard | C07K 14/755 514/1.1 |
| 2009/0118184 A1* | 5/2009 | Fay | A61K 38/37 514/13.7 |
| 2009/0203077 A1* | 8/2009 | Kaufman | C07K 14/755 435/69.6 |
| 2011/0124565 A1 | 5/2011 | Hauser et al. | |
| 2012/0028900 A1 | 2/2012 | Kaufman et al. | |
| 2012/0065136 A1 | 3/2012 | Fay et al. | |
| 2012/0190623 A1 | 7/2012 | Kaufman et al. | |

FOREIGN PATENT DOCUMENTS

| | | |
|---|---|---|
| WO | WO 87/07144 | 12/1987 |
| WO | WO 90/05530 | 5/1990 |
| WO | WO 97/40145 | 10/1997 |
| WO | WO 2003/087161 | 10/2003 |
| WO | WO 2006/027111 | 3/2006 |
| WO | WO 2006/108590 | 10/2006 |

OTHER PUBLICATIONS

Wakabayashi et al., 2012, Enhancing factor VIII and VIIIa stability by combining mutations at the A2 domain interface and A1-C2 domain interface, J Throm Haemost, 10(3): 491-495.*
Thompson, Seminars in Thrombosis and Hemostasis, 29:11-22 (2003).
Gallwitz et al., "The Extended Cleavage Specificity of Human Thrombin", PLoS ONE 7:e31756 (2012).
Kaufman et al., J. Biol. Chem. 263:6352 (1988).
Anderson et al., Proc. Natl. Acad. Sci. 83:2979 (1986).
Ewenstein et al., Semin. Hematol. 41:1-16 (2004).
Mei et al., Blood 116: 270-279 (2010).
Wakabayashi et al., J. Thromb. Haemost. 7:438-444 (2009).
Lind et al., Eur, J. Biochem. 232:19-27 (1995).
Swaroop et al., JBC 272:24121-24124 (1997).
Lollar, Thromb. Haemost. 82:505-508 (1999).
Oh et al., Exp. Mol. Med. 31:95-100 (1999).
Ananyeva et al., TCM 11:251-257 (2001).
Kane et al., "Blood Coagulation Factors V and VIII: Structural and Functional Similarities . . . ", Blood, American Society of Hematology, vol. 71, No. 3, pp. 539-555 (Mar. 1, 1988).
Newell-Caito, J., et al., "P3-P3 Residues Flanking Scissile Bonds in Factor VIII Modulate . . . ", Biochemistry, vol. 51, No. 16, pp. 3451-3459 (Apr. 24, 2012).
Jagannathan I., et al., "Identification of Residues in the 558-Loop of Factor VIIIa A2 . . . ", Journal of Biological Chemistry, vol. 284, No. 47, pp. 32248-32255 (Nov. 20, 2009).
Wakabayashi, et al., "Enhancing Factor VIII and VIIIa Stability by Combining Mutations at the A2 Domain Interface . . . ", J. Thromb.Haemost. 2012, 10(3): 492-5.
Corresponding PCT/US14/27443 International Search Report.
Corresponding EP14770221 Supplementary European Search Report.

* cited by examiner

*Primary Examiner* — Amber D Steele
(74) *Attorney, Agent, or Firm* — Buchanan, Ingersoll & Rooney PC

(57) ABSTRACT

This disclosure relates to variant Factor VIII polypeptides comprising an amino acid substitution at one or more positions within one or both of the thrombin cleavage site and the activation loop. In certain embodiments, the variant Factor VIII polypeptide comprises one or more amino acid substitutions within both the thrombin cleavage site and the activation loop. In further embodiments, the variant factor VIII polypeptide further comprises one or more amino acid substitutions within the A1-A2 domain interface and the A2-A3 domain interface. The present disclosure further relates to methods of producing and/or using such variant Factor VIII polypeptides; nucleic acids encoding the polypeptides; vectors and/or recombinant cells, tissues, or organisms containing such nucleic acids; and kits and pharmaceutical compositions containing such polypeptides and/or nucleic acids.

12 Claims, 11 Drawing Sheets

VARIANT FACTOR VIII POLYPEPTIDES AND METHODS OF THEIR PRODUCTION AND USE

CROSS-REFERENCE TO RELATED APPLICATION

This application claims the benefit of U.S. Provisional Application No. 61/789,112, filed Mar. 15, 2013, which is hereby incorporated by reference herein in its entirety.

FIELD OF THE DISCLOSURE

Human coagulation Factor VIII variants and the polynucleotides encoding such variants, vectors, and host cells comprising and expressing such variants, methods of obtaining such variants, methods of using such variants, compositions of the variants, and additional inventive features related thereto are provided herein.

BACKGROUND

Blood coagulation is a process consisting of complex interactions between various blood components (or factors) that eventually gives rise to a fibrin clot. Generally, the blood components that participate in what is frequently referred to as the coagulation "cascade" are enzymatically inactive proteins (proenzymes or zymogens) that are converted to proteolytic enzymes by the action of an activator, which itself is often an activated clotting factor. One peptide that is critical to the coagulation cascade is Factor VIII or FVIII. In fact, Hemophilia A, which is the most common hereditary coagulation disorder, is caused by deficiency or structural defects in Factor VIII. The biochemistry of Factor VIII allows for a rapid on/off switch for coagulation. It circulates as an inactive cofactor which is activated to FVIIIa by thrombin, the penultimate enzyme of the coagulation cascade. FVIIIa participates in a short-lived enzymatic complex (FXase) with FIXa, a membrane or phospholipid (PL) surface and $Ca^{+2}$ to convert FX to FXa. The major function of FVIIIa as a participant in the FXase complex is to markedly amplify FXa, which then allows for thrombin generation. Factor VIII is encoded by a ~186 kb gene consisting of 26 exons (Thompson, Seminars in Thrombosis and Hemostasis, 29:11-22 (2003) (references 11 and 16-18)). Translation of the mRNA of this gene, followed by removal of a 19 amino acid signal sequence, leads to a mature protein of 2332 amino acids. The protein consists of 6 major domains, which, from the amino terminus, are: A1, A2, B, A3, C1, and C2. Additional short acidic regions a1, a2, and a3, which are involved in activation, are interspersed between the A1 and A2, A2 and B, and B and A3 domains, respectively. The 2332 amino acid primary translation product is processed into a heterodimer consisting of a heterogeneous heavy chain, which contains the intact A1,a1 A2,a2 domains and various lengths of the B-domain, and a homogenous 80 kD light chain, which contains of a3, A3, C1, and C2 domain. The heterogeneity of the B-domain results from proteolysis during secretion.

Activation of Factor VIII to Factor VIIIa generally occurs via proteolysis of the procofactor by thrombin. Thrombin recognizes certain amino acid regions that define thrombin cleavage sites along the Factor VIII peptide chain. Factor VIII has three thrombin cleavage sites. Examination of other thrombin substrates reveals a variety of residues that can be accommodated by thrombin. Though the amino acids within these thrombin cleavage sites can vary to some degree, certain amino acids are much more common within these cleavage sites than others, and certain amino acid residues result in a more efficient cleavage of the peptide by thrombin. (See, e.g., Newell-Caito et al., "P3-P3' Residues flanking Scissile Bonds in Factor VIII Modulate Rates of Substrate Cleavage and Profactor Activation by Thrombin," Biochemistry 51:3451-59 (2012); Gallwitz et al., "The Extended Cleavage Specificity of Human Thrombin," PLoS ONE 7:e31756 (2012)). One of the three thrombin cleavage sites in Factor VIII lies at or near the a1-A2 junction, which is at or near amino acid positions 370-375 of the mature wild-type human Factor VIII peptide.

Following cleavage, active Factor VIIIa is a heterotrimer comprised of the A1 subunit, the A2 subunit, and the A3C1C2 subunit. This heterotrimer is supported by both electrostatic and hydrophobic interactions between the subunits at the regions in which they interact with one another, termed the "domain interfaces." The heterotrimer is known to include at least A1-A2 and A2-A3 domain interfaces. (See, e.g., U.S. Pat. No. 8,338,571 (filed Jul. 25, 2008) (issued Dec. 25, 2012)).

Human Factor VIII has been produced recombinantly as a single-chain molecule of approximately 300 kD. The precursor product is processed into two polypeptide chains of 200 kD (heavy) and 80 kD (light) in the Golgi Apparatus, with the two chains held together by metal ions (Kaufman et al., J. Biol. Chem. 263:6352 (1988); Andersson et al., Proc. Natl. Acad. Sci. 83:2979 (1986)). The B-domain of FVIII seems to be dispensable, as B-domain deleted FVIII (FVIII-BDD; 90 kD A1-A2 heavy chain plus 80 kD light chain) has also been shown to be effective as a replacement therapy for hemophilia A. One well-known B-domain deleted Factor VIII sequence referred to as "BDD-SQ" or simply "BDD" contains a deletion of all but 14 amino acids of the B-domain.

Treatment of hemophilia A currently involves intravenous (iv) administration of Factor VIII on demand or as a prophylactic therapy. Despite its large size of greater than 300 kD for the full-length protein, Factor VIII has a half-life in humans of only about 11 hours. (Ewenstein et al., Semin. Hematol. 41:1-16 (2004)). As such, Factor VIII must be administered relatively frequently for prophylactic treatment of clotting disorders. Factor VIII is typically administered two to three times a week with dosing based upon Factor VIII activity. This need for frequent iv injection creates tremendous barriers to patient compliance. It would be more convenient for patients if a Factor VIII product could be developed that required less frequent administration. Furthermore, reducing the number of dosages required would also reduce the cost of treatment. Additionally, even with these frequent administrations, due to its short half-life, patients undergoing Factor VIII replacement therapy often achieve large swings in plasma Factor VIII activity levels, potentially putting them at risk for thrombosis (at peak levels) and bleeding (at trough levels).

Additionally, an alternate, non-iv route of administration, such as subcutaneous (sc) administration, could both increase ease of treatment and decrease the potential risks of thrombosis and bleeding by maintaining plasma Factor VIII levels at a more constant level. One challenge of sc delivery is increasing the bioavailability of the administered Factor VIII. A Factor VIII peptide with enhanced activity could be useful in enhancing bioavailability, and therefore could be useful in sc delivery of Factor VIII. Due to its higher specific activity, such a Factor VIII peptide could allow for a decrease in the volume needed for administration, as the activity concentration of the drug is higher. Reduced injection volume could decrease patient discomfort. Furthermore, the reduction in volume would also translate to a reduction in the cost of goods. Finally, an enhanced activity Factor VIII molecule could also confer additional protection above that of wild-type Factor VIII, by prolonging the duration of cofactor activity if dosing is by mass rather than by activity. As an example, with equal mass dosing, the enhanced activity FVIII variants with 2-fold specific activity enhancement would offer the same protection at the 0.5% level as the protection provided at the 1% level for the wild-type FVIII, thus extending the interval between Factor VIII doses.

Numerous Factor VIII variants have been produced in an attempt to address one or more shortcomings of the current medical therapy. For example, U.S. Pat. No. 8,338,571 (filed Jul. 25, 2008; issued Dec. 25, 2012) describes a recombinant factor VIII that includes one or more mutations that result in enhanced stability of both Factor VIII and Factor VIIIa. Similarly, U.S. Patent Publication No. 2012/0190623 (filed Jan. 27, 2011) describes Factor VIII muteins that are resistant to inactivation, including muteins "wherein the APC cleavage sites, Arg336 and Ile562, are mutated." U.S. Patent Publication No. 2011/0124565 (filed Apr. 10, 2006) relates to modified nucleic acid sequences coding for coagulation factors, in particular human Factor VIII and their derivatives with improved stability, including a Factor VIII peptide with a modification that reportedly prevents thrombin cleavage between the A1 and the A2 domain of FVIII. Other efforts have produced, for example, modified Factor VIII polypeptides that reportedly have increased circulating half-lives due to the introduction of mutations that permit PEGylation of the peptide (Mei et al., Blood 116:270-279 (2010)) and modified Factor VIII polypeptides that reportedly possess increased stability due to mutations to the amino acids that make up the domain interfaces of the active FVIIIa heterotrimer (Wakabayashi et al., J. Thromb. Haemost. 7:438-444 (2009)).

For the reasons stated above, there exists a need for improved Factor VIII variants, for instance a variant that possesses increased activity and/or a variant that need not be administered as frequently and/or at as high a dose. Furthermore, it is desirable that such a protein be produced as a homogeneous product in a consistent manner.

BRIEF SUMMARY

In one embodiment, the present disclosure relates to a variant of a Factor VIII polypeptide which is a functional Factor VIII, the Factor VIII polypeptide comprising a thrombin cleavage site at amino acid positions 370-375 and an activation loop at amino acid positions 558-565, wherein these amino acid position numbers are in reference to the amino acid sequence set forth in SEQ ID NO: 1; and wherein the variant comprises an amino acid substitution at one or more residues within the thrombin cleavage site and an amino acid substitution at one or more residues within the activation loop.

In certain examples, the substitution within the thrombin cleavage site of the variant Factor VIII polypeptide does not include a substitution at amino acid position 372. In other examples, the substitution within the thrombin cleavage site comprises a substitution at one or more of positions 370, 371, or 374, while in other examples the substitution within the thrombin cleavage site comprises a substitution at two or more of positions 370, 371, or 374.

In further examples, the substitution within the activation loop comprises a substitution at one or more of positions 559, 562, and 565, while in other examples, the substitution within the activation loop comprises a substitution at two or more of positions 559, 562, and 565.

In other examples, the variant Factor VIII polypeptide further comprises an A1-A2 domain interface comprising amino acid residues E272 and D519 and an A2-A3 domain interface comprising amino acid residues E665 and E1984, wherein these amino acid position numbers are in reference to the amino acid sequence set forth in SEQ ID NO: 1; and the variant further comprises a substitution at one or more amino acid residues of the A1-A2 domain interface and a substitution at one or more amino acid residues of the A2-A3 domain interface. In additional examples, the substitution of the A1-A2 domain interface comprises one or more substitutions selected from the group consisting of E272A, E272V, D519A, and D519V. In other examples, the substitution of the A2-A3 domain interface comprises one or more substitutions selected from the group consisting of E665A, E665V, E1984A, and E1984V. In still further examples, the substitution of the A1-A2 domain interface comprises D519V and the substitution of the A2-A3 domain interface comprises E665V.

In particular examples, the variant Factor VIII polypeptide comprises an amino acid substitution at one or more of positions 370, 371, and 374, and an amino acid substitution at one or more of positions 559, 562, and 565. In other examples, the variant comprises an amino acid substitution at two or more of positions 370, 371, and 374, and an amino acid substitution at two or more of positions 559, 562, and 565. In still further examples, the variant comprises amino acid substitutions selected from the group consisting of: Q370M, I371P, V374F, V559L, R562W, R562F, R562K, and Q565E. In additional examples, the variant comprises amino acid substitutions within the thrombin cleavage site selected from the group consisting of: (i) Q370M and I371P, and (ii) I371P and V374F. In further examples, the variant comprises amino acid substitutions within the activation loop selected from the group consisting of: (i) V559L and R562F, (ii) V559L and R562W, (iii) V559L and Q565E, (iv) V559L, R562W, and Q565E, and (v) V559L, R562F, and Q565E.

In certain particular examples, the variant comprises the amino acid substitutions I371P, V374F, V559L, R562W, and Q565E. In other particular examples, the variant comprises the amino acid substitutions I371P, V374F, V559L, R562W, Q565E, D519V, and E665V. In still further examples, the variant further comprises an amino acid substitution at amino acid position 336. In certain examples, the amino acid substitution at amino acid position 336 comprises an R336I substitution.

In certain examples, the variant Factor VIII polypeptide comprises an amino acid sequence at least 90% identical to the sequence of SEQ ID NO: 1, 2, or 3. In other examples, the variant Factor VIII polypeptide comprises the amino acid sequence of SEQ ID NO: 53.

In certain examples the variant Factor VIII polypeptide has increased specific activity as compared to the unmodified Factor VIII polypeptide.

In an additional embodiment, the present disclosure relates to a pharmaceutical composition comprising a variant Factor VIII polypeptide as described herein and a pharmaceutically acceptable excipient.

In another embodiment, the present disclosure relates to an isolated nucleic acid encoding a variant Factor VIII polypeptide as described herein.

In a further embodiment, the present disclosure relates to a vector comprising a nucleic acid sequence encoding a variant Factor VIII polypeptide as described herein. In certain examples, the vector is an expression vector.

In yet another embodiment, the present disclosure relates to a recombinant host cell comprising an isolated nucleic acid or vector as described herein.

In a further embodiment, the present disclosure relates to a method of producing a variant Factor VIII polypeptide, the method comprising culturing a recombinant host cell as described herein under conditions appropriate for expression of the variant Factor VIII polypeptide and isolating the variant.

In still another embodiment, the present disclosure relates to a method for preventing or treating a bleeding disorder comprising administering to a subject an effective amount of a variant Factor VIII polypeptide or the pharmaceutical composition as described herein. In certain examples, the bleeding disorder is a chronic bleeding disorder. In other examples, the bleeding disorder is an acute bleeding episode.

BRIEF DESCRIPTION OF THE SEQUENCES

Figure 1:
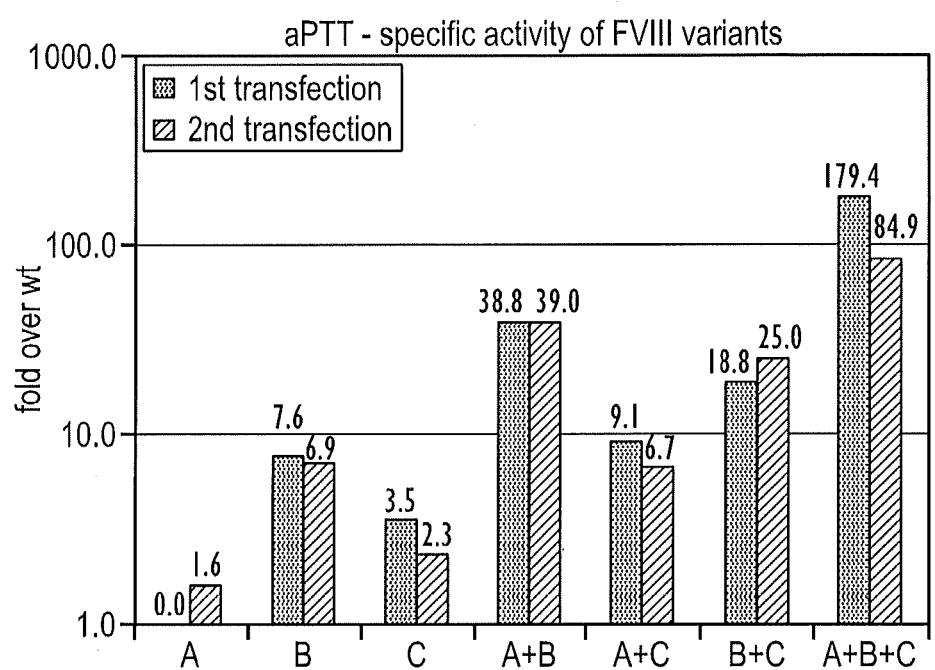
FIG. 1 presents the aPTT specific activities of various Factor VIII polypeptides and variants, presented as fold activity over wild-type Factor VIII. The designations have the following meanings: "A" indicates that the polypeptide possessed I371P and V374F amino acid substitutions in the Thrombin cleavage site; "B" indicates that the polypeptide possessed V559L, R562W, and Q565E amino acid substitutions in the activation site; and "C" indicates that the polypeptide possessed D519V and E665V amino acid substitutions. All amino acid position designations are based upon position numbers in wt-FVIII (SEQ ID NO: 1).

SEQ ID NO: 1 comprises a wild-type human Factor VIII polypeptide sequence. This polypeptide is generally referred to herein as "wild-type Factor VIII," "wt-FVIII," or simply "Factor VIII" or "FVIII."

SEQ ID NO: 2 comprises a nucleotide sequence that encodes for the polypeptide of SEQ ID NO: 1.

SEQ ID NO: 3 comprises a modified form of the wt-FVIII polypeptide sequence of SEQ ID NO: 1 that has a deletion in the B-domain. This is a nearly complete deletion of the B-domain with only 14 amino acids of the B-domain remaining. This polypeptide is generally referred to herein as "B-domain deleted Factor VIII," "Factor VIII BDD," or "FVIII-BDD."

SEQ ID NO: 4 comprises a nucleotide sequence that encodes for the polypeptide of SEQ ID NO: 3.

SEQ ID NO: 5 comprises a modified form of the FVIII-BDD of SEQ ID NO: 3 that contains two amino acid substitutions: D519V and E665V. This polypeptide is generally referred to herein as "D519VE665V Factor VIII" or "D519VE665V-FVIII."

SEQ ID NO: 6 comprises a nucleotide sequence that encodes for the polypeptide of SEQ ID NO: 5.

SEQ ID NO: 7 is a variant of the wt-FVIII of SEQ ID NO: 1 that contains the following amino acid substitutions: Q370M and I371P.

SEQ ID NO: 8 comprises a nucleotide sequence that encodes for the polypeptide of SEQ ID NO: 7.

SEQ ID NO: 9 is a variant of the FVIII-BDD of SEQ ID NO: 3 that contains the following amino acid substitutions: Q370M and I371P.

SEQ ID NO: 10 comprises a nucleotide sequence that encodes for the polypeptide of SEQ ID NO: 9.

SEQ ID NO: 11 is a variant of the D519VE665V-FVIII of SEQ ID NO: 5 that contains the following additional amino acid substitutions: Q370M and I371P.

SEQ ID NO: 12 comprises a nucleotide sequence that encodes for the polypeptide of SEQ ID NO: 11.

SEQ ID NO: 13 is a variant of the wt-FVIII of SEQ ID NO: 1 that contains the following amino acid substitutions: I371 P and V374F.

SEQ ID NO: 14 comprises a nucleotide sequence that encodes for the polypeptide of SEQ ID NO: 13.

SEQ ID NO: 15 is a variant of the FVIII-BDD of SEQ ID NO: 3 that contains the following amino acid substitutions: I371P and V374F.

SEQ ID NO: 16 comprises a nucleotide sequence that encodes for the polypeptide of SEQ ID NO: 15.

SEQ ID NO: 17 is a variant of the D519VE665V-FVIII of SEQ ID NO: 5 that contains the following additional amino acid substitutions: I371 P and V374F.

SEQ ID NO: 18 comprises a nucleotide sequence that encodes for the polypeptide of SEQ ID NO: 17.

SEQ ID NO: 19 is a variant of the wt-FVIII of SEQ ID NO: 1 that contains the following amino acid substitutions: V559L and R562F.

SEQ ID NO: 20 comprises a nucleotide sequence that encodes for the polypeptide of SEQ ID NO: 19.

SEQ ID NO: 21 is a variant of the FVIII-BDD of SEQ ID NO: 3 that contains the following amino acid substitutions: V559L and R562F.

SEQ ID NO: 22 comprises a nucleotide sequence that encodes for the polypeptide of SEQ ID NO: 21.

SEQ ID NO: 23 is a variant of the D519VE665V-FVIII of SEQ ID NO: 5 that contains the following additional amino acid substitutions: V559L and R562F.

SEQ ID NO: 24 comprises a nucleotide sequence that encodes for the polypeptide of SEQ ID NO: 23.

SEQ ID NO: 25 is a variant of the wt-FVIII of SEQ ID NO: 1 that contains the following amino acid substitutions: V559L and R562W.

SEQ ID NO: 26 comprises a nucleotide sequence that encodes for the polypeptide of SEQ ID NO: 25.

SEQ ID NO: 27 is a variant of the FVIII-BDD of SEQ ID NO: 3 that contains the following amino acid substitutions: V559L and R562W.

SEQ ID NO: 28 comprises a nucleotide sequence that encodes for the polypeptide of SEQ ID NO: 27.

SEQ ID NO: 29 is a variant of the D519VE665V-FVIII of SEQ ID NO: 5 that contains the following additional amino acid substitutions: V559L and R562W.

SEQ ID NO: 30 comprises a nucleotide sequence that encodes for the polypeptide of SEQ ID NO: 29.

SEQ ID NO: 31 is a variant of the wt-FVIII of SEQ ID NO: 1 that contains the following amino acid substitutions: V559L and Q565E.

SEQ ID NO: 32 comprises a nucleotide sequence that encodes for the polypeptide of SEQ ID NO: 31.

SEQ ID NO: 33 is a variant of the FVIII-BDD of SEQ ID NO: 3 that contains the following amino acid substitutions: V559L and Q565E.

SEQ ID NO: 34 comprises a nucleotide sequence that encodes for the polypeptide of SEQ ID NO: 33.

SEQ ID NO: 35 is a variant of the D519VE665V-FVIII of SEQ ID NO: 5 that contains the following additional amino acid substitutions: V559L and Q565E.

SEQ ID NO: 36 comprises a nucleotide sequence that encodes for the polypeptide of SEQ ID NO: 35.

SEQ ID NO: 37 is a variant of the wt-FVIII of SEQ ID NO: 1 that contains the following amino acid substitutions: V559L, R562W, and Q565E.

SEQ ID NO: 38 comprises a nucleotide sequence that encodes for the polypeptide of SEQ ID NO: 37.

SEQ ID NO: 39 is a variant of the FVIII-BDD of SEQ ID NO: 3 that contains the following amino acid substitutions: V559L, R562W, and Q565E.

SEQ ID NO: 40 comprises a nucleotide sequence that encodes for the polypeptide of SEQ ID NO: 39.

SEQ ID NO: 41 is a variant of the D519VE665V-FVIII of SEQ ID NO: 5 that contains the following additional amino acid substitutions: V559L, R562W, and Q565E.

SEQ ID NO: 42 comprises a nucleotide sequence that encodes for the polypeptide of SEQ ID NO: 41.

SEQ ID NO: 43 is a variant of the wt-FVIII of SEQ ID NO: 1 that contains the following amino acid substitutions: V559L, R562F, and Q565E.

SEQ ID NO: 44 comprises a nucleotide sequence that encodes for the polypeptide of SEQ ID NO: 43.

SEQ ID NO: 45 is a variant of the FVIII-BDD of SEQ ID NO: 3 that contains the following amino acid substitutions: V559L, R562F, and Q565E.

SEQ ID NO: 46 comprises a nucleotide sequence that encodes for the polypeptide of SEQ ID NO: 45.

SEQ ID NO: 47 is a variant of the D519VE665V-FVIII of SEQ ID NO: 5 that contains the following additional amino acid substitutions: V559L, R562F, and Q565E.

SEQ ID NO: 48 comprises a nucleotide sequence that encodes for the polypeptide of SEQ ID NO: 47.

SEQ ID NO: 49 is a variant of the wt-FVIII of SEQ ID NO: 1 that contains the following amino acid substitutions: I371P, V374F, V559L, R562W, and Q565E.

SEQ ID NO: 50 comprises a nucleotide sequence that encodes for the polypeptide of SEQ ID NO: 49.

SEQ ID NO: 51 is a variant of the FVIII-BDD of SEQ ID NO: 3 that contains the following amino acid substitutions: I371P, V374F, V559L, R562W, and Q565E.

SEQ ID NO: 52 comprises a nucleotide sequence that encodes for the polypeptide of SEQ ID NO: 51.

SEQ ID NO: 53 is a variant of the D519VE665V-FVIII of SEQ ID NO: 5 that contains the following additional amino acid substitutions: I371P, V374F, V559L, R562W, and Q565E.

SEQ ID NO: 54 comprises a nucleotide sequence that encodes for the polypeptide of SEQ ID NO: 53.

SEQ ID NO: 55 is a variant of the D519VE665V-FVIII of SEQ ID NO: 5 that contains the following additional amino acid substitutions: I371P, V374F, V559L, R562W, Q565E, and R336I.

SEQ ID NO: 56 comprises a nucleotide sequence that encodes for the polypeptide of SEQ ID NO: 55.

DETAILED DESCRIPTION

Before describing the present invention in detail, it is to be understood that this disclosure is not limited to particular embodiments, which can, of course, vary. It is also to be understood that the terminology used herein is for the purpose of describing particular embodiments only, and is not intended to be limiting. Unless defined otherwise, all technical and scientific terms used herein generally have the same meaning as commonly understood by one of ordinary skill in the art to which this disclosure belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid and polypeptide synthesis. The nomenclature used herein and the laboratory procedures described below are those well-known and commonly employed in the art. Procedures used for genetic engineering are well known and can be found for example in Sambrook et al., Molecular Cloning: A Laboratory Manual, Cold Spring Harbor, N.Y.).

As used in this specification and the appended claims, terms in the singular and the singular forms "a," "an," and "the," for example, include plural referents unless the content clearly dictates otherwise. Thus, for example, reference to "polypeptide," "the polypeptide," or "a polypeptide" also includes a plurality of polypeptides. Additionally, as used herein, the term "comprises" is intended to indicate a non-exhaustive list of components or steps, thus indicating that the given composition or method includes the listed components or steps and may also include additional components or steps not specifically listed. As an example, a composition "comprising a polypeptide" may also include additional components or polypeptides. The term "comprising" is also intended to encompass embodiments "consisting essentially of" and "consisting of" the listed components or steps. Similarly, the term "consisting essentially of" is also intended to encompass embodiments "consisting of" the listed components or steps.

Numeric ranges recited within the specification are inclusive of the numbers defining the range (the end point numbers) and also are intended to include each integer or any non-integer fraction within the defined range.

In describing and claiming the particular embodiments, the following terminology will be used in accordance with the definitions set out below.

As used herein, "B-domain deleted Factor VIII" or "FVIII-BDD" refers to a Factor VIII polypeptide which contains a deletion of at least some portion of the B-domain. In the examples set forth herein, FVIII-BDD specifically refers to a deletion of all but 14 amino acids of the B-domain of Factor VIII. (Lind et al., Eur. J. Biochem. 232:19-27 (1995)), the polypeptide sequence of which is set forth in SEQ ID NO: 3, which is encoded by the nucleotide sequence of SEQ ID NO: 4. However, while this particular FVIII-BDD sequence was employed in the examples herein, it is to be understood that Factor VIII polypeptides with modifications as compared to SEQ ID NO: 3, including differences in the B-domain deletion, could also be employed. For example, a Factor VIII polypeptide with more or fewer than 14 amino acids of the B-domain remaining could also be useful in some embodiments if Factor VIII procoagulant activity is retained.

As used herein, "Factor VIII" or "FVIII" refers to a blood clotting factor which is a glycoprotein synthesized and released into the bloodstream by the liver. In its immature form, FVIII contains a signal sequence, which is proteolytically cleaved during the translation process. Following removal of that 19 amino acid signal sequence, the Factor VIII polypeptide is in its mature form, in which the first amino acid of the secreted FVIII product is an alanine. This mature form of Factor VIII will be referred to herein as "mature Factor VIII." Mature wild-type human FVIII has the amino acid sequence set forth in SEQ ID NO:1, although allelic variants are possible, as are modified versions, such as those set forth in SEQ ID NOs: 3 and 5.

As used herein, a "functional Factor VIII polypeptide" denotes a polypeptide or combination of polypeptides that is/are capable, in vivo or in vitro, of correcting human Factor VIII deficiencies, characterized, for example, by hemophilia A. Factor VIII has multiple degradation or processed forms in the natural state. These are proteolytically derived from a precursor, one chain protein, as demonstrated herein. A functional Factor VIII polypeptide includes such single chain protein and also provides for these various degradation products that have the biological activity of correcting human factor VIII deficiencies. Allelic variations likely exist. The functional Factor VIII polypeptides include all such allelic variations, glycosylated versions, modifications, and fragments resulting in derivatives of Factor VIII so long as they contain the functional segment of Factor VIII and the essential, characteristic Factor VIII functional activity remains unaffected in kind. Those derivatives of Factor VIII possessing the requisite functional activity can readily be identified by straightforward in vitro tests described herein. Furthermore, functional Factor VIII polypeptide is capable of catalyzing the conversion of Factor X to Xa in the presence of Factor IXa, calcium, and phospholipid, as well as correcting the coagulation defect in plasma derived from hemophilia A affected individuals. From the disclosure of the sequence of the human Factor VIII amino acid sequences and the functional regions herein, the fragments that can be derived via restriction enzyme cutting of the DNA or proteolytic or other degradation of human Factor VIII protein will be apparent to those skilled in the art.

As used herein, "thrombin cleavage site" refers to a portion of the Factor VIII peptide chain which is a target cleavage site for thrombin. In certain embodiments, the thrombin cleavage site is located at or near the a1-A2 junction of the Factor VIII polypeptide. In other embodiments, the thrombin cleavage site is located at amino acid residues 370-375 of the mature wild-type human Factor VIII peptide (SEQ ID NO: 1). In further embodiments, the thrombin cleavage site may be a homologous site in a homologous Factor VIII polypeptide, such as an allelic variant or modified polypeptide.

As used herein, "activation loop" refers to a portion of the A2 subunit of the Factor VIII peptide chain which is capable of interfacing with Factor IXa. In certain embodiments, the activation loop is located at amino acid residues 558-565 of the mature wild-type human Factor VIII peptide (SEQ ID NO: 1). In further embodiments, the activation loop may be a homologous site in a homologous Factor VIII polypeptide, such as an allelic variant or modified polypeptide.

As used herein, "domain interface" refers to the regions or residues on the respective subunits of the Factor VIIIa heterotrimer which interact with the other subunits of the heterotrimer. As such, "A1-A2 domain interface" refers to the regions or residues on each of the A1 and A2 subunits that interact with the corresponding regions or residues on the other subunit. Similarly, "A2-A3 domain interface" refers to the regions or residues on each of the A2 and A3 subunits that interact with the corresponding regions or residues on the other subunit. In certain examples, the A1-A2 domain interface includes residues E272 and D519 (based on the wild-type Factor VIII sequence of SEQ ID NO: 1). In other examples, the A2-A3 domain interface includes residues E665 and E1984 (based on the wild-type Factor VIII sequence of SEQ ID NO: 1).

As used herein, "Factor IX" or "FIX" means Coagulation Factor IX, which is also known as Human Clotting Factor IX or Plasma Thromboplastin Component.

As used herein, "Factor X" or "FX" means Coagulation Factor X, which is also known by the names Human Clotting Factor X and by the eponym Stuart-Prower factor.

"Pharmacokinetics" or "PK" is used herein to describe the properties of absorption, distribution, metabolism, and elimination of a drug in a body. An improvement to a drug's pharmacokinetics means an improvement in those characteristics that make the drug more effective in vivo as a therapeutic agent, especially its useful duration in the body.

The terms "polypeptide," "peptide," and "protein" are generally used interchangeably herein and they refer to a polymer in which the monomers are amino acids that are joined together through amide bonds. Additionally, unnatural amino acids, for example, β-alanine, phenylglycine, and homoarginine are also included. Amino acids that are not gene-encoded can also be used with the technology disclosed herein. Furthermore, amino acids that have been modified to include reactive groups, glycosylation sites, polymers, therapeutic moieties, biomolecules, and the like can also be used. All of the amino acids used herein can be either the D- or L-isomer. The L-isomer is generally preferred. As used herein, "polypeptide," "peptide," and "protein" refer to both glycosylated and unglycosylated forms.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

"Variant" and "mutein" are used interchangeably herein and they each refer to a genetically engineered polypeptide or nucleotide sequence encoding a polypeptide arising as a result of a laboratory induced change to the nucleotide or polypeptide sequence. In describing amino acids, the standard one-letter or three-letter amino acid codes that are well-known in the art may be used in place of the full name of an amino acid. Additionally, a one-letter amino acid code followed by a number may be used to indicate a particular amino acid at a particular position in the starting sequence. For instance "V374" would indicate the valine at amino acid position 374 of the wt-FVIII sequence (SEQ ID NO: 1). Further, the one-letter code of the substituted amino acid may be included after the position number to indicate a particular amino acid substitution that was made. For instance, "V374F" would indicate that a phenylalanine residue has been substituted for the valine at position 374. "Substitution" as used herein refers to replacement of one amino acid with another amino acid and does not include deletions or additions unless expressly stated otherwise.

It should also be noted that, unless the language of a particular example specifically indicates otherwise, the amino acid positions disclosed herein are all based on the corresponding position in the amino acid sequence of the mature wild-type Factor VIII peptide, as provided in SEQ ID NO: 1, as is conventionally done in the art.

The variant polypeptides of the present disclosure include one or more amino acid substitutions in one or both of the thrombin cleavage site and the activation loop. In certain examples, the variant polypeptides include one or more amino acid substitutions in one or both of 1) the thrombin cleavage site, represented by amino acid positions 370-375 of SEQ ID NO: 1, and 2) the activation loop, represented by amino acid positions 558-565 of SEQ ID NO: 1. With regard to the thrombin cleavage site at residues 370-375, cleavage typically occurs immediately after the R372 residue, which makes this residue important for proper cleavage at this site. As such, in certain embodiments, the variant polypeptide will include one or more amino acid substitutions within the thrombin cleavage site represented by amino acid positions 370-375 of SEQ ID NO: 1, wherein the substitution is not at position 372. In certain embodiments, the amino acid substitution may be a substitution at one or more of the following positions in the starting sequence (with the position numbers based on the wt-FVIII sequence of SEQ ID NO: 1): Q370, I371, S373, V374, A375, S558, V559, D560, Q561, R562, G563, N564, and Q565. In certain other embodiments, there may be substitutions at 2, 3, 4, 5, 6, 7, 8, 9, 10, 11, 12, or 13 of those positions. In additional embodiments, the variant may comprise at least one substitution in each of the thrombin cleavage site (370-375) and the activation loop (558-565). In certain examples, the variant may comprise a substitution of at least one of Q370, I1371, S373, V374, and A375, and a substitution of at least one of S558, V559, D560, Q561, R562, G563, N564, and Q565. In further embodiments, the variant may comprise more than one substitution within either the thrombin cleavage site (370-375) or the activation loop (558-565), for example 2, 3, 4, 5, 6, 7, or 8 substitutions. In particular examples, the variant comprises two substitutions within the thrombin cleavage site (370-375) and two substitutions within the activation loop (558-565). In other examples, the variant comprises two substitutions within the thrombin cleavage site (370-375) and three substitutions within the activation loop (558-565). In particular examples, the substitutions within the thrombin cleavage site are Q370M, I371P, V374F, Q370M/I371P, or I371P/V374F. In other examples, the substitutions within the activation loop are V559L, R562W, R562F, R562K, Q565E, V559L/R562F, V559L/R562W, V559L/Q565E, V559L/R562W/Q565E, or V559L/R562F/Q565E.

In further examples, the variant Factor VIII polypeptide further includes one or more substitutions to amino acid residues within each of the A1-A2 and A2-A3 domain interfaces. In particular examples, the substitution within the A1-A2 domain interface comprises a substitution of one or both of residues E272 and D519 (based on the wild-type Factor VIII sequence of SEQ ID NO: 1). In certain embodiments, these substitutions replace one or both of the charged aspartic acid (D) or glutamic acid (E) residues at E272 and D519 with a hydrophobic residue, and particularly a hydrophobic residue such as alanine, leucine, proline, methionine, glycine, valine, isoleucine, phenylalanine, or tryptophan. In certain examples, the one or more substitutions within the A1-A2 domain interface are selected from the group consisting of E272A, E272V, D519A, and D519V. In additional examples, the substitution within the A2-A3 domain interface comprises a substitution of one or both of residues E665 and E1984 (based on the wild-type Factor VIII sequence of SEQ ID NO: 1). In certain embodiments, these substitutions replace one or both of the charged glutamic acid (E) residues at E665 and E1984 with a hydrophobic residue, and particularly a hydrophobic residue such as alanine, leucine, proline, methionine, glycine, valine, isoleucine, phenylalanine, or tryptophan. In further examples, the one or more substitutions within the A2-A3 domain interface are selected from the group consisting of E665A, E665V, E1984A, and E1984V. In certain examples, the variant Factor VIII polypeptide comprises D519A/E665A substitutions, D519A/E665V substitutions, D519V/E665A substitutions, or D519V/E665V substitutions.

In certain examples, preparation of the variant Factor VIII polypeptides involves site-directed mutagenesis of a nucleic acid sequence encoding a Factor VIII polypeptide. Such site-directed mutation of a nucleotide sequence may occur by any method known in the art and persons skilled in the art would be capable of readily determining an appropriate mutagenesis technique to employ for the specific application at hand. In certain examples, the mutagenesis is accomplished using a commercially available site-directed mutagenesis kit such as the Stratagene QuickChange™ II site-directed mutagenesis kit, the Clontech Transformer site-directed mutagenesis kit no. K1600-1, the Invitrogen GenTaylor site-directed mutagenesis system no. 12397014, the Promega Altered Sites II in vitro mutagenesis system kit no. Q6210, or the Takara Minis Bio LA PCR mutagenesis kit no. TAK RR016.

In certain embodiments, the variant Factor VIII polypeptides will have an increased activity in at least one activity assay when compared with the starting Factor VIII polypeptide. Any suitable assay for testing Factor VIII activity can be employed with the variant polypeptides of the present disclosure, and such assays are well known in the art. Such activity assays include, but are not limited to: aPTT; chromogenic or fluorogenic substrate assay for FVIII, either assembled from individual components of the FXase complex or as a kit; thrombin generation assay or test (TGA or TGT) or calibrated automated thrombography (CAT); and rotational thromboelastometry (ROTEM) or rotational thromboelastography (ROTEG).

The aPTT can refer to the one-stage or the less common two-stage assay, where coagulation is detected as the time needed to achieve a predefined sample turbidity or viscosity (clot time or CT). As the aPTT is a plasma-based assay, it has been used to assess potential Factor VIII activity and function in plasma. In the typical one-stage aPTT, a plasma sample containing FVIII is incubated with a negatively charged surface or particles and $Ca^{+2}$ to initiate coagulation. In the one-stage assay, FXIa, FVIIIa, FXa, thrombin, and fibrin generation occur in one reaction. In the two-stage assay FXIa, FVIIIa, and FXa generation occur at the first stage and thrombin and fibrin formation occur in the second stage. Modifications of the one-stage and two-stage aPTT may be possible to make the assays specific for FVIII quantitation, as in a FVIII-specific factor assay.

The chromogenic substrate assay (chromo assay) is a two-stage assay designed to assess FVIII function in the context of FXase complex (FIXa, PL, Ca+2, and FX). In this assay, FVIIIa is fully activated, and FIXa and PL are in excess, a situation not typically encountered physiologically. In this assay, FVIIIa is combined with purified or relatively purified components of the FXase complex to generate FXa in the first stage. In the second stage, the level of FXa generated is quantified by a substrate that yields color when cleaved by FXa. Variation of the chromogenic assay includes replacement of the chromogenic substrate with a fluorogenic substrate, and fluorescence emission is detected (fluorogenic assay).

TGA, another assay of FVIII procoagulant function, is performed by activating plasma containing FVIII with a physiologic initiator such as tissue factor (TF) or FXIa in the presence of phospholipid (PL) (40:40:20, v/v/v phosphatidylserine:phosphatidylcholine:phosphatidylethanolamine) to simulate the membrane surface of activated platelets. Thrombin generation (and coagulation) commences with the addition of $Ca^{+2}$ and a fluorogenic substrate for thrombin to the sample. In CAT, the fluorescence change over time is then related back to thrombin concentration by monitoring the rate of fluorescence change in parallel samples containing defined levels of thrombin. Parameters describing the kinetic change in thrombin generation profiles can include the time before the onset of the response (lag) and the peak thrombin achieved (peak).

ROTEM/ROTEG is analogous to TGA, except that the development of viscosity with coagulation is monitored rather than thrombin generation. Again, coagulation is initiated in plasma containing FVIII by $Ca^{+2}$, or TF-PL mixture. Parameters describing the kinetic changes in viscosity can include clot initiation time (CT) and the rate of viscosity change ($\alpha$ angle).

In certain examples, activity of the variant Factor VIII polypeptide will be tested by one or more assays. Note that due to the changes in the mechanism of action for these FVIII variants and to the differences in the ability of assays to detect specific aspects of FVIII function, only certain assays will detect marked enhancements in Factor VIII activity. As such, in certain examples, the variant Factor VIII polypeptide may have comparable activity to wt-FVIII in one assay while possessing increased activity in another assay. For example, the variant may have activity that is comparable to that of wt-FVIII in a chromogenic assay while possessing increased activity when tested using an aPTT assay or thrombin generation assay. This can occur, for example, when a variant has enhanced catalytic activity but is also more susceptible to proteolytic degradation. For some variants, the assays most sensitive to enhanced activity may be the one-stage aPTT and the TGA, but not the chromogenic assay. Such a discrepancy in assay performance of coagulation proteins is not uncommon, particularly when mutations are in domains impacting specific functions but not others (Leong et al., Biochemistry 31:2567 (1992); Stone et al., Biochemistry 30:6392 (1991); Henriksen and Mann, Biochemistry 28:2078 (1989)). These results may suggest that these variants may have the advantage of being easier to activate, i.e., the conversion from FVIII to FVIIIa is accelerated, which could then translate to enhanced thrombin generation.

In certain examples, the variant Factor VIII polypeptide will possess an activity greater than that of the starting Factor VIII polypeptide, wt-FVIII, FVIII-BDD, or D519VE665E-FVIII. These activities will be measured using polypeptides produced under comparable conditions, such as recombinant expression of the variant and starting polypeptide in the same type of cell line under comparable conditions. In certain embodiments, the activity will be increased by at least 1.1-fold over that of the starting Factor VIII polypeptide, wt-FVIII, FVIII-BDD, or D519VE665E-FVIII in at least one assay. In other embodiments, the activity will be increased by at least about 1.2-fold, 1.3-fold, 1.4-fold, 1.5-fold, 1.6-fold, 1.7-fold, 1.8-fold, 1.9-fold, 2.0-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 55-fold, 60-fold, 65-fold, 70-fold, 75-fold, 80-fold, 85-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 450-fold, 500-fold, or more over that of the starting Factor VIII polypeptide, wt-FVIII, FVIII-BDD, or D519VE665E-FVIII in at least one assay.

In still further embodiments, the activity will be increased by about 1.2 to 10-fold, 1.2 to 12-fold, 1.2 to 14-fold, 1.2 to 16-fold, 1.2 to 18-fold, 1.2 to 20-fold, 1.2 to 30-fold, 1.2 to 40-fold, 1.2 to 50-fold, 1.2 to 60-fold, 1.2 to 70-fold, 1.2 to 80-fold, 1.2 to 90-fold, 1.2 to 100-fold, 1.3 to 10-fold, 1.3 to 12-fold, 1.3 to 14-fold, 1.3 to 16-fold, 1.3 to 18-fold, 1.3 to 20-fold, 1.3 to 30-fold, 1.3 to 40-fold, 1.3 to 50-fold, 1.3 to 60-fold, 1.3 to 70-fold, 1.3 to 80-fold, 1.3 to 90-fold, 1.3 to 100-fold, 1.4 to 10-fold, 1.4 to 12-fold, 1.4 to 14-fold, 1.4 to 16-fold, 1.4 to 18-fold, 1.4 to 20-fold, 1.4 to 30-fold, 1.4 to 40-fold, 1.4 to 50-fold, 1.4 to 60-fold, 1.4 to 70-fold, 1.4 to 80-fold, 1.4 to 90-fold, 1.4 to 100-fold, 1.5 to 10-fold, 1.5 to 12-fold, 1.5 to 14-fold, 1.5 to 16-fold, 1.5 to 18-fold, 1.5 to 20-fold, 1.5 to 30-fold, 1.5 to 40-fold, 1.5 to 50-fold, 1.5 to 60-fold, 1.5 to 70-fold, 1.5 to 80-fold, 1.5 to 90-fold, 1.5 to 100-fold, 1.6 to 10-fold, 1.6 to 12-fold, 1.6 to 14-fold, 1.6 to 16-fold, 1.6 to 18-fold, 1.6 to 20-fold, 1.6 to 30-fold, 1.6 to 40-fold, 1.6 to 50-fold, 1.6 to 60-fold, 1.6 to 70-fold, 1.6 to 80-fold, 1.6 to 90-fold, 1.6 to 100-fold, 1.8 to 10-fold, 1.8 to 12-fold, 1.8 to 14-fold, 1.8 to 16-fold, 1.8 to 18-fold, 1.8 to 20-fold, 1.8 to 30-fold, 1.8 to 40-fold, 1.8 to 50-fold, 1.8 to 60-fold, 1.8 to 70-fold, 1.8 to 80-fold, 1.8 to 90-fold, 1.8 to 100-fold, 2 to 10-fold, 2 to 12-fold, 2 to 14-fold, 2 to 16-fold, 2 to 18-fold, 2 to 20-fold, 2 to 30-fold, 2 to 40-fold, 2 to 50-fold, 2 to 60-fold, 2 to 70-fold, 22 to 80-fold, 2 to 90-fold, 2 to 100-fold, 4 to 10-fold, 4 to 12-fold, 4 to 14-fold, 4 to 16-fold, 4 to 18-fold, 4 to 20-fold, 4 to 30-fold, 4 to 40-fold, 4 to 50-fold, 4 to 60-fold, 4 to 70-fold, 4 to 80-fold, 4 to 90-fold, 4 to 100-fold, 5 to 10-fold, 5 to 12-fold, 5 to 14-fold, 5 to 16-fold, 5 to 18-fold, 5 to 20-fold, 5 to 30-fold, 5 to 40-fold, 5 to 50-fold, 5 to 60-fold, 5 to 70-fold, 5 to 80-fold, 5 to 90-fold, 5 to 100-fold, 6 to 12-fold, 6 to 14-fold, 6 to 16-fold, 6 to 18-fold, 6 to 20-fold, 6 to 30-fold, 6 to 40-fold, 6 to 50-fold, 6 to 60-fold, 6 to 70-fold, 6 to 80-fold, 6 to 90-fold, 6 to 100-fold, 8 to 16-fold, 8 to 18-fold, 8 to 20-fold, 8 to 30-fold, 8 to 40-fold, 8 to 50-fold, 8 to 60-fold, 8 to 70-fold, 8 to 80-fold, 8 to 90-fold, 8 to 100-fold, 10 to 20-fold, 10 to 30-fold, 10 to 40-fold, 10 to 50-fold, 10 to 60-fold, 10 to 70-fold, 10 to 80-fold, 10 to 90-fold, 10 to 100-fold, 12 to 20-fold, 12 to 30-fold, 12 to 40-fold, 12 to 50-fold, 12 to 60-fold, 12 to 70-fold, 12 to 80-fold, 12 to 90-fold, 12 to 100-fold, 15 to 30-fold, 15 to 40-fold, 15 to 50-fold, 15 to 60-fold, 5 to 70-fold, 15 to 80-fold, 15 to 90-fold, 15 to 100-fold, 20 to 40-fold, 20 to 50-fold, 20 to 60-fold, 20 to 70-fold, 20 to 80-fold, 20 to 90-fold, 20 to 100-fold, 30 to 40-fold, 30 to 50-fold, 30 to 60-fold, 30 to 70-fold, 30 to 80-fold, 30 to 90-fold, 30 to 100-fold, 40 to 60-fold, 40 to 70-fold, 40 to 80-fold, 40 to 90-fold, 40 to 100-fold, 50 to 80-fold, 50 to 90-fold, 50 to 100-fold, 60 to 80-fold, 60 to 90-fold, 60 to 100-fold, 70 to 100-fold, 70 to 200-fold, 90 to 100-fold, 90 to 120-fold, 90 to 140-fold, 100 to 150-fold, 100 to 160-fold, 100 to 180-fold, 100 to 200-fold, 100 to 250-fold, 100 to 300-fold, 100 to 350-fold, 100 to 400-fold, 100 to 500-fold, 120 to 150-fold, 120 to 160-fold, 120 to 180-fold, 120 to 200-fold, 120 to 250-fold, 120 to 300-fold, 120 to 350-fold, 120 to 400-fold, 120 to 500-fold, 150 to 200-fold, 150 to 250-fold, 150 to 300-fold, 150 to 350-fold, 150 to 400-fold, 150 to 500-fold, 200 to 300-fold, 200 to 400-fold, 200 to 500-fold, 00 to 400-fold, 300 to 500-fold, or 400 to 500-fold over that of the starting Factor VIII polypeptide, wt-FVIII, FVIII-BDD, or D519VE665E-FVIII in at least one assay.

The Factor VIII variants described herein can be designed using any functional Factor VIII polypeptide as a starting polypeptide. In certain embodiments, the Factor VIII polypeptide is a human Factor VIII polypeptide. In further embodiments, the Factor VIII polypeptide is human wt-FVIII (SEQ ID NO: 1), FVIII-BDD (SEQ ID NO: 3), or D519VE665E-FVIII (SEQ ID NO: 5). The starting polypeptide may have deletions, insertions, and/or additions compared with the amino acid sequence of wild type Factor VIII. As non-limiting examples, the starting polypeptide may include Factor VIII mutants with mutations further stabilizing the A2 domain (see, e.g., WO 97/40145), Factor VIII mutants resulting in increased expression (see, e.g., Swaroop et al., JBC 272:24121-24124 (1997)), Factor VIII mutants reducing the immunogenicity relative to wild type (see, e.g., Lollar, Thromb. Haemost. 82:505-508 (1999)), Factor VIII reconstituted from differently expressed heavy and light chains (see, e.g., Oh et al., Exp. Mol. Med. 31:95-100 (1999), or Factor VIII mutants having reduced binding to receptors leading to catabolism of Factor VIII like HSPG (heparan sulfate proteoglycans) and/or LRP (low density lipoprotein receptor related protein) (see, e.g., Ananyeva et al., TCM 11:251-257 (2001)). In certain examples, the Factor VIII polypeptide may also contain additional amino acid substitutions, such as, for example, a substitution at or near the R336 residue, for example an R336I substitution. Additionally, useful starting polypeptides can be modified forms of these that still possess Factor VIII functionality, including polypeptides comprising an amino acid sequence at least about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% identical to the sequence of wt-FVIII (SEQ ID NO: 1), FVIII-BDD (SEQ ID NO: 3), or D519VE665E-FVIII (SEQ ID NO: 5). Further, variant Factor VIII polypeptides of the present disclosure include any variant polypeptide with at least about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% identity to the sequence of wt-FVIII (SEQ ID NO: 1), FVIII-BDD (SEQ ID NO: 3), or D519VE665E-FVIII (SEQ ID NO: 5) and which also contain one or more of the amino acid substitutions discussed herein, or in a further embodiment contain one or more amino acid substitutions in both the thrombin cleavage site and the activation loop. In another embodiment, variant Factor VIII polypeptides of the present disclosure include any variant polypeptide with more than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% identity to the sequence of wt-FVIII (SEQ ID NO: 1), FVIII-BDD (SEQ ID NO: 3), or D519VE665E-FVIII (SEQ ID NO: 5) and which also contain one or more of the amino acid substitutions discussed herein, or in a further embodiment contain one or more amino acid substitutions in both the thrombin cleavage site and the activation loop.

In another embodiment, the present disclosure relates to nucleic acid sequences encoding the variant Factor VIII polypeptides. In one embodiment, the Factor VIII variants are encoded by a nucleotide sequence having at least about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% identity across the full length to the nucleotide sequence of wt-FVIII (SEQ ID NO: 2), FVIII-BDD (SEQ ID NO: 4), or D519VE665E-FVIII (SEQ ID NO: 6), and which encodes a polypeptide containing one or more of the amino acid alterations discussed herein, or in a further embodiment contain one or more amino acid substitutions in both the thrombin cleavage site and the activation loop. In another embodiment, the Factor VIII variant is encoded by a nucleotide sequence having more than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, or 66% identity across the full length to the nucleotide sequence of wt-FVIII (SEQ ID NO: 2), FVIII-BDD (SEQ ID NO: 4), or D519VE665E FVIII (SEQ ID NO: 6), and which encodes a polypeptide containing one or more of the amino acid alterations discussed herein, or in a further embodiment contain one or more amino acid substitutions in both the thrombin cleavage site and the activation loop.

The percent identity values are calculated over the entire amino acid or nucleic acid sequence region. A series of programs based on a variety of algorithms is available to the skilled worker for comparing different sequences. In at least one embodiment, the percent identity between two amino acid sequences is determined using the Needleman and Wunsch algorithm (Needleman J. Mol. Biol. 48:444-453 (1970)) which has been incorporated into the needle program in the EMBOSS software package (Rice et al., "EMBOSS: The European Molecular Biology Open Software Suite," Trends in Genetics 16:276-277 (2000)), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap extension penalty of 0.5, 1, 2, 3, 4, 5, or 6. Guides for local installation of the EMBOSS package as well as links to WEB-Services can be found at emboss.sourceforge.net. A non-limiting example of parameters to be used for aligning two amino acid sequences using the needle program are the default parameters, including the EBLOSUM62 scoring matrix, a gap opening penalty of 10 and a gap extension penalty of 0.5. In yet another embodiment, the percent identity between two nucleotide sequences is determined using the needle program in the EMBOSS software package (Rice et al., "EMBOSS: The European Molecular Biology Open Software Suite," Trends in Genetics 16:276-277 (2000)), using the EDNAFULL scoring matrix and a gap opening penalty of 16, 14, 12, 10, 8, 6, or 4 and a gap extension penalty of 0.5, 1, 2, 3, 4, 5, or 6. A non-limiting example of parameters to be used in conjunction for aligning two amino acid sequences using the needle program are the default parameters, including the EDNAFULL scoring matrix, a gap opening penalty of 10 and a gap extension penalty of 0.5. The nucleic acid and protein sequences can further be used as a "query sequence" to perform a search against public databases to, for example, identify other family members or related sequences. Such searches can be performed using the BLAST series of programs (version 2.2) of Altschul (Altschul et al., J. Mol. Biol. 215:403-10 (1990)). BLAST using nucleic acid sequences of the present disclosure as query sequence can be performed with the BLASTn, BLASTx, or the tBLASTx program using default parameters to obtain either nucleotide sequences (BLASTn, tBLASTx) or amino acid sequences (BLASTx) homologous to sequences encoded by the nucleic acid sequences of the present disclosure. BLAST using protein sequences encoded by the nucleic acid sequences of the present disclosure as query sequence can be performed with the BLASTp or the tBLASTn program using default parameters to obtain either amino acid sequences (BLASTp) or nucleic acid sequences (tBLASTn) homologous to sequences of the present disclosure. To obtain gapped alignments for comparison purposes, Gapped BLAST using default parameters can be utilized as described in Altschul et al., Nucleic Acids Res. 25:3389-3402 (1997).

In certain embodiments, the polynucleotides of the present disclosure either essentially consist of the aforementioned nucleotide sequences or comprise the aforementioned nucleotide sequences. Thus, they can contain further nucleotide sequences as well. In certain embodiments, the polynucleotide can comprise, in addition to an open reading frame, further untranslated sequence at the 3' and at the 5' terminus of the coding gene region, for example at least 10, 20, 30, 40, 50, 60, 70, 80, 90, 100, 200, 300, 400, 500, or more nucleotides of the sequence upstream of the 5' terminus of the coding region and/or at least 10, 20, 30, 40, 50, 60, 70, 80, 90, 100, 200, 300, 400, 500, or more nucleotides of the sequence downstream of the 3' terminus of the coding gene region. Furthermore, the polynucleotides can encode proteins that comprise so called "tags" which may serve as a detectable marker or as an auxiliary measure for purification purposes. Tags for different purposes are well known in the art and include, for example, FLAG-tags, 6-histidine-tags, MYC-tags, and the like. In one embodiment, the polynucleotide further comprises an expression control sequence operatively linked to the nucleotide sequence.

In certain embodiments, a nucleic acid sequence encoding the variant Factor VIII polypeptide is inserted into a suitable vector. Numerous vectors useful for various purposes are well known in the art and persons skilled in the art would be able to readily select an appropriate vector for their desired application. In certain examples, the vector may be a cloning vector or an expression vector. In other examples, the vector may be a plasmid, a viral vector, a cosmid, or an artificial chromosome. Examples of suitable vectors include Tat/TaroriP expression vectors, such as pSS185 (Cho et al., Biotechnol. Prog. 19:229-232 (2003)) and pSS207 (Mei et al., Mol. Biotech. 34:165-178 (2006)), as well as pcDNA3.1, pCINeo, pEAK, pCEP4, and pUCOE vectors. In certain examples, the nucleic acid encoding the variant Factor VIII polypeptide may be placed adjacent to and/or under the control of an appropriate promoter. Numerous promoters useful for various purposes are well known in the art and persons skilled in the art would be able to readily select an appropriate promoter for their desired application. In certain examples, the promoter may be a constitutive promoter, an inducible promoter, or a tissue specific promoter. Examples of suitable promoters include the human or murine CMV promoter/enhancer, SV40 promoter/enhancer, EIf1alpha promoter, MPSV promoter, and SRalpha promoter.

In certain embodiments, the variant Factor VIII polypeptides are recombinantly produced in a cell, tissue, or organism. In certain embodiments, such recombinant production is accomplished by transforming or transfecting a host cell with a nucleic acid molecule encoding the variant polypeptide or a vector containing such a nucleic acid. Numerous methods of transformation and transfection are well known in the art and persons skilled in the art would be able to readily select an appropriate method for their desired application. Examples of suitable transformation methods include liposome mediated transfection (e.g., 293Fectin™ from Invitrogen), calcium phosphate transfection, electroporation, and DEAE-dextran transfection.

Such recombinant production can also be accomplished using any suitable host cell, tissue, or organism. Suitable cells, tissues, and organisms are well known in the art and persons skilled in the art would be able to readily select an appropriate host for their desired application. In some embodiments, the host cell is mammalian. Examples of suitable mammalian cell lines are the COS-1 (ATCC CRL 1650), baby hamster kidney (BHK) cell lines, such as BHK21, HKB11 (Cho et al., J. Biomed. Sci. 9:631 (2002)), HEK293 (ATCC CRL-1573; Graham et al., J. Gen. Virol. 36:59-72 (1977)), HEK293T (ATCC CRL 11268; DSM ACC 2494), and HEK293F (Invitrogen R79007) cells. A useful BHK cell line is the tk$^{31}$ ts13 BHK cell line (Waechter and Baserga, Proc. Natl. Acad. Sci. USA 79:1106-1110 (1982), incorporated herein by reference), hereinafter referred to as BHK 570 cells. The BHK 570 cell line has been deposited with the American Type Culture Collection, 12301 Parklawn Dr., Rockville, Md. 20852, under ATCC accession number CRL 10314. A tk$^-$ ts13 BHK cell line is also available from the ATCC under accession number CRL 1632. In addition, a number of other cell lines can be used within the present disclosure, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61), CHO K1 (ATCC CCI61), DUKX cells (Urlaub and Chasin, Proc. Natl. Acad. Sci. USA 77:4216-4220 (1980)) and CHO-DG44 cells (Urlaub et al., Cell 33:405-412 (1983)).

In another embodiment, the present disclosure relates to pharmaceutical formulations of the Factor VIII variants, as well as pharmaceutical compositions comprising a therapeutically effective amount of the Factor VIII variant and a pharmaceutically acceptable excipient or carrier. Pharmaceutically acceptable excipients or carriers generally include substances that may be added to the active ingredient to help formulate or stabilize the preparation and which cause no significant adverse toxicological effects to the patient. Numerous suitable excipients and carriers are well known in the art and persons skilled in the art would be able to readily identify a suitable excipient or carrier to employ for a particular formulation or composition. Examples of suitable excipients or carriers include water, sugars such as maltose or sucrose; albumin; and salts. Specific examples of suitable formulations include the formulations described in U.S. Pat. No. 5,763,401 (filed Jul. 12, 1996; issued Jun. 9, 1998), which is incorporated herein by reference in its entirety.

In one embodiment, the pharmaceutical formulations/compositions are for parenteral administration, such as by iv, sc, or intramuscular (im) administration, and dosing may be as a single bolus dose, intermittent dosing, or as a continuous iv infusion. Topical formulations are also useful. In one embodiment the pharmaceutical formulation comprises an isolated Factor VIII variant as described herein, or comprises a composition of Factor VIII variants as described herein, in a lyophilized preparation that is reconstituted at the time of use. Alternatively, the pharmaceutical formulation can be a stable liquid ready-to-use formulation not requiring reconstitution. The pharmaceutical formulation can be provided in single-use vials of lyophilized powder or vials of ready-to-use solution of about 25 IU, 50 IU, 75 IU, 100 IU, 125 IU, 150 IU, 175 IU, 200 IU, 250 IU, 300 IU, 350 IU, 400 IU, 450 IU, 500 IU, 550 IU, 600 IU, 650 IU, 700 IU, 750 IU, 800 IU, 850 IU, 900 IU, 950 IU, 1000 IU, 1050 IU, 1100 IU, 1150 IU, 1200 IU, 1250 IU, 1300 IU, 1350 IU, 1400 IU, 1450 IU, 1500 IU, 1550 IU, 1600 IU, 1650 IU, 1700 IU, 1750 IU, 1800 IU, 1850 IU, 1900 IU, 1950 IU, 2000 IU, 2050 IU, 2100 IU, 2150 IU, 2200 IU, 2250 IU, 2300 IU, 2350 IU, 2400 IU, 2450 IU, 2500 IU, 2550 IU, 2600 IU, 2650 IU, 2700 IU, 2750 IU, 2800 IU, 2850 IU, 2900 IU, 2950 IU, 3000 IU, 3050 IU, 3100 IU, 3150 IU, 3200 IU, 3250 IU, 3300 IU, 3350 IU, 3400 IU, 3450 IU, 3500 IU, 3550 IU, 3600 IU, 3650 IU, 3700 IU, 3750 IU, 3800 IU, 3850 IU, 3900 IU, 3950 IU, 4000 IU, 4050 IU, 4100 IU, 4150 IU, 4200 IU, 4250 IU, 4300 IU, 4350 IU, 4400 IU, 4450 IU, 4500 IU, 4550 IU, 4600 IU, 4650 IU, 4700 IU, 4750 IU, 4800 IU, 4850 IU, 4900 IU, 4950 IU, 5000 IU, 5500 IU, 6000 IU, 6500 IU, 7000 IU, 7500 IU, 8000 IU, 8500 IU, 9000 IU, 9500 IU, 10000 IU, 10500 IU, 11000 IU, 11500 IU, 12000 IU, 12500 IU, 13000 IU, 13500 IU, 14000 IU, 14500 IU, or 15000 IU, and vials containing any range of the above amounts identified by two of the above numbers are included herein (e.g., a range of 25-75 IU, 100-200 IU, etc.). "IU" is understood in the field as an International Unit and is defined by the WHO International Standard. Actual methods for preparing parenterally administrable compositions will be known or apparent to those skilled in the art and are described in more detail in, for example, Remington's Pharmaceutical Sciences, 21st ed., published by Lippincott Williams & Wilkins (2005). Topical application, such as can be advisable in the case of trauma or surgery, can be carried out by means of a spray, perfusion, catheters, stent, vascular graft or stent, ointment, or other preparation known in the art. In certain examples, topical administration can be by way of a solid or semi-solid matrix, such as a surgical sponge or collagen matrix, which has been treated with, infused with, coated with, or soaked in a composition comprising the variant Factor VIII polypeptide. Methods of preparing such matrices are well known in the art (see, e.g., Thrombosis/Hemostasis 12:445 (2006)). The composition of the disclosure would then be applied to the matrix using known technology, such as spraying an aqueous formulation onto the matrix.

In one embodiment, the present disclosure relates to kits comprising the variant Factor VIII polypeptide. In certain examples, the kit contains a vial containing the lyophilized variant Factor VIII polypeptide, or a lyophilized formulation comprising the polypeptide, and also a diluent for reconstitution. In other examples, the kit contains a topical formulation of the Factor VIII polypeptide, for example, an ointment, spray, or liquid, and a matrix such as a sponge or other medical matrix to which the topical formulation may be applied before administration to the patient.

Proper dosage for administration to a patient suffering from Hemophilia A or another clotting disorder caused by a deficiency in a particular clotting factor can be readily determined by persons skilled in the art based upon, for example, the weight of the patient, the severity of the bleeding episode, the factor deficiency, and the specific activity of the particular variant being employed. In certain examples, dosing can be about 5 IU/kg, 10 IU/kg, 15 IU/kg, 20 IU/kg, 25 IU/kg, 30 IU/kg, 35 IU/kg, 40 IU/kg, 45 IU/kg, 50 IU/kg, 55 IU/kg, 60 IU/kg, 65 IU/kg, 70 IU/kg, 75 IU/kg, 80 IU/kg, 85 IU/kg, 90 IU/kg, 95 IU/kg, 100 IU/kg, or more when administered parenterally. The dosage may also be within a range of dosages in which each endpoint of the range is selected from the above dosages, such as, i.e., 5-15 IU/kg, 10-20 IU/kg, etc. In certain embodiments, for a patient having hemophilia A, the dosages administered iv are about 40 IU per kilogram for pre-operative indications, 15 to 20 IU per kilogram for minor hemorrhaging, and 20 to 40 IU per kilogram administered over an 8-hour period for a maintenance dose. These dosages may be administered as frequently as needed based on the pharmacokinetic profile of the variant Factor VIII preparation being administered. For example, such preparations may be administered intravenously twice per day, daily, every other day, every third day, three times per week, twice per week, or once per week for prophylactic use. Frequency of dosaging would be determined based upon the severity of the Hemophilia A condition, the pharmacokinetics of the variant being administered, and the prolongation of action achieved due to enhanced activity.

The Factor VIII variants and compositions herein are useful for the treatment of blood clotting disorders and those disorders that benefit from blood coagulation, and are particularly useful in situations where a Factor VIII with increased clotting activity is needed. Accordingly, the Factor VIII variants and compositions herein are useful for prophylactic treatment in patients with clotting disorders, as well as for treatment of acute bleeding episodes in patients with or without an underlying clotting deficiency. In certain embodiments, the variant Factor VIII polypeptides can be employed to treat bleeding caused by or related to penetrating traumatic injury; blunt traumatic injury; bleeding in elective surgery; bleeding in cardiac surgery; bleeding in spinal surgery; orthopedic surgery; neurosurgery; oncology surgery; post-partum surgery; menorrhagia; bleeding in stem cell transplantation; bleeding in liver transplantation; gastrointestinal bleeding; active variceal bleeding in cirrhosis; non variceal bleeding in cirrhosis; diffuse alveolar hemorrhage; aortic aneurysm; intracerebral hemorrhage; traumatic brain injury; brain contusion; reversal of warfarin; reversal of heparin; reversal of anticoagulants; reversal of antithrombotics; Factor VIII deficiency; specific types of von Willebrand disease; hereditary hemorrhagic telangiectasis; various arteriovenous malformations; burns; prophylaxis in hemophilia patients with inhibitors; partial hepatectomy for non-cirrhotic and cirrhotic patients; acquired hemophilia; idiopathic thrombocytopenic purpura; defects in plateletmediated hemostasis (e.g., defects in platelet number or response); Glanzmann's Thrombasthenia; Glanzmann's Thrombasthenia refractory to platelet transfusion; BernardSoulier Syndrome; and Dengue hemorrhagic fever.

The following examples are offered to illustrate, but not to limit, the claimed embodiments. It is to be understood that the examples and embodiments described herein are for illustrative purposes only, and persons skilled in the art will recognize various parameters that can be altered without departing from the spirit of the disclosure or the scope of the appended claims.

EXAMPLES

Example 1: Mutagenesis of Thrombin Cleavage Site and Activation Loop

Thrombin Cleavage Site Mutagenesis

Expression constructs for a variety of FVIII variants carrying amino acid substitutions at positions within the thrombin cleavage site were generated by standard sitedirected mutagenesis using the Quick Change Site-Directed Mutagenesis Kit (Agilent Technologies cat. #200251) and using FVIII-BDD as a starting polypeptide. The constructs were originally created in a pcDNA3.1 vector. Following mutagenesis, the nucleic acid sequence encoding the variant Factor VIII was cut out of the pcDNA3.1 using appropriate restriction enzymes and was ligated into a pSS207 expression vector. The resulting plasmids were transiently transfected into HEK293 cells in a 96 well-based format. FVIII expression levels were quantitated by standard sandwich ELISAs.

Activation Loop Mutagenesis

Gene libraries individually randomizing amino acid positions 558-65 were generated using FVIII-BDD as a starting polypeptide and the standard mutagenesis technique described above. Clonal DNA preparations of the eight libraries were transiently transfected into HEK293 cells. FVIII expression levels were quantitated by standard sandwich ELISAs, as described above.

Inclusion of Additional Mutations

In addition to producing substitutions within the thrombin cleavage site and activation loop, certain substitutions at other positions along the Factor VIII polypeptide chain were also made in order to investigate the effects of such additional mutations. In one instance, a pcDNA3.1 vector containing a nucleic acid encoding a D519VE665V-FVIII polypeptide with I371P, V374F, V559L, R562W, and Q565E substitutions was further subjected to site directed mutagenesis, as described above, to produce an R336I substitution. The resulting nucleic acid was then transferred to the expression vector pSS207.

Combination of Mutations of Interest

Following creation of the distinct variant sets, mutations of interest were combined and characterized in a variety of permutations using essentially identical protocols. Overall, roughly 2000 FVIII variants were generated and characterized.

Factor VIII Activity Assays

FVIII activity was measured by both chromogenic and aPTT assays. For purified proteins, chromogenic activity was determined by Coatest FVIII:C (Instrumentation Laboratory; Bedford, Mass.), using 02-122 as a calibrator (NIBSC; Potters Bar, Hertfordshire, UK). Details of the chromogenic assay principles are described above. The aPTT activity of purified proteins was determined on the ACL TOP, using FVIII-BDD as a calibrator and the APTT-SP kit (Instrumentation Laboratory; Bedford, Mass.). Further details of the one-stage aPTT assay principles are described above. Specific activity of purified proteins was calculated using A280 to determine the protein concentrations.

Results

Numerous variants of FVIII-BDD with amino acid substitutions at positions within the thrombin cleavage site at amino acids 370-375 were produced and investigated (see Table 1). Preferred thrombin cleavage sequences were based on the ability of thrombin to cleave specific linear peptide sequences over others using kinetic fluorogenic substrate assay (Bianchini et al., J. Biol. Chem. 277:20527 (2002)). Surprisingly, one variant that was previously predicted to be containing an "optimal" thrombin cleavage site (Bianchini et al., J. Biol. Chem. 277:20527 (2002)) showed poor aPTT activity (variant "a" in Table 1). Other variants with partial correspondence to the predicted "optimal" consensus sequence (variants b and c in Table 1) displayed enhanced aPTT activity. Without wanting to be limited in any way by theory, the discrepancy from the predicted "optimal" thrombin cleavage site may be due partly to the limited capacity to extrapolate from thrombin interaction with small, linear peptide sequences to thrombin's interaction with large, three-dimensional proteins. Nevertheless, the enhanced aPTT activity of "b" and "c" indicated that these FVIII mutants were more efficiently activated under aPTT conditions, e.g., limited activated coagulation factor initiation.

TABLE 1

| Variant Name | Specific Activity (aPTT, fold over FVIII-BDD) |
|---|---|
| FVIII-BDD (SEQ ID NO. 3) | 1 |
| Q370M, I371P, S373F, V374S, A375R | 0.27 |
| Q370M, I371P, | 2.0 |
| I371P, V374F | 2.5 |

Roughly 1600 Factor VIII variants with amino acid substitutions in the activation loop at positions 558-565 were produced and characterized. While the primary screen was done using a chromogenic assay, aPTT assays identified variants with enhanced procoagulant activity. Table 2 lists the aPTT activities of certain variants produced and characterized.

TABLE 2

| Variant | Specific Activity (aPTT, fold over FVIII-BDD) |
|---|---|
| FVIII-BDD | 1 |
| R562W | 1.7 |
| R562F | 2.0 |
| Q565E | 2.0 |
| R562K | 2.8 |
| V559L | 3.6 |

Subsequently, the effects of combining multiple amino acid substitutions within the activation loop was investigated. Table 3 lists the activities of selected combinations of variants.

TABLE 3

| Variant | Specific Activity (aPTT, fold over FVIII-BDD) |
|---|---|
| FVIII-BDD | 1 |
| V559L, R562F | 3.2 |
| V559L, R562W | 3.1 |
| V559L, Q565E | 4.8 |
| V559L, R562W, Q565E | 7.9 |
| V559L, R562F, Q565E | 9.5 |

Figure 2:
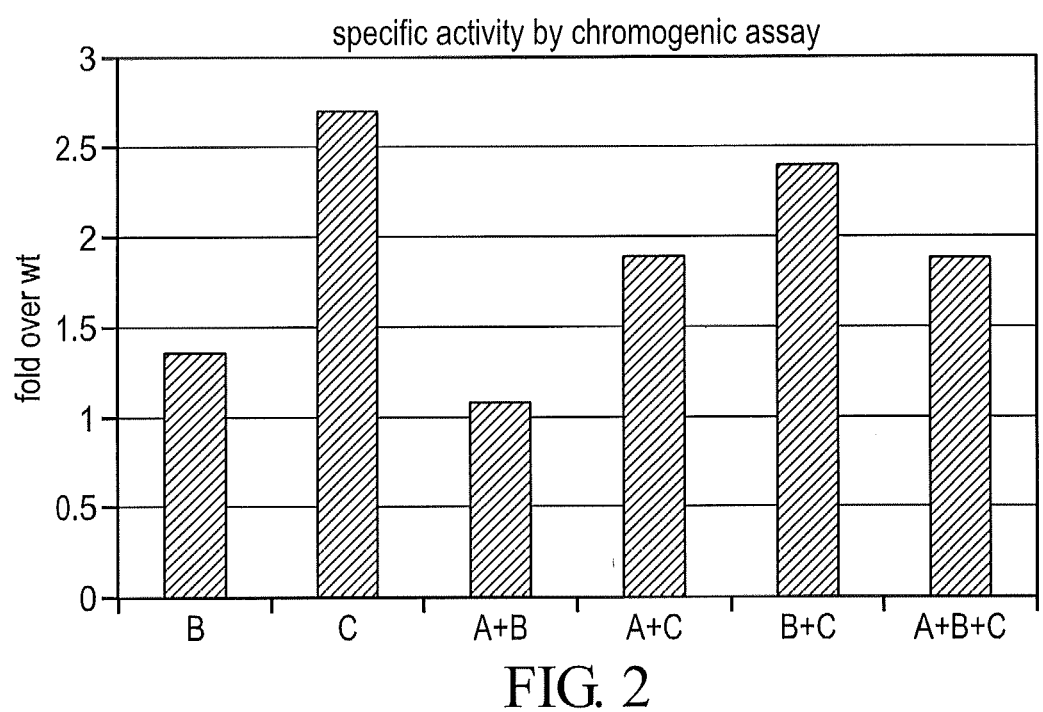
FIG. 2 presents specific activities of various Factor VIII polypeptides and variants, presented as fold activity over wild-type Factor VIII, as determined by a chromogenic assay. The designations have the same meanings as for FIG. 1.

Finally, combinations of variants at both the thrombin cleavage site and the activation loop were characterized. Many of the resulting variants showed only modest activity increases as assessed by chromogenic assay (FIG. 2), but showed substantial activity increases when characterized by the aPTT assay (FIG. 1). The modest change in chromogenic assay activity versus the markedly enhanced aPTT activity might be consistent with the activation advantage of these FVIII variants, as FVIII is fully pre-activated in the chromogenic assay but not in the aPTT assay.

Example 2: Further Characterization of Var97

Another particular variant, termed Var97, which utilized D519VE665V-FVIII as the starting polypeptide and which possessed I371P, V374F, V559L, R562W, and Q565E amino acid substitutions, was further characterized. The selected variant was first cloned into the pSS207 expression vector and transfected into HKB11 cells to obtain a stably expressing pool of cells used to inoculate a 10 L wave fermenter. Purified Var97 protein was obtained and characterized both in vitro and in vivo as described below.

In the initial studies, it was found that purified Var97 protein has significantly enhanced aPTT activity compared to its chromogenic assay activity relative to the starting Factor VIII polypeptide. The ratio of specific activity for both these assays indicated that the degree of aPTT activity over chromogenic assay activity for the variant Var97 protein was about 30 times that of FVIII-BDD activity (Table 4).

TABLE 4

| Protein | Ratio of aPTT activity to chromogenic assay activity | Standard deviation of ratio |
|---|---|---|
| FVIII-BDD | 0.76 | 0.40 |
| D519VE665V-FVIII | 2.01 | 0.18 |
| Var97 | 33.1 | 2.69 |

Figure 3:
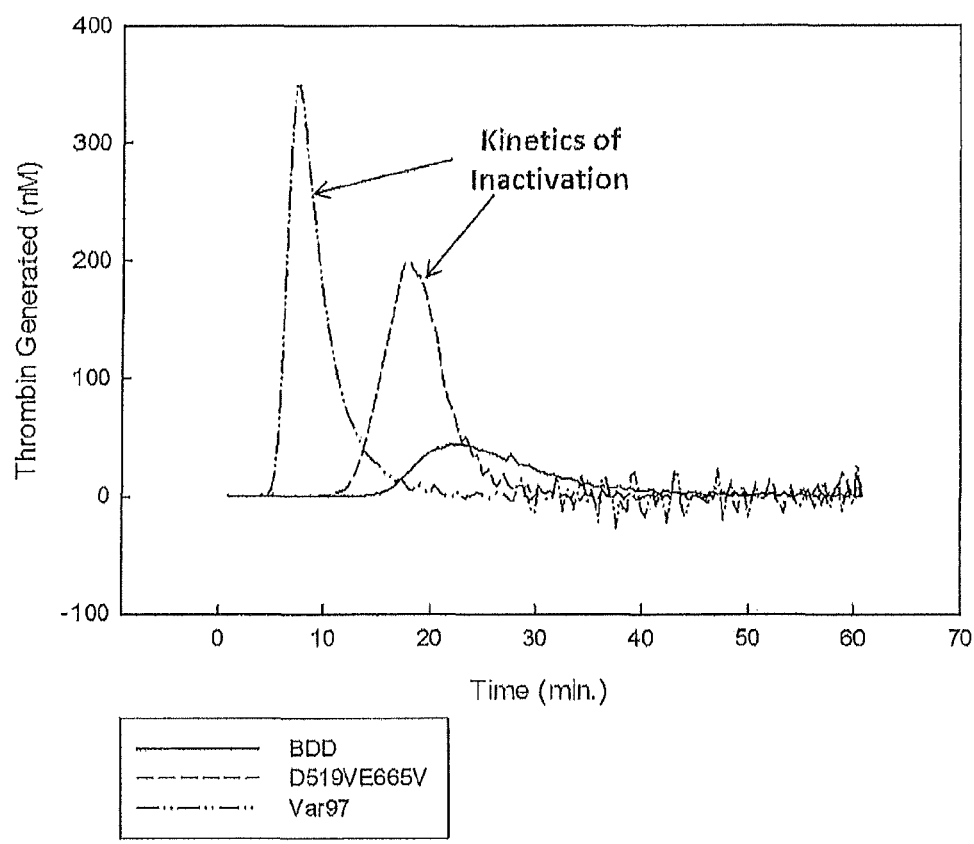
FIG. 3 presents thrombin generation profiles for FVIII-BDD (SEQ ID NO: 3), D519VE665V-FVIII (SEQ ID NO: 5), and Var97, a variant of D519VE665V-FVIII which possesses the following amino acid substitutions: I371P, V374F, V559L, R562W, and Q565E (SEQ ID NO: 53).

Further assessment of Var97 potency in coagulation was performed by TGA using tissue factor (TF) as an initiator. TGA was performed as recommended by the manufacturer (Diagnostica Stago; Asnières sur Seine, France). In brief, FVIII (BDD, D519VE665V, or variant) was spiked into human hemophilia A plasma with 1 pM TF 4 µM PL mixture, final concentration, as described above. Reactions were initiated by adding a mixture of thrombin substrate and $CaCl_2$ (Flu-Ca), and monitored for 60 min. The TGA results reported herein represent the mean of triplicate experiments. Due to the use of low levels of TF, the TGA is likely to more closely reflect physiologic coagulation. By TGA, Var97 was clearly more potent than either FVIII-BDD or D519VE665V-FVIII proteins, eliciting a very rapid increase in thrombin generation relative to those parent molecules (FIG. 3). Comparison of the thrombin profiles between Var97 and its parent, D519VE665V-FVIII, clearly demonstrated the contribution of the additional mutations by increasing the ease of thrombin activation (shorter lag) and the enhanced FXa generation (faster rate of rise, and the larger extent of thrombin generation).

Despite its enhanced capacity to elicit a thrombin response, the overall Var97 thrombin profile was qualitatively very similar to FVIII-BDD and D519VE665V-FVIII, where the rate of return toward baseline thrombin levels was related to peak thrombin levels (FIG. 3). This suggests that Var97 did not alter the mechanisms regulating thrombin levels in plasma. These results predict that Var97 is likely to pose no additional thrombogenic risk or systemic coagulation risk above that of the FVIII-BDD or D519VE665V-FVIII proteins.

Figure 4:
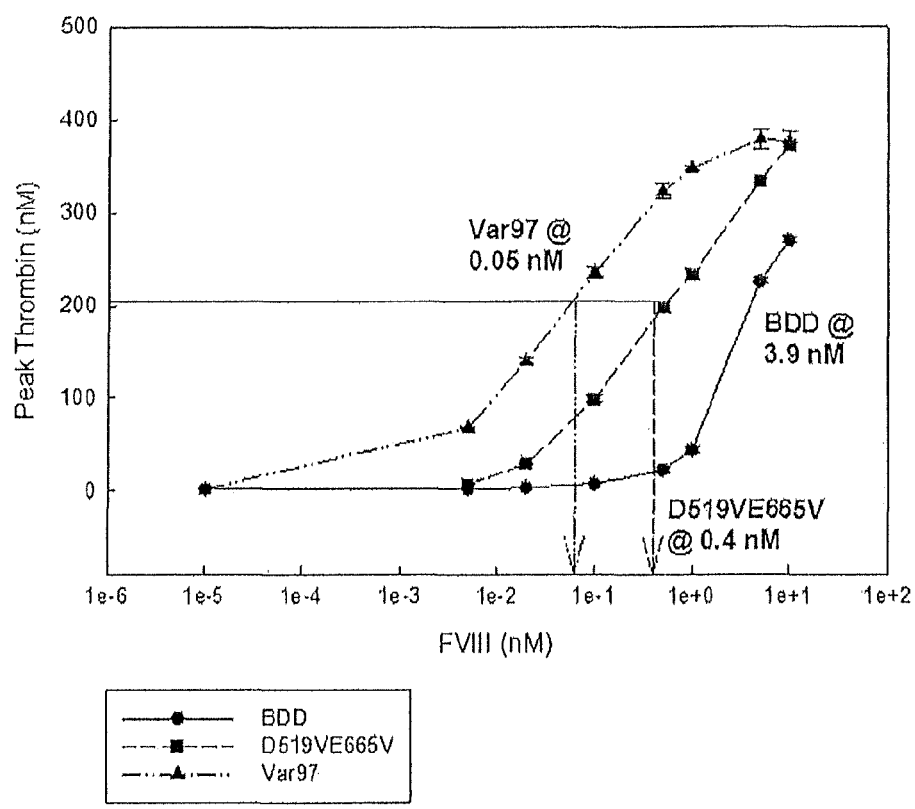
FIG. 4 presents data demonstrating the concentration of various Factor VIII polypeptides and variants needed to elicit a defined quantity of peak thrombin. The Factor VIII polypeptides investigated are FVIII-BDD (SEQ ID NO: 3), D519VE665V-FVIII (SEQ ID NO: 5), a modified FVIII-BDD with D519V and E665V amino acid substitutions, and Var97, a variant of D519VE665V-FVIII which possesses the following amino acid substitutions: I371P, V374F, V559L, R562W, and Q565E (SEQ ID NO: 53).
Figure 5:
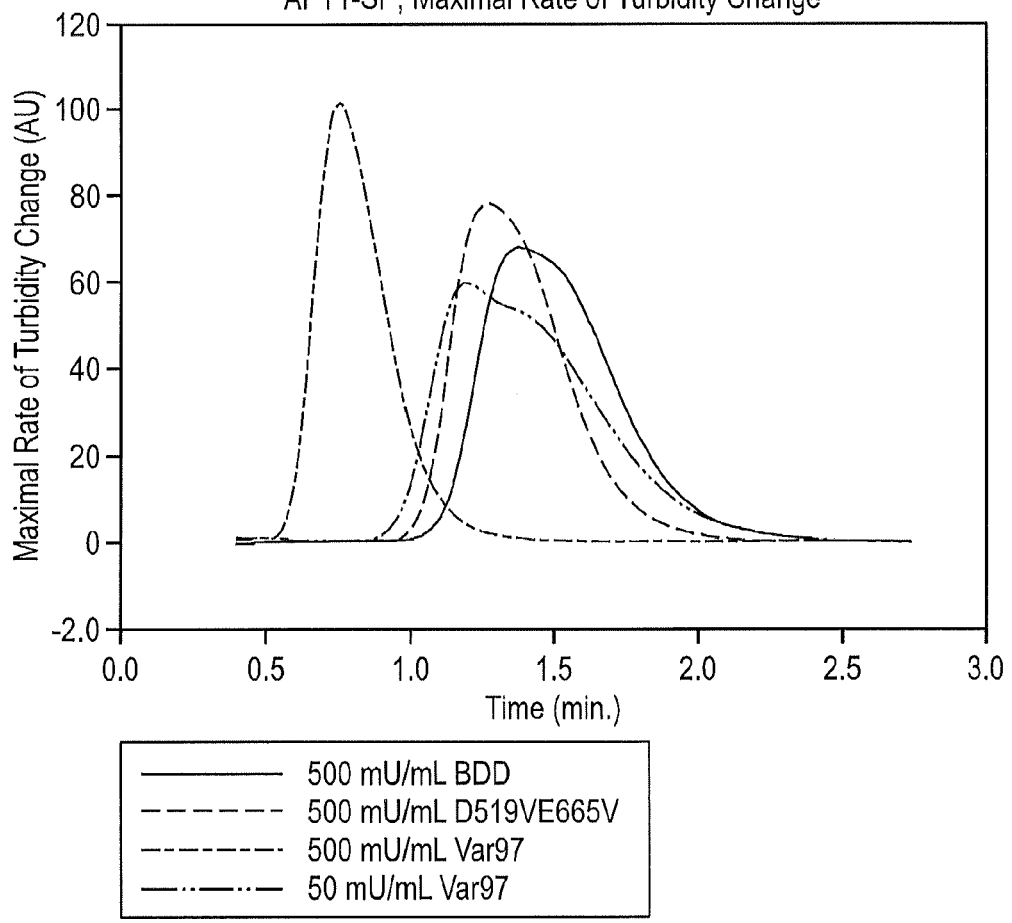
FIG. 5 presents kinetic profiles of the clot formation rates for FVIII-BDD (SEQ ID NO: 3), D519VE665V-FVIII (SEQ ID NO: 5), and Var97, a variant of D519VE665V-FVIII which possesses the following additional amino acid substitutions: I371P, V374F, V559L, R562W, and Q565E (SEQ ID NO: 53). The approximately 10-fold greater activity of Var97 relative to BDD and D519VE665V is evident in the time needed to achieve maximal rate of clot formation.

Quantitative comparisons of Var97 potency relative to other FVIII molecules tested indicate agreement between the procoagulant assay (TGA and aPTT) results. Comparison of the concentration of Var97 needed to elicit a defined quantity of peak thrombin indicated that Var97 was ~10× more potent than its parent D519VE665V-FVIII, and ~100× more potent than FVIII-BDD (FIG. 4). A similar assessment by aPTT indicated that ~10× less Var97 was required to elicit the same clot time as D519VE665V-FVIII (FIG. 5).

Figure 6:
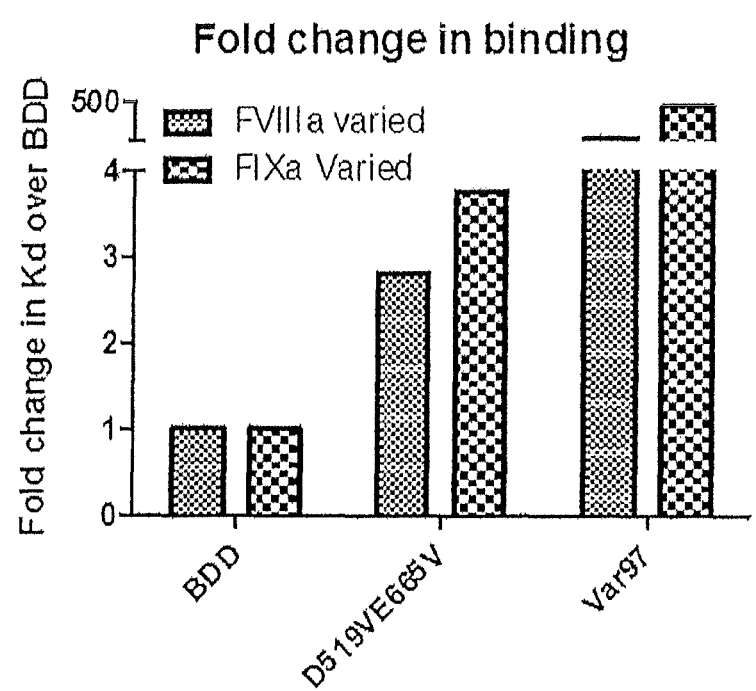
FIG. 6 presents binding affinity results for FVIII-BDD (SEQ ID NO: 3), D519VE665V-FVIII (SEQ ID NO: 5), and Var97, a variant of D519VE665V-FVIII which possesses the following additional amino acid substitutions: I371P, V374F, V559L, R562W, and Q565E (SEQ ID NO: 53).

The function of the Var97 variant in its physiologic enzyme complex was examined using FXase kinetic assays. These FXase kinetic assays were performed in 10 mM HEPES pH 7.4, 150 mM NaCl, 5 mM CaCl2, 0.01% Tween 20, 0.01% BSA and 10 µM PL (40:40:20, v/v/v PS:PC:PE). In these FXase kinetic assays, purified FVIIIa proteins were generated by incubation with 20 nM thrombin. The FVIII level was held fixed at 10 pM and reacted with varying concentrations of FIXa (0-10 nM), or the FIXa level was held fixed at (100 pM) and the level of thrombin activated FVIIIa was varied (0-10 nM). FX (150 nM) was added to either types of reactions, and after 1 min., the FXase reactions were stopped by addition to EDTA. The amount of FXa generated in these reactions were measured using the S-2765 chromogenic substrate. FXa generation was then extrapolated from a standard curve relating FXa level to rates of chromogenic substrate cleavage. The data was fit to a standard Michaelis-Menten equation to derive kinetic constants. This data was plotted to show how FXa activity generation varied with FIXa concentration. Results of this analysis are shown in Table 5 and FIG. 6. As Table 5 demonstrates, the Var97 variant has an enhanced rate of FX activation as opposed to the wt-FVIII or FVIII-BDD polypeptides. Additionally, FIG. 6 illustrates that the Var97 variant shows an increased binding affinity for FIXa. In fact, Var97 shows at least a 4-fold greater binding affinity for FIXa over the FVIII-BDD polypeptide.

TABLE 5

|  | Vmax (nM/sec) | sem | Km (nM) | sem | Kcat (s-1) | sem |
| --- | --- | --- | --- | --- | --- | --- |
| Var97 | 0.325 | 0.007 | 16.770 | 1.554 | 3.25 | 0.067 |
| D519VE665V-FVIII | 0.186 | 0.003 | 10.990 | 0.894 | 1.859 | 0.031 |
| FVIII-BDD | 0.147 | 0.002 | 9.493 | 0.779 | 1.472 | 0.023 |

Figure 7:
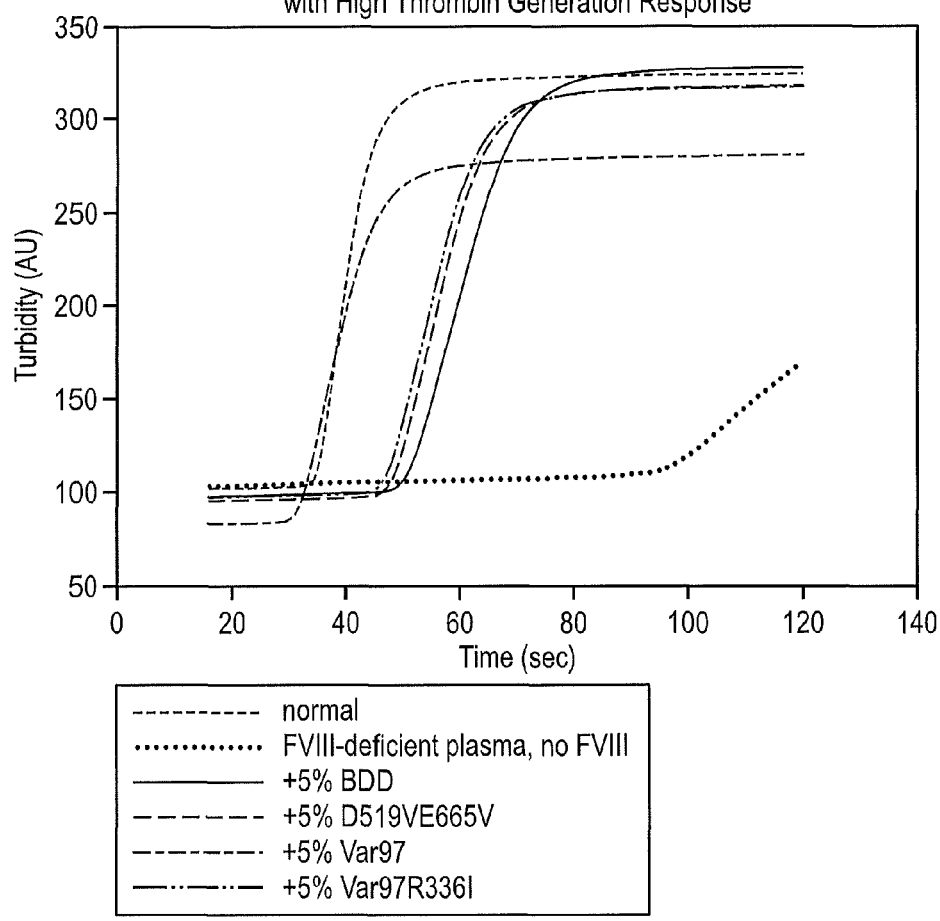
FIG. 7 presents turbidity profiles (absorbance units versus time) for clot formation using either normal plasma, FVIII-deficient plasma, or FVIII-deficient plasma containing 50 mU/mL (5%) of one of the following FVIII variants: FVIII-BDD, D519VE665V-FVIII, Var97, or Var97-R336I.

The turbidity of a clotting solution over a time course can be analyzed to investigate both clotting kinetics and the structure of a resulting clot. It has been previously demonstrated that changes in the turbidity versus time profile during clotting can be induced by lowering the concentration of clotting factors as compared to physiological levels, and further that such changes in the turbidity profile correlate with changes in the fibrin structure of the clot. See, e.g., Weisel and Nagsawami, Biophys. J., 63:111-28 (1992). Turbidity analysis was performed as described by Weisel and Nagsawami using either normal plasma, FVIII-deficient plasma, or FVIII-deficient plasma containing 50 mU/mL of the various Factor VIII variants. As shown in FIG. 7, introduction of either 50 mU/mL BDD or D519VE665V to FVIII-deficient plasma produced a turbidity profile (absorbance units [AU] versus time [sec]) which differs from that of normal serum; the rise in turbidity in these two variants was not nearly as rapid as was observed in the normal serum sample. In addition to indicating that the clotting kinetics of BDD and D519VE665V are not as rapid as in normal serum, this suggests that the presence of 50 mU/mL of the BDD or D519VE665V variant may produce a different clot structure and architecture than is produced during normal clotting. In contrast, introduction of 50 mU/mL Var97 Factor VIII variant produced a turbidity profile that is quite similar to that of the normal serum sample, indicating clotting kinetics and clot structure that closely resembles that of a normal clot.

Figure 8:
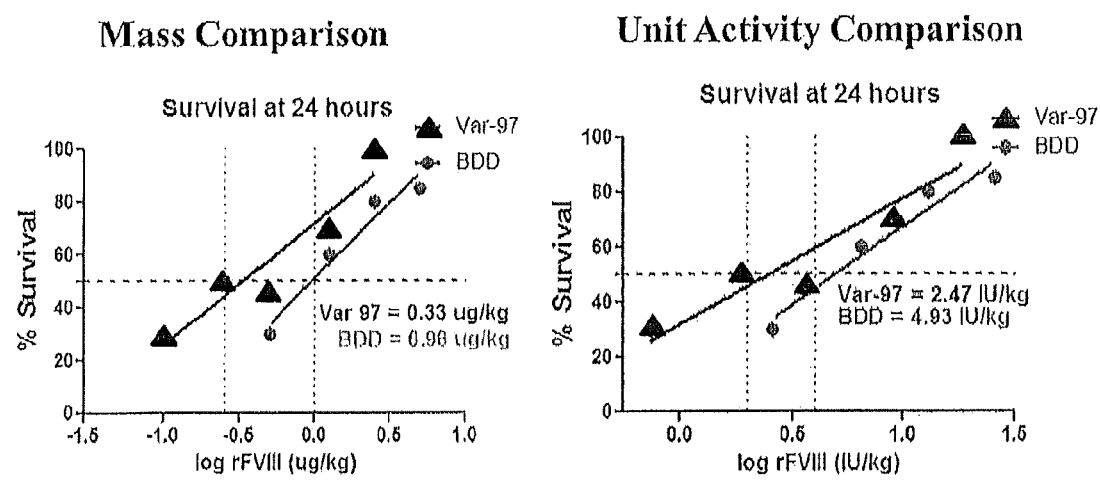
FIG. 8 presents plots of 24-hour survival (%) of HemA mice following vascular injury after administration of various dosages, measured either by mass (left panel) or units (right panel), of either FVIII-BDD (gray circles) or Var97 (black triangles).

As a further characterization of the Var97 variant, a study was performed to compare the ability of BDD and Var97 to protect against death from vascular injury in HemA mice. HemA mice were dosed with different concentrations of the various FVIII and 24 hours later, tail veins of HemA mice were transected as described (Mei et al., Blood (2010) 116: 270-279.). HemA mice survival was monitored for 24 hours and FVIII variant efficacy was assessed as 24 hour survival. The survival rate at the various dosages administered was then plotted (both in µg/kg and IU/kg) and the dosage of BDD and Var97 required to result in 50% survival (ED50) was determined from the plot (FIG. 8 and Table 6). As this shows, a 50% survival rate is achieved at ~2-3-fold lower dose with Var97 than with BDD. This correlates well with the results of the other tests discussed herein, which indicated enhanced potency of Var97 and improved clot structure produced by Var97.

TABLE 6

|  | ED50 (µg/kg) | ED50 (IU/kg) |
| --- | --- | --- |
| Var97 | 0.33 | 2.47 |
| BDD | 0.96 | 4.93 |
| Difference | ~3-fold | ~2-fold |

Figure 9:
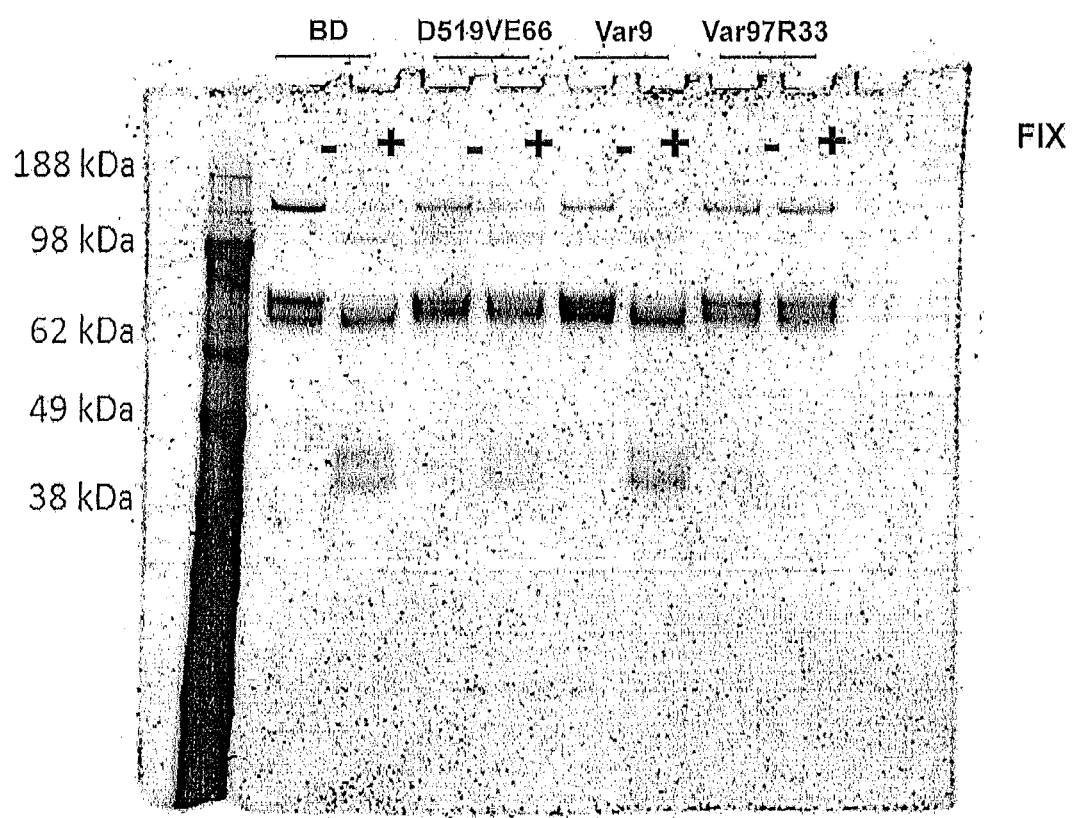
FIG. 9 presents an image of an SDS-PAGE gel of variant Factor VIII polypeptides from an FXase reaction in the presence (+) or absence (−) of excess FIXa. The FVIII polypeptides investigated are FVIII-BDD (lanes 2 and 3), D519VE665V-FVIII (lanes 4 and 5), Var97 (lanes 6 and 7), and Var97-R336I (lanes 8 and 9), with a mass marker in lane 1.

The kinetic FXase results (not shown) with variable FIXa and fixed FVIIIa suggested that proteolysis might account for the discrepant aPTT versus chromogenic assay activity of Var97. To investigate cleavage of the variant Factor VIII polypeptide, the physical changes in FVIII in the presence of excess FIXa in a FXase reaction were visualized. For the detection of FVIIIa cleavage by FIXa present in FXase, Factor VIII polypeptides being examined were adjusted to 0.1 µg/ml final concentration in the standard Xase reaction buffer without bovine serum albumin present. The FVIII solution (25 µL) was added to 5 µl of 120 nM IXa or buffer. The reactants were allowed to incubate at 37° C. for 1 hr., and 4× nupage buffer was added to stop the reaction. The samples were then subjected to SDS-PAGE, followed by Coomassie Blue staining (FIG. 9). This analysis demonstrated that the Var97 Factor VIII variant shows enhanced proteolytic cleavage by FIXa relative to one or both of BDD and D519VE665V variant FVIII.

Example 3: Characterization of Var97-R336I

In an attempt to reduce the enhanced proteolytic cleavage of Var97, an additional substitution, R336I, was made within the Var97 peptide chain (Var97-R336I; SEQ ID NO: 55). This is a substitution within a known cleavage site for activated protein C (aPC). As can be seen in the SDS-PAGE gel image of FIG. 9, in the FIXa digestion assay, proteolytic cleavage of Var97-R336I was markedly reduced as compared to Var97.

Figure 10:
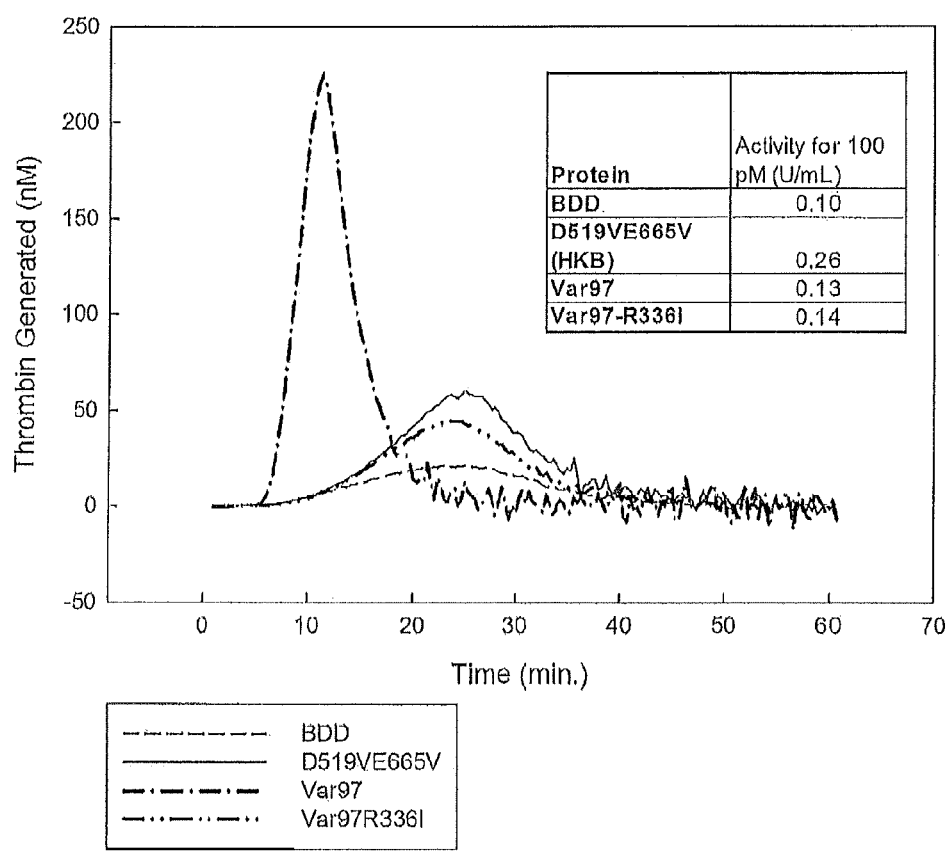
FIG. 10 presents thrombin generation profiles for FVIII-BDD (SEQ ID NO: 3), D519VE665V-FVIII (SEQ ID NO: 5), Var97 (SEQ ID NO: 53), and Var97-R336I (SEQ ID NO: 55).
Figure 11:
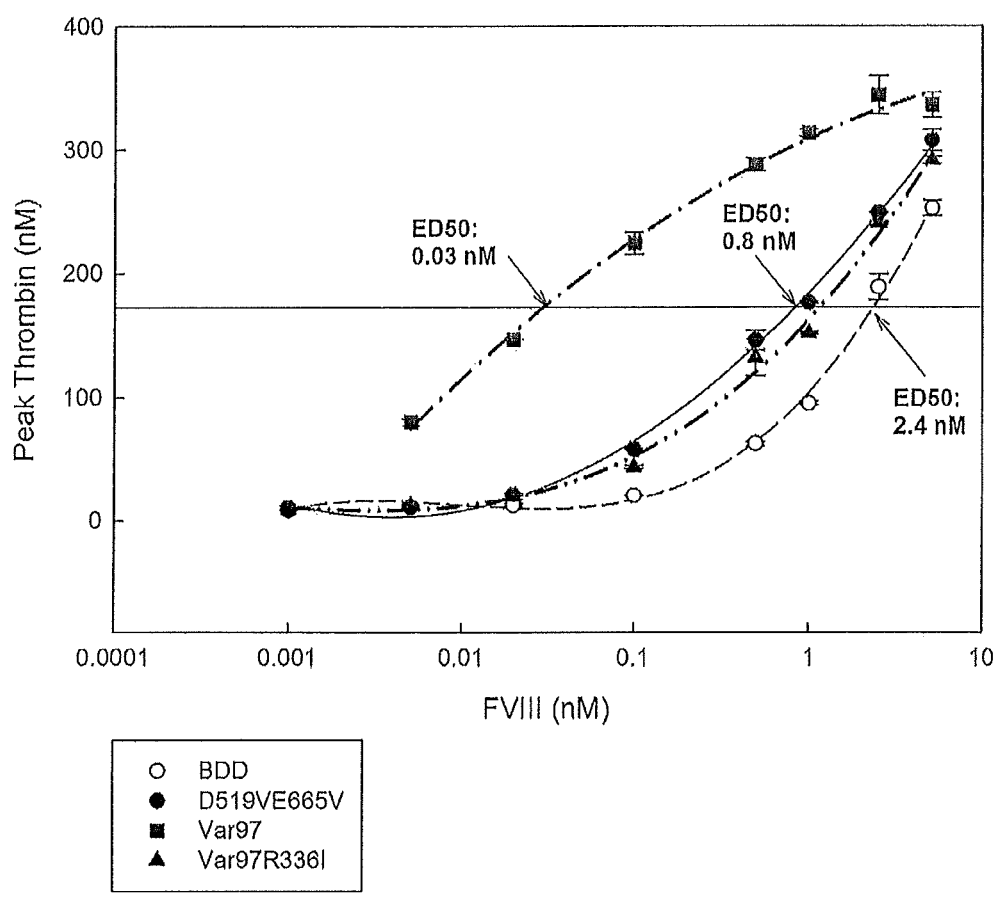
FIG. 11 presents data demonstrating the concentration of various Factor VIII polypeptides and variants needed to elicit a defined quantity of peak thrombin. The Factor VIII polypeptides investigated are FVIII-BDD (SEQ ID NO: 3), D519VE665V-FVIII (SEQ ID NO: 5), Var97 (SEQ ID NO: 53), and Var97-R336I (SEQ ID NO: 55).

The potency of the Var97-R336I variant in coagulation variant was also assessed by TGA using tissue factor (TF) as an initiator, as described above. By TGA, Var97-R336I was more potent than BDD, though somewhat less potent than Var97 and D519VE665V (FIG. 10). Additionally, the overall Var97-R336I thrombin profile was again qualitatively very similar to BDD, D519VE665V, and Var97, where the rate of return toward baseline thrombin levels was related to peak thrombin levels (FIG. 10). Quantitative comparisons of the concentration of BDD, D519VE665V, Var97, and Var97-R336I Factor VIII variants needed to elicit a defined quantity of peak thrombin indicated that Var97-R336I was of similar potency to D519VE665V-FVIII (FIG. 11).

To further characterize the Var97-R336I variant, the turbidity profile of this variant was compared to the other variants, as well as normal serum control, as described above. As shown in FIG. 7, the turbidity profile of the Var97-R336I variant closely resembles that of the BDD and D519VE665V variants, indicating similar clotting kinetics and clot structure.

The variant polypeptides described herein, including Var97, have application for a variety of clinical indications. For hemophilia A, such a molecule with a rapid and enhanced thrombin response profile could be used either acutely or prophylactically, with either iv or sc routes of administration. These variants also could be used to treat other bleeding disorders, whether arising from a platelet or coagulation defect. In the cases of defects in platelet-mediated hemostasis, whether due to insufficiency in platelet number or response, the enhanced capacity of these variants to generate thrombin could potentially compensate by enhancing platelet activity and by providing more fibrin "glue" to hold the platelet plug needed for effective hemostasis.

In addition to hemophilia and other hemostatic disorders, the ability of these variants to elicit such a rapid thrombin response suggests possible utility in more acute situations, such as trauma and surgery. In those settings, the rapidity and robustness with which these variants can support a thrombin response, with minimal impact on the mechanisms regulating thrombin levels, could be an advantage. In those settings, these variants could be administered in a variety of manners, including iv, sc, and topically, either in the form of a spray or soaked in matrices, such as surgical sponges or collagen. Other indications where these variants could have utility include the treatment of hemorrhagic syndromes, such as Dengue hemorrhagic fever, where massive vascular permeability, impaired platelet function, and enhanced fibrinolysis can result in life-threatening internal bleeding.

We claim:

1. A variant of a Factor VIII polypeptide, wherein said Factor VIII polypeptide is a functional Factor VIII comprising a thrombin cleavage site at amino acid positions 370-375 and an activation loop at amino acid positions 558-565, wherein said amino acid position numbering is with reference to the amino acid sequence set forth in SEQ ID NO: 1; and wherein said variant comprises amino acid substitutions within the thrombin cleavage site selected from the group consisting of:
   (i) Q370M and I371P, and
   (ii) I371P and V374F;
and comprises amino acid substitutions within the activation loop selected from the group consisting of:
   (i) V559L and R562F,
   (ii) V559L and R562W,
   (iii) V559L and Q565E,
   (iv) V559L, R562W, and Q565E, and
   (v) V559L, R562F, and Q565E.

2. The variant of claim 1, wherein said substitution within the thrombin cleavage site does not include a substitution at amino acid position 372.

3. The variant of claim 1, wherein said Factor VIII polypeptide further comprises an A1-A2 domain interface comprising amino acid residues E272 and D519 and an A2-A3 domain interface comprising amino acid residues E665 and E1984, wherein said amino acid position numbering is with reference to the amino acid sequence set forth in SEQ ID NO: 1; and wherein said variant further comprises a substitution at one or more amino acid residues of the A1-A2 domain interface and a substitution at one or more amino acid residues of the A2-A3 domain interface.

4. The variant of claim 3, wherein said substitution of the A1-A2 domain interface comprises one or more substitutions selected from the group consisting of E272A, E272V, D519A, and D519V, and wherein said substitution of the A2-A3 domain interface comprises one or more substitutions selected from the group consisting of E665A, E665V, E1984A, and E1984V.

5. The variant of claim 3, wherein said substitution of the A1-A2 domain interface comprises D519V and wherein said substitution of the A2-A3 domain interface comprises E665V.

6. The variant of claim 1, wherein said variant comprises the amino acid substitutions I371P, V374F, V559L, R562W, and Q565E.

7. The variant of claim 3, wherein said variant comprises the amino acid substitutions I371P, V374F, V559L, R562W, Q565E, D519V, and E665V.

8. The variant of claim 1, wherein said variant further comprises an amino acid substitution at amino acid position 336, wherein said amino acid substitution at amino acid position 336 comprises an R336I substitution.

9. The variant of claim 1, wherein said Factor VIII polypeptide comprises an amino acid sequence at least 90% identical to the sequence of SEQ ID NO: 1, 2, or 3.

10. The variant of claim 1, wherein said Factor VIII polypeptide comprises the amino acid sequence of SEQ ID NO: 53.

11. A pharmaceutical composition comprising the variant Factor VIII polypeptide of claim 1 and a pharmaceutically acceptable excipient.

12. A method for preventing or treating a bleeding disorder comprising administering to a subject an effective amount of the pharmaceutical composition of claim 11.

* * * * *

SEQUENCE LISTING

```
<160> NUMBER OF SEQ ID NOS: 56

<210> SEQ ID NO 1
<211> LENGTH: 2332
<212> TYPE: PRT
<213> ORGANISM: Homo sapiens

<400> SEQUENCE: 1

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
```

-continued

```
                275                 280                 285
Ser Pro Ile Thr Phe Leu Thr Ala Gln Thr Leu Leu Met Asp Leu Gly
290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asp Asn Ser Pro Ser Phe
            355                 360                 365
Ile Gln Ile Arg Ser Val Ala Lys Lys His Pro Lys Thr Trp Val His
370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
690                 695                 700
```

```
Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Ser Lys Asn Asn Ala
            725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
                915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110
```

-continued

```
Gly Lys Asn Ser Leu Asn Ser Gly Gln Gly Pro Ser Pro Lys Gln
1115                1120                    1125

Leu Val Ser Leu Gly Pro Glu Lys Ser Val Glu Gly Gln Asn Phe
1130                1135                    1140

Leu Ser Glu Lys Asn Lys Val Val Val Gly Lys Gly Glu Phe Thr
1145                1150                    1155

Lys Asp Val Gly Leu Lys Glu Met Val Phe Pro Ser Ser Arg Asn
1160                1165                    1170

Leu Phe Leu Thr Asn Leu Asp Asn Leu His Glu Asn Asn Thr His
1175                1180                    1185

Asn Gln Glu Lys Lys Ile Gln Glu Glu Ile Glu Lys Lys Glu Thr
1190                1195                    1200

Leu Ile Gln Glu Asn Val Val Leu Pro Gln Ile His Thr Val Thr
1205                1210                    1215

Gly Thr Lys Asn Phe Met Lys Asn Leu Phe Leu Leu Ser Thr Arg
1220                1225                    1230

Gln Asn Val Glu Gly Ser Tyr Asp Gly Ala Tyr Ala Pro Val Leu
1235                1240                    1245

Gln Asp Phe Arg Ser Leu Asn Asp Ser Thr Asn Arg Thr Lys Lys
1250                1255                    1260

His Thr Ala His Phe Ser Lys Lys Gly Glu Glu Glu Asn Leu Glu
1265                1270                    1275

Gly Leu Gly Asn Gln Thr Lys Gln Ile Val Glu Lys Tyr Ala Cys
1280                1285                    1290

Thr Thr Arg Ile Ser Pro Asn Thr Ser Gln Gln Asn Phe Val Thr
1295                1300                    1305

Gln Arg Ser Lys Arg Ala Leu Lys Gln Phe Arg Leu Pro Leu Glu
1310                1315                    1320

Glu Thr Glu Leu Glu Lys Arg Ile Ile Val Asp Asp Thr Ser Thr
1325                1330                    1335

Gln Trp Ser Lys Asn Met Lys His Leu Thr Pro Ser Thr Leu Thr
1340                1345                    1350

Gln Ile Asp Tyr Asn Glu Lys Glu Lys Gly Ala Ile Thr Gln Ser
1355                1360                    1365

Pro Leu Ser Asp Cys Leu Thr Arg Ser His Ser Ile Pro Gln Ala
1370                1375                    1380

Asn Arg Ser Pro Leu Pro Ile Ala Lys Val Ser Ser Phe Pro Ser
1385                1390                    1395

Ile Arg Pro Ile Tyr Leu Thr Arg Val Leu Phe Gln Asp Asn Ser
1400                1405                    1410

Ser His Leu Pro Ala Ala Ser Tyr Arg Lys Lys Asp Ser Gly Val
1415                1420                    1425

Gln Glu Ser Ser His Phe Leu Gln Gly Ala Lys Lys Asn Asn Leu
1430                1435                    1440

Ser Leu Ala Ile Leu Thr Leu Glu Met Thr Gly Asp Gln Arg Glu
1445                1450                    1455

Val Gly Ser Leu Gly Thr Ser Ala Thr Asn Ser Val Thr Tyr Lys
1460                1465                    1470

Lys Val Glu Asn Thr Val Leu Pro Lys Pro Asp Leu Pro Lys Thr
1475                1480                    1485

Ser Gly Lys Val Glu Leu Leu Pro Lys Val His Ile Tyr Gln Lys
1490                1495                    1500

Asp Leu Phe Pro Thr Glu Thr Ser Asn Gly Ser Pro Gly His Leu
```

-continued

```
                1505                1510                1515

Asp Leu Val Glu Gly Ser Leu Leu Gln Gly Thr Glu Gly Ala Ile
        1520                1525                1530

Lys Trp Asn Glu Ala Asn Arg Pro Gly Lys Val Pro Phe Leu Arg
        1535                1540                1545

Val Ala Thr Glu Ser Ser Ala Lys Thr Pro Ser Lys Leu Leu Asp
        1550                1555                1560

Pro Leu Ala Trp Asp Asn His Tyr Gly Thr Gln Ile Pro Lys Glu
        1565                1570                1575

Glu Trp Lys Ser Gln Glu Lys Ser Pro Glu Lys Thr Ala Phe Lys
        1580                1585                1590

Lys Lys Asp Thr Ile Leu Ser Leu Asn Ala Cys Glu Ser Asn His
        1595                1600                1605

Ala Ile Ala Ala Ile Asn Glu Gly Gln Asn Lys Pro Glu Ile Glu
        1610                1615                1620

Val Thr Trp Ala Lys Gln Gly Arg Thr Glu Arg Leu Cys Ser Gln
        1625                1630                1635

Asn Pro Pro Val Leu Lys Arg His Gln Arg Glu Ile Thr Arg Thr
        1640                1645                1650

Thr Leu Gln Ser Asp Gln Glu Glu Ile Asp Tyr Asp Asp Thr Ile
        1655                1660                1665

Ser Val Glu Met Lys Lys Glu Asp Phe Asp Ile Tyr Asp Glu Asp
        1670                1675                1680

Glu Asn Gln Ser Pro Arg Ser Phe Gln Lys Lys Thr Arg His Tyr
        1685                1690                1695

Phe Ile Ala Ala Val Glu Arg Leu Trp Asp Tyr Gly Met Ser Ser
        1700                1705                1710

Ser Pro His Val Leu Arg Asn Arg Ala Gln Ser Gly Ser Val Pro
        1715                1720                1725

Gln Phe Lys Lys Val Val Phe Gln Glu Phe Thr Asp Gly Ser Phe
        1730                1735                1740

Thr Gln Pro Leu Tyr Arg Gly Glu Leu Asn Glu His Leu Gly Leu
        1745                1750                1755

Leu Gly Pro Tyr Ile Arg Ala Glu Val Glu Asp Asn Ile Met Val
        1760                1765                1770

Thr Phe Arg Asn Gln Ala Ser Arg Pro Tyr Ser Phe Tyr Ser Ser
        1775                1780                1785

Leu Ile Ser Tyr Glu Glu Asp Gln Arg Gln Gly Ala Glu Pro Arg
        1790                1795                1800

Lys Asn Phe Val Lys Pro Asn Glu Thr Lys Thr Tyr Phe Trp Lys
        1805                1810                1815

Val Gln His His Met Ala Pro Thr Lys Asp Glu Phe Asp Cys Lys
        1820                1825                1830

Ala Trp Ala Tyr Phe Ser Asp Val Asp Leu Glu Lys Asp Val His
        1835                1840                1845

Ser Gly Leu Ile Gly Pro Leu Leu Val Cys His Thr Asn Thr Leu
        1850                1855                1860

Asn Pro Ala His Gly Arg Gln Val Thr Val Gln Glu Phe Ala Leu
        1865                1870                1875

Phe Phe Thr Ile Phe Asp Glu Thr Lys Ser Trp Tyr Phe Thr Glu
        1880                1885                1890

Asn Met Glu Arg Asn Cys Arg Ala Pro Cys Asn Ile Gln Met Glu
        1895                1900                1905
```

-continued

```
Asp Pro Thr Phe Lys Glu Asn Tyr Arg Phe His Ala Ile Asn Gly
    1910            1915            1920

Tyr Ile Met Asp Thr Leu Pro Gly Leu Val Met Ala Gln Asp Gln
    1925            1930            1935

Arg Ile Arg Trp Tyr Leu Leu Ser Met Gly Ser Asn Glu Asn Ile
    1940            1945            1950

His Ser Ile His Phe Ser Gly His Val Phe Thr Val Arg Lys Lys
    1955            1960            1965

Glu Glu Tyr Lys Met Ala Leu Tyr Asn Leu Tyr Pro Gly Val Phe
    1970            1975            1980

Glu Thr Val Glu Met Leu Pro Ser Lys Ala Gly Ile Trp Arg Val
    1985            1990            1995

Glu Cys Leu Ile Gly Glu His Leu His Ala Gly Met Ser Thr Leu
    2000            2005            2010

Phe Leu Val Tyr Ser Asn Lys Cys Gln Thr Pro Leu Gly Met Ala
    2015            2020            2025

Ser Gly His Ile Arg Asp Phe Gln Ile Thr Ala Ser Gly Gln Tyr
    2030            2035            2040

Gly Gln Trp Ala Pro Lys Leu Ala Arg Leu His Tyr Ser Gly Ser
    2045            2050            2055

Ile Asn Ala Trp Ser Thr Lys Glu Pro Phe Ser Trp Ile Lys Val
    2060            2065            2070

Asp Leu Leu Ala Pro Met Ile Ile His Gly Ile Lys Thr Gln Gly
    2075            2080            2085

Ala Arg Gln Lys Phe Ser Ser Leu Tyr Ile Ser Gln Phe Ile Ile
    2090            2095            2100

Met Tyr Ser Leu Asp Gly Lys Lys Trp Gln Thr Tyr Arg Gly Asn
    2105            2110            2115

Ser Thr Gly Thr Leu Met Val Phe Phe Gly Asn Val Asp Ser Ser
    2120            2125            2130

Gly Ile Lys His Asn Ile Phe Asn Pro Pro Ile Ile Ala Arg Tyr
    2135            2140            2145

Ile Arg Leu His Pro Thr His Tyr Ser Ile Arg Ser Thr Leu Arg
    2150            2155            2160

Met Glu Leu Met Gly Cys Asp Leu Asn Ser Cys Ser Met Pro Leu
    2165            2170            2175

Gly Met Glu Ser Lys Ala Ile Ser Asp Ala Gln Ile Thr Ala Ser
    2180            2185            2190

Ser Tyr Phe Thr Asn Met Phe Ala Thr Trp Ser Pro Ser Lys Ala
    2195            2200            2205

Arg Leu His Leu Gln Gly Arg Ser Asn Ala Trp Arg Pro Gln Val
    2210            2215            2220

Asn Asn Pro Lys Glu Trp Leu Gln Val Asp Phe Gln Lys Thr Met
    2225            2230            2235

Lys Val Thr Gly Val Thr Thr Gln Gly Val Lys Ser Leu Leu Thr
    2240            2245            2250

Ser Met Tyr Val Lys Glu Phe Leu Ile Ser Ser Ser Gln Asp Gly
    2255            2260            2265

His Gln Trp Thr Leu Phe Phe Gln Asn Gly Lys Val Lys Val Phe
    2270            2275            2280

Gln Gly Asn Gln Asp Ser Phe Thr Pro Val Val Asn Ser Leu Asp
    2285            2290            2295
```

Pro Pro Leu Leu Thr Arg Tyr Leu Arg Ile His Pro Gln Ser Trp
2300           2305            2310

Val His Gln Ile Ala Leu Arg Met Glu Val Leu Gly Cys Glu Ala
2315           2320            2325

Gln Asp Leu Tyr
2330

<210> SEQ ID NO 2
<211> LENGTH: 6996
<212> TYPE: DNA
<213> ORGANISM: Homo sapiens

<400> SEQUENCE: 2

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggttca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg gagccctact agtatgtaga     540
gaagggagtc tggccaagga aaagacacag accttgcaca aatttatact acttttttgct    600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca aacactcttg     900
atggaccttg acagtttctc actgttttgt catatctctt cccaccaaca tgatggcatg     960
gaagcttatg tcaaagtaga cagctgtcca gaggaacccc aactacgaat gaaaaataat    1020
gaagaagcgg aagactatga tgatgatctt actgattctg aaatggatgt ggtcaggttt    1080
gatgatgaca actctccttc ctttatccaa attcgctcag ttgccaagaa gcatcctaaa    1140
acttgggtac attacattgc tgctgaagag gaggactggg actatgctcc cttagtcctc    1200
gccccccgatg acagaagtta taaagtcaa tatttgaaca atggccctca gcggattggt    1260
aggaagtaca aaaagtccg atttatggca tacacagatg aaacctttaa gactcgtgaa    1320
gctattcagc atgaatcagg aatcttggga ccttttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagatggg    1560
ccaactaaat cagatcctcg gtgcctgacc cgctattact ctagtttcgt taatatggag    1620
agagatctag cttcaggact cattggccct ctcctcatct gctacaaaga atctgtagat    1680
caaagaggaa accagataat gtcagacaag aggaatgtca tcctgttttc tgtatttgat    1740
gagaaccgaa gctggtacct cacagagaat atacaacgtt tctcccccaa tccagctgga    1800
gtgcagcttg aggatccaga gttccaagcc tccaacatca tgcacagcat caatggctat    1860
```

```
gttttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcacccta ttcccattct caggagaaac tgtcttcatg    2040
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttatg aagatatttc agcatacttg ctgagtaaaa acaatgccat gaaccaaga    2220
agcttctccc agaattcaag cacccctagc actaggcaaa agcaatttaa tgccaccaca    2280
attccagaaa atgacataga gaagactgac ccttggtttg cacacagaac acctatgcct    2340
aaaatacaaa atgtctcctc tagtgatttg ttgatgctct tgcgacagag tcctactcca    2400
catgggctat ccttatctga tctccaagaa gccaaatatg gactttttc tgatgatcca    2460
tcacctggag caatagacag taataacagc ctgtctgaaa tgacacactt caggccacag    2520
ctccatcaca gtggggacat ggtatttacc cctgagtcag gcctccaatt aagattaaat    2580
gagaaactgg ggacaactgc agcaacagag ttgaagaaac ttgatttcaa agtttctagt    2640
acatcaaata atctgatttc aacaattcca tcagacaatt tggcagcagg tactgataat    2700
acaagttcct taggaccccc aagtatgcca gttcattatg atagtcaatt agataccact    2760
ctatttggca aaagtcatc tccccttact gagtctggtg gacctctgag cttgagtgaa    2820
gaaaataatg attcaaagtt gttagaatca ggtttaatga atagccaaga aagttcatgg    2880
ggaaaaatg tatcgtcaac agagagtggt aggttattta agggaaaag agctcatgga    2940
cctgcttttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaa ttcaggaaga aatagaaaag    3600
aaggaaacat taatccaaga gaatgtagtt ttgcctcaga tacatacagt gactggcact    3660
aagaatttca tgaagaacct tttcttactg agcactaggc aaaatgtaga aggttcatat    3720
gacgggcat atgctccagt acttcaagat tttaggtcat taaatgattc aacaaataga    3780
acaaagaaac acacagctca tttctcaaaa aaggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctccctta tcagattgcc ttacgaggag tcatagcatc    4140
cctcaagcaa atagatctcc attacccatt gcaaaggtat catcatttcc atctattaga    4200
cctatatatc tgaccagggt cctattccaa gacaactctt ctcatcttcc agcagcatct    4260
```

```
tatagaaaga aagattctgg ggtccaagaa agcagtcatt tcttacaagg agccaaaaaa    4320 aataacctttt ctttagccat tctaaccttg gagatgactg gtgatcaaag agaggttggc   4380
tccctgggga caagtgccac aaattcagtc acatacaaga aagttgagaa cactgttctc    4440
ccgaaaccag acttgcccaa aacatctggc aaagttgaat tgcttccaaa agttcacatt    4500
tatcagaagg acctattccc tacggaaact agcaatgggt ctcctggcca tctggatctc    4560
gtggaaggga gccttcttca gggaacagag ggagcgatta gtggaatgaa gcaaacaga    4620 cctggaaaag ttccctttct gagagtagca acagaaagct ctgcaaagac tccctccaag    4680
ctattggatc tcttgcttg ggataaccac tatggtactc agataccaaa agaagagtgg     4740
aaatcccaag agaagtcacc agaaaaaaca gcttttaaga aaaggatac cattttgtcc     4800 ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga acgccatca acgggaaata actcgtacta ctcttcagtc agatcaagag     4980
gaaattgact atgatgatac catatcagtt gaaatgaaga aggaagattt tgacatttat    5040
gatgaggatg aaaatcagag ccccccgcagc tttcaaaaga aaacacgaca ctattttatt   5100
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagcccctt ataccgtgga gaactaaatg aacatttggg actcctgggg   5280
ccatatataa gagcagaagt tgaagataat atcatggtaa cttttcagaaa tcaggcctct   5340 cgtccctatt ccttctattc tagccttatt tcttatgagg aagatcagag gcaaggagca    5400
gaacctagaa aaaactttgt caagcctaat gaaaccaaaa cttacttttg gaaagtgcaa    5460
catcatatgg cacccactaa agatgagttt gactgcaaag cctgggctta tttctctgat    5520
gttgacctgg aaaaagatgt gcactcaggc ctgattggac cccttctggt ctgccacact    5580
aacacactga accctgctca tgggagacaa gtgacagtac aggaatttgc tctgttttc    5640 accatctttg atgagaccaa aagctggtac ttcactgaaa atatggaaag aaactgcagg    5700
gctccctgca atatccagat ggaagatccc acttttaaag agaattatcg cttccatgca   5760
atcaatggct acataatgga tacactacct ggcttagtaa tggctcagga tcaaaggatt    5820
cgatggtatc tgctcagcat gggcagcaat gaaaacatcc attctattca tttcagtgga   5880
catgtgttca ctgtacgaaa aaaagaggag tataaaatgg cactgtacaa tctctatcca    5940 ggtgttttttg agacagtgga aatgttacca tccaaagctg gaatttggcg ggtggaatgc    6000
cttattggcg agcatctaca tgctgggatg agcacacttt ttctggtgta cagcaataag    6060
tgtcagactc ccctgggaat ggcttctgga cacattagg attttcagat tacagcttca     6120
ggacaatatg gacagtgggc cccaaagctg gccagacttc attattccgg atcaatcaat    6180
gcctggagca ccaaggagcc cttttcttgg atcaaggtgg atctgttggc accaatgatt   6240
attcacggca tcaagaccca gggtgcccgt cagaagttct ccagcctcta catctctcag   6300
tttatcatca tgtatagtct tgatgggaag aagtggcaga cttatcgagg aaattccact    6360
ggaaccttaa tggtcttctt tggcaatgtg gattcatctg gataaaaca caatattttt    6420 aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
```

-continued

```
gccacctggt ctccttcaaa agctcgactt cacctccaag ggaggagtaa tgcctggaga      6660
cctcaggtga ataatccaaa agagtggctg caagtggact tccagaagac aatgaaagtc      6720
acaggagtaa ctactcaggg agtaaaatct ctgcttacca gcatgtatgt gaaggagttc      6780
ctcatctcca gcagtcaaga tggccatcag tggactctct tttttcagaa tggcaaagta      6840
aaggtttttc agggaaatca agactccttc acacctgtgg tgaactctct agacccaccg      6900
ttactgactc gctaccttcg aattcacccc cagagttggg tgcaccagat tgccctgagg      6960
atggaggttc tgggctgcga ggcacaggac ctctac                                6996
```

<210> SEQ ID NO 3
<211> LENGTH: 1438
<212> TYPE: PRT
<213> ORGANISM: Artificial Sequence
<220> FEATURE:
<223> OTHER INFORMATION: Variant peptide

<400> SEQUENCE: 3

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
```

-continued

```
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Leu Thr Asp
                340                 345                 350
Ser Glu Met Asp Val Val Arg Phe Asp Asp Asn Ser Pro Ser Phe
            355                 360                 365
Ile Gln Ile Arg Ser Val Ala Lys Lys His Pro Lys Thr Trp Val His
        370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
        530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
```

-continued

```
Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125
```

```
Thr Pro Leu Gly Met Ala Ser Gly His Ile Arg Asp Phe Gln Ile
        1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 4
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 4
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
```

```
atcgctaagc caaggccacc ctggatgggt ctgctaggtc ctaccatcca ggctgaggtt    240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttgct     600 gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg acagtttctt actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaaagtccg atttatggca tacacagatg aaacctttaa gactcgtgaa   1320
gctattcagc atgaatcagg aatcttggga ccttttacttt atggggaagt tggagacaca   1380
ctgttgatta tatttaagaa tcaagcaagc agaccatata acatctaccc tcacggaatc   1440
actgatgtcc gtccttttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctgtagat   1680
caaagaggaa accagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860 gttttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg ggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat gaaccaaga    2220 agcttctccc agaacccacc agtcttgaaa cgccatcaac gggaaataac tcgtactact   2280
cttcagtcag atcaagagga aattgactat gatgatacca tatcagttga aatgaagaag   2340
gaagattttg acatttatga tgaggatgaa aatcagagcc cccgcagctt tcaaaagaaa   2400
acacgacact attttattgc tgcagtggag aggctctggg attatgggat gagtagctcc   2460
ccacatgttc taagaaacag ggctcagagt ggcagtgtcc ctcagttcaa gaaagttgtt   2520
ttccaggaat ttactgatgg ctccttttact cagcccttat accgtggaga actaaatgaa   2580
```

-continued

```
catttgggac tcctgggggcc atatataaga gcagaagttg aagataatat catggtaact    2640
ttcagaaatc aggcctctcg tccctattcc ttctattcta gccttatttc ttatgaggaa    2700
gatcagaggc aaggagcaga acctagaaaa aactttgtca agcctaatga aaccaaaact    2760
tacttttgga aagtgcaaca tcatatggca cccactaaag atgagtttga ctgcaaagcc    2820
tgggcttatt tctctgatgt tgacctggaa aaagatgtgc actcaggcct gattggaccc    2880
cttctggtct gccacactaa cacactgaac cctgctcatg ggagacaagt gacagtacag    2940
gaatttgctc tgttttcac catctttgat gagaccaaaa gctggtactt cactgaaaat    3000
atggaaagaa actgcagggc tccctgcaat atccagatgg aagatcccac ttttaaagag    3060
aattatcgct ccatgcaat caatggctac ataatggata cactacctgg cttagtaatg    3120
gctcaggatc aaaggattcg atggtatctg ctcagcatgg gcagcaatga aaacatccat    3180
tctattcatt tcagtggaca tgtgttcact gtacgaaaaa aagaggagta taaaatggca    3240
ctgtacaatc tctatccagg tgttttgag acagtggaaa tgttaccatc aaagctgga    3300
atttggcggg tggaatgcct tattggcgag catctacatg ctgggatgag cacactttt    3360
ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct tttcttggat caaggtggat    3540
ctgttggcac caatgattat tcacggcatc aagacccagg gtgcccgtca agttctcc    3600
agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atatttttaa ccctccaatt attgctcgat acatccgttt gcacccaact    3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggag taaatctct gcttaccagc    4080
atgtatgtga aggagttcct catctccagc agtcaagatg ccatcagtg gactctcttt    4140
tttcagaatg gcaaagtaaa ggtttttcag ggaaatcaag actccttcac acctgtggtg    4200
aactctctag acccaccgtt actgactcgc taccttcgaa ttcaccccca gagttgggtg    4260
caccagattg ccctgaggat ggaggttctg ggctgcgagg cacaggacct ctac           4314
```

<210> SEQ ID NO 5
<211> LENGTH: 1438
<212> TYPE: PRT
<213> ORGANISM: Artificial Sequence
<220> FEATURE:
<223> OTHER INFORMATION: Variant peptide

<400> SEQUENCE: 5

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
```

```
                  50                  55                  60
Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                     85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
                115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
                195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
                275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asn Ser Pro Ser Phe
                355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
                450                 455                 460

Phe Lys Asn Gln Ala Ser Arg Pro Tyr Asn Ile Tyr Pro His Gly Ile
465                 470                 475                 480
```

```
Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
        500                 505                 510

Trp Thr Val Thr Val Glu Val Gly Pro Thr Lys Ser Asp Pro Arg Cys
            515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Val Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
        770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
            805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
        850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
            885                 890                 895
```

```
Ser Tyr Glu Glu Asp Gln Arg Gln Gly Ala Glu Pro Arg Lys Asn Phe
        900                 905                 910

Val Lys Pro Asn Glu Thr Lys Thr Tyr Phe Trp Lys Val Gln His His
    915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
```

Trp Ser Pro Ser Lys Ala Arg Leu His Leu Gln Gly Arg Ser Asn
    1310                1315                1320
Ala Trp Arg Pro Gln Val Asn Asn Pro Lys Glu Trp Leu Gln Val
    1325                1330                1335
Asp Phe Gln Lys Thr Met Lys Val Thr Gly Val Thr Thr Gln Gly
    1340                1345                1350
Val Lys Ser Leu Leu Thr Ser Met Tyr Val Lys Glu Phe Leu Ile
    1355                1360                1365
Ser Ser Ser Gln Asp Gly His Gln Trp Thr Leu Phe Phe Gln Asn
    1370                1375                1380
Gly Lys Val Lys Val Phe Gln Gly Asn Gln Asp Ser Phe Thr Pro
    1385                1390                1395
Val Val Asn Ser Leu Asp Pro Pro Leu Leu Thr Arg Tyr Leu Arg
    1400                1405                1410
Ile His Pro Gln Ser Trp Val His Gln Ile Ala Leu Arg Met Glu
    1415                1420                1425
Val Leu Gly Cys Glu Ala Gln Asp Leu Tyr
    1430                1435

<210> SEQ ID NO 6
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 6

| | | | | | |
|---|---|---|---|---|---|
| gccaccagaa | gatactacct | gggtgcagtg | gaactgtcat | gggactatat | gcaaagtgat | 60 |
| ctcggtgagc | tgcctgtgga | cgcaagattt | cctcctagag | tgccaaaatc | ttttccattc | 120 |
| aacacctcag | tcgtgtacaa | aaagactctg | tttgtagaat | tcacggatca | ccttttcaac | 180 |
| atcgctaagc | caaggccacc | ctggatgggt | ctgctaggtc | ctaccatcca | ggctgaggtt | 240 |
| tatgatacag | tggtcattac | acttaagaac | atggcttccc | atcctgtcag | tcttcatgct | 300 |
| gttggtgtat | cctactggaa | agcttctgag | ggagctgaat | atgatgatca | gaccagtcaa | 360 |
| agggagaaag | aagatgataa | agtcttccct | ggtggaagcc | atacatatgt | ctggcaggtc | 420 |
| ctgaaagaga | atggtccaat | ggcctctgac | ccactgtgcc | ttacctactc | atatctttct | 480 |
| catgtggacc | tggtaaaaga | cttgaattca | ggcctcattg | gagccctact | agtatgtaga | 540 |
| gaagggagtc | tggccaagga | aaagacacag | accttgcaca | aatttatact | acttttgct | 600 |
| gtatttgatg | aagggaaaag | ttggcactca | gaaacaaaga | actccttgat | gcaggatagg | 660 |
| gatgctgcat | ctgctcgggc | ctggcctaaa | atgcacacag | tcaatggtta | tgtaaacagg | 720 |
| tctctaccag | gtctgattgg | atgccacagg | aaatcagtct | attggcatgt | gattggaatg | 780 |
| ggcaccactc | ctgaagtgca | ctcaatattc | ctcgaaggtc | acacatttct | gtgtgaggaac | 840 |
| catcgccagg | cgtccttgga | aatctcgcca | ataactttcc | ttactgctca | aacactcttg | 900 |
| atggaccttg | acagtttcct | actgttttgt | catatctctt | cccaccaaca | tgatggcatg | 960 |
| gaagcttatg | tcaaagtaga | cagctgtcca | gaggaacccc | aactacgaat | gaaaaataat | 1020 |
| gaagaagcgg | aagactatga | tgatgatctt | actgattctg | aaatggatgt | ggtcaggttt | 1080 |
| gatgatgaca | actctcctcc | tttatccaa | attcgctcag | ttgccaagaa | gcatcctaaa | 1140 |
| acttgggtac | attacattgc | tgctgaagag | gaggactggg | actatgctcc | cttagtcctc | 1200 |

```
gcccccgatg acagaagtta taaaagtcaa tatttgaaca atggccctca gcggattggt    1260
aggaagtaca aaaaagtccg atttatggca tacacagatg aaacctttaa gacgcgtgaa    1320
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagttggg    1560
ccaactaaat cagatccgcg gtgcctgacc cgctattact ctagtttcgt taatatggag    1620
agagatctag cttcaggact cattggccct ctcctcatct gctacaaaga atctgtagat    1680
caaagaggaa accagataat gtcagacaag aggaatgtca tcctgttttc tgtatttgat    1740
gagaaccgaa gctggtacct cacagagaat atacaacgct ttctcccaa tccagctgga    1800
gtgcagcttg aggatccaga gttccaagcc tccaacatca tgcacagcat caatggctat    1860
gttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgtagacac actcacccta ttcccattct caggagaaac tgtcttcatg    2040
tcgatggaaa cccaggtct atggattctg ggtgccaca actcagactt tcggaacaga    2100
ggcatgaccg ccttactgaa ggtttctagt tgtgacaaga acactggtga ttattacgag    2160
gacagttacg aagatatttc agcatacttg ctgagtaaaa acaatgccat gaacctagg    2220
agcttctctc agaatccacc agtcttgaaa cgccatcaac gggaaataac tcgtacgact    2280
cttcagtcag atcaagagga aattgactat gatgatacca tcagttgaa aatgaagaag    2340
gaagattttg acatttatga tgaggatgaa aatcagagcc cccgcagctt tcaaaagaaa    2400
acacgacact attttattgc tgcagtggag aggctctggg attatgggat gagtagctcc    2460
ccacatgttc taagaaacag ggctcagagt ggcagtgtcc ctcagttcaa gaaagttgtt    2520
ttccaggaat ttactgatgg ctcctttact cagcccttat accgtggaga actaaatgaa    2580
catttgggac tcctggggcc atatataaga gcagaagttg aagataatat catggtaact    2640
ttcagaaatc aggcctctcg tccctattcc ttctattcta gccttatttc ttatgaggaa    2700
gatcagaggc aaggagcaga acctagaaaa aactttgtca gcctaatga aaccaaaact    2760
tactttttgga aagtgcaaca tcatatggca cccactaaag atgagtttga ctgcaaagcc    2820
tgggcttatt tctctgatgt tgacctggaa aaagatgtgc actcaggcct gattggaccc    2880
cttctggtct gccacactaa cacactgaac cctgctcatg ggagacaagt gacagtacag    2940
gaatttgctc tgttttcac catctttgat gagaccaaaa gctggtactt cactgaaaat    3000
atggaaagaa actgcagggc tccctgcaat atccagatgg aagatcccac ttttaaagag    3060
aattatcgct tccatgcaat caatggctac ataatggata cactacctgg cttagtaatg    3120
gctcaggatc aaaggattcg atggtatctg ctcagcatgg gcagcaatga aacatccat    3180
tctattcatt tcagtggaca tgttcact gtacgaaaaa agaggagta taaaatggca    3240
ctgtacaatc tctatccagg tgtttttgag acagtggaaa tgttaccatc caaagctgga    3300
atttggcggg tggaatgcct tattggcgag catctacatg ctgggatgag cacacttttt    3360
ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct tttcttggat caaggtggat    3540
ctgttggcac caatgattat tcacggcatc aagacccagg gtgcccgtca gaagttctcc    3600
```

```
agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atatttttaa ccctccaatt attgctcgat acatccgttt gcacccaact    3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctcaaggg     3960 aggagtaatg cctggagacc tcaggtgaat aatccaaaag agtggctgca agtggacttc    4020
cagaagacaa tgaaagtcac aggagtaact actcagggga taaaatctct gcttaccagc    4080
atgtatgtga aggagttcct catctccagc agtcaagatg ccatcagtg gactctcttt     4140 tttcagaatg gcaaagtaaa ggttttcag ggaaatcaag actccttcac acctgtggtg     4200
aactctctag acccaccgtt actgactcgc taccttcgaa ttcaccccca gagttgggtg    4260
caccagattg ccctgaggat ggaggttctg ggctgcgagg cacaggacct ctac           4314
```

<210> SEQ ID NO 7
<211> LENGTH: 2332
<212> TYPE: PRT
<213> ORGANISM: Artificial Sequence
<220> FEATURE:
<223> OTHER INFORMATION: Variant peptide

<400> SEQUENCE: 7

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240
```

```
Ser Leu Pro Gly Leu Ile Gly Cys His Arg Lys Ser Val Tyr Trp His
            245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
            325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
            355                 360                 365
Ile Met Pro Arg Ser Val Ala Lys Lys His Pro Lys Thr Trp Val His
            370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
            405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
            450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
            485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
            565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
            610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
            645                 650                 655
```

```
Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Ser Lys Asn Asn Ala
                725                 730                 735

Ile Glu Pro Arg Ser Phe Ser Gln Asn Ser Arg His Pro Ser Thr Arg
        740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
        770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
        930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
```

-continued

```
            1070                1075                1080
Pro Ile Pro Pro Asp Ala Gln Asn Pro Asp Met Ser Phe Phe Lys
            1085                1090                1095
Met Leu Phe Leu Pro Glu Ser Ala Arg Trp Ile Gln Arg Thr His
            1100                1105                1110
Gly Lys Asn Ser Leu Asn Ser Gly Gln Gly Pro Ser Pro Lys Gln
            1115                1120                1125
Leu Val Ser Leu Gly Pro Glu Lys Ser Val Glu Gly Gln Asn Phe
            1130                1135                1140
Leu Ser Glu Lys Asn Lys Val Val Val Gly Lys Gly Glu Phe Thr
            1145                1150                1155
Lys Asp Val Gly Leu Lys Glu Met Val Phe Pro Ser Ser Arg Asn
            1160                1165                1170
Leu Phe Leu Thr Asn Leu Asp Asn Leu His Glu Asn Asn Thr His
            1175                1180                1185
Asn Gln Glu Lys Lys Ile Gln Glu Glu Ile Glu Lys Lys Glu Thr
            1190                1195                1200
Leu Ile Gln Glu Asn Val Val Leu Pro Gln Ile His Thr Val Thr
            1205                1210                1215
Gly Thr Lys Asn Phe Met Lys Asn Leu Phe Leu Leu Ser Thr Arg
            1220                1225                1230
Gln Asn Val Glu Gly Ser Tyr Asp Gly Ala Tyr Ala Pro Val Leu
            1235                1240                1245
Gln Asp Phe Arg Ser Leu Asn Asp Ser Thr Asn Arg Thr Lys Lys
            1250                1255                1260
His Thr Ala His Phe Ser Lys Lys Gly Glu Glu Glu Asn Leu Glu
            1265                1270                1275
Gly Leu Gly Asn Gln Thr Lys Gln Ile Val Glu Lys Tyr Ala Cys
            1280                1285                1290
Thr Thr Arg Ile Ser Pro Asn Thr Ser Gln Gln Asn Phe Val Thr
            1295                1300                1305
Gln Arg Ser Lys Arg Ala Leu Lys Gln Phe Arg Leu Pro Leu Glu
            1310                1315                1320
Glu Thr Glu Leu Glu Lys Arg Ile Ile Val Asp Asp Thr Ser Thr
            1325                1330                1335
Gln Trp Ser Lys Asn Met Lys His Leu Thr Pro Ser Thr Leu Thr
            1340                1345                1350
Gln Ile Asp Tyr Asn Glu Lys Glu Lys Gly Ala Ile Thr Gln Ser
            1355                1360                1365
Pro Leu Ser Asp Cys Leu Thr Arg Ser His Ser Ile Pro Gln Ala
            1370                1375                1380
Asn Arg Ser Pro Leu Pro Ile Ala Lys Val Ser Ser Phe Pro Ser
            1385                1390                1395
Ile Arg Pro Ile Tyr Leu Thr Arg Val Leu Phe Gln Asp Asn Ser
            1400                1405                1410
Ser His Leu Pro Ala Ala Ser Tyr Arg Lys Lys Asp Ser Gly Val
            1415                1420                1425
Gln Glu Ser Ser His Phe Leu Gln Gly Ala Lys Lys Asn Asn Leu
            1430                1435                1440
Ser Leu Ala Ile Leu Thr Leu Glu Met Thr Gly Asp Gln Arg Glu
            1445                1450                1455
Val Gly Ser Leu Gly Thr Ser Ala Thr Asn Ser Val Thr Tyr Lys
            1460                1465                1470
```

```
Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860
```

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
2015                2020                2025

Ser Gly His Ile Arg Asp Phe Gln Ile Thr Ala Ser Gly Gln Tyr
2030                2035                2040

Gly Gln Trp Ala Pro Lys Leu Ala Arg Leu His Tyr Ser Gly Ser
2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
2075                2080                2085

Ala Arg Gln Lys Phe Ser Ser Leu Tyr Ile Ser Gln Phe Ile Ile
2090                2095                2100

Met Tyr Ser Leu Asp Gly Lys Lys Trp Gln Thr Tyr Arg Gly Asn
2105                2110                2115

Ser Thr Gly Thr Leu Met Val Phe Phe Gly Asn Val Asp Ser Ser
2120                2125                2130

Gly Ile Lys His Asn Ile Phe Asn Pro Pro Ile Ile Ala Arg Tyr
2135                2140                2145

Ile Arg Leu His Pro Thr His Tyr Ser Ile Arg Ser Thr Leu Arg
2150                2155                2160

Met Glu Leu Met Gly Cys Asp Leu Asn Ser Cys Ser Met Pro Leu
2165                2170                2175

Gly Met Glu Ser Lys Ala Ile Ser Asp Ala Gln Ile Thr Ala Ser
2180                2185                2190

Ser Tyr Phe Thr Asn Met Phe Ala Thr Trp Ser Pro Ser Lys Ala
2195                2200                2205

Arg Leu His Leu Gln Gly Arg Ser Asn Ala Trp Arg Pro Gln Val
2210                2215                2220

Asn Asn Pro Lys Glu Trp Leu Gln Val Asp Phe Gln Lys Thr Met
2225                2230                2235

Lys Val Thr Gly Val Thr Thr Gln Gly Val Lys Ser Leu Leu Thr
2240                2245                2250

Ser Met Tyr Val Lys Glu Phe Leu Ile Ser Ser Ser Gln Asp Gly

|  |  |  |  | 2255 |  |  |  | 2260 |  |  |  | 2265 |  |
|---|---|---|---|---|---|---|---|---|---|---|---|---|---|

His Gln Trp Thr Leu Phe Phe Gln Asn Gly Lys Val Lys Val Phe
    2270                        2275                        2280

Gln Gly Asn Gln Asp Ser Phe Thr Pro Val Val Asn Ser Leu Asp
2285                        2290                        2295

Pro Pro Leu Leu Thr Arg Tyr Leu Arg Ile His Pro Gln Ser Trp
2300                        2305                        2310

Val His Gln Ile Ala Leu Arg Met Glu Val Leu Gly Cys Glu Ala
2315                        2320                        2325

Gln Asp Leu Tyr
    2330

<210> SEQ ID NO 8
<211> LENGTH: 6996
<212> TYPE: DNA
<213> ORGANISM: Artificial Sequence
<220> FEATURE:
<223> OTHER INFORMATION: Variant nucleotide

<400> SEQUENCE: 8

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggttca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg gagccctact agtatgtaga     540
gaagggagtc tggccaagga aaagacacag accttgcaca aatttatact acttttgct      600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780
ggcaccactc tgaagtgca ctcaatattc ctcgaaggtc acatttcct gtgaggaac       840
catcgccagg cgtccttgga aatctcgcca ataactttcc ttactgctca aacactcttg     900
atggaccttg acagtttct actgttttgt catatctctt cccaccaaca tgatggcatg     960
gaagcttatg tcaaagtaga cagctgtcca gaggaacccc aactacgaat gaaaataat    1020
gaagaagcgg aagactatga tgatgatctt actgattctg aaatggatgt ggtcaggttt    1080
gatgatgaca actctccttc ctttatcatg ccccgctcag ttgccaagaa gcatcctaaa    1140
acttgggtac attacattgc tgctgaagag gaggactggg actatgctcc cttagtcctc    1200
gcccccgatg acagaagtta taaagtcaa tatttgaaca atggccctca gcggattggt    1260
aggaagtaca aaaagtccg atttatggca tacacagatg aaacctttaa gactcgtgaa    1320
gctattcagc atgaatcagg aatcttggga cctttacttt atgggaagt tggagacaca    1380
ctgttgatta tatttaagaa tcaagcaagc agaccatata acatctaccc tcacggaatc    1440
actgatgtcc gtccttgta ttcaaggaga ttaccaaaag gtgtaaaaca tttgaaggat    1500
tttccaattc tgccaggaga aatattcaaa tataaatgga cagtgactgt agaagatggg    1560
```

```
ccaactaaat cagatcctcg gtgcctgacc cgctattact ctagtttcgt taatatggag    1620
agagatctag cttcaggact cattggccct ctcctcatct gctacaaaga atctgtagat    1680
caaagaggaa accagataat gtcagacaag aggaatgtca tcctgttttc tgtatttgat    1740
gagaaccgaa gctggtacct cacagagaat atacaacgct ttctccccaa tccagctgga    1800
gtgcagcttg aggatccaga gttccaagcc tccaacatca tgcacagcat caatggctat    1860 gttttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcacccta ttcccattct caggagaaac tgtcttcatg    2040
tcgatggaaa acccaggtct atggattctg ggtgccaca  actcagactt tcggaacaga    2100
ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
agcttctccc agaattcaag acaccctagc actaggcaaa agcaatttaa tgccaccaca    2280
attccagaaa atgacataga gaagactgac ccttggtttg cacacagaac acctatgcct    2340
aaaatacaaa atgtctcctc tagtgatttg ttgatgctct tgcgacagag tcctactcca    2400
catgggctat ccttatctga tctccaagaa gccaaatatg acttttttc tgatgatcca    2460 tcacctggag caatagacag taataacagc ctgtctgaaa tgacacactt caggccacag    2520
ctccatcaca gtggggacat ggtatttacc cctgagtcag gcctccaatt aagattaaat    2580
gagaaactgg ggacaactgc agcaacagag ttgaagaaac ttgatttcaa agtttctagt    2640
acatcaaata atctgatttc aacaattcca tcagacaatt tggcagcagg tactgataat    2700
acaagttcct taggaccccc aagtatgcca gttcattatg atagtcaatt agataccact    2760
ctatttggca aaaagtcatc tccccttact gagtctggtg gacctctgag cttgagtgaa    2820
gaaaataatg attcaaagtt gttagaatca ggtttaatga atagccaaga aagttcatgg    2880
ggaaaaaatg tatcgtcaac agagagtggt aggttattta aagggaaaag agctcatgga    2940
cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agcttttgagg    3180 ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtgaaggt    3420 cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaaa ttcaggaaga aatagaaaag    3600
aaggaaacat taatccaaga gaatgtagtt ttgcctcaga tacatacagt gactggcact    3660
aagaatttca tgaagaacct tttccttactg agcactaggc aaaatgtaga aggttcatat    3720
gacggggcat atgctccagt acttcaagat tttaggtcat taaatgattc aacaaataga    3780
acaaagaaac acacagctca tttctcaaaa aagggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
```

```
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctcccttca tcagattgcc ttacgaggag tcatagcatc    4140
cctcaagcaa atagatctcc attacccatt gcaaaggtat catcatttcc atctattaga    4200
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320
aataaccttt cttttagccat tctaaccttg gagatgactg gtgatcaaag agaggttggc    4380
tccctgggga caagtgccac aaattcagtc acatacaaga agttgagaa cactgttctc    4440 ccgaaaccag acttgcccaa acatctggc aaagttgaat tgcttccaaa agttcacatt    4500
tatcagaagg acctattccc tacgaaaact agcaatgggc tcctggcca tctggatctc    4560 gtggaaggga gccttcttca gggaacagag ggagcgatta agtggaatga agcaaacaga    4620
cctggaaaag ttcccttctct gagagtagca acagaaagct ctgcaaagac tccctccaag    4680
ctattggatc ctcttgcttg ggataaccac tatggtactc agataccaaa agaagagtgg    4740
aaatcccaag agaagtcacc agaaaaaaca gcttttaaga aaaaggatac cattttgtcc    4800
ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga aacgccatca acgggaaata actcgtacta ctcttcagtc agatcaagag    4980
gaaattgact atgatgatac catatcagtt gaaatgaaga aggaagattt tgacatttat    5040
gatgaggatg aaaatcagag ccccccgcagc tttcaaaaga aaacacgaca ctattttatt    5100
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagccctt ataccgtgga gaactaaatg aacatttggg actcctgggg    5280
ccatatataa gagcagaagt tgaagataat atcatggtaa ctttcagaaa tcaggcctct    5340
cgtccctatt ccttctattc tagccttatt tcttatgagg aagatcagag gcaaggagca    5400
gaacctagaa aaaactttgt caagcctaat gaaaccaaaa cttactttttg gaaagtgcaa    5460 catcatatgg cacccactaa agatgagttt gactgcaaag cctgggctta tttctctgat    5520
gttgacctgg aaaagatgt gcactcaggc ctgattggac cccttctggt ctgccacact    5580
aacacactga accctgctca tgggagacaa gtgacagtac aggaatttgc tctgttttttc    5640 accatctttg atgagaccaa aagctggtac ttcactgaaa atatggaaag aaactgcagg    5700
gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaagaggag tataaatgg cactgtacaa tctctatcca    5940 ggtgttttg agacagtgga aatgttacca tccaaagctg gaatttggcg ggtggaatgc    6000
cttattggcg agcatctaca tgctgggatg agcacctttt ttctggtgta cagcaataag    6060
tgtcagactc ccctgggaat ggcttctgga cacattagaa attttcagat tacagcttca    6120
ggacaatatg gacagtgggc cccaaagctg gccagacttc attattccgg atcaatcaat    6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
```

```
tttatcatca tgtatagtct tgatgggaag aagtggcaga cttatcgagg aaattccact     6360
ggaaccttaa tggtcttctt tggcaatgtg gattcatctg ggataaaaca caatatttt      6420 aaccctccaa ttattgctcg atacatccgt ttgcacccaa ctcattatag cattcgcagc     6480
actcttcgca tggagttgat gggctgtgat ttaaatagtt gcagcatgcc attgggaatg     6540
gagagtaaag caatatcaga tgcacagatt actgcttcat cctactttac caatatgttt     6600
gccacctggt ctccttcaaa agctcgactt cacctccaag ggaggagtaa tgcctggaga     6660
cctcaggtga ataatccaaa agagtggctg caagtggact tccagaagac aatgaaagtc     6720
acaggagtaa ctactcaggg agtaaaatct ctgcttacca gcatgtatgt gaaggagttc     6780
ctcatctcca gcagtcaaga tggccatcag tggactctct tttttcagaa tggcaaagta     6840
aaggtttttc agggaaatca agactccttc acacctgtgg tgaactctct agacccaccg     6900
ttactgactc gctaccttcg aattcacccc cagagttggg tgcaccagat tgccctgagg     6960
atggaggttc tgggctgcga ggcacaggac ctctac                              6996
```

<210> SEQ ID NO 9
<211> LENGTH: 1438
<212> TYPE: PRT
<213> ORGANISM: Artificial Sequence
<220> FEATURE:
<223> OTHER INFORMATION: Variant peptide

<400> SEQUENCE: 9

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240
```

-continued

```
Ser Leu Pro Gly Leu Ile Gly Cys His Arg Lys Ser Val Tyr Trp His
            245                 250                 255
Val Ile Gly Met Gly Thr Thr Pro Glu Val His Ser Ile Phe Leu Glu
        260                 265                 270
Gly His Thr Phe Leu Val Arg Asn His Arg Gln Ala Ser Leu Glu Ile
    275                 280                 285
Ser Pro Ile Thr Phe Leu Thr Ala Gln Thr Leu Leu Met Asp Leu Gly
290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Met Pro Arg Ser Val Ala Lys Lys His Pro Lys Thr Trp Val His
    370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
```

-continued

```
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Pro Val Leu Lys Arg His
            740                 745                 750
Gln Arg Glu Ile Thr Arg Thr Thr Leu Gln Ser Asp Gln Glu Ile
        755                 760                 765
Asp Tyr Asp Asp Thr Ile Ser Val Glu Met Lys Lys Gly Asp Phe Asp
    770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Pro His Val Leu Arg Asn Arg Ala Gln Ser Gly Ser
            820                 825                 830
Val Pro Gln Phe Lys Lys Val Val Phe Gln Glu Phe Thr Asp Gly Ser
        835                 840                 845
Phe Thr Gln Pro Leu Tyr Arg Gly Glu Leu Asn Glu His Leu Gly Leu
    850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
Ser Tyr Glu Glu Asp Gln Arg Gln Gly Ala Glu Pro Arg Lys Asn Phe
            900                 905                 910
Val Lys Pro Asn Glu Thr Lys Thr Tyr Phe Trp Lys Val Gln His His
        915                 920                 925
Met Ala Pro Thr Lys Asp Glu Phe Asp Cys Lys Ala Trp Ala Tyr Phe
    930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                965                 970                 975
Val Thr Val Gln Glu Phe Ala Leu Phe Phe Thr Ile Phe Asp Glu Thr
            980                 985                 990
Lys Ser Trp Tyr Phe Thr Glu Asn  Met Glu Arg Asn Cys  Arg Ala Pro
        995                 1000                1005
Cys Asn Ile Gln Met Glu Asp Pro Thr Phe Lys Glu Asn Tyr Arg
    1010                1015                1020
Phe His Ala Ile Asn Gly Tyr Ile Met Asp Thr Leu Pro Gly Leu
    1025                1030                1035
Val Met Ala Gln Asp Gln Arg Ile Arg Trp Tyr Leu Leu Ser Met
    1040                1045                1050
Gly Ser Asn Glu Asn Ile His Ser Ile His Phe Ser Gly His Val
    1055                1060                1065
Phe Thr Val Arg Lys Lys Glu Glu Tyr Lys Met Ala Leu Tyr Asn
    1070                1075                1080
```

Leu Tyr Pro Gly Val Phe Glu Thr Val Glu Met Leu Pro Ser Lys
1085                1090                1095

Ala Gly Ile Trp Arg Val Glu Cys Leu Ile Gly Glu His Leu His
1100                1105                1110

Ala Gly Met Ser Thr Leu Phe Leu Val Tyr Ser Asn Lys Cys Gln
1115                1120                1125

Thr Pro Leu Gly Met Ala Ser Gly His Ile Arg Asp Phe Gln Ile
1130                1135                1140

Thr Ala Ser Gly Gln Tyr Gly Gln Trp Ala Pro Lys Leu Ala Arg
1145                1150                1155

Leu His Tyr Ser Gly Ser Ile Asn Ala Trp Ser Thr Lys Glu Pro
1160                1165                1170

Phe Ser Trp Ile Lys Val Asp Leu Leu Ala Pro Met Ile Ile His
1175                1180                1185

Gly Ile Lys Thr Gln Gly Ala Arg Gln Lys Phe Ser Ser Leu Tyr
1190                1195                1200

Ile Ser Gln Phe Ile Ile Met Tyr Ser Leu Asp Gly Lys Lys Trp
1205                1210                1215

Gln Thr Tyr Arg Gly Asn Ser Thr Gly Thr Leu Met Val Phe Phe
1220                1225                1230

Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser
1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
1280                1285                1290

Ala Gln Ile Thr Ala Ser Ser Tyr Phe Thr Asn Met Phe Ala Thr
1295                1300                1305

Trp Ser Pro Ser Lys Ala Arg Leu His Leu Gln Gly Arg Ser Asn
1310                1315                1320

Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
1400                1405                1410

Ile His Pro Gln Ser Trp Val His Gln Ile Ala Leu Arg Met Glu
1415                1420                1425

Val Leu Gly Cys Glu Ala Gln Asp Leu Tyr
1430                1435

<210> SEQ ID NO 10
<211> LENGTH: 4314
<212> TYPE: DNA
<213> ORGANISM: Artificial Sequence
<220> FEATURE:

<223> OTHER INFORMATION: Variant nucleotide

<400> SEQUENCE: 10

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg gagccctact agtatgtaga     540
gaagggagtc tggccaagga aaagacacag accttgcaca aatttatact acttttttgct    600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca aacactcttg     900
atggaccttg gacagtttct actgttttgt catatctctt cccaccaaca tgatggcatg     960
gaagcttatg tcaaagtaga cagctgtcca gaggaacccc aactacgaat gaaaaataat    1020
gaagaagcgg aagactatga tgatgatctt actgattctg aaatggatgt ggtcaggttt    1080
gatgatgaca actctccttc ctttatcatg ccccgctcag ttgccaagaa gcatcctaaa    1140
acttgggtac attacattgc tgctgaagag gaggactggg actatgctcc cttagtcctc    1200
gcccccgatg acagaagtta taaaagtcaa tatttgaaca atggccctca gcggattggt    1260
aggaagtaca aaaagtccg atttatggca tacacagatg aaacctttaa gactcgtgaa    1320
gctattcagc atgaatcagg aatcttggga ccttttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagatggg    1560
ccaactaaat cagatcctcg gtgcctgacc cgctattact ctagtttcgt taatatggag    1620
agagatctag cttcaggact cattggccct ctcctcatct gctacaaaga atctgtagat    1680
caaagaggaa accagataat gtcagacaag aggaatgtca tcctgttttc tgtatttgat    1740
gagaaccgaa gctggtacct cacagagaat atacaacgct ttctcccaa tccagctgga    1800
gtgcagcttg aggatccaga gttccaagcc tccaacatca tgcacagcat caatggctat    1860
gttttgata gtttgcagtt gtcagttttgt ttgcatgagg tggcatactg gtacattcta    1920
agcattggag cacagactga cttccttttct gtcttcttct ctggatatac cttcaaacac    1980
aaaatggtct atgaagacac actcaccctca ttcccattct caggagaaac tgtcttcatg    2040
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttatg aagatatttc agcatacttg ctgagtaaaa caatgccat gaaccaaga    2220
agcttctccc agaacccacc agtcttgaaa cgccatcaac gggaaataac tcgtactact    2280
```

| | | | |
|---|---|---|---|
| cttcagtcag atcaagagga aattgactat gatgatacca tatcagttga aatgaagaag | 2340 |
| gaagattttg acatttatga tgaggatgaa atcagagcc cccgcagctt tcaaaagaaa | 2400 |
| acacgacact attttattgc tgcagtggag aggctctggg attatgggat gagtagctcc | 2460 |
| ccacatgttc taagaaacag ggctcagagt ggcagtgtcc ctcagttcaa gaaagttgtt | 2520 |
| ttccaggaat ttactgatgg ctcctttact cagcccttat accgtggaga actaaatgaa | 2580 |
| catttgggac tcctggggcc atatataaga gcagaagttg aagataatat catggtaact | 2640 |
| ttcagaaatc aggcctctcg tccctattcc ttctattcta gccttatttc ttatgaggaa | 2700 |
| gatcagaggc aaggagcaga acctagaaaa aactttgtca agcctaatga aaccaaaact | 2760 |
| tactttggga aagtgcaaca tcatatggca cccactaaag atgagtttga ctgcaaagcc | 2820 |
| tgggcttatt tctctgatgt tgacctggaa aaagatgtgc actcaggcct gattggaccc | 2880 |
| cttctggtct gccacactaa cacactgaac cctgctcatg ggagacaagt gacagtacag | 2940 |
| gaatttgctc tgtttttcac catctttgat gagaccaaaa gctggtactt cactgaaaat | 3000 |
| atggaaagaa actgcagggc tccctgcaat atccagatgg aagatcccac ttttaaagag | 3060 |
| aattatcgct tccatgcaat caatggctac ataatggata cactacctgg cttagtaatg | 3120 |
| gctcaggatc aaaggattcg atggtatctg ctcagcatgg gcagcaatga aacatccat | 3180 |
| tctattcatt tcagtggaca tgtgttcact gtacgaaaaa aagaggagta taaaatggca | 3240 |
| ctgtacaatc tctatccagg tgttttgag acagtggaaa tgttaccatc caaagctgga | 3300 |
| atttggcggg tggaatgcct tattggcgag catctacatg ctgggatgag cacactttt | 3360 |
| ctggtgtaca gcaataagtg tcagactccc ctgggaatgg cttctggaca cattagagat | 3420 |
| tttcagatta cagcttcagg acaatatgga cagtgggccc caaagctggc cagacttcat | 3480 |
| tattccggat caatcaatgc ctggagcacc aaggagccct tttcttggat caaggtggat | 3540 |
| ctgttggcac caatgattat tcacggcatc aagacccagg gtgcccgtca gaagttctcc | 3600 |
| agcctctaca tctctcagtt tatcatcatg tatagtcttg atgggaagaa gtggcagact | 3660 |
| tatcgaggaa attccactgg aaccttaatg gtcttctttg gcaatgtgga ttcatctggg | 3720 |
| ataaaacaca atatttttaa ccctccaatt attgctcgat acatccgttt gcacccaact | 3780 |
| cattatagca ttcgcagcac tcttcgcatg gagttgatgg gctgtgattt aaatagttgc | 3840 |
| agcatgccat tgggaatgga gagtaaagca atatcagatg cacagattac tgcttcatcc | 3900 |
| tactttacca atatgtttgc cacctggtct ccttcaaaag ctcgacttca cctccaaggg | 3960 |
| aggagtaatg cctggagacc tcaggtgaat aatccaaaag agtggctgca agtggacttc | 4020 |
| cagaagacaa tgaaagtcac aggagtaact actcagggag taaatctct gcttaccagc | 4080 |
| atgtatgtga aggagttcct catctccagc agtcaagatg gccatcagtg gactctcttt | 4140 |
| tttcagaatg gcaaagtaaa ggttttcag ggaaatcaag actccttcac acctgtggtg | 4200 |
| aactctctag acccaccgtt actgactcgc taccttcgaa ttcaccccca gagttgggtg | 4260 |
| caccagattg ccctgaggat ggaggttctg ggctgcgagg cacaggacct ctac | 4314 |

<210> SEQ ID NO 11
<211> LENGTH: 1438
<212> TYPE: PRT
<213> ORGANISM: Artificial Sequence
<220> FEATURE:
<223> OTHER INFORMATION: Variant peptide

<400> SEQUENCE: 11

-continued

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asn Ser Pro Ser Phe
        355                 360                 365

Ile Met Pro Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
```

```
                420             425             430
Asp Glu Thr Phe Lys Thr Arg Glu Ala Ile Gln His Glu Ser Gly Ile
            435             440             445

Leu Gly Pro Leu Leu Tyr Gly Glu Val Gly Asp Thr Leu Leu Ile Ile
450             455             460

Phe Lys Asn Gln Ala Ser Arg Pro Tyr Asn Ile Tyr Pro His Gly Ile
465             470             475             480

Thr Asp Val Arg Pro Leu Tyr Ser Arg Arg Leu Pro Lys Gly Val Lys
            485             490             495

His Leu Lys Asp Phe Pro Ile Leu Pro Gly Glu Ile Phe Lys Tyr Lys
            500             505             510

Trp Thr Val Thr Val Glu Val Gly Pro Thr Lys Ser Asp Pro Arg Cys
            515             520             525

Leu Thr Arg Tyr Tyr Ser Ser Phe Val Asn Met Glu Arg Asp Leu Ala
            530             535             540

Ser Gly Leu Ile Gly Pro Leu Leu Ile Cys Tyr Lys Glu Ser Val Asp
545             550             555             560

Gln Arg Gly Asn Gln Ile Met Ser Asp Lys Arg Asn Val Ile Leu Phe
            565             570             575

Ser Val Phe Asp Glu Asn Arg Ser Trp Tyr Leu Thr Glu Asn Ile Gln
            580             585             590

Arg Phe Leu Pro Asn Pro Ala Gly Val Gln Leu Glu Asp Pro Glu Phe
            595             600             605

Gln Ala Ser Asn Ile Met His Ser Ile Asn Gly Tyr Val Phe Asp Ser
            610             615             620

Leu Gln Leu Ser Val Cys Leu His Glu Val Ala Tyr Trp Tyr Ile Leu
625             630             635             640

Ser Ile Gly Ala Gln Thr Asp Phe Leu Ser Val Phe Phe Ser Gly Tyr
            645             650             655

Thr Phe Lys His Lys Met Val Tyr Val Asp Thr Leu Thr Leu Phe Pro
            660             665             670

Phe Ser Gly Glu Thr Val Phe Met Ser Met Glu Asn Pro Gly Leu Trp
            675             680             685

Ile Leu Gly Cys His Asn Ser Asp Phe Arg Asn Arg Gly Met Thr Ala
            690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
            725             730             735

Ile Glu Pro Arg Ser Phe Ser Gln Asn Pro Pro Val Leu Lys Arg His
            740             745             750

Gln Arg Glu Ile Thr Arg Thr Thr Leu Gln Ser Asp Gln Glu Glu Ile
            755             760             765

Asp Tyr Asp Asp Thr Ile Ser Val Glu Met Lys Lys Glu Asp Phe Asp
            770             775             780

Ile Tyr Asp Glu Asp Glu Asn Gln Ser Pro Arg Ser Phe Gln Lys Lys
785             790             795             800

Thr Arg His Tyr Phe Ile Ala Ala Val Glu Arg Leu Trp Asp Tyr Gly
            805             810             815

Met Ser Ser Ser Pro His Val Leu Arg Asn Arg Ala Gln Ser Gly Ser
            820             825             830

Val Pro Gln Phe Lys Lys Val Val Phe Gln Glu Phe Thr Asp Gly Ser
            835             840             845
```

```
Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
                900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
            930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
                980                 985                 990

Lys Ser Trp Tyr Phe Thr Glu Asn Met Glu Arg Asn Cys Arg Ala Pro
            995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245
```

```
Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 12
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 12
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca cctttcaac      180 atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg agcctact agtatgtaga      540 gaagggagtc tggccaagga aaagacacag accttgcaca aatttatact acttttgct      600 gtatttgatg aagggaaag ttggcactca gaaacaaaga actccttgat gcaggatagg     660
gatgctgcat ctgctcgggc ctggcctaaa atgcacacag tcaatggtta tgtaaacagg     720
tctctaccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca aacactcttg     900
```

```
atggaccttg gacagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatcatg ccccgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaagtccg atttatggca tacacagatg aaacctttaa gacgcgtgaa    1320
gctattcagc atgaatcagg aatcttggga cctttacttt atggggaagt tggagacaca   1380
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagttggg   1560
ccaactaaat cagatccgcg gtgcctgacc cgctattact ctagtttcgt taatatggag   1620
agagatctag cttcaggact cattggccct ctcctcatct gctacaaaga atctgtagat   1680
caaagaggaa accagataat gtcagacaag aggaatgtca tcctgttttc tgtatttgat   1740
gagaaccgaa gctggtacct cacagagaat atacaacgct tctcccccaa tccagctgga   1800
gtgcagcttg aggatccaga gttccaagcc tccaacatca tgcacagcat caatggctat   1860 gttttgata gtttgcagtt gtcagtttgt ttgcatgagg tggcatactg gtacattcta    1920
agcattggag cacagactga cttcctttct gtcttcttct ctggatatac cttcaaacac   1980
aaaatggtct atgtagacac actcacccta ttcccattct caggagaaac tgtcttcatg   2040
tcgatggaaa acccaggtct atggattctg ggtgccaca actcagactt cggaacaga    2100 ggcatgaccg ccttactgaa ggtttctagt tgtgacaaga acactggtga ttattacgag   2160
gacagttacg aagatatttc agcatacttg ctgagtaaaa acaatgccat tgaacctagg   2220
agcttctctc agaatccacc agtccttgaaa cgccatcaac gggaaataac tcgtacgact   2280
cttcagtcag atcaagagga aattgactat gatgatacca tatcagttga aatgaagaag   2340
gaagattttg acatttatga tgaggatgaa aatcagagcc cccgcagctt tcaaaagaaa   2400
acacgacact atttttattgc tgcagtggag aggctctggg attatgggat gagtagctcc   2460
ccacatgttc taagaaacag ggctcagagt ggcagtgtcc ctcagttcaa gaaagttgtt   2520
ttccaggaat ttactgatgg ctcctttact cagcccttat accgtggaga actaaatgaa   2580
catttgggac tcctgggcc atatataaga gcagaagttg aagataatat catggtaact    2640
ttcagaaatc aggcctctcg tccctattcc ttctattcta gccttatttc ttatgaggaa   2700
gatcagaggc aaggagcaga acctagaaaa aactttgtca agcctaatga aaccaaaact   2760
tacttttgga aagtgcaaca tcatatggca cccactaaag atgagtttga ctgcaaagcc   2820
tgggcttatt tctctgatgt tgacctggaa aaagatgtgc actcaggcct gattggaccc   2880
cttctggtct gccacactaa cacactgaac cctgctcatg ggagacaagt gacagtacag   2940
gaatttgctc tgtttttcac catctttgat gagaccaaaa gctggtactt cactgaaaat   3000
atggaaagaa actgcagggc tccctgcaat atccagatgg aagatcccac ttttaaagag   3060
aattatcgct tccatgcaat caatggctac ataatggata cactacctgg cttagtaatg   3120
gctcaggatc aaaggattcg atggtatctg ctcagcatgg gcagcaatga aacatccat    3180 tctattcatt tcagtggaca tgtgttcact gtacgaaaaa agaggagtta taaatggca    3240 ctgtacaatc tctatccagg tgttttttgag acagtggaaa tgttaccatc caaagctgga   3300
```

-continued

```
atttggcggg tggaatgcct tattggcgag catctacatg ctgggatgag cacactttt   3360
ctggtgtaca gcaataagtg tcagactccc ctgggaatgg cttctggaca cattagagat   3420
tttcagatta cagcttcagg acaatatgga cagtgggccc caaagctggc cagacttcat   3480
tattccggat caatcaatgc ctggagcacc aaggagccct tttcttggat caaggtggat   3540
ctgttggcac caatgattat tcacggcatc aagacccagg gtgcccgtca gaagttctcc   3600
agcctctaca tctctcagtt tatcatcatg tatagtcttg atgggaagaa gtggcagact   3660
tatcgaggaa attccactgg aaccttaatg gtcttctttg gcaatgtgga ttcatctggg   3720
ataaaacaca atattttaa ccctccaatt attgctcgat acatccgttt gcacccaact   3780
cattatagca ttcgcagcac tcttcgcatg gagttgatgg gctgtgattt aaatagttgc   3840
agcatgccat tgggaatgga gagtaaagca atatcagatg cacagattac tgcttcatcc   3900
tactttacca atatgtttgc cacctggtct ccttcaaaag ctcgacttca cctccaaggg   3960
aggagtaatg cctggagacc tcaggtgaat aatccaaaag agtggctgca agtggacttc   4020
cagaagacaa tgaaagtcac aggagtaact actcagggag taaaatctct gcttaccagc   4080
atgtatgtga aggagttcct catctccagc agtcaagatg ccatcagtg gactctcttt    4140
tttcagaatg gcaaagtaaa ggttttcag ggaaatcaag actccttcac acctgtggtg    4200
aactctctag acccaccgtt actgactcgc taccttcgaa ttcacccca gagttgggtg    4260
caccagattg ccctgaggat ggaggttctg ggctgcgagg cacaggacct ctac         4314
```

<210> SEQ ID NO 13
<211> LENGTH: 2332
<212> TYPE: PRT
<213> ORGANISM: Artificial Sequence
<220> FEATURE:
<223> OTHER INFORMATION: Variant peptide

<400> SEQUENCE: 13

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
```

```
                180                 185                 190
His Lys Phe Ile Leu Phe Ala Val Phe Asp Glu Gly Lys Ser Trp
            195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Pro Arg Ser Phe Ala Lys Lys His Pro Lys Thr Trp Val His
            370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605
```

-continued

```
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
        755                 760                 765
Thr Asp Pro Trp Phe Ala His Arg Thr Pro Met Pro Lys Ile Gln Asn
770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
        835                 840                 845
Phe Thr Pro Glu Ser Gly Leu Gln Leu Arg Leu Asn Glu Lys Leu Gly
850                 855                 860
Thr Thr Ala Ala Thr Glu Leu Lys Lys Leu Asp Phe Lys Val Ser Ser
865                 870                 875                 880
Thr Ser Asn Asn Leu Ile Ser Thr Ile Pro Ser Asp Asn Leu Ala Ala
                885                 890                 895
Gly Thr Asp Asn Thr Ser Ser Leu Gly Pro Pro Ser Met Pro Val His
            900                 905                 910
Tyr Asp Ser Gln Leu Asp Thr Thr Leu Phe Gly Lys Lys Ser Ser Pro
        915                 920                 925
Leu Thr Glu Ser Gly Gly Pro Leu Ser Leu Ser Glu Glu Asn Asn Asp
930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
            980                 985                 990
Val Ser Ile Ser Leu Leu Lys Thr Asn Lys Thr Ser Asn Asn Ser Ala
        995                 1000                1005
Thr Asn Arg Lys Thr His Ile Asp Gly Pro Ser Leu Leu Ile Glu
    1010                1015                1020
```

```
Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
```

-continued

| | | | | | | | | | |
|---|---|---|---|---|---|---|---|---|---|
| | 1415 | | | | 1420 | | | | 1425 |
| Gln | Glu | Ser | Ser | His | Phe | Leu | Gln | Gly | Ala | Lys | Lys | Asn | Asn | Leu |
| 1430 | | | | | 1435 | | | | | 1440 | | | | |
| Ser | Leu | Ala | Ile | Leu | Thr | Leu | Glu | Met | Thr | Gly | Asp | Gln | Arg | Glu |
| 1445 | | | | | 1450 | | | | | 1455 | | | | |
| Val | Gly | Ser | Leu | Gly | Thr | Ser | Ala | Thr | Asn | Ser | Val | Thr | Tyr | Lys |
| 1460 | | | | | 1465 | | | | | 1470 | | | | |
| Lys | Val | Glu | Asn | Thr | Val | Leu | Pro | Lys | Pro | Asp | Leu | Pro | Lys | Thr |
| 1475 | | | | | 1480 | | | | | 1485 | | | | |
| Ser | Gly | Lys | Val | Glu | Leu | Leu | Pro | Lys | Val | His | Ile | Tyr | Gln | Lys |
| 1490 | | | | | 1495 | | | | | 1500 | | | | |
| Asp | Leu | Phe | Pro | Thr | Glu | Thr | Ser | Asn | Gly | Ser | Pro | Gly | His | Leu |
| 1505 | | | | | 1510 | | | | | 1515 | | | | |
| Asp | Leu | Val | Glu | Gly | Ser | Leu | Leu | Gln | Gly | Thr | Glu | Gly | Ala | Ile |
| 1520 | | | | | 1525 | | | | | 1530 | | | | |
| Lys | Trp | Asn | Glu | Ala | Asn | Arg | Pro | Gly | Lys | Val | Pro | Phe | Leu | Arg |
| 1535 | | | | | 1540 | | | | | 1545 | | | | |
| Val | Ala | Thr | Glu | Ser | Ser | Ala | Lys | Thr | Pro | Ser | Lys | Leu | Leu | Asp |
| 1550 | | | | | 1555 | | | | | 1560 | | | | |
| Pro | Leu | Ala | Trp | Asp | Asn | His | Tyr | Gly | Thr | Gln | Ile | Pro | Lys | Glu |
| 1565 | | | | | 1570 | | | | | 1575 | | | | |
| Glu | Trp | Lys | Ser | Gln | Glu | Lys | Ser | Pro | Glu | Lys | Thr | Ala | Phe | Lys |
| 1580 | | | | | 1585 | | | | | 1590 | | | | |
| Lys | Lys | Asp | Thr | Ile | Leu | Ser | Leu | Asn | Ala | Cys | Glu | Ser | Asn | His |
| 1595 | | | | | 1600 | | | | | 1605 | | | | |
| Ala | Ile | Ala | Ala | Ile | Asn | Glu | Gly | Gln | Asn | Lys | Pro | Glu | Ile | Glu |
| 1610 | | | | | 1615 | | | | | 1620 | | | | |
| Val | Thr | Trp | Ala | Lys | Gln | Gly | Arg | Thr | Glu | Arg | Leu | Cys | Ser | Gln |
| 1625 | | | | | 1630 | | | | | 1635 | | | | |
| Asn | Pro | Pro | Val | Leu | Lys | Arg | His | Gln | Arg | Glu | Ile | Thr | Arg | Thr |
| 1640 | | | | | 1645 | | | | | 1650 | | | | |
| Thr | Leu | Gln | Ser | Asp | Gln | Glu | Glu | Ile | Asp | Tyr | Asp | Asp | Thr | Ile |
| 1655 | | | | | 1660 | | | | | 1665 | | | | |
| Ser | Val | Glu | Met | Lys | Lys | Glu | Asp | Phe | Asp | Ile | Tyr | Asp | Glu | Asp |
| 1670 | | | | | 1675 | | | | | 1680 | | | | |
| Glu | Asn | Gln | Ser | Pro | Arg | Ser | Phe | Gln | Lys | Lys | Thr | Arg | His | Tyr |
| 1685 | | | | | 1690 | | | | | 1695 | | | | |
| Phe | Ile | Ala | Ala | Val | Glu | Arg | Leu | Trp | Asp | Tyr | Gly | Met | Ser | Ser |
| 1700 | | | | | 1705 | | | | | 1710 | | | | |
| Ser | Pro | His | Val | Leu | Arg | Asn | Arg | Ala | Gln | Ser | Gly | Ser | Val | Pro |
| 1715 | | | | | 1720 | | | | | 1725 | | | | |
| Gln | Phe | Lys | Lys | Val | Val | Phe | Gln | Glu | Phe | Thr | Asp | Gly | Ser | Phe |
| 1730 | | | | | 1735 | | | | | 1740 | | | | |
| Thr | Gln | Pro | Leu | Tyr | Arg | Gly | Glu | Leu | Asn | Glu | His | Leu | Gly | Leu |
| 1745 | | | | | 1750 | | | | | 1755 | | | | |
| Leu | Gly | Pro | Tyr | Ile | Arg | Ala | Glu | Val | Glu | Asp | Asn | Ile | Met | Val |
| 1760 | | | | | 1765 | | | | | 1770 | | | | |
| Thr | Phe | Arg | Asn | Gln | Ala | Ser | Arg | Pro | Tyr | Ser | Phe | Tyr | Ser | Ser |
| 1775 | | | | | 1780 | | | | | 1785 | | | | |
| Leu | Ile | Ser | Tyr | Glu | Glu | Asp | Gln | Arg | Gln | Gly | Ala | Glu | Pro | Arg |
| 1790 | | | | | 1795 | | | | | 1800 | | | | |
| Lys | Asn | Phe | Val | Lys | Pro | Asn | Glu | Thr | Lys | Thr | Tyr | Phe | Trp | Lys |
| 1805 | | | | | 1810 | | | | | 1815 | | | | |

Val Gln His His Met Ala Pro Thr Lys Asp Glu Phe Asp Cys Lys
1820                     1825                1830

Ala Trp Ala Tyr Phe Ser Asp Val Asp Leu Glu Lys Asp Val His
1835                     1840                1845

Ser Gly Leu Ile Gly Pro Leu Leu Val Cys His Thr Asn Thr Leu
1850                     1855                1860

Asn Pro Ala His Gly Arg Gln Val Thr Val Gln Glu Phe Ala Leu
1865                     1870                1875

Phe Phe Thr Ile Phe Asp Glu Thr Lys Ser Trp Tyr Phe Thr Glu
1880                     1885                1890

Asn Met Glu Arg Asn Cys Arg Ala Pro Cys Asn Ile Gln Met Glu
1895                     1900                1905

Asp Pro Thr Phe Lys Glu Asn Tyr Arg Phe His Ala Ile Asn Gly
1910                     1915                1920

Tyr Ile Met Asp Thr Leu Pro Gly Leu Val Met Ala Gln Asp Gln
1925                     1930                1935

Arg Ile Arg Trp Tyr Leu Leu Ser Met Gly Ser Asn Glu Asn Ile
1940                     1945                1950

His Ser Ile His Phe Ser Gly His Val Phe Thr Val Arg Lys Lys
1955                     1960                1965

Glu Glu Tyr Lys Met Ala Leu Tyr Asn Leu Tyr Pro Gly Val Phe
1970                     1975                1980

Glu Thr Val Glu Met Leu Pro Ser Lys Ala Gly Ile Trp Arg Val
1985                     1990                1995

Glu Cys Leu Ile Gly Glu His Leu His Ala Gly Met Ser Thr Leu
2000                     2005                2010

Phe Leu Val Tyr Ser Asn Lys Cys Gln Thr Pro Leu Gly Met Ala
2015                     2020                2025

Ser Gly His Ile Arg Asp Phe Gln Ile Thr Ala Ser Gly Gln Tyr
2030                     2035                2040

Gly Gln Trp Ala Pro Lys Leu Ala Arg Leu His Tyr Ser Gly Ser
2045                     2050                2055

Ile Asn Ala Trp Ser Thr Lys Glu Pro Phe Ser Trp Ile Lys Val
2060                     2065                2070

Asp Leu Leu Ala Pro Met Ile Ile His Gly Ile Lys Thr Gln Gly
2075                     2080                2085

Ala Arg Gln Lys Phe Ser Ser Leu Tyr Ile Ser Gln Phe Ile Ile
2090                     2095                2100

Met Tyr Ser Leu Asp Gly Lys Lys Trp Gln Thr Tyr Arg Gly Asn
2105                     2110                2115

Ser Thr Gly Thr Leu Met Val Phe Phe Gly Asn Val Asp Ser Ser
2120                     2125                2130

Gly Ile Lys His Asn Ile Phe Asn Pro Pro Ile Ile Ala Arg Tyr
2135                     2140                2145

Ile Arg Leu His Pro Thr His Tyr Ser Ile Arg Ser Thr Leu Arg
2150                     2155                2160

Met Glu Leu Met Gly Cys Asp Leu Asn Ser Cys Ser Met Pro Leu
2165                     2170                2175

Gly Met Glu Ser Lys Ala Ile Ser Asp Ala Gln Ile Thr Ala Ser
2180                     2185                2190

Ser Tyr Phe Thr Asn Met Phe Ala Thr Trp Ser Pro Ser Lys Ala
2195                     2200                2205

| | | | | | | | | | | | |
|---|---|---|---|---|---|---|---|---|---|---|---|
|Arg|Leu|His|Leu|Gln|Gly|Arg|Ser|Asn|Ala|Trp|Arg Pro Gln Val|
| |2210| | | |2215| | | |2220| | |

Asn Asn Pro Lys Glu Trp Leu Gln Val Asp Phe Gln Lys Thr Met
    2225            2230            2235

Lys Val Thr Gly Val Thr Thr Gln Gly Val Lys Ser Leu Leu Thr
    2240            2245            2250

Ser Met Tyr Val Lys Glu Phe Leu Ile Ser Ser Gln Asp Gly
    2255            2260            2265

His Gln Trp Thr Leu Phe Phe Gln Asn Gly Lys Val Lys Val Phe
    2270            2275            2280

Gln Gly Asn Gln Asp Ser Phe Thr Pro Val Val Asn Ser Leu Asp
    2285            2290            2295

Pro Pro Leu Leu Thr Arg Tyr Leu Arg Ile His Pro Gln Ser Trp
    2300            2305            2310

Val His Gln Ile Ala Leu Arg Met Glu Val Leu Gly Cys Glu Ala
    2315            2320            2325

Gln Asp Leu Tyr
    2330

<210> SEQ ID NO 14
<211> LENGTH: 6996
<212> TYPE: DNA
<213> ORGANISM: Artificial Sequence
<220> FEATURE:
<223> OTHER INFORMATION: Variant nucleotide

<400> SEQUENCE: 14

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggttca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga tggtccaat ggcctctgac ccactgtgcc ttacctactc atatctttct     480
catgtgacc tggtaaaaga cttgaattca ggcctcattg agccctact agtatgtaga     540
gaagggagtc tggccaagga aaagacacag accttgcaca aatttatact acttttgct     600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca aacactcttg     900
atggaccttg acagtttct actgtttgt catatctctt cccaccaaca tgatggcatg     960
gaagcttatg tcaaagtaga cagctgtcca gaggaacccc aactacgaat gaaaaataat    1020
gaagaagcgg aagactatga tgatgatctt actgattctg aaatggatgt ggtcaggttt    1080
gatgatgaca actctcctt ctttatccaa ccccgctcat cgccaagaa gcatcctaaa    1140
acttgggtac attacattgc tgctgaagag gaggactggg actatgctcc cttagtcctc    1200
gcccccgatg acagaagtta taaaagtcaa tatttgaaca atggccctca gcggattggt    1260
```

```
aggaagtaca aaaaagtccg atttatggca tacacagatg aaacctttaa gactcgtgaa    1320
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagatggg    1560
ccaactaaat cagatcctcg gtgcctgacc cgctattact ctagtttcgt taatatggag    1620
agagatctag cttcaggact cattggccct ctcctcatct gctacaaaga atctgtagat    1680
caaagaggaa accagataat gtcagacaag aggaatgtca tcctgttttc tgtatttgat    1740
gagaaccgaa gctggtacct cacagagaat atacaacgct ttctccccaa tccagctgga    1800
gtgcagcttg aggatccaga gttccaagcc tccaacatca tgcacagcat caatggctat    1860
gtttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcacccta ttcccattct caggagaaac tgtcttcatg    2040
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttatg aagatatttc agcatacttg ctgagtaaaa acaatgccat gaaccaaga    2220 agcttctccc agaattcaag cacccctagc actaggcaaa gcaatttaa tgccaccaca    2280 attccagaaa atgacataga gaagactgac ccttggtttg cacacagaac acctatgcct    2340
aaaatacaaa atgtctcctc tagtgatttg ttgatgctct gcgacagag tcctactcca    2400 catgggctat ccttatctga tctccaagaa gccaaatatg agacttttc tgatgatcca    2460 tcacctggag caatagacag taataacagc ctgtctgaaa tgcacacttt caggccacag    2520
ctccatcaca gtggggacat ggtatttacc cctgagtcag gcctccaatt aagattaaat    2580
gagaaactgg ggacaactgc agcaacagag ttgaagaaac ttgatttcaa agttctagt    2640 acatcaaata atctgatttc aacaattcca tcagacaatt tggcagcagg tactgataat    2700
acaagttcct taggaccccc aagtatgcca gttcattatg atagtcaatt agataccact    2760
ctatttggca aaaagtcatc tcccttact gagtctggtg gacctctgag cttgagtgaa    2820
gaaaataatg attcaaagtt gttagaatca ggtttaatga atagccaaga aagttcatgg    2880 ggaaaaatg tatcgtcaac agagagtggt aggttattta agggaaaag agctcatgga    2940 cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg aaagaactc tctgaactct    3360 gggcaaggcc ccagtccaaa gcaattagta tccttaggac agaaaaatc tgtggaaggt    3420 cagaatttct tgtctgagaa aaacaaagtg gtagtaggaa agggtgaatt tacaaaggac    3480
gtaggactca agagatggt ttttccaagc agcagaaacc tatttcttac taacttggat    3540
aatttacatg aaaataatac acacaatcaa gaaaaaaaa ttcaggaaga aatagaaaag    3600
aaggaaacat taatccaaga gaatgtagtt ttgcctcaga tacatacagt gactggcact    3660
```

```
aagaatttca tgaagaacct tttcttactg agcactaggc aaaatgtaga aggttcatat    3720 gacgggcat atgctccagt acttcaagat tttaggtcat taaatgattc aacaaataga    3780
acaaagaaac acacagctca tttctcaaaa aaggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctccctta tcagattgcc ttacgaggag tcatagcatc    4140
cctcaagcaa atagatctcc attacccatt gcaaaggtat catcatttcc atctattaga    4200
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320
aataaccttt ctttagccat tctaaccttg gagatgactg tgatcaaag agaggttggc    4380 tccctgggga caagtgccac aaattcagtc acatacaaga aagttgagaa cactgttctc    4440
ccgaaaccag acttgcccaa acatctggc aaagttgaat tgcttccaaa agttcacatt    4500
tatcagaagg acctattccc tacggaaact agcaatgggt ctcctggcca tctggatctc    4560
gtggaaggga gccttcttca gggaacagag ggagcgatta agtggaatga agcaaacaga    4620
cctggaaaag ttcccttct gagagtagca acagaaagct ctgcaaagac tccctccaag    4680
ctattggatc ctcttgcttg ggataaccac tatggtactc agataccaaa agaagagtgg    4740
aaatcccaag agaagtcacc agaaaaaaca gcttttaaga aaaaggatac cattttgtcc    4800
ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga acgccatca acgggaaata actcgtacta ctcttcagtc agatcaagag    4980
gaaattgact atgatgatac catatcagtt gaaatgaaga aggaagattt tgacatttat    5040
gatgaggatg aaaatcagag ccccgcagc tttcaaaaga aaacacgaca ctattttatt    5100
gctgcagtgg agaggctctg ggattatggg atgagtagct ccccacatgt tctaagaaac    5160
agggctcaga gtggcagtgt ccctcagttc aagaaagttg ttttccagga atttactgat    5220 ggctcccttta ctcagccctt ataccgtgga gaactaaatg aacatttggg actcctgggg    5280
ccatatataa gagcagaagt tgaagataat atcatggtaa ctttcagaaa tcaggcctct    5340
cgtccctatt ccttctattc tagccttatt tcttatgagg aagatcagag gcaaggagca    5400
gaacctagaa aaaactttgt caagcctaat gaaaccaaaa cttacttttg gaaagtgcaa    5460
catcatatgg cacccactaa agatgagttt gactgcaaag cctgggctta tttctctgat    5520
gttgacctgg aaaagatgt gcactcaggc ctgattggac cccttctggt ctgccacact    5580
aacacactga accctgctca tgggagacaa gtgacagtac aggaatttgc tctgttttc    5640 accatctttg atgagaccaa agctggtac ttcactgaaa atatggaaag aaactgcagg    5700
gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaaagaggag tataaaatgg cactgtacaa tctctatcca    5940 ggtgttttttg agacagtgga aatgttacca tccaaagctg gaatttggcg ggtggaatgc    6000
```

```
cttattggcg agcatctaca tgctgggatg agcacacttt ttctggtgta cagcaataag    6060
tgtcagactc ccctgggaat ggcttctgga cacattagag attttcagat tacagcttca    6120
ggacaatatg gacagtgggc cccaaagctg gccagacttc attattccgg atcaatcaat    6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg ggataaaaca caatattttt    6420
aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840
aaggtttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctac                               6996
```

<210> SEQ ID NO 15
<211> LENGTH: 1438
<212> TYPE: PRT
<213> ORGANISM: Artificial Sequence
<220> FEATURE:
<223> OTHER INFORMATION: Variant peptide

<400> SEQUENCE: 15

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190
```

```
His Lys Phe Ile Leu Phe Ala Val Phe Asp Glu Gly Lys Ser Trp
        195                 200                 205
His Ser Glu Thr Lys Asn Ser Leu Met Gln Asp Arg Asp Ala Ala Ser
    210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
                275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asn Ser Pro Ser Phe
                355                 360                 365
Ile Gln Pro Arg Ser Phe Ala Lys Lys His Pro Lys Thr Trp Val His
    370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
            595                 600                 605
```

-continued

```
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Ser Gly Tyr
                    645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                    725                 730                 735
Ile Glu Pro Arg Ser Phe Ser Gln Asn Pro Pro Val Leu Lys Arg His
                740                 745                 750
Gln Arg Glu Ile Thr Arg Thr Thr Leu Gln Ser Asp Gln Glu Glu Ile
            755                 760                 765
Asp Tyr Asp Asp Thr Ile Ser Val Glu Met Lys Lys Glu Asp Phe Asp
770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                    805                 810                 815
Met Ser Ser Ser Pro His Val Leu Arg Asn Arg Ala Gln Ser Gly Ser
                820                 825                 830
Val Pro Gln Phe Lys Lys Val Val Phe Gln Glu Phe Thr Asp Gly Ser
            835                 840                 845
Phe Thr Gln Pro Leu Tyr Arg Gly Glu Leu Asn Glu His Leu Gly Leu
        850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                    885                 890                 895
Ser Tyr Glu Glu Asp Gln Arg Gln Gly Ala Glu Pro Arg Lys Asn Phe
                900                 905                 910
Val Lys Pro Asn Glu Thr Lys Thr Tyr Phe Trp Lys Val Gln His His
            915                 920                 925
Met Ala Pro Thr Lys Asp Glu Phe Asp Cys Lys Ala Trp Ala Tyr Phe
930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                    965                 970                 975
Val Thr Val Gln Glu Phe Ala Leu Phe Phe Thr Ile Phe Asp Glu Thr
                980                 985                 990
Lys Ser Trp Tyr Phe Thr Glu Asn  Met Glu Arg Asn Cys  Arg Ala Pro
            995                 1000                1005
Cys Asn Ile Gln Met Glu Asp  Pro Thr Phe Lys Glu  Asn Tyr Arg
        1010                1015                1020
Phe His Ala Ile Asn Gly Tyr  Ile Met Asp Thr Leu  Pro Gly Leu
```

```
                    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425
```

```
Val Leu Gly Cys Glu Ala Gln  Asp Leu Tyr
    1430            1435

<210> SEQ ID NO 16
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 16
gccaccagaa gatactacct gggtgcagtg gaactgtcat gggactatat gcaaagtgat      60
ctcggtgagc tgcctgtgga cgcaagattt cctcctagag tgccaaaatc tttttccattc    120 aacacctcag tcgtgtacaa aaagactctg tttgtagaat tcacggatca ccttttcaac    180
atcgctaagc caaggccacc ctggatgggt ctgctaggtc ctaccatcca ggctgaggtt    240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttgct    600 gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc tgaagtgca ctcaatattc ctcgaaggtc acacatttct tgtgaggaac    840
catcgccagg cgtccttgga aatctcgcca ataactttcc ttactgctca aacactcttg    900
atggaccttg acagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa ccccgctcat cgccaagaa gcatcctaaa    1140 acttgggtac attacattgc tgctgaagag gaggactggg actatgctcc cttagtcctc    1200
gcccccgatg acagaagtta taaagtcaa tatttgaaca atggccctca gcggattggt    1260
aggaagtaca aaaagtccg atttatggca tacacagatg aaacctttaa gactcgtgaa    1320
gctattcagc atgaatcagg aatcttggga ctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat   1500
tttccaattc tgccaggaga aatattcaaa tataaatgga cagtgactgt agaagatggg    1560
ccaactaaat cagatcctcg gtgcctgacc cgctattact ctagtttcgt taatatggag    1620
agagatctag cttcaggact cattggcccc tcctcatct gctacaaaga atctgtagat   1680
caaagaggaa accagataat gtcagacaag aggaatgtca tcctgttttc tgtatttgat   1740
gagaaccgaa gctggtacct cacagagaat atacaacgct ttctcccaa tccagctgga    1800 gtgcagcttg aggatccaga gttccaagcc tccaacatca tgcacagcat caatggctat    1860 gttttttgata gtttgcagtt gtcagtttgt ttgcatgagg tggcatactg gtacattcta    1920
agcattggag cacagactga cttcctttct gtcttcttct ctggatatac cttcaaacac    1980
```

```
aaaatggtct atgaagacac actcaccata ttcccattct caggagaaac tgtcttcatg    2040
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
agcttctccc agaacccacc agtcttgaaa cgccatcaac gggaaataac tcgtactact    2280
cttcagtcag atcaagagga aattgactat gatgatacca tatcagttga aatgaagaag    2340
gaagattttg acatttatga tgaggatgaa aatcagagcc cccgcagctt tcaaaagaaa    2400
acacgacact attttattgc tgcagtggag aggctctggg attatgggat gagtagctcc    2460
ccacatgttc taagaaacag ggctcagagt ggcagtgtcc ctcagttcaa gaaagttgtt    2520
ttccaggaat ttactgatgg ctcctttact cagcccttat accgtggaga actaaatgaa    2580
catttgggac tcctggggcc atatataaga gcagaagttg aagataatat catggtaact    2640
ttcagaaatc aggcctctcg tccctattcc ttctattcta gccttatttc ttatgaggaa    2700
gatcagaggc aaggagcaga acctagaaaa aactttgtca agcctaatga aaccaaaact    2760 tactttttgga aagtgcaaca tcatatggca cccactaaag atgagtttga ctgcaaagcc    2820
tgggcttatt tctctgatgt tgacctggaa aaagatgtgc actcaggcct gattggaccc    2880
cttctggtct gccacactaa cacactgaac cctgctcatg ggagacaagt gacagtacag    2940
gaatttgctc tgttttttcac catctttgat gagaccaaaa gctggtactt cactgaaaat    3000
atggaaagaa actgcagggc tccctgcaat atccagatgg aagatcccac ttttaaagag    3060
aattatcgct tccatgcaat caatggctac ataatggata cactacctgg cttagtaatg    3120
gctcaggatc aaaggattcg atggtatctg ctcagcatgg gcagcaatga aaacatccat    3180
tctattcatt tcagtggaca tgtgttcact gtacgaaaaa aagaggagta taaaatggca    3240
ctgtacaatc tctatccagg tgtttttgag acagtgaaaa tgttaccatc caaagctgga    3300
atttggcggg tggaatgcct tattggcgag catctacatg ctgggatgag cacactttt    3360 ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct tttcttggat caaggtggat    3540
ctgttggcac caatgattat tcacggcatc aagacccagg gtgcccgtca gaagttctcc    3600
agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atattttttaa ccctccaatt attgctcgat acatccgttt gcacccaact    3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggag taaaatctct gcttaccagc    4080
atgtatgtga aggagttcct catctccagc agtcaagatg gccatcagtg gactctcttt    4140
tttcagaatg gcaaagtaaa ggttttttcag ggaaatcaag actccttcac acctgtggtg    4200
aactctctag acccaccgtt actgactcgc taccttcgaa ttcacccca gagttgggtg    4260 caccagattg ccctgaggat ggaggttctg ggctgcgagg cacaggacct ctac          4314
```

<210> SEQ ID NO 17
<211> LENGTH: 1438
<212> TYPE: PRT
<213> ORGANISM: Artificial Sequence
<220> FEATURE:
<223> OTHER INFORMATION: Variant peptide

<400> SEQUENCE: 17

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asp Asn Ser Pro Ser Phe
        355                 360                 365
```

-continued

```
Ile Gln Pro Arg Ser Phe Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                    405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Val Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Val Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
                740                 745                 750

Gln Arg Glu Ile Thr Arg Thr Thr Leu Gln Ser Asp Gln Glu Glu Ile
            755                 760                 765

Asp Tyr Asp Asp Thr Ile Ser Val Glu Met Lys Lys Glu Asp Phe Asp
770                 775                 780

Ile Tyr Asp Glu Asp Glu Asn Gln Ser Pro Arg Ser Phe Gln Lys Lys
```

-continued

```
            785                 790                 795                 800
      Thr Arg His Tyr Phe Ile Ala Ala Val Glu Arg Leu Trp Asp Tyr Gly
                            805                 810                 815
      Met Ser Ser Ser Pro His Val Leu Arg Asn Arg Ala Gln Ser Gly Ser
                            820                 825                 830
      Val Pro Gln Phe Lys Lys Val Phe Gln Glu Phe Thr Asp Gly Ser
                            835                 840                 845
      Phe Thr Gln Pro Leu Tyr Arg Gly Glu Leu Asn Glu His Leu Gly Leu
                            850                 855                 860
      Leu Gly Pro Tyr Ile Arg Ala Glu Val Glu Asp Asn Ile Met Val Thr
      865                 870                 875                 880
      Phe Arg Asn Gln Ala Ser Arg Pro Tyr Ser Phe Tyr Ser Ser Leu Ile
                            885                 890                 895
      Ser Tyr Glu Glu Asp Gln Arg Gln Gly Ala Glu Pro Arg Lys Asn Phe
                            900                 905                 910
      Val Lys Pro Asn Glu Thr Lys Thr Tyr Phe Trp Lys Val Gln His His
                            915                 920                 925
      Met Ala Pro Thr Lys Asp Glu Phe Asp Cys Lys Ala Trp Ala Tyr Phe
                            930                 935                 940
      Ser Asp Val Asp Leu Glu Lys Asp Val His Ser Gly Leu Ile Gly Pro
      945                 950                 955                 960
      Leu Leu Val Cys His Thr Asn Thr Leu Asn Pro Ala His Gly Arg Gln
                            965                 970                 975
      Val Thr Val Gln Glu Phe Ala Leu Phe Phe Thr Ile Phe Asp Glu Thr
                            980                 985                 990
      Lys Ser Trp Tyr Phe Thr Glu Asn Met Glu Arg Asn Cys Arg Ala Pro
                            995                1000                1005
      Cys Asn Ile Gln Met Glu Asp Pro Thr Phe Lys Glu Asn Tyr Arg
                           1010                1015                1020
      Phe His Ala Ile Asn Gly Tyr Ile Met Asp Thr Leu Pro Gly Leu
                           1025                1030                1035
      Val Met Ala Gln Asp Gln Arg Ile Arg Trp Tyr Leu Leu Ser Met
                           1040                1045                1050
      Gly Ser Asn Glu Asn Ile His Ser Ile His Phe Ser Gly His Val
                           1055                1060                1065
      Phe Thr Val Arg Lys Lys Glu Glu Tyr Lys Met Ala Leu Tyr Asn
                           1070                1075                1080
      Leu Tyr Pro Gly Val Phe Glu Thr Val Glu Met Leu Pro Ser Lys
                           1085                1090                1095
      Ala Gly Ile Trp Arg Val Glu Cys Leu Ile Gly Glu His Leu His
                           1100                1105                1110
      Ala Gly Met Ser Thr Leu Phe Leu Val Tyr Ser Asn Lys Cys Gln
                           1115                1120                1125
      Thr Pro Leu Gly Met Ala Ser Gly His Ile Arg Asp Phe Gln Ile
                           1130                1135                1140
      Thr Ala Ser Gly Gln Tyr Gly Gln Trp Ala Pro Lys Leu Ala Arg
                           1145                1150                1155
      Leu His Tyr Ser Gly Ser Ile Asn Ala Trp Ser Thr Lys Glu Pro
                           1160                1165                1170
      Phe Ser Trp Ile Lys Val Asp Leu Leu Ala Pro Met Ile Ile His
                           1175                1180                1185
      Gly Ile Lys Thr Gln Gly Ala Arg Gln Lys Phe Ser Ser Leu Tyr
                           1190                1195                1200
```

```
Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 18
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 18
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg gagccctact agtatgtaga     540
gaagggagtc tggccaagga aaagacacag accttgcaca aatttatact acttttgct      600
```

```
gtatttgatg aagggaaaag ttggcactca gaaacaaaga actccttgat gcaggatagg      660
gatgctgcat ctgctcgggc ctggcctaaa atgcacacag tcaatggtta tgtaaacagg      720
tctctaccag gtctgattgg atgccacagg aaatcagtct attggcatgt gattggaatg      780
ggcaccactc ctgaagtgca ctcaatattc ctcgaaggtc acacatttct tgtgaggaac      840
catcgccagg cgtccttgga aatctcgcca ataactttcc ttactgctca aacactcttg      900
atggaccttg gacagtttct actgttttgt catatctctt cccaccaaca tgatggcatg      960
gaagcttatg tcaaagtaga cagctgtcca gaggaacccc aactacgaat gaaaaataat     1020
gaagaagcgg aagactatga tgatgatctt actgattctg aaatggatgt ggtcaggttt     1080
gatgatgaca actctccttc ctttatccaa ccccgctcat tcgccaagaa gcatcctaaa     1140
acttgggtac attacattgc tgctgaagag gaggactggg actatgctcc cttagtcctc     1200 gccccccgatg acagaagtta taaaagtcaa tatttgaaca atggccctca gcggattggt     1260
aggaagtaca aaaaagtccg atttatggca tacacagatg aaaccttttaa gacgcgtgaa     1320 gctattcagc atgaatcagg aatcttggga cctttacttt atggggaagt tggagacaca     1380
ctgttgatta tatttaagaa tcaagcaagc agaccatata acatctaccc tcacggaatc     1440
actgatgtcc gtcctttgta ttcaaggaga ttaccaaaag gtgtaaaaca tttgaaggat     1500
tttccaattc tgccaggaga aatattcaaa tataaatgga cagtgactgt agaagttggg     1560
ccaactaaat cagatccgcg gtgcctgacc cgctattact ctagtttcgt taatatggag     1620
agagatctag cttcaggact cattggccct ctcctcatct gctacaaaga atctgtagat     1680
caaagaggaa accagataat gtcagacaag aggaatgtca tcctgttttc tgtatttgat     1740
gagaaccgaa gctggtacct cacagagaat atacaacgct ttctccccaa tccagctgga     1800
gtgcagcttg aggatccaga gttccaagcc tccaacatca tgcacagcat caatggctat     1860 gttttttgata gtttgcagtt gtcagtttgt ttgcatgagg tggcatactg gtacattcta     1920
agcattggag cacagactga cttcctttct gtcttcttct ctggatatac cttcaaacac     1980
aaaatggtct atgtagacac actcaccccta ttcccattct caggagaaac tgtcttcatg     2040
tcgatggaaa acccaggtct atggattctg gggtgccaca actcagactt tcggaacaga     2100
ggcatgaccg ccttactgaa ggtttctagt tgtgacaaga acactggtga ttattacgag     2160
gacagttacg aagatatttc agcatacttg ctgagtaaaa acaatgccat tgaacctagg     2220
agcttctctc agaatccacc agtcttgaaa cgccatcaac gggaaataac tcgtacgact     2280
cttcagtcag atcaagagga aattgactat gatgatacca tatcagttga aatgaagaag     2340
gaagattttg acatttatga tgaggatgaa aatcagagcc cccgcagctt tcaaaagaaa     2400
acacgacact attttattgc tgcagtggag aggctctggg attatgggat gagtagctcc     2460
ccacatgttc taagaaacag ggctcagagt ggcagtgtcc ctcagttcaa gaaagttgtt     2520
ttccaggaat ttactgatgg ctccttcact cagcccttat accgtggaga actaaatgaa     2580
catttgggac tcctggggcc atatataaga gcagaagttg aagataatat catggtaact     2640
ttcagaaatc aggcctctcg tccctattcc ttctattcta gccttatttc ttatgaggaa     2700
gatcagagga aggagcagaa acctagaaaa aactttgtca agcctaatga aaccaaaact     2760
tacttttgga aagtgcaaca tcatatggca cccactaaag atgagtttga ctgcaaagcc     2820
tgggcttatt tctctgatgt tgacctgaaa aaagatgtgc actcaggcct gattggaccc     2880
cttctggtct gccacactaa cacactgaac cctgctcatg ggacacaagt gacagtacag     2940
gaatttgctc tgttttttcac catctttgat gagaccaaaa gctggtactt cactgaaaat     3000
```

```
atggaaagaa actgcagggc tccctgcaat atccagatgg aagatcccac ttttaaagag    3060
aattatcgct tccatgcaat caatggctac ataatggata cactacctgg cttagtaatg    3120
gctcaggatc aaaggattcg atggtatctg ctcagcatgg gcagcaatga aacatccat     3180
tctattcatt tcagtggaca tgtgttcact gtacgaaaaa aagaggagta taaaatggca    3240
ctgtacaatc tctatccagg tgtttttgag acagtggaaa tgttaccatc caaagctgga    3300
atttggcggg tggaatgcct tattggcgag catctacatg ctgggatgag cacactttt    3360
ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct tttcttggat caaggtggat    3540
ctgttggcac caatgattat tcacggcatc aagacccagg gtgcccgtca gaagttctcc    3600
agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atatttttaa ccctccaatt attgctcgat acatccgttt gcacccaact    3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggag taaaatctct gcttaccagc    4080
atgtatgtga aggagttcct catctccagc agtcaagatg ccatcagtg gactctcttt    4140
tttcagaatg gcaaagtaaa ggttttcag ggaaatcaag actccttcac acctgtggtg    4200
aactctctag acccaccgtt actgactcgc taccttcgaa ttcaccccca gagttgggtg    4260
caccagattg ccctgaggat ggaggttctg ggctgcgagg cacaggacct ctac          4314
```

<210> SEQ ID NO 19
<211> LENGTH: 2332
<212> TYPE: PRT
<213> ORGANISM: Artificial Sequence
<220> FEATURE:
<223> OTHER INFORMATION: Variant peptide

<400> SEQUENCE: 19

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125
```

```
Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
```

```
545                 550                 555                 560
Gln Phe Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
                755                 760                 765

Thr Asp Pro Trp Phe Ala His Arg Thr Pro Met Pro Lys Ile Gln Asn
                770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
        850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
                915                 920                 925

Leu Thr Glu Ser Gly Gly Pro Leu Ser Leu Ser Glu Glu Asn Asn Asp
                930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975
```

-continued

```
Arg Ala His Gly Pro Ala Leu Leu Thr Lys Asp Asn Ala Leu Phe Lys
            980             985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010            1015                1020

Asn Ser Pro Ser Val Trp Gln Asn Ile Leu Glu Ser Asp Thr Glu
    1025            1030                1035

Phe Lys Lys Val Thr Pro Leu Ile His Asp Arg Met Leu Met Asp
    1040            1045                1050

Lys Asn Ala Thr Ala Leu Arg Leu Asn His Met Ser Asn Lys Thr
    1055            1060                1065

Thr Ser Ser Lys Asn Met Glu Met Val Gln Gln Lys Lys Glu Gly
    1070            1075                1080

Pro Ile Pro Pro Asp Ala Gln Asn Pro Asp Met Ser Phe Phe Lys
    1085            1090                1095

Met Leu Phe Leu Pro Glu Ser Ala Arg Trp Ile Gln Arg Thr His
    1100            1105                1110

Gly Lys Asn Ser Leu Asn Ser Gly Gln Gly Pro Ser Pro Lys Gln
    1115            1120                1125

Leu Val Ser Leu Gly Pro Glu Lys Ser Val Glu Gly Gln Asn Phe
    1130            1135                1140

Leu Ser Glu Lys Asn Lys Val Val Val Gly Lys Gly Glu Phe Thr
    1145            1150                1155

Lys Asp Val Gly Leu Lys Glu Met Val Phe Pro Ser Ser Arg Asn
    1160            1165                1170

Leu Phe Leu Thr Asn Leu Asp Asn Leu His Glu Asn Asn Thr His
    1175            1180                1185

Asn Gln Glu Lys Lys Ile Gln Glu Glu Ile Glu Lys Lys Glu Thr
    1190            1195                1200

Leu Ile Gln Glu Asn Val Val Leu Pro Gln Ile His Thr Val Thr
    1205            1210                1215

Gly Thr Lys Asn Phe Met Lys Asn Leu Phe Leu Leu Ser Thr Arg
    1220            1225                1230

Gln Asn Val Glu Gly Ser Tyr Asp Gly Ala Tyr Ala Pro Val Leu
    1235            1240                1245

Gln Asp Phe Arg Ser Leu Asn Asp Ser Thr Asn Arg Thr Lys Lys
    1250            1255                1260

His Thr Ala His Phe Ser Lys Lys Gly Glu Glu Glu Asn Leu Glu
    1265            1270                1275

Gly Leu Gly Asn Gln Thr Lys Gln Ile Val Glu Lys Tyr Ala Cys
    1280            1285                1290

Thr Thr Arg Ile Ser Pro Asn Thr Ser Gln Gln Asn Phe Val Thr
    1295            1300                1305

Gln Arg Ser Lys Arg Ala Leu Lys Gln Phe Arg Leu Pro Leu Glu
    1310            1315                1320

Glu Thr Glu Leu Glu Lys Arg Ile Ile Val Asp Asp Thr Ser Thr
    1325            1330                1335

Gln Trp Ser Lys Asn Met Lys His Leu Thr Pro Ser Thr Leu Thr
    1340            1345                1350

Gln Ile Asp Tyr Asn Glu Lys Glu Lys Gly Ala Ile Thr Gln Ser
    1355            1360                1365
```

```
Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
```

|   |   |   |
|---|---|---|
| 1760 | 1765 | 1770 |

Thr Phe Arg Asn Gln Ala Ser Arg Pro Tyr Ser Phe Tyr Ser Ser
 1775                1780                1785

Leu Ile Ser Tyr Glu Glu Asp Gln Arg Gln Gly Ala Glu Pro Arg
 1790                1795                1800

Lys Asn Phe Val Lys Pro Asn Glu Thr Lys Thr Tyr Phe Trp Lys
 1805                1810                1815

Val Gln His His Met Ala Pro Thr Lys Asp Glu Phe Asp Cys Lys
 1820                1825                1830

Ala Trp Ala Tyr Phe Ser Asp Val Asp Leu Glu Lys Asp Val His
 1835                1840                1845

Ser Gly Leu Ile Gly Pro Leu Leu Val Cys His Thr Asn Thr Leu
 1850                1855                1860

Asn Pro Ala His Gly Arg Gln Val Thr Val Gln Glu Phe Ala Leu
 1865                1870                1875

Phe Phe Thr Ile Phe Asp Glu Thr Lys Ser Trp Tyr Phe Thr Glu
 1880                1885                1890

Asn Met Glu Arg Asn Cys Arg Ala Pro Cys Asn Ile Gln Met Glu
 1895                1900                1905

Asp Pro Thr Phe Lys Glu Asn Tyr Arg Phe His Ala Ile Asn Gly
 1910                1915                1920

Tyr Ile Met Asp Thr Leu Pro Gly Leu Val Met Ala Gln Asp Gln
 1925                1930                1935

Arg Ile Arg Trp Tyr Leu Leu Ser Met Gly Ser Asn Glu Asn Ile
 1940                1945                1950

His Ser Ile His Phe Ser Gly His Val Phe Thr Val Arg Lys Lys
 1955                1960                1965

Glu Glu Tyr Lys Met Ala Leu Tyr Asn Leu Tyr Pro Gly Val Phe
 1970                1975                1980

Glu Thr Val Glu Met Leu Pro Ser Lys Ala Gly Ile Trp Arg Val
 1985                1990                1995

Glu Cys Leu Ile Gly Glu His Leu His Ala Gly Met Ser Thr Leu
 2000                2005                2010

Phe Leu Val Tyr Ser Asn Lys Cys Gln Thr Pro Leu Gly Met Ala
 2015                2020                2025

Ser Gly His Ile Arg Asp Phe Gln Ile Thr Ala Ser Gly Gln Tyr
 2030                2035                2040

Gly Gln Trp Ala Pro Lys Leu Ala Arg Leu His Tyr Ser Gly Ser
 2045                2050                2055

Ile Asn Ala Trp Ser Thr Lys Glu Pro Phe Ser Trp Ile Lys Val
 2060                2065                2070

Asp Leu Leu Ala Pro Met Ile Ile His Gly Ile Lys Thr Gln Gly
 2075                2080                2085

Ala Arg Gln Lys Phe Ser Ser Leu Tyr Ile Ser Gln Phe Ile Ile
 2090                2095                2100

Met Tyr Ser Leu Asp Gly Lys Lys Trp Gln Thr Tyr Arg Gly Asn
 2105                2110                2115

Ser Thr Gly Thr Leu Met Val Phe Phe Gly Asn Val Asp Ser Ser
 2120                2125                2130

Gly Ile Lys His Asn Ile Phe Asn Pro Pro Ile Ile Ala Arg Tyr
 2135                2140                2145

Ile Arg Leu His Pro Thr His Tyr Ser Ile Arg Ser Thr Leu Arg
 2150                2155                2160

Met Glu Leu Met Gly Cys Asp Leu Asn Ser Cys Ser Met Pro Leu
2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
2315                2320                2325

Gln Asp Leu Tyr
    2330

<210> SEQ ID NO 20
<211> LENGTH: 6996
<212> TYPE: DNA
<213> ORGANISM: Artificial Sequence
<220> FEATURE:
<223> OTHER INFORMATION: Variant nucleotide

<400> SEQUENCE: 20
gccaccagaa gatactacct gggtgcagtg gaactgtcat ggactatat gcaaagtgat      60 ctcggtgagc tgcctgtgga cgcaagattt cctcctagag tgccaaaatc ttttccattc     120
aacacctcag tcgtgtacaa aaagactctg tttgtagaat tcacggttca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg agccctact agtatgtaga     540 gaagggagtc tggccaagga aaagacacag accttgcaca aatttatact acttttgct      600 gtatttgatg aagggaaaag ttggcactca gaaacaaaga actccttgat gcaggatagg      660
gatgctgcat ctgctcgggc ctggcctaaa atgcacacag tcaatggtta tgtaaacagg      720
tctctgccag gtctgattgg atgccacagg aaatcagtct attggcatgt gattggaatg      780
ggcaccactc ctgaagtgca ctcaatattc ctcgaaggtc acacatttct tgtgaggaac      840
catcgccagg cgtccttgga aatctcgcca ataactttcc ttactgctca aacactcttg      900
atggaccttg acagtttct actgtttgt catatctctt cccaccaaca tgatggcatg      960

```
gaagcttatg tcaaagtaga cagctgtcca gaggaaccc  aactacgaat gaaaaataat    1020
gaagaagcgg aagactatga tgatgatctt actgattctg aaatggatgt ggtcaggttt    1080
gatgatgaca actctccttc ctttatccaa attcgctcag ttgccaagaa gcatcctaaa    1140
acttgggtac attacattgc tgctgaagag gaggactggg actatgctcc cttagtcctc    1200
gcccccgatg acagaagtta taaaagtcaa tatttgaaca atggccctca gcggattggt    1260
aggaagtaca aaaagtccg atttatggca tacacagatg aaacctttaa gactcgtgaa    1320
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagatggg    1560
ccaactaaat cagatcctcg gtgcctgacc cgctattact ctagtttcgt taatatggag    1620
agagatctag cttcaggact cattggcct ctcctcatct gctacaaaga atctctggat    1680
caattcggaa accagataat gtcagacaag aggaatgtca tcctgttttc tgtatttgat    1740
gagaaccgaa gctggtacct cacagagaat atacaacgct ttctccccaa tccagctgga    1800
gtgcagcttg aggatccaga gttccaagcc tccaacatca tgcacagcat caatggctat    1860 gttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcacccta ttcccattct caggagaaac tgtcttcatg    2040
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttatg aagatatttc agcatacttg ctgagtaaaa acaatgccat gaaccaaga    2220 agcttctccc agaattcaag cacccctagc actaggcaaa agcaatttaa tgccaccaca    2280
attccagaaa atgacataga gaagactgac ccttggtttg cacacagaac acctatgcct    2340
aaaatacaaa atgtctcctc tagtgatttg ttgatgctct tgcgacagag tcctactcca    2400
catgggctat ccttatctga tctccaagaa gccaaatatg agactttttc tgatgatcca    2460
tcacctggag caatagacag taataacagc ctgtctgaaa tgacacactt caggccacag    2520
ctccatcaca gtggggacat ggtatttacc cctgagtcag gcctccaatt aagattaaat    2580
gagaaactgg ggacaactgc agcaacagag ttgaagaaac ttgatttcaa agtttctagt    2640
acatcaaata atctgatttc aacaattcca tcagacaatt tggcagcagg tactgataat    2700
acaagttcct taggacccc aagtatgcca gttcattatg atagtcaatt agataccact    2760
ctatttggca aaaagtcatc tccccttact gagtctggtg gacctctgag cttgagtgaa    2820
gaaaataatg attcaaagtt gttagaatca ggtttaatga atagccaaga aagttcatgg    2880
ggaaaaaatg tatcgtcaac agagagtggt aggttattta agggaaaag agctcatgga    2940 cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagttaa    3120 aaagtgacac ctttgattca tgcagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
```

```
gggcaaggcc ccagtccaaa gcaattagta tccttaggac cagaaaaatc tgtggaaggt   3420
cagaatttct tgtctgagaa aaacaaagtg gtagtaggaa agggtgaatt tacaaaggac   3480
gtaggactca aagagatggt ttttccaagc agcagaaacc tatttcttac taacttggat   3540
aatttacatg aaaataatac acacaatcaa gaaaaaaaaa ttcaggaaga aatagaaaag   3600
aaggaaacat taatccaaga gaatgtagtt ttgcctcaga tacatacagt gactggcact   3660
aagaatttca tgaagaacct tttcttactg agcactaggc aaaatgtaga aggttcatat   3720 gacgggcat atgctccagt acttcaagat tttaggtcat taaatgattc aacaaataga    3780
acaaagaaac acacagctca tttctcaaaa aaggggagg aagaaaactt ggaaggcttg    3840
ggaaatcaaa ccaagcaaat tgtagagaaa tatgcatgca ccacaaggat atctcctaat   3900
acaagccagc agaattttgt cacgcaacgt agtaagagag cttttgaaaca attcagactc   3960 ccactagaag aaacagaact tgaaaaaagg ataattgtgg atgacacctc aacccagtgg   4020
tccaaaaaca tgaaacattt gaccccgagc accctcacac agatagacta caatgagaag   4080
gagaaagggg ccattactca gtctcccta tcagattgcc ttacgaggag tcatagcatc    4140
cctcaagcaa atagatctcc attacccatt gcaaaggtat catcatttcc atctattaga   4200
cctatatatc tgaccagggt cctattccaa gacaactctt ctcatcttcc agcagcatct   4260
tatagaaaga aagattctgg ggtccaagaa agcagtcatt tcttacaagg agccaaaaaa   4320
aataaccttt ctttagccat tctaaccttg gagatgactg gtgatcaaag agaggttggc   4380
tccctgggga caagtgccac aaattcagtc acatacaaga aagttgagaa cactgttctc   4440
ccgaaaccag acttgcccaa acatctggc aaagttgaat tgcttccaaa agttcacatt    4500
tatcagaagg acctattccc tacggaaact agcaatgggt ctcctggcca tctggatctc   4560
gtggaaggga gccttcttca gggaacagag ggagcgatta agtggaatga agcaaacaga   4620
cctgaaaaag ttcccttcct gagagtagca acagaaaagct ctgcaaagac tccctccaag   4680
ctattggatc ctcttgcttg ggataaccac tatggtactc agataccaaa agaagagtgg   4740
aaatcccaag agaagtcacc agaaaaaaca gcttttaaga aaaaggatac cattttgtcc   4800
ctgaacgctt gtgaaagcaa tcatgcaata gcagcaataa atgagggaca aaataagccc   4860
gaaatagaag tcacctgggc aaagcaaggt aggactgaaa ggctgtgctc tcaaaaccca   4920
ccagtcttga aacgccatca acgggaaata actcgtacta ctcttcagtc agatcaagag   4980
gaaattgact atgatgatac catatcagtt gaaatgaaga aggaagattt tgacatttat   5040
gatgaggatg aaaatcagag cccccgcagc tttcaaaaga aaacacgaca ctatttatt   5100 gctgcagtgg agaggctctg ggattatggg atgagtagct ccccacatgt tctaagaaac   5160
agggctcaga gtggcagtgt ccctcagttc aagaaagttg ttttccagga atttactgat   5220
ggctccttta ctcagcccctt ataccgtgga gaactaaatg aacatttggg actcctgggg   5280
ccatatataa gagcagaagt tgaagataat atcatggtaa ctttcagaaa tcaggcctct   5340
cgtccctatt ccttctattc tagccttatt tcttatgagg aagatcagag gcaaggagca   5400
gaacctagaa aaaactttgt caagcctaat gaaaccaaaa cttacttttg gaaagtgcaa   5460
catcatatgg cacccactaa agatgagttt gactgcaaag cctgggctta tttctctgat   5520
gttgacctgg aaaaagatgt gcactcaggc ctgattggac cccttctggt ctgccacact   5580
aacacactga accctgctca tgggagacaa gtgcacagta aggaatttgc tctgtttttc   5640
accatctttg atgagaccaa aagctggtac ttcactgaaa atatggaaag aaactgcagg   5700
```

```
gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaagaggag tataaaatgg cactgtacaa tctctatcca     5940 ggtgttttg agacagtgga atgttacca tccaaagctg gaatttggcg ggtggaatgc      6000
cttattggcg agcatctaca tgctgggatg agcacacttt ttctggtgta cagcaataag    6060
tgtcagactc ccctgggaat ggcttctgga cacattagag attttcagat tacagcttca    6120
ggacaatatg gacagtgggc cccaaagctg ccagacttc attattccgg atcaatcaat     6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg gataaaaca caatatttt      6420 aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840
aaggtttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac tctac                               6996
```

<210> SEQ ID NO 21
<211> LENGTH: 1438
<212> TYPE: PRT
<213> ORGANISM: Artificial Sequence
<220> FEATURE:
<223> OTHER INFORMATION: Variant peptide

<400> SEQUENCE: 21

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
```

```
            130                 135                 140
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560
```

```
Gln Phe Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975
```

-continued

Val Thr Val Gln Glu Phe Ala Leu Phe Phe Thr Ile Phe Asp Glu Thr
                    980                 985                 990

Lys Ser Trp Tyr Phe Thr Glu Asn Met Glu Arg Asn Cys Arg Ala Pro
            995                1000                1005

Cys Asn Ile Gln Met Glu Asp Pro Thr Phe Lys Glu Asn Tyr Arg
        1010                1015                1020

Phe His Ala Ile Asn Gly Tyr Ile Met Asp Thr Leu Pro Gly Leu
        1025                1030                1035

Val Met Ala Gln Asp Gln Arg Ile Arg Trp Tyr Leu Leu Ser Met
        1040                1045                1050

Gly Ser Asn Glu Asn Ile His Ser Ile His Phe Ser Gly His Val
        1055                1060                1065

Phe Thr Val Arg Lys Lys Glu Glu Tyr Lys Met Ala Leu Tyr Asn
        1070                1075                1080

Leu Tyr Pro Gly Val Phe Glu Thr Val Glu Met Leu Pro Ser Lys
        1085                1090                1095

Ala Gly Ile Trp Arg Val Glu Cys Leu Ile Gly Glu His Leu His
        1100                1105                1110

Ala Gly Met Ser Thr Leu Phe Leu Val Tyr Ser Asn Lys Cys Gln
        1115                1120                1125

Thr Pro Leu Gly Met Ala Ser Gly His Ile Arg Asp Phe Gln Ile
        1130                1135                1140

Thr Ala Ser Gly Gln Tyr Gly Gln Trp Ala Pro Lys Leu Ala Arg
        1145                1150                1155

Leu His Tyr Ser Gly Ser Ile Asn Ala Trp Ser Thr Lys Glu Pro
        1160                1165                1170

Phe Ser Trp Ile Lys Val Asp Leu Leu Ala Pro Met Ile Ile His
        1175                1180                1185

Gly Ile Lys Thr Gln Gly Ala Arg Gln Lys Phe Ser Ser Leu Tyr
        1190                1195                1200

Ile Ser Gln Phe Ile Ile Met Tyr Ser Leu Asp Gly Lys Lys Trp
        1205                1210                1215

Gln Thr Tyr Arg Gly Asn Ser Thr Gly Thr Leu Met Val Phe Phe
        1220                1225                1230

Gly Asn Val Asp Ser Ser Gly Ile Lys His Asn Ile Phe Asn Pro
        1235                1240                1245

Pro Ile Ile Ala Arg Tyr Ile Arg Leu His Pro Thr His Tyr Ser
        1250                1255                1260

Ile Arg Ser Thr Leu Arg Met Glu Leu Met Gly Cys Asp Leu Asn
        1265                1270                1275

Ser Cys Ser Met Pro Leu Gly Met Glu Ser Lys Ala Ile Ser Asp
        1280                1285                1290

Ala Gln Ile Thr Ala Ser Ser Tyr Phe Thr Asn Met Phe Ala Thr
        1295                1300                1305

Trp Ser Pro Ser Lys Ala Arg Leu His Leu Gln Gly Arg Ser Asn
        1310                1315                1320

Ala Trp Arg Pro Gln Val Asn Asn Pro Lys Glu Trp Leu Gln Val
        1325                1330                1335

Asp Phe Gln Lys Thr Met Lys Val Thr Gly Val Thr Thr Gln Gly
        1340                1345                1350

Val Lys Ser Leu Leu Thr Ser Met Tyr Val Lys Glu Phe Leu Ile
        1355                1360                1365

Ser Ser Ser Gln Asp Gly His Gln Trp Thr Leu Phe Phe Gln Asn

|  |  |  |
|---|---|---|
| 1370 | 1375 | 1380 |

Gly Lys Val Lys Val Phe Gln Gly Asn Gln Asp Ser Phe Thr Pro
    1385                       1390                       1395

Val Val Asn Ser Leu Asp Pro Pro Leu Leu Thr Arg Tyr Leu Arg
    1400                       1405                       1410

Ile His Pro Gln Ser Trp Val His Gln Ile Ala Leu Arg Met Glu
    1415                       1420                       1425

Val Leu Gly Cys Glu Ala Gln Asp Leu Tyr
    1430                       1435

<210> SEQ ID NO 22
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 22

| | | | | | |
|---|---|---|---|---|---|
| gccaccagaa | gatactacct | gggtgcagtg | gaactgtcat | ggactatat | gcaaagtgat | 60 |
| ctcggtgagc | tgcctgtgga | cgcaagattt | cctcctagag | tgccaaaatc | ttttccattc | 120 |
| aacacctcag | tcgtgtacaa | aaagactctg | tttgtagaat | tcacggatca | ccttttcaac | 180 |
| atcgctaagc | caaggccacc | ctggatgggt | ctgctaggtc | ctaccatcca | ggctgaggtt | 240 |
| tatgatacag | tggtcattac | acttaagaac | atggcttccc | atcctgtcag | tcttcatgct | 300 |
| gttggtgtat | cctactggaa | agcttctgag | ggagctgaat | atgatgatca | gaccagtcaa | 360 |
| agggagaaag | aagatgataa | agtcttccct | ggtggaagcc | atacatatgt | ctggcaggtc | 420 |
| ctgaaagaga | tggtccaat | ggcctctgac | ccactgtgcc | ttacctactc | atatctttct | 480 |
| catgtggacc | tggtaaaaga | cttgaattca | ggcctcattg | gagccctact | agtatgtaga | 540 |
| gaagggagtc | tggccaagga | aaagacacag | accttgcaca | aatttatact | acttttgct | 600 |
| gtatttgatg | aagggaaaag | ttggcactca | gaaacaaaga | actccttgat | gcaggatagg | 660 |
| gatgctgcat | ctgctcgggc | ctggcctaaa | atgcacacag | tcaatggtta | tgtaaacagg | 720 |
| tctctgccag | gtctgattgg | atgccacagg | aaatcagtct | attggcatgt | gattggaatg | 780 |
| ggcaccactc | ctgaagtgca | ctcaatattc | ctcgaaggtc | acacatttct | tgtgaggaac | 840 |
| catcgccagg | cgtccttgga | aatctcgcca | ataactttcc | ttactgctca | aacactcttg | 900 |
| atggaccttg | acagtttct | actgttttgt | catatctctt | cccaccaaca | tgatggcatg | 960 |
| gaagcttatg | tcaaagtaga | cagctgtcca | gaggaacccc | aactacgaat | gaaaaataat | 1020 |
| gaagaagcgg | aagactatga | tgatgatctt | actgattctg | aaatggatgt | ggtcaggttt | 1080 |
| gatgatgaca | actctccttc | ctttatccaa | attcgctcag | ttgccaagaa | gcatcctaaa | 1140 |
| acttgggtac | attacattgc | tgctgaagag | gaggactggg | actatgctcc | cttagtcctc | 1200 |
| gcccccgatg | acagaagtta | taaaagtcaa | tatttgaaca | atggcccctca | gcggattggt | 1260 |
| aggaagtaca | aaaaagtccg | atttatggca | tacacagatg | aaacctttaa | gactcgtgaa | 1320 |
| gctattcagc | atgaatcagg | aatcttggga | cctttacttt | atgggaagt | tggagacaca | 1380 |
| ctgttgatta | tatttaagaa | tcaagcaagc | agaccatata | acatctaccc | tcacggaatc | 1440 |
| actgatgtcc | gtcctttgta | ttcaaggaga | ttaccaaaag | gtgtaaaaca | tttgaaggat | 1500 |
| tttccaattc | tgccaggaga | aatattcaaa | tataaatgga | cagtgactgt | agaagatggg | 1560 |
| ccaactaaat | cagatcctcg | gtgcctgacc | cgctattact | ctagtttcgt | taatatggag | 1620 |
| agagatctag | cttcaggact | cattggccct | ctcctcatct | gctacaaaga | atctctggat | 1680 |

```
caattcggaa accagataat gtcagacaag aggaatgtca tcctgttttc tgtatttgat    1740
gagaaccgaa gctggtacct cacagagaat atacaacgct ttctccccaa tccagctgga    1800
gtgcagcttg aggatccaga gttccaagcc tccaacatca tgcacagcat caatggctat    1860
gtttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcaccta ttcccattct caggagaaac tgtcttcatg    2040
tcgatggaaa acccaggtct atggattctg gggtgccaca actcagactt cggaacaga     2100 ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
agcttctccc agaacccacc agtcttgaaa cgccatcaac gggaaataac tcgtactact    2280
cttcagtcag atcaagagga aattgactat gatgatacca tatcagttga aatgaagaag    2340
gaagattttg acatttatga tgaggatgaa aatcagagcc cccgcagctt tcaaaagaaa    2400
acacgacact attttattgc tgcagtggag aggctctggg attatgggat gagtagctcc    2460
ccacatgttc taagaaacag ggctcagagt ggcagtgtcc ctcagttcaa gaaagttgtt    2520
ttccaggaat ttactgatgg ctcctttact cagcccttat accgtggaga actaaatgaa    2580
catttgggac tcctggggcc atatataaga gcagaagttg aagataatat catggtaact    2640
ttcagaaatc aggcctctcg tccctattcc ttctattcta gccttatttc ttatgaggaa    2700
gatcagaggc aaggagcaga acctagaaaa aactttgtca agcctaatga aaccaaaact    2760
tacttttgga aagtgcaaca tcatatggca cccactaaag atgagtttga ctgcaaagcc    2820
tgggcttatt tctctgatgt tgacctggaa aaagatgtgc actcaggcct gattggaccc    2880
cttctggtct gccacactaa cacactgaac cctgctcatg ggagacaagt gacagtacag    2940
gaatttgctc tgtttttcac catctttgat gagaccaaaa gctggtactt cactgaaaat    3000
atggaaagaa actgcagggc tccctgcaat atccagatgg aagatcccac ttttaaagag    3060
aattatcgct tccatgcaat caatggctac ataatggata cactacctgg cttagtaatg    3120
gctcaggatc aaaggattcg atggtatctg ctcagcatgg gcagcaatga aacatccat     3180 tctattcatt tcagtggaca tgtgttcact gtacgaaaaa aagaggagta taaaatggca    3240
ctgtacaatc tctatccagg tgttttttgag acagtgaaaa tgttaccatc caaagctgga    3300
atttggcggg tggaatgcct tattggcgag catctacatg ctgggatgag cacactttttt  3360 ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct ttcttggat caaggtggat     3540 ctgttggcac caatgattat tcacggcatc aagacccagg gtgcccgtca agttctcc      3600 agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atattttaa ccctccaatt attgctcgat acatccgttt gcacccaact     3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
```

-continued

```
cagaagacaa tgaaagtcac aggagtaact actcagggag taaaatctct gcttaccagc    4080
atgtatgtga aggagttcct catctccagc agtcaagatg ccatcagtg gactctcttt     4140 tttcagaatg gcaaagtaaa ggttttcag ggaaatcaag actccttcac acctgtggtg     4200
aactctctag acccaccgtt actgactcgc taccttcgaa ttcacccca gagttgggtg     4260 caccagattg ccctgaggat ggaggttctg ggctgcgagg cacaggacct ctac           4314
```

<210> SEQ ID NO 23
<211> LENGTH: 1438
<212> TYPE: PRT
<213> ORGANISM: Artificial Sequence
<220> FEATURE:
<223> OTHER INFORMATION: Variant peptide

<400> SEQUENCE: 23

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320
```

-continued

```
Glu Ala Tyr Val Lys Val Asp Ser Cys Pro Glu Pro Gln Leu Arg
            325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Val Gly Pro Thr Lys Ser Asp Pro Arg Cys
    515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Leu Asp
545                 550                 555                 560

Gln Phe Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Val Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735
```

-continued

Ile Glu Pro Arg Ser Phe Ser Gln Asn Pro Val Leu Lys Arg His
                740                 745                 750

Gln Arg Glu Ile Thr Arg Thr Thr Leu Gln Ser Asp Gln Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Pro His Val Leu Arg Asn Arg Ala Gln Ser Gly Ser
        820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
        900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
        930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
        980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg

| | | | | | | | | | |
|---|---|---|---|---|---|---|---|---|---|
| | | 1145 | | | 1150 | | | 1155 | |

Leu His Tyr Ser Gly Ser Ile Asn Ala Trp Ser Thr Lys Glu Pro
        1160                1165                1170

Phe Ser Trp Ile Lys Val Asp Leu Leu Ala Pro Met Ile Ile His
        1175                1180                1185

Gly Ile Lys Thr Gln Gly Ala Arg Gln Lys Phe Ser Ser Leu Tyr
        1190                1195                1200

Ile Ser Gln Phe Ile Ile Met Tyr Ser Leu Asp Gly Lys Lys Trp
        1205                1210                1215

Gln Thr Tyr Arg Gly Asn Ser Thr Gly Thr Leu Met Val Phe Phe
        1220                1225                1230

Gly Asn Val Asp Ser Ser Gly Ile Lys His Asn Ile Phe Asn Pro
        1235                1240                1245

Pro Ile Ile Ala Arg Tyr Ile Arg Leu His Pro Thr His Tyr Ser
        1250                1255                1260

Ile Arg Ser Thr Leu Arg Met Glu Leu Met Gly Cys Asp Leu Asn
        1265                1270                1275

Ser Cys Ser Met Pro Leu Gly Met Glu Ser Lys Ala Ile Ser Asp
        1280                1285                1290

Ala Gln Ile Thr Ala Ser Ser Tyr Phe Thr Asn Met Phe Ala Thr
        1295                1300                1305

Trp Ser Pro Ser Lys Ala Arg Leu His Leu Gln Gly Arg Ser Asn
        1310                1315                1320

Ala Trp Arg Pro Gln Val Asn Asn Pro Lys Glu Trp Leu Gln Val
        1325                1330                1335

Asp Phe Gln Lys Thr Met Lys Val Thr Gly Val Thr Thr Gln Gly
        1340                1345                1350

Val Lys Ser Leu Leu Thr Ser Met Tyr Val Lys Glu Phe Leu Ile
        1355                1360                1365

Ser Ser Ser Gln Asp Gly His Gln Trp Thr Leu Phe Phe Gln Asn
        1370                1375                1380

Gly Lys Val Lys Val Phe Gln Gly Asn Gln Asp Ser Phe Thr Pro
        1385                1390                1395

Val Val Asn Ser Leu Asp Pro Pro Leu Leu Thr Arg Tyr Leu Arg
        1400                1405                1410

Ile His Pro Gln Ser Trp Val His Gln Ile Ala Leu Arg Met Glu
        1415                1420                1425

Val Leu Gly Cys Glu Ala Gln Asp Leu Tyr
        1430                1435

<210> SEQ ID NO 24
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 24
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca cctttttcaac   180 atcgctaagc caaggccacc ctggatgggt ctgctaggtc ctaccatcca ggctgaggtt     240
tatgatacag tggtcattac acttaagaac atggcttccc atcctgtcag tcttcatgct     300

-continued

```
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttgct    600 gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctaccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg acagtttct actgttttgt catatctctt cccaccaaca tgatggcatg    960
gaagcttatg tcaaagtaga cagctgtcca ggaaccccc aactacgaat gaaaaataat    1020
gaagaagcgg aagactatga tgatgatctt actgattctg aaatggatgt ggtcaggttt    1080
gatgatgaca actctccttc ctttatccaa attcgctcag ttgccaagaa gcatcctaaa    1140
acttgggtac attacattgc tgctgaagag gaggactggg actatgctcc cttagtcctc    1200
gcccccgatg acagaagtta taaaagtcaa tatttgaaca atggccctca gcggattggt    1260
aggaagtaca aaaaagtccg atttatggca tacacagatg aaacctttaa gacgcgtgaa    1320
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagttggg    1560
ccaactaaat cagatccgcg gtgcctgacc cgctattact ctagtttcgt taatatggag    1620
agagatctag cttcaggact cattggccct ctcctcatct gctacaaaga atctctggat    1680
caattcggaa accagataat gtcagacaag aggaatgtca tcctgttttc tgtatttgat    1740
gagaaccgaa gctggtacct cacagagaat atacaacgct ttctcccccaa tccagctgga    1800 gtgcagcttg aggatccaga gttccaagcc tccaacatca tgcacagcat caatggctat    1860 gttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgtagacac actcacccta ttcccattct caggagaaac tgtcttcatg    2040
tcgatggaaa acccaggtct atggattctg ggtgccaca actcagactt tcggaacaga    2100
ggcatgaccg ccttactgaa ggtttctagt tgtgacaaga acactggtga ttattacgag    2160
gacagttacg aagatatttc agcatacttg ctgagtaaaa acaatgccat tgaacctagg    2220
agcttctctc agaatccacc agtcttgaaa cgccatcaac gggaaataac tcgtacgact    2280
cttcagtcag atcaagagga aattgactat gatgatacca tatcagttga aatgaagaag    2340
gaagattttg acatttatga tgaggatgaa aatcagagcc cccgcagctt tcaaaagaaa    2400
acacgacact attttattgc tgcagtggag aggctctggg attatgggat gagtagctcc    2460
ccacatgttc taagaaacag ggctcagagt ggcagtgtcc ctcagttcaa gaaagttgtt    2520
ttccaggaat ttactgatgg ctccttact cagcccttat accgtggaga actaaatgaa    2580
catttgggac tcctggggcc atatataaga gcagaagttg aagataatat catggtaact    2640
ttcagaaatc aggcctctcg tccctattcc ttctattcta gccttatttc ttatgaggaa    2700
```

```
gatcagaggc aaggagcaga acctagaaaa aactttgtca agcctaatga aaccaaaact   2760
tacttttgga aagtgcaaca tcatatggca cccactaaag atgagtttga ctgcaaagcc   2820
tgggcttatt tctctgatgt tgacctggaa aaagatgtgc actcaggcct gattggaccc   2880
cttctggtct gccacactaa cacactgaac cctgctcatg ggagacaagt gacagtacag   2940
gaatttgctc tgttttttcac catctttgat gagaccaaaa gctggtactt cactgaaaat   3000
atggaaagaa actgcagggc tccctgcaat atccagatgg aagatcccac ttttaaagag   3060
aattatcgct ccatgcaat caatggctac ataatggata cactacctgg cttagtaatg   3120
gctcaggatc aaaggattcg atggtatctg ctcagcatgg gcagcaatga aacatccat   3180 tctattcatt tcagtggaca tgtgttcact gtacgaaaaa aagaggagta taaaatggca   3240
ctgtacaatc tctatccagg tgttttttgag acagtggaaa tgttaccatc caaagctgga   3300
atttggcggg tggaatgcct tattggcgag catctacatg ctgggatgag cacttttt   3360 ctggtgtaca gcaataagtg tcagactccc ctgggaatgg cttctggaca cattagagat   3420
tttcagatta cagcttcagg acaatatgga cagtgggccc caaagctggc cagacttcat   3480
tattccggat caatcaatgc ctggagcacc aaggagccct tttcttggat caaggtggat   3540
ctgttggcac caatgattat tcacggcatc aagacccagg gtgcccgtca aagttctcc   3600 agcctctaca tctctcagtt tatcatcatg tatagtcttg atgggaagaa gtggcagact   3660
tatcgaggaa attccactgg aaccttaatg gtcttctttg gcaatgtgga ttcatctggg   3720
ataaaacaca atatttttaa ccctccaatt attgctcgat acatccgttt gcacccaact   3780
cattatagca ttcgcagcac tcttcgcatg gagttgatgg gctgtgattt aaatagttgc   3840
agcatgccat tgggaatgga gagtaaagca atatcagatg cacagattac tgcttcatcc   3900
tactttacca atatgtttgc cacctggtct ccttcaaaag ctcgacttca cctccaaggg   3960
aggagtaatg cctggagacc tcaggtgaat aatccaaaag agtggctgca agtggacttc   4020
cagaagacaa tgaaagtcac aggagtaact actcagggag taaatctct gcttaccagc   4080 atgtatgtga aggagttcct catctccagc agtcaagatg ccatcagtg gactctcttt   4140 tttcagaatg gcaaagtaaa ggttttcag ggaaatcaag actccttcac acctgtggtg   4200
aactctctag acccaccgtt actgactcgc taccttcgaa ttcaccccca gagttgggtg   4260
caccagattg ccctgaggat ggaggttctg ggctgcgagg cacaggacct ctac           4314
```

<210> SEQ ID NO 25
<211> LENGTH: 2332
<212> TYPE: PRT
<213> ORGANISM: Artificial Sequence
<220> FEATURE:
<223> OTHER INFORMATION: Variant peptide

<400> SEQUENCE: 25

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80
```

-continued

```
Tyr Asp Thr Val Val Ile Thr Leu Lys Asn Met Ala Ser His Pro Val
                 85                  90                  95
Ser Leu His Ala Val Gly Val Ser Tyr Trp Lys Ala Ser Glu Gly Ala
            100                 105                 110
Glu Tyr Asp Asp Gln Thr Ser Gln Arg Glu Lys Glu Asp Asp Lys Val
        115                 120                 125
Phe Pro Gly Gly Ser His Thr Tyr Val Trp Gln Val Leu Lys Glu Asn
130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
            180                 185                 190
His Lys Phe Ile Leu Leu Phe Ala Val Phe Asp Glu Gly Lys Ser Trp
        195                 200                 205
His Ser Glu Thr Lys Asn Ser Leu Met Gln Asp Arg Asp Ala Ala Ser
    210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
        275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Leu Thr Asp
            340                 345                 350
Ser Glu Met Asp Val Val Arg Phe Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
```

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560

Gln Trp Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro

-continued

```
            915                 920                 925
Leu Thr Glu Ser Gly Gly Pro Leu Ser Leu Ser Glu Glu Asn Asn Asp
        930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
            980                 985                 990
Val Ser Ile Ser Leu Leu Lys Thr Asn Lys Thr Ser Asn Asn Ser Ala
        995                 1000                1005
Thr Asn Arg Lys Thr His Ile Asp Gly Pro Ser Leu Leu Ile Glu
    1010                1015                1020
Asn Ser Pro Ser Val Trp Gln Asn Ile Leu Glu Ser Asp Thr Glu
    1025                1030                1035
Phe Lys Lys Val Thr Pro Leu Ile His Asp Arg Met Leu Met Asp
    1040                1045                1050
Lys Asn Ala Thr Ala Leu Arg Leu Asn His Met Ser Asn Lys Thr
    1055                1060                1065
Thr Ser Ser Lys Asn Met Glu Met Val Gln Gln Lys Lys Glu Gly
    1070                1075                1080
Pro Ile Pro Pro Asp Ala Gln Asn Pro Asp Met Ser Phe Phe Lys
    1085                1090                1095
Met Leu Phe Leu Pro Glu Ser Ala Arg Trp Ile Gln Arg Thr His
    1100                1105                1110
Gly Lys Asn Ser Leu Asn Ser Gly Gln Gly Pro Ser Pro Lys Gln
    1115                1120                1125
Leu Val Ser Leu Gly Pro Glu Lys Ser Val Glu Gly Gln Asn Phe
    1130                1135                1140
Leu Ser Glu Lys Asn Lys Val Val Val Gly Lys Gly Glu Phe Thr
    1145                1150                1155
Lys Asp Val Gly Leu Lys Glu Met Val Phe Pro Ser Ser Arg Asn
    1160                1165                1170
Leu Phe Leu Thr Asn Leu Asp Asn Leu His Glu Asn Asn Thr His
    1175                1180                1185
Asn Gln Glu Lys Lys Ile Gln Glu Glu Ile Glu Lys Lys Glu Thr
    1190                1195                1200
Leu Ile Gln Glu Asn Val Val Leu Pro Gln Ile His Thr Val Thr
    1205                1210                1215
Gly Thr Lys Asn Phe Met Lys Asn Leu Phe Leu Leu Ser Thr Arg
    1220                1225                1230
Gln Asn Val Glu Gly Ser Tyr Asp Gly Ala Tyr Ala Pro Val Leu
    1235                1240                1245
Gln Asp Phe Arg Ser Leu Asn Asp Ser Thr Asn Arg Thr Lys Lys
    1250                1255                1260
His Thr Ala His Phe Ser Lys Lys Gly Glu Glu Glu Asn Leu Glu
    1265                1270                1275
Gly Leu Gly Asn Gln Thr Lys Gln Ile Val Glu Lys Tyr Ala Cys
    1280                1285                1290
Thr Thr Arg Ile Ser Pro Asn Thr Ser Gln Gln Asn Phe Val Thr
    1295                1300                1305
Gln Arg Ser Lys Arg Ala Leu Lys Gln Phe Arg Leu Pro Leu Glu
    1310                1315                1320
```

```
Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710
```

-continued

| | | | | | | | | | | |
|---|---|---|---|---|---|---|---|---|---|---|
| Ser | Pro | His | Val | Leu | Arg | Asn | Arg | Ala | Gln | Ser | Gly | Ser | Val | Pro |
| | 1715 | | | | 1720 | | | | 1725 | |
| Gln | Phe | Lys | Lys | Val | Val | Phe | Gln | Glu | Phe | Thr | Asp | Gly | Ser | Phe |
| | 1730 | | | | 1735 | | | | 1740 | |
| Thr | Gln | Pro | Leu | Tyr | Arg | Gly | Glu | Leu | Asn | Glu | His | Leu | Gly | Leu |
| | 1745 | | | | 1750 | | | | 1755 | |
| Leu | Gly | Pro | Tyr | Ile | Arg | Ala | Glu | Val | Glu | Asp | Asn | Ile | Met | Val |
| | 1760 | | | | 1765 | | | | 1770 | |
| Thr | Phe | Arg | Asn | Gln | Ala | Ser | Arg | Pro | Tyr | Ser | Phe | Tyr | Ser | Ser |
| | 1775 | | | | 1780 | | | | 1785 | |
| Leu | Ile | Ser | Tyr | Glu | Glu | Asp | Gln | Arg | Gln | Gly | Ala | Glu | Pro | Arg |
| | 1790 | | | | 1795 | | | | 1800 | |
| Lys | Asn | Phe | Val | Lys | Pro | Asn | Glu | Thr | Lys | Thr | Tyr | Phe | Trp | Lys |
| | 1805 | | | | 1810 | | | | 1815 | |
| Val | Gln | His | His | Met | Ala | Pro | Thr | Lys | Asp | Glu | Phe | Asp | Cys | Lys |
| | 1820 | | | | 1825 | | | | 1830 | |
| Ala | Trp | Ala | Tyr | Phe | Ser | Asp | Val | Asp | Leu | Glu | Lys | Asp | Val | His |
| | 1835 | | | | 1840 | | | | 1845 | |
| Ser | Gly | Leu | Ile | Gly | Pro | Leu | Leu | Val | Cys | His | Thr | Asn | Thr | Leu |
| | 1850 | | | | 1855 | | | | 1860 | |
| Asn | Pro | Ala | His | Gly | Arg | Gln | Val | Thr | Val | Gln | Glu | Phe | Ala | Leu |
| | 1865 | | | | 1870 | | | | 1875 | |
| Phe | Phe | Thr | Ile | Phe | Asp | Glu | Thr | Lys | Ser | Trp | Tyr | Phe | Thr | Glu |
| | 1880 | | | | 1885 | | | | 1890 | |
| Asn | Met | Glu | Arg | Asn | Cys | Arg | Ala | Pro | Cys | Asn | Ile | Gln | Met | Glu |
| | 1895 | | | | 1900 | | | | 1905 | |
| Asp | Pro | Thr | Phe | Lys | Glu | Asn | Tyr | Arg | Phe | His | Ala | Ile | Asn | Gly |
| | 1910 | | | | 1915 | | | | 1920 | |
| Tyr | Ile | Met | Asp | Thr | Leu | Pro | Gly | Leu | Val | Met | Ala | Gln | Asp | Gln |
| | 1925 | | | | 1930 | | | | 1935 | |
| Arg | Ile | Arg | Trp | Tyr | Leu | Leu | Ser | Met | Gly | Ser | Asn | Glu | Asn | Ile |
| | 1940 | | | | 1945 | | | | 1950 | |
| His | Ser | Ile | His | Phe | Ser | Gly | His | Val | Phe | Thr | Val | Arg | Lys | Lys |
| | 1955 | | | | 1960 | | | | 1965 | |
| Glu | Glu | Tyr | Lys | Met | Ala | Leu | Tyr | Asn | Leu | Tyr | Pro | Gly | Val | Phe |
| | 1970 | | | | 1975 | | | | 1980 | |
| Glu | Thr | Val | Glu | Met | Leu | Pro | Ser | Lys | Ala | Gly | Ile | Trp | Arg | Val |
| | 1985 | | | | 1990 | | | | 1995 | |
| Glu | Cys | Leu | Ile | Gly | Glu | His | Leu | His | Ala | Gly | Met | Ser | Thr | Leu |
| | 2000 | | | | 2005 | | | | 2010 | |
| Phe | Leu | Val | Tyr | Ser | Asn | Lys | Cys | Gln | Thr | Pro | Leu | Gly | Met | Ala |
| | 2015 | | | | 2020 | | | | 2025 | |
| Ser | Gly | His | Ile | Arg | Asp | Phe | Gln | Ile | Thr | Ala | Ser | Gly | Gln | Tyr |
| | 2030 | | | | 2035 | | | | 2040 | |
| Gly | Gln | Trp | Ala | Pro | Lys | Leu | Ala | Arg | Leu | His | Tyr | Ser | Gly | Ser |
| | 2045 | | | | 2050 | | | | 2055 | |
| Ile | Asn | Ala | Trp | Ser | Thr | Lys | Glu | Pro | Phe | Ser | Trp | Ile | Lys | Val |
| | 2060 | | | | 2065 | | | | 2070 | |
| Asp | Leu | Leu | Ala | Pro | Met | Ile | Ile | His | Gly | Ile | Lys | Thr | Gln | Gly |
| | 2075 | | | | 2080 | | | | 2085 | |
| Ala | Arg | Gln | Lys | Phe | Ser | Ser | Leu | Tyr | Ile | Ser | Gln | Phe | Ile | Ile |
| | 2090 | | | | 2095 | | | | 2100 | |
| Met | Tyr | Ser | Leu | Asp | Gly | Lys | Lys | Trp | Gln | Thr | Tyr | Arg | Gly | Asn |

|  | 2105 |  |  |  | 2110 |  |  |  | 2115 |  |  |
|---|---|---|---|---|---|---|---|---|---|---|---|

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 26
<211> LENGTH: 6996
<212> TYPE: DNA
<213> ORGANISM: Artificial Sequence
<220> FEATURE:
<223> OTHER INFORMATION: Variant nucleotide

<400> SEQUENCE: 26
gccaccagaa gatactacct gggtgcagtg gaactgtcat gggactatat gcaaagtgat     60
ctcggtgagc tgcctgtgga cgcaagattt cctcctagag tgccaaaatc ttttccattc    120
aacacctcag tcgtgtacaa aaagactctg tttgtagaat tcacggttca ccttttcaac    180
atcgctaagc caaggccacc ctggatgggt ctgctaggtc ctaccatcca ggctgaggtt    240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg agccctacta gtatgtaga     540 gaagggagtc tggccaagga aaagacacag accttgcaca aatttatact acttttgct     600 gtatttgatg aagggaaaag ttggcactca gaaacaaaga actccttgat gcaggatagg    660

```
gatgctgcat ctgctcgggc ctggcctaaa atgcacacag tcaatggtta tgtaaacagg      720
tctctgccag gtctgattgg atgccacagg aaatcagtct attggcatgt gattggaatg      780
ggcaccactc ctgaagtgca ctcaatattc ctcgaaggtc acacatttct tgtgaggaac      840
catcgccagg cgtccttgga aatctcgcca ataactttcc ttactgctca aacactcttg      900
atggaccttg gacagtttct actgttttgt catatctctt cccaccaaca tgatggcatg      960
gaagcttatg tcaaagtaga cagctgtcca gaggaacccc aactacgaat gaaaaataat     1020
gaagaagcgg aagactatga tgatgatctt actgattctg aaatggatgt ggtcaggttt     1080
gatgatgaca actctccttc ctttatccaa attcgctcag ttgccaagaa gcatcctaaa     1140
acttgggtac attacattgc tgctgaagag gaggactggg actatgctcc cttagtcctc     1200
gcccccgatg acagaagtta taaaagtcaa tatttgaaca atggccctca gcggattggt     1260
aggaagtaca aaaagtccg atttatggca tacacagatg aaacctttaa gactcgtgaa     1320
gctattcagc atgaatcagg aatcttggga cctttacttt atggggaagt tggagacaca     1380
ctgttgatta tatttaagaa tcaagcaagc agaccatata acatctaccc tcacggaatc     1440
actgatgtcc gtcctttgta ttcaaggaga ttaccaaaag gtgtaaaaca tttgaaggat     1500
tttccaattc tgccaggaga aatattcaaa tataaatgga cagtgactgt agaagatggg     1560
ccaactaaat cagatcctcg gtgcctgacc cgctattact ctagtttcgt taatatggag     1620
agagatctag cttcaggact cattggccct ctcctcatct gctacaaaga atctctggat     1680
caatggggaa accagataat gtcagacaag aggaatgtca tcctgttttc tgtatttgat     1740
gagaaccgaa gctggtacct cacagagaat atacaacgct ttctccccaa tccagctgga     1800
gtgcagcttg aggatccaga gttccaagcc tccaacatca tgcacagcat caatggctat     1860 gttttgata gtttgcagtt gtcagtttgt ttgcatgagg tggcatactg gtacattcta     1920
agcattggag cacagactga cttccttcct gtcttcttct ctggatatac cttcaaacac     1980
aaaatggtct atgaagacac actcacccta ttcccattct caggagaaac tgtcttcatg     2040
tcgatggaaa acccaggtct atggattctg ggtgccaca actcagactt tcggaacaga     2100
ggcatgaccg ccttactgaa ggtttctagt tgtgacaaga acactggtga ttattacgag     2160
gacagttatg aagatatttc agcatacttg ctgagtaaaa acaatgccat tgaaccaaga     2220
agcttctccc agaattcaag acaccctagc actaggcaaa agcaatttaa tgccaccaca     2280
attccagaaa atgacataga gaagactgac ccttggtttg cacacagaac acctatgcct     2340
aaaatacaaa atgtctcctc tagtgatttg ttgatgctct tgcgacagag tcctactcca     2400
catgggctat ccttatctga tctccaagaa gccaaatatg agacttttc tgatgatcca     2460 tcacctggag caatagacag taataacagc ctgtctgaaa tgacacactt caggccacag     2520
ctccatcaca gtggggacat ggtatttacc cctgagtcag gcctccaatt aagattaaat     2580
gagaaactgg gacaactgc agcaacagag ttgaagaaac ttgatttcaa agtttctagt     2640
acatcaaata atctgatttc aacaattcca tcagacaatt tggcagcagg tactgataat     2700
acaagttcct taggaccccc aagtatgcca gttcattatg atagtcaatt agataccact     2760
ctatttggca aaaagtcatc tccccttact gagtctggtg gacctctgag cttgagtgaa     2820
gaaaataatg attcaaagtt gttagaatca ggtttaatga atagccaaga agttcatgg     2880 ggaaaaatg tatcgtcaac agagagtggt aggttattta agggaaaag agctcatgga     2940 cctgctttgt tgactaaaga taatgcctta ttcaaagtta gcatctcttt gttaaagaca     3000
aacaaaactt ccaataattc agcaactaat agaaagactc acattgatgg cccatcatta     3060
```

```
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaaa ttcaggaaga aatagaaaag    3600
aaggaaacat taatccaaga gaatgtagtt ttgcctcaga tacatacagt gactggcact    3660
aagaatttca tgaagaacct tttcttactg agcactaggc aaaatgtaga aggttcatat    3720
gacggggcat atgctccagt acttcaagat tttaggtcat taaatgattc aacaaataga    3780
acaaagaaac acacagctca tttctcaaaa aaggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctccctta tcagattgcc ttacgaggag tcatagcatc    4140
cctcaagcaa atagatctcc attacccatt gcaaaggtat catcatttcc atctattaga    4200
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320
aataaccttt ctttagccat tctaaccttg gagatgactg gtgatcaaag agaggttggc    4380
tccctgggga caagtgccac aaattcagtc acatacaaga aagttgagaa cactgttctc    4440
ccgaaaccag acttgcccaa acatctggc aaagttgaat tgcttccaaa agttcacatt    4500
tatcagaagg acctattccc tacgaaaact agcaatgggt ctcctggcca tctggatctc    4560
gtggaaggga gccttcttca gggaacagag ggagcgatta agtggaatga agcaaacaga    4620
cctggaaaag ttccctttct gagagtagca acagaaagct ctgcaaagac tccctccaag    4680
ctattggatc ctcttgcttg ggataaccac tatggtactc agataccaaa agaagagtgg    4740
aaatcccaag agaagtcacc agaaaaaaca gcttttaaga aaaaggatac cattttgtcc    4800
ctgaacgctt gtgaaagcaa tcatgcaata gcagcaataa atgagggaca aaataagccc    4860
gaaatagaag tcacctggc aaagcaaggt aggactgaaa ggctgtgctc tcaaaaccca    4920
ccagtcttga acgccatca acgggaaata actcgtacta ctcttcagtc agatcaagag    4980
gaaattgact atgatgatac catatcagtt gaaatgaaga aggaagattt tgacatttat    5040
gatgaggatg aaaatcagag cccccgcagc tttcaaaaga aaacacgaca ctattttatt    5100
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagcccct taccgtgga gaactaaatg aacatttggg actcctgggg    5280
ccatatataa gagcagaagt tgaagataat atcatggtaa ctttcagaaa tcaggcctct    5340
cgtcccctatt ccttctattc tagccttatt tcttatgagg aagatcagag gcaaggagca    5400
```

-continued

```
gaacctagaa aaaactttgt caagcctaat gaaaccaaaa cttactttg gaaagtgcaa    5460
catcatatgg cacccactaa agatgagttt gactgcaaag cctgggctta tttctctgat    5520
gttgacctgg aaaagatgt gcactcaggc ctgattggac cccttctggt ctgccacact    5580
aacacactga accctgctca tgggagacaa gtgacagtac aggaatttgc tctgtttttc    5640
accatctttg atgagaccaa aagctggtac ttcactgaaa atatggaaag aaactgcagg    5700
gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaaagaggag tataaaatgg cactgtacaa tctctatcca    5940
ggtgttttg agacagtgga atgttacca tccaaagctg gaatttggcg ggtggaatgc    6000
cttattggcg agcatctaca tgctgggatg agcacacttt ttctggtgta cagcaataag    6060
tgtcagactc ccctgggaat ggcttctgga cacattagag attttcagat tacagcttca    6120
ggacaatatg gacagtgggc cccaaagctg gccagacttc attattccgg atcaatcaat    6180
gcctggagca ccaaggagcc ctttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg gataaaaaca caatatttt    6420
aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaaatct ctgcttacca gcatgtatgt gaaggagttc    6780
ctcatctcca gcagtcaaga tggccatcag tggactctct ttttcagaa tggcaaagta    6840
aaggttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctac                              6996
```

<210> SEQ ID NO 27
<211> LENGTH: 1438
<212> TYPE: PRT
<213> ORGANISM: Artificial Sequence
<220> FEATURE:
<223> OTHER INFORMATION: Variant peptide

<400> SEQUENCE: 27

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

```
Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
```

```
                500             505             510
Trp Thr Val Thr Val Glu Asp Gly Pro Thr Lys Ser Asp Pro Arg Cys
            515             520             525

Leu Thr Arg Tyr Tyr Ser Ser Phe Val Asn Met Glu Arg Asp Leu Ala
            530             535             540

Ser Gly Leu Ile Gly Pro Leu Leu Ile Cys Tyr Lys Glu Ser Leu Asp
545             550             555             560

Gln Trp Gly Asn Gln Ile Met Ser Asp Lys Arg Asn Val Ile Leu Phe
            565             570             575

Ser Val Phe Asp Glu Asn Arg Ser Trp Tyr Leu Thr Glu Asn Ile Gln
            580             585             590

Arg Phe Leu Pro Asn Pro Ala Gly Val Gln Leu Glu Asp Pro Glu Phe
            595             600             605

Gln Ala Ser Asn Ile Met His Ser Ile Asn Gly Tyr Val Phe Asp Ser
            610             615             620

Leu Gln Leu Ser Val Cys Leu His Glu Val Ala Tyr Trp Tyr Ile Leu
625             630             635             640

Ser Ile Gly Ala Gln Thr Asp Phe Leu Ser Val Phe Phe Ser Gly Tyr
            645             650             655

Thr Phe Lys His Lys Met Val Tyr Glu Asp Thr Leu Thr Leu Phe Pro
            660             665             670

Phe Ser Gly Glu Thr Val Phe Met Ser Met Glu Asn Pro Gly Leu Trp
            675             680             685

Ile Leu Gly Cys His Asn Ser Asp Phe Arg Asn Arg Gly Met Thr Ala
            690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
            725             730             735

Ile Glu Pro Arg Ser Phe Ser Gln Asn Pro Pro Val Leu Lys Arg His
            740             745             750

Gln Arg Glu Ile Thr Arg Thr Thr Leu Gln Ser Asp Gln Glu Glu Ile
            755             760             765

Asp Tyr Asp Asp Thr Ile Ser Val Glu Met Lys Lys Glu Asp Phe Asp
            770             775             780

Ile Tyr Asp Glu Asp Glu Asn Gln Ser Pro Arg Ser Phe Gln Lys Lys
785             790             795             800

Thr Arg His Tyr Phe Ile Ala Ala Val Glu Arg Leu Trp Asp Tyr Gly
            805             810             815

Met Ser Ser Ser Pro His Val Leu Arg Asn Arg Ala Gln Ser Gly Ser
            820             825             830

Val Pro Gln Phe Lys Lys Val Val Phe Gln Glu Phe Thr Asp Gly Ser
            835             840             845

Phe Thr Gln Pro Leu Tyr Arg Gly Glu Leu Asn Glu His Leu Gly Leu
            850             855             860

Leu Gly Pro Tyr Ile Arg Ala Glu Val Glu Asp Asn Ile Met Val Thr
865             870             875             880

Phe Arg Asn Gln Ala Ser Arg Pro Tyr Ser Phe Tyr Ser Ser Leu Ile
            885             890             895

Ser Tyr Glu Glu Asp Gln Arg Gln Gly Ala Glu Pro Arg Lys Asn Phe
            900             905             910

Val Lys Pro Asn Glu Thr Lys Thr Tyr Phe Trp Lys Val Gln His His
            915             920             925
```

```
Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
                980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320
```

| Ala | Trp | Arg | Pro | Gln | Val | Asn | Asn | Pro | Lys | Glu | Trp | Leu | Gln | Val |
|  | 1325 |  |  |  | 1330 |  |  |  | 1335 |  |  |  |  |  |

| Asp | Phe | Gln | Lys | Thr | Met | Lys | Val | Thr | Gly | Val | Thr | Thr | Gln | Gly |
| 1340 |  |  |  |  | 1345 |  |  |  |  | 1350 |  |  |  |  |

| Val | Lys | Ser | Leu | Leu | Thr | Ser | Met | Tyr | Val | Lys | Glu | Phe | Leu | Ile |
| 1355 |  |  |  |  | 1360 |  |  |  |  | 1365 |  |  |  |  |

| Ser | Ser | Ser | Gln | Asp | Gly | His | Gln | Trp | Thr | Leu | Phe | Phe | Gln | Asn |
| 1370 |  |  |  |  | 1375 |  |  |  |  | 1380 |  |  |  |  |

| Gly | Lys | Val | Lys | Val | Phe | Gln | Gly | Asn | Gln | Asp | Ser | Phe | Thr | Pro |
| 1385 |  |  |  |  | 1390 |  |  |  |  | 1395 |  |  |  |  |

| Val | Val | Asn | Ser | Leu | Asp | Pro | Pro | Leu | Leu | Thr | Arg | Tyr | Leu | Arg |
| 1400 |  |  |  |  | 1405 |  |  |  |  | 1410 |  |  |  |  |

| Ile | His | Pro | Gln | Ser | Trp | Val | His | Gln | Ile | Ala | Leu | Arg | Met | Glu |
| 1415 |  |  |  |  | 1420 |  |  |  |  | 1425 |  |  |  |  |

| Val | Leu | Gly | Cys | Glu | Ala | Gln | Asp | Leu | Tyr |
| 1430 |  |  |  |  | 1435 |  |  |  |  |

<210> SEQ ID NO 28
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 28

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg gagccctact agtatgtaga     540
gaagggagtc tggccaagga aaagacacag accttgcaca aatttatact actttttgct     600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca acactcttg      900
atggaccttg acagtttct actgttttgt catatctctt cccaccaaca tgatggcatg      960
gaagcttatg tcaaagtaga cagctgtcca gaggaacccc aactacgaat gaaaaataat    1020
gaagaagcgg aagactatga tgatgatctt actgattctg aaatggatgt ggtcaggttt    1080
gatgatgaca ctctccttc ctttatccaa attcgctcag ttgccaagaa gcatcctaaa    1140
acttgggtac attacattgc tgctgaagag gaggactggg actatgctcc cttagtcctc    1200
gcccccgatg acagaagtta taaagtcaa tatttgaaca atggccctca gcggattggt    1260
aggaagtaca aaaaagtccg atttatggca tacacagatg aaacctttaa gactcgtgaa    1320
gctattcagc atgaatcagg aatcttggga cctttacttt atggggaagt tggagacaca    1380
```

```
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctctggat   1680
caatggggaa accagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860 gttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg gggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat tgaaccaaga   2220
agcttctccc agaacccacc agtcttgaaa cgccatcaac gggaaataac tcgtactact   2280
cttcagtcag atcaagagga aattgactat gatgatacca tatcagttga aatgaagaag   2340
gaagattttg acatttatga tgaggatgaa aatcagagcc ccgcagcttt caaaagaaa   2400 acacgacact attttattgc tgcagtggag aggctctggg attatgggat gagtagctcc   2460
ccacatgttc taagaaacag ggctcagagt ggcagtgtcc ctcagttcaa gaaagttgtt   2520
ttccaggaat ttactgatgg ctcctttact cagcccttat accgtggaga actaaatgaa   2580
catttgggac tcctggggcc atatataaga gcagaagttg aagataatat catggtaact   2640
ttcagaaatc aggcctctcg tccctattcc ttctattcta gccttatttc ttatgaggaa   2700
gatcagaggc aaggagcaga acctagaaaa aactttgtca gcctaatga aaccaaaact   2760 tacttttgga agtgcaaca tcatatggca cccactaaag atgagtttga ctgcaaagcc   2820
tgggcttatt tctctgatgt tgacctggaa aaagatgtgc actcaggcct gattggaccc   2880
cttctggtct gccacactaa cacactgaac cctgctcatg ggagacaagt gacagtacag   2940
gaatttgctc tgttttcac catctttgat gagaccaaaa gctggtactt cactgaaaat   3000
atggaaagaa actgcagggc tccctgcaat atccagatgg aagatccac tttaaagag   3060 aattatcgct tccatgcaat caatggctac ataatggata cactacctgg cttagtaatg   3120
gctcaggatc aaaggattcg atggtatctg ctcagcatgg gcagcaatga aacatccat   3180 tctattcatt tcagtggaca tgtgttcact gtacgaaaaa aagaggagta taaatggca   3240 ctgtacaatc tctatccagg tgttttgag acagtggaaa tgttaccatc caaagctgga   3300
atttggcggg tggaatgcct tattggcgag catctacatg ctgggatgag cacacttttt   3360
ctggtgtaca gcaataagtg tcagactccc ctgggaatgg cttctggaca cattagagat   3420
tttcagatta cagcttcagg acaatatgga cagtgggccc caaagctggc cagacttcat   3480
tattccggat caatcaatgc ctggagcacc aaggagccct ttcttggat caaggtggat   3540 ctgttggcac caatgattat tcacggcatc aagacccagg gtgcccgtca gaagttctcc   3600
agcctctaca tctctcagtt tatcatcatg tatagtcttg atgggaagaa gtggcagact   3660
tatcgaggaa attccactgg aacccttaatg gtcttctttg gcaatgtgga ttcatctggg   3720
```

| | | |
|---|---|---|
| ataaaacaca atattttaa ccctccaatt attgctcgat acatccgttt gcacccaact | | 3780 |
| cattatagca ttcgcagcac tcttcgcatg gagttgatgg gctgtgattt aaatagttgc | | 3840 |
| agcatgccat tgggaatgga gagtaaagca atatcagatg cacagattac tgcttcatcc | | 3900 |
| tactttacca atatgtttgc cacctggtct ccttcaaaag ctcgacttca cctccaaggg | | 3960 |
| aggagtaatg cctggagacc tcaggtgaat aatccaaaag agtggctgca agtggacttc | | 4020 |
| cagaagacaa tgaaagtcac aggagtaact actcagggag taaaatctct gcttaccagc | | 4080 |
| atgtatgtga aggagttcct catctccagc agtcaagatg ccatcagtg gactctcttt | | 4140 |
| tttcagaatg gcaaagtaaa ggttttcag ggaaatcaag actccttcac acctgtggtg | | 4200 |
| aactctctag acccaccgtt actgactcgc taccttcgaa ttcaccccca gagttgggtg | | 4260 |
| caccagattg ccctgaggat ggaggttctg ggctgcgagg cacaggacct ctac | | 4314 |

<210> SEQ ID NO 29
<211> LENGTH: 1438
<212> TYPE: PRT
<213> ORGANISM: Artificial Sequence
<220> FEATURE:
<223> OTHER INFORMATION: Variant peptide

<400> SEQUENCE: 29

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
```

```
            260                 265                 270
Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Val Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560

Gln Trp Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Val Asp Thr Leu Thr Leu Phe Pro
            660                 665                 670

Phe Ser Gly Glu Thr Val Phe Met Ser Met Glu Asn Pro Gly Leu Trp
        675                 680                 685
```

```
Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Val Leu Lys Arg His
            740                 745                 750

Gln Arg Glu Ile Thr Arg Thr Thr Leu Gln Ser Asp Gln Glu Ile
        755                 760                 765

Asp Tyr Asp Asp Thr Ile Ser Val Glu Met Lys Lys Gly Asp Phe Asp
770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
                820                 825                 830

Val Pro Gln Phe Lys Lys Val Val Phe Gln Glu Phe Thr Asp Gly Ser
            835                 840                 845

Phe Thr Gln Pro Leu Tyr Arg Gly Glu Leu Asn Glu His Leu Gly Leu
850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
                900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
                995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095
```

Ala Gly Ile Trp Arg Val Glu Cys Leu Ile Gly Glu His Leu His
1100             1105            1110

Ala Gly Met Ser Thr Leu Phe Leu Val Tyr Ser Asn Lys Cys Gln
1115             1120            1125

Thr Pro Leu Gly Met Ala Ser Gly His Ile Arg Asp Phe Gln Ile
1130             1135            1140

Thr Ala Ser Gly Gln Tyr Gly Gln Trp Ala Pro Lys Leu Ala Arg
1145             1150            1155

Leu His Tyr Ser Gly Ser Ile Asn Ala Trp Ser Thr Lys Glu Pro
1160             1165            1170

Phe Ser Trp Ile Lys Val Asp Leu Leu Ala Pro Met Ile Ile His
1175             1180            1185

Gly Ile Lys Thr Gln Gly Ala Arg Gln Lys Phe Ser Ser Leu Tyr
1190             1195            1200

Ile Ser Gln Phe Ile Ile Met Tyr Ser Leu Asp Gly Lys Lys Trp
1205             1210            1215

Gln Thr Tyr Arg Gly Asn Ser Thr Gly Thr Leu Met Val Phe Phe
1220             1225            1230

Gly Asn Val Asp Ser Ser Gly Ile Lys His Asn Ile Phe Asn Pro
1235             1240            1245

Pro Ile Ile Ala Arg Tyr Ile Arg Leu His Pro Thr His Tyr Ser
1250             1255            1260

Ile Arg Ser Thr Leu Arg Met Glu Leu Met Gly Cys Asp Leu Asn
1265             1270            1275

Ser Cys Ser Met Pro Leu Gly Met Glu Ser Lys Ala Ile Ser Asp
1280             1285            1290

Ala Gln Ile Thr Ala Ser Ser Tyr Phe Thr Asn Met Phe Ala Thr
1295             1300            1305

Trp Ser Pro Ser Lys Ala Arg Leu His Leu Gln Gly Arg Ser Asn
1310             1315            1320

Ala Trp Arg Pro Gln Val Asn Asn Pro Lys Glu Trp Leu Gln Val
1325             1330            1335

Asp Phe Gln Lys Thr Met Lys Val Thr Gly Val Thr Thr Gln Gly
1340             1345            1350

Val Lys Ser Leu Leu Thr Ser Met Tyr Val Lys Glu Phe Leu Ile
1355             1360            1365

Ser Ser Ser Gln Asp Gly His Gln Trp Thr Leu Phe Phe Gln Asn
1370             1375            1380

Gly Lys Val Lys Val Phe Gln Gly Asn Gln Asp Ser Phe Thr Pro
1385             1390            1395

Val Val Asn Ser Leu Asp Pro Pro Leu Leu Thr Arg Tyr Leu Arg
1400             1405            1410

Ile His Pro Gln Ser Trp Val His Gln Ile Ala Leu Arg Met Glu
1415             1420            1425

Val Leu Gly Cys Glu Ala Gln Asp Leu Tyr
1430             1435

<210> SEQ ID NO 30
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 30

-continued

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatcttcct     480
catgtggacc tggtaaaaga cttgaattca ggcctcattg gagccctact agtatgtaga     540
gaagggagtc tggccaagga aaagacacag accttgcaca aatttatact acttttttgct    600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctaccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca aacactcttg     900
atggaccttg acagtttcct actgttttgt catatctctt cccaccaaca tgatggcatg     960
gaagcttatg tcaaagtaga cagctgtcca gaggaaccc aactacgaat gaaaaataat     1020
gaagaagcgg aagactatga tgatgatctt actgattctg aaatggatgt ggtcaggttt    1080
gatgatgaca actctccttc ctttatccaa attcgctcag ttgccaagaa gcatcctaaa    1140
acttgggtac attacattgc tgctgaagag gaggactggg actatgctcc cttagtcctc    1200
gcccccgatg acagaagtta taaaagtcaa tatttgaaca atggccctca gcggattggt    1260
aggaagtaca aaaagtccg atttatggca tacacagatg aaacctttaa gacgcgtgaa    1320
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtccttgta ttcaaggaga ttaccaaaag gtgtaaaaca tttgaaggat    1500
tttccaattc tgccaggaga aatattcaaa tataaatgga cagtgactgt agaagttggg    1560
ccaactaaat cagatccgcg gtgcctgacc cgctattact ctagtttcgt taatatggag    1620
agagatctag cttcaggact cattggccct ctcctcatct gctacaaaga atctctggat    1680
caatggggaa accagataat gtcagacaag aggaatgtca tcctgttttc tgtatttgat    1740
gagaaccgaa gctggtacct cacagagaat atacaacgct ttctcccaa tccagctgga    1800
gtgcagcttg aggatccaga gttccaagcc tccaacatca tgcacagcat caatggctat    1860
gttttgata gttgcagtt gtcagttgt ttgcatgagg tggcatactg gtacattcta    1920
agcattggag cacagactga cttcttttct gtcttctct ctggatatac cttcaaacac    1980
aaaatggtct atgtagacac actcaccta ttcccattct caggagaaac tgtcttcatg     2040
tcgatggaaa acccaggtct atggattctg ggtgccaca actcagactt tcggaacaga   2100
ggcatgaccg ccttactgaa ggtttctagt tgtgacaaga acactggtga ttattacgag   2160
gacagttacg aagatatttc agcatacttg ctgagtaaaa acaatgccat tgaacctagg   2220
agcttctctc agaatccacc agtcttgaaa cgccatcaac gggaaataac tcgtacgact   2280
cttcagtcag atcaagagga aattgactat gatgatacca tcagttga aatgaagaag    2340
gaagattttg acatttatga tgaggatgaa aatcagagcc cccgcagctt tcaaaagaaa   2400
```

```
acacgacact attttattgc tgcagtggag aggctctggg attatgggat gagtagctcc    2460
ccacatgttc taagaaacag ggctcagagt ggcagtgtcc ctcagttcaa gaaagttgtt    2520
ttccaggaat ttactgatgg ctcctttact cagcccttat accgtggaga actaaatgaa    2580
catttgggac tcctgggcc atatataaga gcagaagttg aagataatat catggtaact     2640
ttcagaaatc aggcctctcg tccctattcc ttctattcta gccttatttc ttatgaggaa    2700
gatcagaggc aaggagcaga acctagaaaa aactttgtca agcctaatga aaccaaaact    2760 tactttgga aagtgcaaca tcatatggca cccactaaag atgagtttga ctgcaaagcc     2820
tgggcttatt tctctgatgt tgacctggaa aaagatgtgc actcaggcct gattggaccc    2880
cttctggtct gccacactaa cacactgaac cctgctcatg ggagacaagt gacagtacag    2940
gaatttgctc tgttttcac catctttgat gagaccaaaa gctggtactt cactgaaaat     3000
atggaaagaa actgcagggc tccctgcaat atccagatgg aagatcccac ttttaaagag    3060
aattatcgct tccatgcaat caatggctac ataatggata cactacctgg cttagtaatg    3120
gctcaggatc aaaggattcg atggtatctg ctcagcatgg gcagcaatga aacatccat     3180 tctattcatt tcagtggaca tgtgttcact gtacgaaaaa aagaggagta taaaatggca    3240
ctgtacaatc tctatccagg tgttttttgag acagtggaaa tgttaccatc caaagctgga    3300
atttggcggg tggaatgcct tattggcgag catctacatg ctgggatgag cacactttt     3360 ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct ttcttggat caaggtggat     3540 ctgttggcac caatgattat tcacggcatc aagacccagg gtgcccgtca gaagttctcc    3600
agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atattttaa ccctccaatt attgctcgat acatccgttt gcacccaact     3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggag taaaatctct gcttaccagc    4080
atgtatgtga aggagttcct catctccagc agtcaagatg gccatcagtg gactctcttt    4140
tttcagaatg gcaaagtaaa ggttttttcag ggaaatcaag actccttcac acctgtggtg    4200
aactctctag acccaccgtt actgactcgc taccttcgaa ttcaccccca gagttgggtg    4260
caccagattg ccctgaggat ggaggttctg ggctgcgagg cacaggacct ctac          4314
```

<210> SEQ ID NO 31
<211> LENGTH: 2332
<212> TYPE: PRT
<213> ORGANISM: Artificial Sequence
<220> FEATURE:
<223> OTHER INFORMATION: Variant peptide

<400> SEQUENCE: 31

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
```

-continued

```
                20                  25                  30
Arg Val Pro Lys Ser Phe Pro Phe Asn Thr Ser Val Val Tyr Lys Lys
             35                  40                  45
Thr Leu Phe Val Glu Phe Thr Asp His Leu Phe Asn Ile Ala Lys Pro
 50                  55                  60
Arg Pro Pro Trp Met Gly Leu Leu Gly Pro Thr Ile Gln Ala Glu Val
 65                  70                  75                  80
Tyr Asp Thr Val Ile Thr Leu Lys Asn Met Ala Ser His Pro Val
             85                  90                  95
Ser Leu His Ala Val Gly Val Ser Tyr Trp Lys Ala Ser Glu Gly Ala
            100                 105                 110
Glu Tyr Asp Asp Gln Thr Ser Gln Arg Glu Lys Glu Asp Asp Lys Val
            115                 120                 125
Phe Pro Gly Gly Ser His Thr Tyr Val Trp Gln Val Leu Lys Glu Asn
            130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
            165                 170                 175
Leu Val Cys Arg Glu Gly Ser Leu Ala Lys Glu Lys Thr Gln Thr Leu
            180                 185                 190
His Lys Phe Ile Leu Leu Phe Ala Val Phe Asp Glu Gly Lys Ser Trp
            195                 200                 205
His Ser Glu Thr Lys Asn Ser Leu Met Gln Asp Arg Asp Ala Ala Ser
            210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
            245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
            325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
            355                 360                 365
Ile Gln Ile Arg Ser Val Ala Lys Lys His Pro Lys Thr Trp Val His
            370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
            405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
            435                 440                 445
```

```
Leu Gly Pro Leu Leu Tyr Gly Glu Val Gly Asp Thr Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560

Gln Arg Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
    850                 855                 860
```

```
Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
```

```
            1265                1270                1275

Gly Leu Gly Asn Gln Thr Lys Gln Ile Val Glu Lys Tyr Ala Cys
        1280                1285                1290

Thr Thr Arg Ile Ser Pro Asn Thr Ser Gln Gln Asn Phe Val Thr
        1295                1300                1305

Gln Arg Ser Lys Arg Ala Leu Lys Gln Phe Arg Leu Pro Leu Glu
        1310                1315                1320

Glu Thr Glu Leu Glu Lys Arg Ile Ile Val Asp Asp Thr Ser Thr
        1325                1330                1335

Gln Trp Ser Lys Asn Met Lys His Leu Thr Pro Ser Thr Leu Thr
        1340                1345                1350

Gln Ile Asp Tyr Asn Glu Lys Glu Lys Gly Ala Ile Thr Gln Ser
        1355                1360                1365

Pro Leu Ser Asp Cys Leu Thr Arg Ser His Ser Ile Pro Gln Ala
        1370                1375                1380

Asn Arg Ser Pro Leu Pro Ile Ala Lys Val Ser Ser Phe Pro Ser
        1385                1390                1395

Ile Arg Pro Ile Tyr Leu Thr Arg Val Leu Phe Gln Asp Asn Ser
        1400                1405                1410

Ser His Leu Pro Ala Ala Ser Tyr Arg Lys Lys Asp Ser Gly Val
        1415                1420                1425

Gln Glu Ser Ser His Phe Leu Gln Gly Ala Lys Lys Asn Asn Leu
        1430                1435                1440

Ser Leu Ala Ile Leu Thr Leu Glu Met Thr Gly Asp Gln Arg Glu
        1445                1450                1455

Val Gly Ser Leu Gly Thr Ser Ala Thr Asn Ser Val Thr Tyr Lys
        1460                1465                1470

Lys Val Glu Asn Thr Val Leu Pro Lys Pro Asp Leu Pro Lys Thr
        1475                1480                1485

Ser Gly Lys Val Glu Leu Leu Pro Lys Val His Ile Tyr Gln Lys
        1490                1495                1500

Asp Leu Phe Pro Thr Glu Thr Ser Asn Gly Ser Pro Gly His Leu
        1505                1510                1515

Asp Leu Val Glu Gly Ser Leu Leu Gln Gly Thr Glu Gly Ala Ile
        1520                1525                1530

Lys Trp Asn Glu Ala Asn Arg Pro Gly Lys Val Pro Phe Leu Arg
        1535                1540                1545

Val Ala Thr Glu Ser Ser Ala Lys Thr Pro Ser Lys Leu Leu Asp
        1550                1555                1560

Pro Leu Ala Trp Asp Asn His Tyr Gly Thr Gln Ile Pro Lys Glu
        1565                1570                1575

Glu Trp Lys Ser Gln Glu Lys Ser Pro Glu Lys Thr Ala Phe Lys
        1580                1585                1590

Lys Lys Asp Thr Ile Leu Ser Leu Asn Ala Cys Glu Ser Asn His
        1595                1600                1605

Ala Ile Ala Ala Ile Asn Glu Gly Gln Asn Lys Pro Glu Ile Glu
        1610                1615                1620

Val Thr Trp Ala Lys Gln Gly Arg Thr Glu Arg Leu Cys Ser Gln
        1625                1630                1635

Asn Pro Pro Val Leu Lys Arg His Gln Arg Glu Ile Thr Arg Thr
        1640                1645                1650

Thr Leu Gln Ser Asp Gln Glu Glu Ile Asp Tyr Asp Asp Thr Ile
        1655                1660                1665
```

```
Ser Val Glu Met Lys Lys Glu Asp Phe Asp Ile Tyr Asp Glu Asp
    1670            1675               1680

Glu Asn Gln Ser Pro Arg Ser Phe Gln Lys Lys Thr Arg His Tyr
    1685            1690               1695

Phe Ile Ala Ala Val Glu Arg Leu Trp Asp Tyr Gly Met Ser Ser
    1700            1705               1710

Ser Pro His Val Leu Arg Asn Arg Ala Gln Ser Gly Ser Val Pro
    1715            1720               1725

Gln Phe Lys Lys Val Val Phe Gln Glu Phe Thr Asp Gly Ser Phe
    1730            1735               1740

Thr Gln Pro Leu Tyr Arg Gly Glu Leu Asn Glu His Leu Gly Leu
    1745            1750               1755

Leu Gly Pro Tyr Ile Arg Ala Glu Val Glu Asp Asn Ile Met Val
    1760            1765               1770

Thr Phe Arg Asn Gln Ala Ser Arg Pro Tyr Ser Phe Tyr Ser Ser
    1775            1780               1785

Leu Ile Ser Tyr Glu Glu Asp Gln Arg Gln Gly Ala Glu Pro Arg
    1790            1795               1800

Lys Asn Phe Val Lys Pro Asn Glu Thr Lys Thr Tyr Phe Trp Lys
    1805            1810               1815

Val Gln His His Met Ala Pro Thr Lys Asp Glu Phe Asp Cys Lys
    1820            1825               1830

Ala Trp Ala Tyr Phe Ser Asp Val Asp Leu Glu Lys Asp Val His
    1835            1840               1845

Ser Gly Leu Ile Gly Pro Leu Leu Val Cys His Thr Asn Thr Leu
    1850            1855               1860

Asn Pro Ala His Gly Arg Gln Val Thr Val Gln Glu Phe Ala Leu
    1865            1870               1875

Phe Phe Thr Ile Phe Asp Glu Thr Lys Ser Trp Tyr Phe Thr Glu
    1880            1885               1890

Asn Met Glu Arg Asn Cys Arg Ala Pro Cys Asn Ile Gln Met Glu
    1895            1900               1905

Asp Pro Thr Phe Lys Glu Asn Tyr Arg Phe His Ala Ile Asn Gly
    1910            1915               1920

Tyr Ile Met Asp Thr Leu Pro Gly Leu Val Met Ala Gln Asp Gln
    1925            1930               1935

Arg Ile Arg Trp Tyr Leu Leu Ser Met Gly Ser Asn Glu Asn Ile
    1940            1945               1950

His Ser Ile His Phe Ser Gly His Val Phe Thr Val Arg Lys Lys
    1955            1960               1965

Glu Glu Tyr Lys Met Ala Leu Tyr Asn Leu Tyr Pro Gly Val Phe
    1970            1975               1980

Glu Thr Val Glu Met Leu Pro Ser Lys Ala Gly Ile Trp Arg Val
    1985            1990               1995

Glu Cys Leu Ile Gly Glu His Leu His Ala Gly Met Ser Thr Leu
    2000            2005               2010

Phe Leu Val Tyr Ser Asn Lys Cys Gln Thr Pro Leu Gly Met Ala
    2015            2020               2025

Ser Gly His Ile Arg Asp Phe Gln Ile Thr Ala Ser Gly Gln Tyr
    2030            2035               2040

Gly Gln Trp Ala Pro Lys Leu Ala Arg Leu His Tyr Ser Gly Ser
    2045            2050               2055
```

Ile Asn Ala Trp Ser Thr Lys Glu Pro Phe Ser Trp Ile Lys Val
2060              2065              2070

Asp Leu Leu Ala Pro Met Ile Ile His Gly Ile Lys Thr Gln Gly
2075              2080              2085

Ala Arg Gln Lys Phe Ser Ser Leu Tyr Ile Ser Gln Phe Ile Ile
2090              2095              2100

Met Tyr Ser Leu Asp Gly Lys Lys Trp Gln Thr Tyr Arg Gly Asn
2105              2110              2115

Ser Thr Gly Thr Leu Met Val Phe Phe Gly Asn Val Asp Ser Ser
2120              2125              2130

Gly Ile Lys His Asn Ile Phe Asn Pro Pro Ile Ile Ala Arg Tyr
2135              2140              2145

Ile Arg Leu His Pro Thr His Tyr Ser Ile Arg Ser Thr Leu Arg
2150              2155              2160

Met Glu Leu Met Gly Cys Asp Leu Asn Ser Cys Ser Met Pro Leu
2165              2170              2175

Gly Met Glu Ser Lys Ala Ile Ser Asp Ala Gln Ile Thr Ala Ser
2180              2185              2190

Ser Tyr Phe Thr Asn Met Phe Ala Thr Trp Ser Pro Ser Lys Ala
2195              2200              2205

Arg Leu His Leu Gln Gly Arg Ser Asn Ala Trp Arg Pro Gln Val
2210              2215              2220

Asn Asn Pro Lys Glu Trp Leu Gln Val Asp Phe Gln Lys Thr Met
2225              2230              2235

Lys Val Thr Gly Val Thr Thr Gln Gly Val Lys Ser Leu Leu Thr
2240              2245              2250

Ser Met Tyr Val Lys Glu Phe Leu Ile Ser Ser Ser Gln Asp Gly
2255              2260              2265

His Gln Trp Thr Leu Phe Phe Gln Asn Gly Lys Val Lys Val Phe
2270              2275              2280

Gln Gly Asn Gln Asp Ser Phe Thr Pro Val Val Asn Ser Leu Asp
2285              2290              2295

Pro Pro Leu Leu Thr Arg Tyr Leu Arg Ile His Pro Gln Ser Trp
2300              2305              2310

Val His Gln Ile Ala Leu Arg Met Glu Val Leu Gly Cys Glu Ala
2315              2320              2325

Gln Asp Leu Tyr
2330

<210> SEQ ID NO 32
<211> LENGTH: 6996
<212> TYPE: DNA
<213> ORGANISM: Artificial Sequence
<220> FEATURE:
<223> OTHER INFORMATION: Variant nucleotide

<400> SEQUENCE: 32
gccaccagaa gatactacct gggtgcagtg gaactgtcat gggactatat gcaaagtgat    60
ctcggtgagc tgcctgtgga cgcaagattt cctcctagag tgccaaaatc ttttccattc   120
aacacctcag tcgtgtacaa aaagactctg tttgtagaat tcacggttca ccttttcaac   180
atcgctaagc caaggccacc ctggatgggt ctgctaggtc ctaccatcca ggctgaggtt   240
tatgatacag tggtcattac acttaagaac atggcttccc atcctgtcag tcttcatgct   300
gttggtgtat cctactggaa agcttctgag ggagctgaat atgatgatca gaccagtcaa   360

```
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttgct     600 gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg acagtttct  actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaagtccg  atttatggca tacacagatg aaacctttaa gactcgtgaa   1320
gctattcagc atgaatcagg aatcttggga ccttactttt atggggaagt ggagacaca    1380 ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctctggat   1680
caaagaggaa acgagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860
gtttttgata gtttgcagtt gtcagttgt  ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg ggtgccaca  actcagactt tcggaacaga   2100
ggcatgaccg ccttactgaa ggtttctagt tgtgacaaga cactggtga  ttattacgag   2160 gacagttatg aagatatttc agcatacttg ctgagtaaaa acaatgccat gaaccaaga    2220 agcttctccc agaattcaag acaccctagc actaggcaaa agcaatttaa tgccaccaca   2280
attccagaaa atgacataga gaagactgac ccttggtttg cacacagaac acctatgcct   2340
aaaatacaaa atgtctcctc tagtgatttg ttgatgctct gcgacagag  tcctactcca   2400 catgggctat ccttatctga tctccaagaa gccaaatatg agacttttc  tgatgatcca   2460 tcacctggag caatagacag taataacagc ctgtctgaaa tgcacacttt caggccacag   2520
ctccatcaca gtggggacat ggtatttacc cctgagtcag gcctccaatt aagattaaat   2580
gagaaactgg ggcaactgc  agcaacagag ttgaagaaac ttgatttcaa agtttctagt   2640
acatcaaata atctgatttc aacaattcca tcagacaatt tggcagcagg tactgataat   2700
acaagttcct taggaccccc aagtatgcca gttcattatg atagtcaatt agataccact   2760
```

```
ctatttggca aaaagtcatc tccccttact gagtctggtg gacctctgag cttgagtgaa    2820
gaaaataatg attcaaagtt gttagaatca ggtttaatga atagccaaga aagttcatgg    2880
ggaaaaaatg tatcgtcaac agagagtggt aggttattta aagggaaaag agctcatgga    2940
cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaaa ttcaggaaga aatagaaaag    3600
aaggaaacat taatccaaga gaatgtagtt ttgcctcaga tacatacagt gactggcact    3660
aagaatttca tgaagaacct tttcttactg agcactaggc aaaatgtaga aggttcatat    3720 gacgggcat atgctccagt acttcaagat tttaggtcat taaatgattc aacaaataga    3780
acaaagaaac acacagctca tttctcaaaa aagggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctccctta tcagattgcc ttacgaggag tcatagcatc    4140
cctcaagcaa atagatctcc attacccatt gcaaaggtat catcatttcc atctattaga    4200
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320
aataaccttt ctttagccat tctaaccttg gagatgactg tgatcaaag agaggttggc    4380 tccctgggga caagtgccac aaattcagtc acatacaaga aagttgagaa cactgttctc    4440
ccgaaaccag acttgcccaa aacatctggc aaagttgaat tgcttccaaa agttcacatt    4500
tatcagaagg acctattccc tacggaaact agcaatgggt ctcctggcca tctggatctc    4560
gtggaaggga gccttcttca gggaacagag ggagcgatta gtggaatga agcaaacaga    4620 cctggaaaag ttcccttcct gagagtagca acagaaagct ctgcaaagac tccctccaag    4680
ctattggatc ctcttgcttg ggataaccac tatggtactc agataccaaa agaagagtgg    4740
aaatcccaag agaagtcacc agaaaaaaca gcttttaaga aaaggatac cattttgtcc    4800 ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga aacgccatca acgggaaata actcgtacta ctcttcagtc agatcaagag    4980
gaaattgact atgatgatac catatcagtt gaaatgaaga aggaagattt tgacatttat    5040
gatgaggatg aaaatcagag cccccgcagc tttcaaaaga aaacacgaca ctatttttat    5100
```

```
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagccctt ataccgtgga gaactaaatg aacatttggg actcctgggg    5280
ccatatataa gagcagaagt tgaagataat atcatggtaa ctttcagaaa tcaggcctct    5340
cgtccctatt ccttctattc tagccttatt tcttatgagg aagatcagag gcaaggagca    5400
gaacctagaa aaaactttgt caagcctaat gaaaccaaaa cttacttttg gaaagtgcaa    5460
catcatatgg cacccactaa agatgagttt gactgcaaag cctgggctta tttctctgat    5520
gttgacctgg aaaagatgt gcactcaggc ctgattggac cccttctggt ctgccacact    5580
aacacactga accctgctca tgggagacaa gtgacagtac aggaatttgc tctgttttc    5640 accatctttg atgagaccaa agctggtac ttcactgaaa atatggaaag aaactgcagg    5700
gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaagaggag tataaaatgg cactgtacaa tctctatcca    5940 ggtgttttg agacagtgga atgttacca tccaaagctg gaatttggcg ggtggaatgc    6000
cttattggcg agcatctaca tgctgggatg agcacttt ttctggtgta cagcaataag    6060
tgtcagactc ccctgggaat ggcttctgga cacattagag attttcagat tacagcttca    6120
ggacaatatg gacagtgggc cccaaagctg gccagacttc attattccgg atcaatcaat    6180
gcctggagca ccaaggagcc ctttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg gataaaaaca caatattttt    6420
aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840 aaggttttt agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctac                            6996
```

<210> SEQ ID NO 33
<211> LENGTH: 1438
<212> TYPE: PRT
<213> ORGANISM: Artificial Sequence
<220> FEATURE:
<223> OTHER INFORMATION: Variant peptide

<400> SEQUENCE: 33

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

```
Arg Val Pro Lys Ser Phe Pro Phe Asn Thr Ser Val Val Tyr Lys Lys
             35                  40                  45

Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
 65                  70                  75                  80

Tyr Asp Thr Val Ile Thr Leu Lys Asn Met Ala Ser His Pro Val
                 85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Lys Val
             115                 120                 125

Phe Pro Gly Gly Ser His Thr Tyr Val Trp Gln Val Leu Lys Glu Asn
 130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                 165                 170                 175

Leu Val Cys Arg Glu Gly Ser Leu Ala Lys Glu Lys Thr Gln Thr Leu
             180                 185                 190

His Lys Phe Ile Leu Leu Phe Ala Val Phe Asp Glu Gly Lys Ser Trp
             195                 200                 205

His Ser Glu Thr Lys Asn Ser Leu Met Gln Asp Arg Asp Ala Ala Ser
 210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                 245                 250                 255

Val Ile Gly Met Gly Thr Thr Pro Glu Val His Ser Ile Phe Leu Glu
             260                 265                 270

Gly His Thr Phe Leu Val Arg Asn His Arg Gln Ala Ser Leu Glu Ile
             275                 280                 285

Ser Pro Ile Thr Phe Leu Thr Ala Gln Thr Leu Leu Met Asp Leu Gly
 290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                 325                 330                 335

Met Lys Asn Asn Glu Glu Ala Glu Asp Tyr Asp Asp Leu Thr Asp
             340                 345                 350

Ser Glu Met Asp Val Val Arg Phe Asp Asp Asn Ser Pro Ser Phe
             355                 360                 365

Ile Gln Ile Arg Ser Val Ala Lys Lys His Pro Lys Thr Trp Val His
 370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                 405                 410                 415

Gln Arg Ile Gly Arg Lys Tyr Lys Lys Val Arg Phe Met Ala Tyr Thr
             420                 425                 430

Asp Glu Thr Phe Lys Thr Arg Glu Ala Ile Gln His Glu Ser Gly Ile
             435                 440                 445
```

```
Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560

Gln Arg Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
```

```
                           865                 870                 875                 880
              Phe Arg Asn Gln Ala Ser Arg Pro Tyr Ser Phe Tyr Ser Ser Leu Ile
                                  885                 890                 895

Ser Tyr Glu Glu Asp Gln Arg Gln Gly Ala Glu Pro Arg Lys Asn Phe
                                  900                 905                 910

Val Lys Pro Asn Glu Thr Lys Thr Tyr Phe Trp Lys Val Gln His His
                                  915                 920                 925

Met Ala Pro Thr Lys Asp Glu Phe Asp Cys Lys Ala Trp Ala Tyr Phe
                                  930                 935                 940

Ser Asp Val Asp Leu Glu Lys Asp Val His Ser Gly Leu Ile Gly Pro
              945                 950                 955                 960

Leu Leu Val Cys His Thr Asn Thr Leu Asn Pro Ala His Gly Arg Gln
                                  965                 970                 975

Val Thr Val Gln Glu Phe Ala Leu Phe Phe Thr Ile Phe Asp Glu Thr
                                  980                 985                 990

Lys Ser Trp Tyr Phe Thr Glu Asn Met Glu Arg Asn Cys Arg Ala Pro
                                  995                1000                1005

Cys Asn Ile Gln Met Glu Asp Pro Thr Phe Lys Glu Asn Tyr Arg
                            1010                1015                1020

Phe His Ala Ile Asn Gly Tyr Ile Met Asp Thr Leu Pro Gly Leu
                            1025                1030                1035

Val Met Ala Gln Asp Gln Arg Ile Arg Trp Tyr Leu Leu Ser Met
                            1040                1045                1050

Gly Ser Asn Glu Asn Ile His Ser Ile His Phe Ser Gly His Val
                            1055                1060                1065

Phe Thr Val Arg Lys Lys Glu Glu Tyr Lys Met Ala Leu Tyr Asn
                            1070                1075                1080

Leu Tyr Pro Gly Val Phe Glu Thr Val Glu Met Leu Pro Ser Lys
                            1085                1090                1095

Ala Gly Ile Trp Arg Val Glu Cys Leu Ile Gly Glu His Leu His
                            1100                1105                1110

Ala Gly Met Ser Thr Leu Phe Leu Val Tyr Ser Asn Lys Cys Gln
                            1115                1120                1125

Thr Pro Leu Gly Met Ala Ser Gly His Ile Arg Asp Phe Gln Ile
                            1130                1135                1140

Thr Ala Ser Gly Gln Tyr Gly Gln Trp Ala Pro Lys Leu Ala Arg
                            1145                1150                1155

Leu His Tyr Ser Gly Ser Ile Asn Ala Trp Ser Thr Lys Glu Pro
                            1160                1165                1170

Phe Ser Trp Ile Lys Val Asp Leu Leu Ala Pro Met Ile Ile His
                            1175                1180                1185

Gly Ile Lys Thr Gln Gly Ala Arg Gln Lys Phe Ser Ser Leu Tyr
                            1190                1195                1200

Ile Ser Gln Phe Ile Ile Met Tyr Ser Leu Asp Gly Lys Lys Trp
                            1205                1210                1215

Gln Thr Tyr Arg Gly Asn Ser Thr Gly Thr Leu Met Val Phe Phe
                            1220                1225                1230

Gly Asn Val Asp Ser Ser Gly Ile Lys His Asn Ile Phe Asn Pro
                            1235                1240                1245

Pro Ile Ile Ala Arg Tyr Ile Arg Leu His Pro Thr His Tyr Ser
                            1250                1255                1260

Ile Arg Ser Thr Leu Arg Met Glu Leu Met Gly Cys Asp Leu Asn
                            1265                1270                1275
```

| Ser | Cys | Ser | Met | Pro | Leu | Gly | Met | Glu | Ser | Lys | Ala | Ile | Ser | Asp |
|     | 1280|     |     |     |     | 1285|     |     |     | 1290|     |     |     |     |

Ala Gln Ile Thr Ala Ser Ser Tyr Phe Thr Asn Met Phe Ala Thr
    1295            1300                1305

Trp Ser Pro Ser Lys Ala Arg Leu His Leu Gln Gly Arg Ser Asn
    1310            1315                1320

Ala Trp Arg Pro Gln Val Asn Asn Pro Lys Glu Trp Leu Gln Val
    1325            1330                1335

Asp Phe Gln Lys Thr Met Lys Val Thr Gly Val Thr Thr Gln Gly
    1340            1345                1350

Val Lys Ser Leu Leu Thr Ser Met Tyr Val Lys Glu Phe Leu Ile
    1355            1360                1365

Ser Ser Ser Gln Asp Gly His Gln Trp Thr Leu Phe Phe Gln Asn
    1370            1375                1380

Gly Lys Val Lys Val Phe Gln Gly Asn Gln Asp Ser Phe Thr Pro
    1385            1390                1395

Val Val Asn Ser Leu Asp Pro Pro Leu Leu Thr Arg Tyr Leu Arg
    1400            1405                1410

Ile His Pro Gln Ser Trp Val His Gln Ile Ala Leu Arg Met Glu
    1415            1420                1425

Val Leu Gly Cys Glu Ala Gln Asp Leu Tyr
    1430            1435

<210> SEQ ID NO 34
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 34

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg agccctact agtatgtaga     540
gaagggagtc tggccaagga aaagacacag accttgcaca aatttatact acttttgct      600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780
ggcaccactc ctgaagtgca ctcaatattc ctcgaaggtc acacatttct gtgtgggaac     840
catcgccagg cgtccttgga aatctcgcca ataactttcc ttactgctca acactcttg      900
atggaccttg acagtttct actgttttgt catatctctt cccaccaaca tgatggcatg     960
gaagcttatg tcaaagtaga cagctgtcca gaggaacccc aactacgaat gaaaaataat    1020
gaagaagcgg aagactatga tgatgatctt actgattctg aaatggatgt ggtcaggttt    1080
```

-continued

```
gatgatgaca actctccttc ctttatccaa attcgctcag ttgccaagaa gcatcctaaa    1140
acttgggtac attacattgc tgctgaagag gaggactggg actatgctcc cttagtcctc    1200
gcccccgatg acagaagtta taaaagtcaa tatttgaaca atggccctca gcggattggt    1260
aggaagtaca aaaaagtccg atttatggca tacacagatg aaacctttaa gactcgtgaa    1320
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagatggg    1560
ccaactaaat cagatcctcg gtgcctgacc cgctattact ctagtttcgt taatatggag    1620
agagatctag cttcaggact cattggccct ctcctcatct gctacaaaga atctctggat    1680
caaagaggaa acgagataat gtcagacaag aggaatgtca tcctgttttc tgtatttgat    1740
gagaaccgaa gctggtacct cacagagaat atacaacgct ttctccccaa tccagctgga    1800
gtgcagcttg aggatccaga gttccaagcc tccaacatca tgcacagcat caatggctat    1860 gttttgata gtttgcagtt gtcagttgt ttgcatgagg tggcatactg gtacattcta    1920
agcattggag cacagactga cttcctttct gtcttcttct ctggatatac cttcaaacac    1980
aaaatggtct atgaagacac actcacccta ttcccattct caggagaaac tgtcttcatg    2040
tcgatggaaa acccaggtct atggattctg gggtgccaca actcagactt cggaacagaa    2100
ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
agcttctccc agaacccacc agtcttgaaa cgccatcaac gggaaataac tcgtactact    2280
cttcagtcag atcaagagga aattgactat gatgatacca tatcagttga aatgaagaag    2340
gaagattttg acatttatga tgaggatgaa aatcagagcc cccgcagctt tcaaaagaaa    2400
acacgacact attttattgc tgcagtggag aggctctggg attatgggat gagtagctcc    2460
ccacatgttc taagaaacag ggctcagagt ggcagtgtcc ctcagttcaa gaaagttgtt    2520
ttccaggaat ttactgatgg ctcctttact cagcccttat accgtggaga actaaatgaa    2580
catttgggac tcctggggcc atatataaga gcagaagttg aagataatat catggtaact    2640
ttcagaaatc aggcctctcg tccctattcc ttctattcta gccttatttc ttatgaggaa    2700
gatcagaggc aaggagcaga acctagaaaa aactttgtca agcctaatga aaccaaaact    2760
tactttggaa agtgcaaca tcatatgcca cccactaaag atgagtttga ctgcaaagcc    2820
tgggcttatt tctctgatgt tgacctggaa aaagatgtgc actcaggcct gattggaccc    2880
cttctggtct gccacactaa cacactgaac cctgctcatg ggagacaagt gacagtacag    2940
gaatttgctc tgttttcac catctttgat gagaccaaaa gctggtactt cactgaaaat    3000
atggaaagaa actgcagggc tccctgcaat atccagatgg aagatccac ttttaaagag    3060 aattatcgct tccatgcaat caatggctac ataatggata cactacctgg cttagtaatg    3120
gctcaggatc aaaggattcg atggtatctg ctcagcatgg gcagcaatga aacatccat    3180 tctattcatt tcagtggaca tgtgttcact gtacgaaaaa aagaggagta taaaatggca    3240
ctgtacaatc tctatccagg tgttttgag acagtggaaa tgttaccatc caaagctgga    3300
atttggcggg tggaatgcct tattggcgag catctcacatg ctgggatgag cacacttttt    3360
ctggtgtaca gcaataagtg tcagactccc ctgggaatgg cttctggaca cattagagat    3420
```

-continued

```
tttcagatta cagcttcagg acaatatgga cagtgggccc caaagctggc cagacttcat    3480
tattccggat caatcaatgc ctggagcacc aaggagccct tttcttggat caaggtggat    3540
ctgttggcac caatgattat tcacggcatc aagacccagg gtgcccgtca gaagttctcc    3600
agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atattttaa ccctccaatt attgctcgat acatccgttt gcacccaact    3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggag taaaatctct gcttaccagc    4080
atgtatgtga aggagttcct catctccagc agtcaagatg ccatcagtg gactctcttt    4140 tttcagaatg gcaaagtaaa ggttttcag ggaaatcaag actccttcac acctgtggtg    4200
aactctctag acccaccgtt actgactcgc taccttcgaa ttcaccccca gagttgggtg    4260
caccagattg ccctgaggat ggaggttctg ggctgcgagg cacaggacct ctac          4314
```

<210> SEQ ID NO 35
<211> LENGTH: 1438
<212> TYPE: PRT
<213> ORGANISM: Artificial Sequence
<220> FEATURE:
<223> OTHER INFORMATION: Variant peptide

<400> SEQUENCE: 35

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205
```

-continued

```
His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Val Gly Pro Thr Lys Ser Asp Pro Arg Cys
    515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Leu Asp
545                 550                 555                 560

Gln Arg Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
```

```
625             630             635             640
Ser Ile Gly Ala Gln Thr Asp Phe Leu Ser Val Phe Ser Gly Tyr
            645             650             655

Thr Phe Lys His Lys Met Val Tyr Val Asp Thr Leu Thr Leu Phe Pro
            660             665             670

Phe Ser Gly Glu Thr Val Phe Met Ser Met Glu Asn Pro Gly Leu Trp
            675             680             685

Ile Leu Gly Cys His Asn Ser Asp Phe Arg Arg Gly Met Thr Ala
690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
            725             730             735

Ile Glu Pro Arg Ser Phe Ser Gln Asn Pro Val Leu Lys Arg His
            740             745             750

Gln Arg Glu Ile Thr Arg Thr Leu Gln Ser Asp Gln Glu Glu Ile
            755             760             765

Asp Tyr Asp Asp Thr Ile Ser Val Glu Met Lys Lys Glu Asp Phe Asp
            770             775             780

Ile Tyr Asp Glu Asp Glu Asn Gln Ser Pro Arg Ser Phe Gln Lys Lys
785             790             795             800

Thr Arg His Tyr Phe Ile Ala Ala Val Glu Arg Leu Trp Asp Tyr Gly
            805             810             815

Met Ser Ser Ser Pro His Val Leu Arg Asn Arg Ala Gln Ser Gly Ser
            820             825             830

Val Pro Gln Phe Lys Lys Val Val Phe Gln Glu Phe Thr Asp Gly Ser
            835             840             845

Phe Thr Gln Pro Leu Tyr Arg Gly Glu Leu Asn Glu His Leu Gly Leu
            850             855             860

Leu Gly Pro Tyr Ile Arg Ala Glu Val Glu Asp Asn Ile Met Val Thr
865             870             875             880

Phe Arg Asn Gln Ala Ser Arg Pro Tyr Ser Phe Tyr Ser Ser Leu Ile
            885             890             895

Ser Tyr Glu Glu Asp Gln Arg Gln Gly Ala Glu Pro Arg Lys Asn Phe
            900             905             910

Val Lys Pro Asn Glu Thr Lys Thr Tyr Phe Trp Lys Val Gln His His
            915             920             925

Met Ala Pro Thr Lys Asp Glu Phe Asp Cys Lys Ala Trp Ala Tyr Phe
930             935             940

Ser Asp Val Asp Leu Glu Lys Asp Val His Ser Gly Leu Ile Gly Pro
945             950             955             960

Leu Leu Val Cys His Thr Asn Thr Leu Asn Pro Ala His Gly Arg Gln
            965             970             975

Val Thr Val Gln Glu Phe Ala Leu Phe Phe Thr Ile Phe Asp Glu Thr
            980             985             990

Lys Ser Trp Tyr Phe Thr Glu Asn Met Glu Arg Asn Cys Arg Ala Pro
            995             1000            1005

Cys Asn Ile Gln Met Glu Asp Pro Thr Phe Lys Glu Asn Tyr Arg
            1010            1015            1020

Phe His Ala Ile Asn Gly Tyr Ile Met Asp Thr Leu Pro Gly Leu
            1025            1030            1035

Val Met Ala Gln Asp Gln Arg Ile Arg Trp Tyr Leu Leu Ser Met
            1040            1045            1050
```

```
Gly Ser Asn Glu Asn Ile His Ser Ile His Phe Ser Gly His Val
1055                1060                1065

Phe Thr Val Arg Lys Lys Glu Glu Tyr Lys Met Ala Leu Tyr Asn
1070                1075                1080

Leu Tyr Pro Gly Val Phe Glu Thr Val Glu Met Leu Pro Ser Lys
1085                1090                1095

Ala Gly Ile Trp Arg Val Glu Cys Leu Ile Gly Glu His Leu His
1100                1105                1110

Ala Gly Met Ser Thr Leu Phe Leu Val Tyr Ser Asn Lys Cys Gln
1115                1120                1125

Thr Pro Leu Gly Met Ala Ser Gly His Ile Arg Asp Phe Gln Ile
1130                1135                1140

Thr Ala Ser Gly Gln Tyr Gly Gln Trp Ala Pro Lys Leu Ala Arg
1145                1150                1155

Leu His Tyr Ser Gly Ser Ile Asn Ala Trp Ser Thr Lys Glu Pro
1160                1165                1170

Phe Ser Trp Ile Lys Val Asp Leu Leu Ala Pro Met Ile Ile His
1175                1180                1185

Gly Ile Lys Thr Gln Gly Ala Arg Gln Lys Phe Ser Ser Leu Tyr
1190                1195                1200

Ile Ser Gln Phe Ile Ile Met Tyr Ser Leu Asp Gly Lys Lys Trp
1205                1210                1215

Gln Thr Tyr Arg Gly Asn Ser Thr Gly Thr Leu Met Val Phe Phe
1220                1225                1230

Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser
1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
1280                1285                1290

Ala Gln Ile Thr Ala Ser Ser Tyr Phe Thr Asn Met Phe Ala Thr
1295                1300                1305

Trp Ser Pro Ser Lys Ala Arg Leu His Leu Gln Gly Arg Ser Asn
1310                1315                1320

Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
1400                1405                1410

Ile His Pro Gln Ser Trp Val His Gln Ile Ala Leu Arg Met Glu
1415                1420                1425

Val Leu Gly Cys Glu Ala Gln Asp Leu Tyr
1430                1435
```

<210> SEQ ID NO 36
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 36

```
gccaccagaa gatactacct gggtgcagtg gaactgtcat gggactatat gcaaagtgat      60
ctcggtgagc tgcctgtgga cgcaagattt cctcctagag tgccaaaatc tttttccattc    120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttttgct  600
gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctaccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg acagtttcct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaaagtccg atttatggca tacacagatg aaacctttaa gacgcgtgaa   1320
gctattcagc atgaatcagg aatcttggga cctttacttt atggggaagt ggagacaca    1380
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagttggg   1560
ccaactaaat cagatccgcg gtgcctgacc cgctattact ctagtttcgt taatatggag   1620
agagatctag cttcaggact cattggcccc ctcctcatct gctacaaaga atctctggat   1680
caaagaggaa acgagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860
gttttttgata gtttgcagtt gtcagtttgt ttgcatgagg tggcatactg gtacattcta   1920
agcattggag cacagactga cttccttttct gtcttcttct ctggatatac cttcaaacac   1980
aaaatggtct atgtagacac actcaccccta ttcccattct caggagaaac tgtcttcatg   2040
tcgatggaaa acccaggtct atggattctg gggtgccaca actcagactt tcggaacaga   2100
```

```
ggcatgaccg ccttactgaa ggtttctagt tgtgacaaga acactggtga ttattacgag   2160
gacagttacg aagatatttc agcatacttg ctgagtaaaa acaatgccat tgaacctagg   2220
agcttctctc agaatccacc agtcttgaaa cgccatcaac gggaaataac tcgtacgact   2280
cttcagtcag atcaagagga aattgactat gatgatacca tatcagttga aatgaagaag   2340
gaagattttg acatttatga tgaggatgaa aatcagagcc cccgcagctt tcaaaagaaa   2400
acacgacact attttattgc tgcagtggag aggctctggg attatgggat gagtagctcc   2460
ccacatgttc taagaaacag gctcagagt ggcagtgtcc ctcagttcaa gaaagttgtt    2520
ttccaggaat ttactgatgg ctcctttact cagcccttat accgtggaga actaaatgaa   2580
catttgggac tcctggggcc atatataaga gcagaagttg aagataatat catggtaact   2640
ttcagaaatc aggcctctcg tccctattcc ttctattcta gccttatttc ttatgaggaa   2700
gatcagaggc aaggagcaga acctagaaaa aactttgtca agcctaatga aaccaaaact   2760
tacttttgga aagtgcaaca tcatatggca cccactaaag atgagtttga ctgcaaagcc   2820
tgggcttatt tctctgatgt tgacctggaa aaagatgtgc actcaggcct gattggaccc   2880
cttctggtct gccacactaa cacactgaac cctgctcatg ggagacaagt gacagtacag   2940
gaatttgctc tgttttcac catctttgat gagaccaaaa gctggtactt cactgaaaat   3000
atggaaagaa actgcagggc tccctgcaat atccagatgg aagatcccac ttttaaagag   3060
aattatcgct tccatgcaat caatggctac ataatggata cactacctgg cttagtaatg   3120
gctcaggatc aaaggattcg atggtatctg ctcagcatgg gcagcaatga aaacatccat   3180
tctattcatt tcagtggaca tgtgttcact gtacgaaaaa aagaggagta taaaatggca   3240
ctgtacaatc tctatccagg tgttttttgag acagtgaaaa tgttaccatc caaagctgga   3300
atttggcggg tggaatgcct tattggcgag catctacatg ctgggatgag cacacttttt   3360
ctggtgtaca gcaataagtg tcagactccc ctgggaatgg cttctggaca cattagagat   3420
tttcagatta cagcttcagg acaatatgga cagtgggccc caaagctggc cagacttcat   3480
tattccggat caatcaatgc ctggagcacc aaggagccct tttcttggat caaggtggat   3540
ctgttggcac caatgattat tcacggcatc aagacccagg gtgcccgtca gaagttctcc   3600
agcctctaca tctctcagtt tatcatcatg tatagtcttg atgggaagaa gtggcagact   3660
tatcgaggaa attccactgg aaccttaatg gtcttctttg gcaatgtgga ttcatctggg   3720
ataaaacaca atattttaa ccctccaatt attgctcgat acatccgttt gcacccaact    3780
cattatagca ttcgcagcac tcttcgcatg gagttgatgg gctgtgattt aaatagttgc   3840
agcatgccat tgggaatgga gagtaaagca atatcagatg cacagattac tgcttcatcc   3900
tactttacca atatgtttgc cacctggtct ccttcaaaag ctcgacttca cctccaaggg   3960
aggagtaatg cctggagacc tcaggtgaat aatccaaaag agtggctgca agtggacttc   4020
cagaagacaa tgaaagtcac aggagtaact actcagggga taaaatctct gcttaccagc   4080
atgtatgtga aggagttcct catctccagc agtcaagatg gccatcagtg gactctcttt   4140
tttcagaatg gcaaagtaaa ggttttttcag ggaaatcaag actccttcac acctgtggtg   4200
aactctctag acccaccgtt actgactcgc taccttcgaa ttcaccccca gagttgggtg   4260
caccagattg ccctgaggat ggaggttctg ggctgcgagg cacaggacct ctac          4314
```

<210> SEQ ID NO 37
<211> LENGTH: 2332
<212> TYPE: PRT

<213> ORGANISM: Artificial Sequence
<220> FEATURE:
<223> OTHER INFORMATION: Variant peptide

<400> SEQUENCE: 37

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350  Asp

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
```

-continued

```
            385                 390                 395                 400
         Ala Pro Asp Asp Arg Ser Tyr Lys Ser Gln Tyr Leu Asn Asn Gly Pro
                         405                 410                 415

Gln Arg Ile Gly Arg Lys Tyr Lys Val Arg Phe Met Ala Tyr Thr
                         420                 425             430

Asp Glu Thr Phe Lys Thr Arg Glu Ala Ile Gln His Glu Ser Gly Ile
                     435                 440                 445

Leu Gly Pro Leu Leu Tyr Gly Glu Val Gly Asp Thr Leu Leu Ile Ile
                     450                 455                 460

Phe Lys Asn Gln Ala Ser Arg Pro Tyr Asn Ile Tyr Pro His Gly Ile
         465                 470                 475                 480

Thr Asp Val Arg Pro Leu Tyr Ser Arg Arg Leu Pro Lys Gly Val Lys
                         485                 490                 495

His Leu Lys Asp Phe Pro Ile Leu Pro Gly Glu Ile Phe Lys Tyr Lys
                     500                 505                 510

Trp Thr Val Thr Val Glu Asp Gly Pro Thr Lys Ser Asp Pro Arg Cys
                     515                 520                 525

Leu Thr Arg Tyr Tyr Ser Ser Phe Val Asn Met Glu Arg Asp Leu Ala
                     530                 535                 540

Ser Gly Leu Ile Gly Pro Leu Leu Ile Cys Tyr Lys Glu Ser Leu Asp
         545                 550                 555                 560

Gln Trp Gly Asn Glu Ile Met Ser Asp Lys Arg Asn Val Ile Leu Phe
                         565                 570                 575

Ser Val Phe Asp Glu Asn Arg Ser Trp Tyr Leu Thr Glu Asn Ile Gln
                     580                 585                 590

Arg Phe Leu Pro Asn Pro Ala Gly Val Gln Leu Glu Asp Pro Glu Phe
                     595                 600                 605

Gln Ala Ser Asn Ile Met His Ser Ile Asn Gly Tyr Val Phe Asp Ser
                     610                 615                 620

Leu Gln Leu Ser Val Cys Leu His Glu Val Ala Tyr Trp Tyr Ile Leu
         625                 630                 635                 640

Ser Ile Gly Ala Gln Thr Asp Phe Leu Ser Val Phe Phe Ser Gly Tyr
                         645                 650                 655

Thr Phe Lys His Lys Met Val Tyr Glu Asp Thr Leu Thr Leu Phe Pro
                         660                 665                 670

Phe Ser Gly Glu Thr Val Phe Met Ser Met Glu Asn Pro Gly Leu Trp
                     675                 680                 685

Ile Leu Gly Cys His Asn Ser Asp Phe Arg Asn Arg Gly Met Thr Ala
                     690                 695                 700

Leu Leu Lys Val Ser Ser Cys Asp Lys Asn Thr Gly Asp Tyr Tyr Glu
         705                 710                 715                 720

Asp Ser Tyr Glu Asp Ile Ser Ala Tyr Leu Leu Ser Lys Asn Asn Ala
                         725                 730                 735

Ile Glu Pro Arg Ser Phe Ser Gln Asn Ser Arg His Pro Ser Thr Arg
                         740                 745                 750

Gln Lys Gln Phe Asn Ala Thr Thr Ile Pro Glu Asn Asp Ile Glu Lys
                     755                 760                 765

Thr Asp Pro Trp Phe Ala His Arg Thr Pro Met Pro Lys Ile Gln Asn
                     770                 775                 780

Val Ser Ser Ser Asp Leu Leu Met Leu Leu Arg Gln Ser Pro Thr Pro
         785                 790                 795                 800

His Gly Leu Ser Leu Ser Asp Leu Gln Glu Ala Lys Tyr Glu Thr Phe
                         805                 810                 815
```

-continued

```
Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
            850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
            1010                1015                1020

Asn Ser Pro Ser Val Trp Gln Asn Ile Leu Glu Ser Asp Thr Glu
            1025                1030                1035

Phe Lys Lys Val Thr Pro Leu Ile His Asp Arg Met Leu Met Asp
            1040                1045                1050

Lys Asn Ala Thr Ala Leu Arg Leu Asn His Met Ser Asn Lys Thr
            1055                1060                1065

Thr Ser Ser Lys Asn Met Glu Met Val Gln Gln Lys Lys Glu Gly
            1070                1075                1080

Pro Ile Pro Pro Asp Ala Gln Asn Pro Asp Met Ser Phe Phe Lys
            1085                1090                1095

Met Leu Phe Leu Pro Glu Ser Ala Arg Trp Ile Gln Arg Thr His
            1100                1105                1110

Gly Lys Asn Ser Leu Asn Ser Gly Gln Gly Pro Ser Pro Lys Gln
            1115                1120                1125

Leu Val Ser Leu Gly Pro Glu Lys Ser Val Glu Gly Gln Asn Phe
            1130                1135                1140

Leu Ser Glu Lys Asn Lys Val Val Val Gly Lys Gly Glu Phe Thr
            1145                1150                1155

Lys Asp Val Gly Leu Lys Glu Met Val Phe Pro Ser Ser Arg Asn
            1160                1165                1170

Leu Phe Leu Thr Asn Leu Asp Asn Leu His Glu Asn Asn Thr His
            1175                1180                1185

Asn Gln Glu Lys Lys Ile Gln Glu Glu Ile Glu Lys Lys Glu Thr
            1190                1195                1200

Leu Ile Gln Glu Asn Val Val Leu Pro Gln Ile His Thr Val Thr
            1205                1210                1215
```

-continued

```
Gly Thr Lys Asn Phe Met Lys Asn Leu Phe Leu Leu Ser Thr Arg
1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
```

-continued

```
            1610                1615                1620
Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010
```

```
Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 38
<211> LENGTH: 6996
<212> TYPE: DNA
<213> ORGANISM: Artificial Sequence
<220> FEATURE:
<223> OTHER INFORMATION: Variant nucleotide

<400> SEQUENCE: 38
gccaccagaa gatactacct gggtgcagtg gaactgtcat gggactatat gcaaagtgat      60
```

```
ctcggtgagc tgcctgtgga cgcaagattt cctcctagag tgccaaaatc tttttccattc    120
aacacctcag tcgtgtacaa aaagactctg tttgtagaat tcacggttca ccttttcaac    180
atcgctaagc caaggccacc ctggatgggt ctgctaggtc ctaccatcca ggctgaggtt    240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttgct     600
gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg acagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggcccctca gcggattggt   1260
aggaagtaca aaaaagtccg atttatggca tacacagatg aaacctttaa gactcgtgaa   1320
gctattcagc atgaatcagg aatcttggga ccttttacttt atggggaagt tggagacaca   1380
ctgttgatta tatttaagaa tcaagcaagc agaccatata acatctaccc tcacggaatc   1440
actgatgtcc gtccttttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctctggat   1680
caatggggaa acgagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860
gttttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcaccccta ttcccattct caggagaaac tgtcttcatg   2040
tcgatggaaa acccaggtct atggattctg ggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat gaaccaaga    2220
agcttctccc agaattcaag acaccctagc actaggcaaa agcaatttaa tgccaccaca   2280
attccagaaa atgacataga gaagactgac cctggtttg cacacagaac acctatgcct   2340
aaaatacaaa atgtctcctc tagtgatttg ttgatgctct gcgacagag tcctactcca   2400
catgggctat ccttatctga tctccaagaa gccaaatatg agacttttc tgatgatcca   2460
```

```
tcacctggag caatagacag taataacagc ctgtctgaaa tgacacactt caggccacag    2520
ctccatcaca gtggggacat ggtatttacc cctgagtcag gcctccaatt aagattaaat    2580
gagaaactgg ggacaactgc agcaacagag ttgaagaaac ttgatttcaa agtttctagt    2640
acatcaaata atctgatttc aacaattcca tcagacaatt tggcagcagg tactgataat    2700
acaagttcct taggacccccc aagtatgcca gttcattatg atagtcaatt agataccact    2760
ctatttggca aaaagtcatc tccccttact gagtctggtg gacctctgag cttgagtgaa    2820
gaaaataatg attcaaagtt gttagaatca ggtttaatga atagccaaga aagttcatgg    2880
ggaaaaaatg tatcgtcaac agagagtggt aggttattta aagggaaaag agctcatgga    2940
cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaaa ttcaggaaga aatagaaaag    3600
aaggaaacat taatccaaga gaatgtagtt ttgcctcaga tacatacagt gactggcact    3660
aagaatttca tgaagaacct tttcttactg agcactaggc aaaatgtaga aggttcatat    3720 gacgggcat atgctccagt acttcaagat tttaggtcat taaatgattc aacaaataga    3780
acaaagaaac acacagctca tttctcaaaa aaggggagg aagaaaactt ggaaggcttg    3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctcccttt tcagattgcc ttacgaggag tcatagcatc    4140
cctcaagcaa atagatctcc attacccatt gcaaaggtat catcatttcc atctattaga    4200
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320
aataaccttt ctttagccat tctaaccttg gagatgactg gtgatcaaag agaggttggc    4380
tccctgggga caagtgccac aaattcagtc acatacaaga aagttgagaa cactgttctc    4440
ccgaaaccag acttgcccaa acatctggc aaagttgaat tgcttccaaa agttcacatt    4500
tatcagaagg acctattccc tacgaaaact agcaatgggt ctcctggcca tctggatctc    4560
gtggaaggga gccttcttca gggaacagag ggagcgatta agtggaatga agcaaacaga    4620
cctggaaaag ttccctttct gagagtagca acagaaagct ctgcaaagac tccctccaag    4680
ctattggatc ctcttgcttg ggataaccac tatggtactc agataccaaa agaagagtgg    4740
aaatcccaag agaagtcacc agaaaaaaca gcttttaaga aaaaggatac cattttgtcc    4800
```

```
ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga aacgccatca acgggaaata actcgtacta ctcttcagtc agatcaagag    4980
gaaattgact atgatgatac catatcagtt gaaatgaaga aggaagattt tgacattttat   5040 gatgaggatg aaaatcagag cccccgcagc tttcaaaaga aaacacgaca ctattttatt    5100
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagccctt ataccgtgga gaactaaatg aacatttggg actcctgggg    5280
ccatatataa gagcagaagt tgaagataat atcatggtaa ctttcagaaa tcaggcctct    5340
cgtccctatt ccttctattc tagccttatt tcttatgagg aagatcagag gcaaggagca    5400
gaacctagaa aaaactttgt caagcctaat gaaaccaaaa cttacttttg gaaagtgcaa    5460
catcatatgg cacccactaa agatgagttt gactgcaaag cctgggctta tttctctgat    5520
gttgacctgg aaaagatgt gcactcaggc ctgattggac cccttctggt ctgccacact    5580
aacacactga accctgctca tgggagacaa gtgacagtac aggaatttgc tctgtttttc    5640
accatctttg atgagaccaa aagctggtac ttcactgaaa atatgaaag aaactgcagg    5700 gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaaagaggag tataaaatgg cactgtacaa tctctatcca    5940 ggtgttttg agacagtgga aatgttacca tccaaagctg gaatttggcg ggtggaatgc    6000
cttattggcg agcatctaca tgctgggatg agcacacttt ttctggtgta cagcaataag    6060
tgtcagactc ccctgggaat ggcttctgga cacattagag attttcagat tacagcttca    6120
ggacaatatg gacagtgggc cccaaagctg gccagacttc attattccgg atcaatcaat    6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg gataaaaca caatattttt    6420 aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840
aaggtttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctac                              6996
```

<210> SEQ ID NO 39
<211> LENGTH: 1438
<212> TYPE: PRT
<213> ORGANISM: Artificial Sequence
<220> FEATURE:
<223> OTHER INFORMATION: Variant peptide

<400> SEQUENCE: 39

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

-continued

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560

Gln Trp Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

```
Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
            835                 840                 845

Phe Thr Gln Pro Leu Tyr Arg Gly Glu Leu Asn Glu His Leu Gly Leu
        850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
        900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
        930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
                995                 1000                1005

Cys Asn Ile Gln Met Glu Asp Pro Thr Phe Lys Glu Asn Tyr Arg
        1010                1015                1020

Phe His Ala Ile Asn Gly Tyr Ile Met Asp Thr Leu Pro Gly Leu
        1025                1030                1035

Val Met Ala Gln Asp Gln Arg Ile Arg Trp Tyr Leu Leu Ser Met
        1040                1045                1050

Gly Ser Asn Glu Asn Ile His Ser Ile His Phe Ser Gly His Val
        1055                1060                1065

Phe Thr Val Arg Lys Lys Glu Glu Tyr Lys Met Ala Leu Tyr Asn
        1070                1075                1080

Leu Tyr Pro Gly Val Phe Glu Thr Val Glu Met Leu Pro Ser Lys
        1085                1090                1095

Ala Gly Ile Trp Arg Val Glu Cys Leu Ile Gly Glu His Leu His
        1100                1105                1110

Ala Gly Met Ser Thr Leu Phe Leu Val Tyr Ser Asn Lys Cys Gln
        1115                1120                1125

Thr Pro Leu Gly Met Ala Ser Gly His Ile Arg Asp Phe Gln Ile
        1130                1135                1140

Thr Ala Ser Gly Gln Tyr Gly Gln Trp Ala Pro Lys Leu Ala Arg
        1145                1150                1155

Leu His Tyr Ser Gly Ser Ile Asn Ala Trp Ser Thr Lys Glu Pro
        1160                1165                1170

Phe Ser Trp Ile Lys Val Asp Leu Leu Ala Pro Met Ile Ile His
        1175                1180                1185

Gly Ile Lys Thr Gln Gly Ala Arg Gln Lys Phe Ser Ser Leu Tyr
        1190                1195                1200

Ile Ser Gln Phe Ile Ile Met Tyr Ser Leu Asp Gly Lys Lys Trp
        1205                1210                1215

Gln Thr Tyr Arg Gly Asn Ser Thr Gly Thr Leu Met Val Phe Phe
```

Gly Asn Val Asp Ser Ser Gly Ile Lys His Asn Ile Phe Asn Pro
1220                 1225                 1230

Pro Ile Ile Ala Arg Tyr Ile Arg Leu His Pro Thr His Tyr Ser
    1235                 1240                 1245

Ile Arg Ser Thr Leu Arg Met Glu Leu Met Gly Cys Asp Leu Asn
1250                 1255                 1260

Ser Cys Ser Met Pro Leu Gly Met Glu Ser Lys Ala Ile Ser Asp
1265                 1270                 1275

Ala Gln Ile Thr Ala Ser Ser Tyr Phe Thr Asn Met Phe Ala Thr
1280                 1285                 1290

Trp Ser Pro Ser Lys Ala Arg Leu His Leu Gln Gly Arg Ser Asn
1295                 1300                 1305

Ala Trp Arg Pro Gln Val Asn Asn Pro Lys Glu Trp Leu Gln Val
1310                 1315                 1320

Asp Phe Gln Lys Thr Met Lys Val Thr Gly Val Thr Thr Gln Gly
1325                 1330                 1335

Val Lys Ser Leu Leu Thr Ser Met Tyr Val Lys Glu Phe Leu Ile
1340                 1345                 1350

Ser Ser Ser Gln Asp Gly His Gln Trp Thr Leu Phe Phe Gln Asn
1355                 1360                 1365

Gly Lys Val Lys Val Phe Gln Gly Asn Gln Asp Ser Phe Thr Pro
1370                 1375                 1380

Val Val Asn Ser Leu Asp Pro Pro Leu Leu Thr Arg Tyr Leu Arg
1385                 1390                 1395

Ile His Pro Gln Ser Trp Val His Gln Ile Ala Leu Arg Met Glu
1400                 1405                 1410

Val Leu Gly Cys Glu Ala Gln Asp Leu Tyr
1415                 1420                 1425

Val Leu Gly Cys Glu Ala Gln Asp Leu Tyr
1430                 1435

<210> SEQ ID NO 40
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 40
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg gagccctact agtatgtaga     540
gaagggagtc tggccaagga aaagacacag accttgcaca aatttatact acttttgct      600 gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780

```
ggcaccactc ctgaagtgca ctcaatattc ctcgaaggtc acacatttct tgtgaggaac    840
catcgccagg cgtccttgga aatctcgcca ataactttcc ttactgctca acactcttg    900
atggaccttg gacagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaagtccg atttatggca tacacagatg aaaccttta gactcgtgaa    1320
gctattcagc atgaatcagg aatcttggga cctttacttt atggggaagt ggagacaca    1380
ctgttgatta tatttaagaa tcaagcaagc agaccatata acatctaccc tcacggaatc   1440
actgatgtcc gtccttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctctggat   1680
caatggggaa acgagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860
gttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg gggtgccaca actcagactt tcggaacaga   2100
ggcatgaccg ccttactgaa ggtttctagt tgtgacaaga cactggtga ttattacgag    2160
gacagttatg aagatatttc agcatacttg ctgagtaaaa acaatgccat tgaaccaaga   2220
agcttctccc agaacccacc agtcttgaaa cgccatcaac gggaaataac tcgtactact   2280
cttcagtcag atcaagagga aattgactat gatgatacca tatcagttga aatgaagaag   2340
gaagattttg acatttatga tgaggatgaa atcagagcc cccgcagctt tcaaaagaaa    2400
acacgacact attttattgc tgcagtggag aggctctggg attatgggat gagtagctcc   2460
ccacatgttc taagaaacag ggctcagagt ggcagtgtcc ctcagttcaa gaaagttgtt   2520
ttccaggaat ttactgatgg ctcctttact cagcccttat accgtggaga actaaatgaa   2580
catttgggac tcctggggcc atatataaga gcagaagttg aagataatat catggtaact   2640
ttcagaaatc aggcctctcg tcctattcc ttctattcta gccttatttc ttatgaggaa    2700
gatcagaggc aaggagcaga acctagaaaa actttgtca gcctaatga aaccaaaact     2760
tactttggga agtgcaaaca tcatatggca cccactaaag atgagtttga ctgcaaagcc   2820
tgggcttatt ctctctgatgt tgacctgaa aaagatgtgc actcaggcct gattggaccc    2880
cttctggtct gccacactaa cacactgaac cctgctcatg ggacaagt gacagtacag     2940
gaatttgctc tgttttcac catctttgat gagaccaaaa gctggtactt cactgaaaat   3000
atggaaagaa actgcagggc tccctgcaat atccagatgg aagatcccac ttttaaagag   3060
aattatcgct tccatgcaat caatggctac ataatggata cactacctgg cttagtaatg   3120
```

```
gctcaggatc aaaggattcg atggtatctg ctcagcatgg gcagcaatga aaacatccat    3180
tctattcatt tcagtggaca tgtgttcact gtacgaaaaa aagaggagta taaaatggca    3240
ctgtacaatc tctatccagg tgtttttgag acagtggaaa tgttaccatc caaagctgga    3300
atttggcggg tggaatgcct tattggcgag catctacatg ctgggatgag cacactttt    3360 ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct ttcttggat caaggtggat    3540 ctgttggcac caatgattat tcacggcatc aagacccagg gtgcccgtca agttctcc    3600 agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atattttaa ccctccaatt attgctcgat acatccgttt gcacccaact    3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggag taaaatctct gcttaccagc    4080
atgtatgtga aggagttcct catctccagc agtcaagatg ccatcagtg gactctcttt    4140 tttcagaatg gcaaagtaaa ggttttttcag ggaaatcaag actccttcac acctgtggtg    4200
aactctctag acccaccgtt actgactcgc taccttcgaa ttcacccca gagttgggtg    4260 caccagattg ccctgaggat ggaggttctg ggctgcgagg cacaggacct ctac          4314
```

<210> SEQ ID NO 41
<211> LENGTH: 1438
<212> TYPE: PRT
<213> ORGANISM: Artificial Sequence
<220> FEATURE:
<223> OTHER INFORMATION: Variant peptide

<400> SEQUENCE: 41

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160
```

-continued

```
His Val Asp Leu Val Lys Asp Leu Asn Ser Gly Leu Ile Gly Ala Leu
            165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
            210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
            370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Val Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Leu Asp
545                 550                 555                 560

Gln Trp Gly Asn Glu Ile Met Ser Asp Lys Arg Asn Val Ile Leu Phe
            565                 570                 575
```

```
Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Ser Gly Tyr
                645                 650                 655

Thr Phe Lys His Lys Met Val Tyr Val Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn  Met Glu Arg Asn Cys  Arg Ala Pro
```

```
                995                1000              1005
Cys Asn Ile Gln Met Glu Asp Pro Thr Phe Lys Glu Asn Tyr Arg
    1010            1015              1020

Phe His Ala Ile Asn Gly Tyr Ile Met Asp Thr Leu Pro Gly Leu
    1025            1030              1035

Val Met Ala Gln Asp Gln Arg Ile Arg Trp Tyr Leu Leu Ser Met
    1040            1045              1050

Gly Ser Asn Glu Asn Ile His Ser Ile His Phe Ser Gly His Val
    1055            1060              1065

Phe Thr Val Arg Lys Lys Glu Glu Tyr Lys Met Ala Leu Tyr Asn
    1070            1075              1080

Leu Tyr Pro Gly Val Phe Glu Thr Val Glu Met Leu Pro Ser Lys
    1085            1090              1095

Ala Gly Ile Trp Arg Val Glu Cys Leu Ile Gly Glu His Leu His
    1100            1105              1110

Ala Gly Met Ser Thr Leu Phe Leu Val Tyr Ser Asn Lys Cys Gln
    1115            1120              1125

Thr Pro Leu Gly Met Ala Ser Gly His Ile Arg Asp Phe Gln Ile
    1130            1135              1140

Thr Ala Ser Gly Gln Tyr Gly Gln Trp Ala Pro Lys Leu Ala Arg
    1145            1150              1155

Leu His Tyr Ser Gly Ser Ile Asn Ala Trp Ser Thr Lys Glu Pro
    1160            1165              1170

Phe Ser Trp Ile Lys Val Asp Leu Leu Ala Pro Met Ile Ile His
    1175            1180              1185

Gly Ile Lys Thr Gln Gly Ala Arg Gln Lys Phe Ser Ser Leu Tyr
    1190            1195              1200

Ile Ser Gln Phe Ile Ile Met Tyr Ser Leu Asp Gly Lys Lys Trp
    1205            1210              1215

Gln Thr Tyr Arg Gly Asn Ser Thr Gly Thr Leu Met Val Phe Phe
    1220            1225              1230

Gly Asn Val Asp Ser Ser Gly Ile Lys His Asn Ile Phe Asn Pro
    1235            1240              1245

Pro Ile Ile Ala Arg Tyr Ile Arg Leu His Pro Thr His Tyr Ser
    1250            1255              1260

Ile Arg Ser Thr Leu Arg Met Glu Leu Met Gly Cys Asp Leu Asn
    1265            1270              1275

Ser Cys Ser Met Pro Leu Gly Met Glu Ser Lys Ala Ile Ser Asp
    1280            1285              1290

Ala Gln Ile Thr Ala Ser Ser Tyr Phe Thr Asn Met Phe Ala Thr
    1295            1300              1305

Trp Ser Pro Ser Lys Ala Arg Leu His Leu Gln Gly Arg Ser Asn
    1310            1315              1320

Ala Trp Arg Pro Gln Val Asn Asn Pro Lys Glu Trp Leu Gln Val
    1325            1330              1335

Asp Phe Gln Lys Thr Met Lys Val Thr Gly Val Thr Thr Gln Gly
    1340            1345              1350

Val Lys Ser Leu Leu Thr Ser Met Tyr Val Lys Glu Phe Leu Ile
    1355            1360              1365

Ser Ser Ser Gln Asp Gly His Gln Trp Thr Leu Phe Phe Gln Asn
    1370            1375              1380

Gly Lys Val Lys Val Phe Gln Gly Asn Gln Asp Ser Phe Thr Pro
    1385            1390              1395
```

| Val | Val | Asn | Ser | Leu | Asp | Pro | Pro | Leu | Leu | Thr | Arg | Tyr | Leu | Arg |
|     | 1400 |     |     |     | 1405 |     |     |     |     | 1410 |     |     |     |     |

| Ile | His | Pro | Gln | Ser | Trp | Val | His | Gln | Ile | Ala | Leu | Arg | Met | Glu |
|     | 1415 |     |     |     |     | 1420 |     |     |     |     | 1425 |     |     |     |

| Val | Leu | Gly | Cys | Glu | Ala | Gln | Asp | Leu | Tyr |
|     | 1430 |     |     |     |     | 1435 |     |     |     |

<210> SEQ ID NO 42
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 42

```
gccaccagaa gatactacct gggtgcagtg gaactgtcat gggactatat gcaaagtgat        60
ctcggtgagc tgcctgtgga cgcaagattt cctcctagag tgccaaaatc ttttccattc       120
aacacctcag tcgtgtacaa aaagactctg tttgtagaat tcacggatca ccttttcaac       180
atcgctaagc caaggccacc ctggatgggt ctgctaggtc ctaccatcca ggctgaggtt       240
tatgatacag tggtcattac acttaagaac atggcttccc atcctgtcag tcttcatgct       300
gttggtgtat cctactggaa agcttctgag ggagctgaat atgatgatca gaccagtcaa       360
agggagaaag aagatgataa agtcttccct ggtggaagcc atacatatgt ctggcaggtc       420
ctgaaagaga atggtccaat ggcctctgac ccactgtgcc ttacctactc atatctttct       480
catgtggacc tggtaaaaga cttgaattca ggcctcattg gagccctact agtatgtaga       540
gaagggagtc tggccaagga aaagacacag accttgcaca aatttatact acttttgct        600
gtatttgatg aagggaaaag ttggcactca gaaacaaaga actccttgat gcaggatagg       660
gatgctgcat ctgctcgggc ctggcctaaa atgcacacag tcaatggtta tgtaaacagg       720
tctctaccag gtctgattgg atgccacagg aaatcagtct attggcatgt gattggaatg       780
ggcaccactc ctgaagtgca ctcaatattc ctcgaaggtc acacatttct tgtgaggaac       840
catcgccagg cgtccttgga aatctcgcca ataactttcc ttactgctca aacactcttg       900
atggaccttg acagtttcct actgttttgt catatctctt cccaccaaca tgatggcatg       960
gaagcttatg tcaaagtaga cagctgtcca gaggaacccc aactacgaat gaaaaataat      1020
gaagaagcgg aagactatga tgatgatctt actgattctg aaatggatgt ggtcaggttt      1080
gatgatgaca actctccttc ctttatccaa attcgctcag ttgccaagaa gcatcctaaa      1140
acttgggtac attacattgc tgctgaagag gaggactggg actatgctcc cttagtcctc      1200
gcccccgatg acagaagtta taaaagtcaa tatttgaaca atggccctca gcggattggt      1260
aggaagtaca aaaagtccg atttatggca tacacagatg aaacctttaa gacgcgtgaa      1320
gctattcagc atgaatcagg aatcttggga ccttttacttt atgggaagt tggagacaca      1380
ctgttgatta tatttaagaa tcaagcaagc agaccatata catctacccc tcacggaatc      1440
actgatgtcc gtccttgta ttcaaggaga ttaccaaaag gtgtaaaaca tttgaaggat      1500
tttccaattc tgccaggaga aatattcaaa tataatggga cagtgactgt agaagttggg      1560
ccaactaaat cagatccgcg gtgcctgacc cgctattact ctagtttcgt taatatggag      1620
agagatctag cttcaggact cattggccct ctcctcatct gctacaaaga atctctggat      1680
caatggggaa acgagataat gtcagacaag aggaatgtca cctgtttttc tgtatttgat      1740
gagaaccgaa gctggtacct cacagagaat atacaacgct ttctccccaa tccagctgga      1800
```

-continued

| | |
|---|---|
| gtgcagcttg aggatccaga gttccaagcc tccaacatca tgcacagcat caatggctat | 1860 |
| gtttttgata gtttgcagtt gtcagtttgt ttgcatgagg tggcatactg gtacattcta | 1920 |
| agcattggag cacagactga cttcctttct gtcttcttct ctggatatac cttcaaacac | 1980 |
| aaaatggtct atgtagacac actcaccota ttcccattct caggagaaac tgtcttcatg | 2040 |
| tcgatggaaa acccaggtct atggattctg gggtgccaca actcagactt tcggaacaga | 2100 |
| ggcatgaccg ccttactgaa ggtttctagt tgtgacaaga acactggtga ttattacgag | 2160 |
| gacagttacg aagatatttc agcatacttg ctgagtaaaa acaatgccat tgaacctagg | 2220 |
| agcttctctc agaatccacc agtcttgaaa cgccatcaac gggaaataac tcgtacgact | 2280 |
| cttcagtcag atcaagagga aattgactat gatgatacca tatcagttga aatgaagaag | 2340 |
| gaagattttg acatttatga tgaggatgaa aatcagagcc cccgcagctt tcaaaagaaa | 2400 |
| acacgacact attttattgc tgcagtggag aggctctggg attatgggat gagtagctcc | 2460 |
| ccacatgttc taagaaacag ggctcagagt ggcagtgtcc ctcagttcaa gaaagttgtt | 2520 |
| ttccaggaat ttactgatgg ctcctttact cagcccttat accgtggaga actaaatgaa | 2580 |
| catttgggac tcctggggcc atatataaga gcagaagttg aagataatat catggtaact | 2640 |
| ttcagaaatc aggcctctcg tccctattcc ttctattcta gccttatttc ttatgaggaa | 2700 |
| gatcagaggc aaggagcaga acctagaaaa aactttgtca agcctaatga aaccaaaact | 2760 |
| tactttttgga aagtgcaaca tcatatggca cccactaaag atgagtttga ctgcaaagcc | 2820 |
| tgggcttatt tctctgatgt tgacctggaa aaagatgtgc actcaggcct gattggaccc | 2880 |
| cttctggtct gccacactaa cacactgaac cctgctcatg ggagacaagt gacagtacag | 2940 |
| gaatttgctc tgttttttcac catctttgat gagaccaaaa gctggtactt cactgaaaat | 3000 |
| atggaaagaa actgcagggc tccctgcaat atccagatgg aagatcccac ttttaaagag | 3060 |
| aattatcgct tccatgcaat caatggctac ataatggata cactacctgg cttagtaatg | 3120 |
| gctcaggatc aaaggattcg atggtatctg ctcagcatgg gcagcaatga aacatccat | 3180 |
| tctattcatt tcagtggaca tgtgttcact gtacgaaaaa aagaggagta taaaatggca | 3240 |
| ctgtacaatc tctatccagg tgtttttgag acagtggaaa tgttaccatc caaagctgga | 3300 |
| atttggcggg tggaatgcct tattggcgag catctacatg ctgggatgag cacacttttt | 3360 |
| ctggtgtaca gcaataagtg tcagactccc ctgggaatgg cttctggaca cattagagat | 3420 |
| tttcagatta cagcttcagg acaatatgga cagtgggccc caaagctggc cagacttcat | 3480 |
| tattccggat caatcaatgc ctggagcacc aaggagccct tttcttggat caaggtggat | 3540 |
| ctgttggcac caatgattat tcacggcatc aagacccagg gtgcccgtca gaagttctcc | 3600 |
| agcctctaca tctctcagtt tatcatcatg tatagtcttg atgggaagaa gtggcagact | 3660 |
| tatcgaggaa attccactgg aaccttaatg gtcttctttg gcaatgtgga ttcatctggg | 3720 |
| ataaaacaca atattttaa ccctccaatt attgctcgat acatccgttt gcacccaact | 3780 |
| cattatagca ttcgcagcac tcttcgcatg gagttgatgg gctgtgattt aaatagttgc | 3840 |
| agcatgccat tgggaatgga gagtaaagca atatcagatg cacagattac tgcttcatcc | 3900 |
| tactttacca atatgtttgc cacctggtct ccttcaaaag ctcgacttca cctccaaggg | 3960 |
| aggagtaatg cctggagacc tcaggtgaat aatccaaaag agtggctgca agtggacttc | 4020 |
| cagaagacaa tgaaagtcac aggagtaact actcagggga taaatctct gcttaccagc | 4080 |
| atgtatgtga aggagttcct catctccagc agtcaagatg gccatcagtg gactctcttt | 4140 |

```
tttcagaatg gcaaagtaaa ggttttcag ggaaatcaag actccttcac acctgtggtg      4200
aactctctag acccaccgtt actgactcgc taccttcgaa ttcaccccca gagttgggtg      4260
caccagattg ccctgaggat ggaggttctg ggctgcgagg cacaggacct ctac            4314
```

<210> SEQ ID NO 43
<211> LENGTH: 2332
<212> TYPE: PRT
<213> ORGANISM: Artificial Sequence
<220> FEATURE:
<223> OTHER INFORMATION: Variant peptide

<400> SEQUENCE: 43

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
           100                 105                 110

Glu Tyr Asp Asp Gln Thr Ser Gln Arg Glu Lys Glu Asp Asp Lys Val
       115                 120                 125

Phe Pro Gly Gly Ser His Thr Tyr Val Trp Gln Val Leu Lys Glu Asn
   130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335
```

-continued

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560

Gln Phe Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys

-continued

```
            755                 760                 765
Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
                915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
                980                 985                 990

Val Ser Ile Ser Leu Leu Lys Thr Asn Lys Thr Ser Asn Asn Ser Ala
                995                 1000                1005

Thr Asn Arg Lys Thr His Ile Asp Gly Pro Ser Leu Leu Ile Glu
            1010                1015                1020

Asn Ser Pro Ser Val Trp Gln Asn Ile Leu Glu Ser Asp Thr Glu
            1025                1030                1035

Phe Lys Lys Val Thr Pro Leu Ile His Asp Arg Met Leu Met Asp
            1040                1045                1050

Lys Asn Ala Thr Ala Leu Arg Leu Asn His Met Ser Asn Lys Thr
            1055                1060                1065

Thr Ser Ser Lys Asn Met Glu Met Val Gln Gln Lys Lys Glu Gly
            1070                1075                1080

Pro Ile Pro Pro Asp Ala Gln Asn Pro Asp Met Ser Phe Phe Lys
            1085                1090                1095

Met Leu Phe Leu Pro Glu Ser Ala Arg Trp Ile Gln Arg Thr His
            1100                1105                1110

Gly Lys Asn Ser Leu Asn Ser Gly Gln Gly Pro Ser Pro Lys Gln
            1115                1120                1125

Leu Val Ser Leu Gly Pro Glu Lys Ser Val Glu Gly Gln Asn Phe
            1130                1135                1140

Leu Ser Glu Lys Asn Lys Val Val Val Gly Lys Gly Glu Phe Thr
            1145                1150                1155

Lys Asp Val Gly Leu Lys Glu Met Val Phe Pro Ser Ser Arg Asn
            1160                1165                1170
```

-continued

```
Leu Phe Leu Thr Asn Leu Asp Asn Leu His Glu Asn Asn Thr His
1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560
```

-continued

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys 1955                1960                1965

Glu Glu Tyr Lys Met Ala Leu Tyr Asn Leu Tyr Pro Gly Val Phe
    1970            1975            1980

Glu Thr Val Glu Met Leu Pro Ser Lys Ala Gly Ile Trp Arg Val
    1985            1990            1995

Glu Cys Leu Ile Gly Glu His Leu His Ala Gly Met Ser Thr Leu
    2000            2005            2010

Phe Leu Val Tyr Ser Asn Lys Cys Gln Thr Pro Leu Gly Met Ala
    2015            2020            2025

Ser Gly His Ile Arg Asp Phe Gln Ile Thr Ala Ser Gly Gln Tyr
    2030            2035            2040

Gly Gln Trp Ala Pro Lys Leu Ala Arg Leu His Tyr Ser Gly Ser
    2045            2050            2055

Ile Asn Ala Trp Ser Thr Lys Glu Pro Phe Ser Trp Ile Lys Val
    2060            2065            2070

Asp Leu Leu Ala Pro Met Ile Ile His Gly Ile Lys Thr Gln Gly
    2075            2080            2085

Ala Arg Gln Lys Phe Ser Ser Leu Tyr Ile Ser Gln Phe Ile Ile
    2090            2095            2100

Met Tyr Ser Leu Asp Gly Lys Lys Trp Gln Thr Tyr Arg Gly Asn
    2105            2110            2115

Ser Thr Gly Thr Leu Met Val Phe Phe Gly Asn Val Asp Ser Ser
    2120            2125            2130

Gly Ile Lys His Asn Ile Phe Asn Pro Pro Ile Ile Ala Arg Tyr
    2135            2140            2145

Ile Arg Leu His Pro Thr His Tyr Ser Ile Arg Ser Thr Leu Arg
    2150            2155            2160

Met Glu Leu Met Gly Cys Asp Leu Asn Ser Cys Ser Met Pro Leu
    2165            2170            2175

Gly Met Glu Ser Lys Ala Ile Ser Asp Ala Gln Ile Thr Ala Ser
    2180            2185            2190

Ser Tyr Phe Thr Asn Met Phe Ala Thr Trp Ser Pro Ser Lys Ala
    2195            2200            2205

Arg Leu His Leu Gln Gly Arg Ser Asn Ala Trp Arg Pro Gln Val
    2210            2215            2220

Asn Asn Pro Lys Glu Trp Leu Gln Val Asp Phe Gln Lys Thr Met
    2225            2230            2235

Lys Val Thr Gly Val Thr Thr Gln Gly Val Lys Ser Leu Leu Thr
    2240            2245            2250

Ser Met Tyr Val Lys Glu Phe Leu Ile Ser Ser Ser Gln Asp Gly
    2255            2260            2265

His Gln Trp Thr Leu Phe Phe Gln Asn Gly Lys Val Lys Val Phe
    2270            2275            2280

Gln Gly Asn Gln Asp Ser Phe Thr Pro Val Val Asn Ser Leu Asp
    2285            2290            2295

Pro Pro Leu Leu Thr Arg Tyr Leu Arg Ile His Pro Gln Ser Trp
    2300            2305            2310

Val His Gln Ile Ala Leu Arg Met Glu Val Leu Gly Cys Glu Ala
    2315            2320            2325

Gln Asp Leu Tyr
    2330

<210> SEQ ID NO 44

<211> LENGTH: 6996
<212> TYPE: DNA
<213> ORGANISM: Artificial Sequence
<220> FEATURE:
<223> OTHER INFORMATION: Variant nucleotide

<400> SEQUENCE: 44

| | | | | | |
|---|---|---|---|---|---|
| gccaccagaa | gatactacct | gggtgcagtg | gaactgtcat | gggactatat | gcaaagtgat | 60 |
| ctcggtgagc | tgcctgtgga | cgcaagattt | cctcctagag | tgccaaaatc | ttttccattc | 120 |
| aacacctcag | tcgtgtacaa | aaagactctg | tttgtagaat | tcacggttca | ccttttcaac | 180 |
| atcgctaagc | caaggccacc | ctggatgggt | ctgctaggtc | ctaccatcca | ggctgaggtt | 240 |
| tatgatacag | tggtcattac | acttaagaac | atggcttccc | atcctgtcag | tcttcatgct | 300 |
| gttggtgtat | cctactggaa | agcttctgag | ggagctgaat | atgatgatca | gaccagtcaa | 360 |
| agggagaaag | aagatgataa | agtcttccct | ggtggaagcc | atacatatgt | ctggcaggtc | 420 |
| ctgaaagaga | atggtccaat | ggcctctgac | ccactgtgcc | ttacctactc | atatctttct | 480 |
| catgtggacc | tggtaaaaga | cttgaattca | ggcctcattg | agccctact | agtatgtaga | 540 |
| gaagggagtc | tggccaagga | aaagacacag | accttgcaca | aatttatact | acttttgct | 600 |
| gtatttgatg | aagggaaaag | ttggcactca | gaaacaaaga | actccttgat | gcaggatagg | 660 |
| gatgctgcat | ctgctcgggc | ctggcctaaa | atgcacacag | tcaatggtta | tgtaaacagg | 720 |
| tctctgccag | tctgattgg | atgccacagg | aaatcagtct | attggcatgt | gattggaatg | 780 |
| ggcaccactc | ctgaagtgca | ctcaatattc | ctcgaaggtc | acacatttct | tgtgaggaac | 840 |
| catcgccagg | cgtccttgga | aatctcgcca | ataactttcc | ttactgctca | aacactcttg | 900 |
| atggaccttg | gacagtttct | actgttttgt | catatctctt | cccaccaaca | tgatggcatg | 960 |
| gaagcttatg | tcaaagtaga | cagctgtcca | gaggaacccc | aactacgaat | gaaaaataat | 1020 |
| gaagaagcgg | aagactatga | tgatgatctt | actgattctg | aaatggatgt | ggtcaggttt | 1080 |
| gatgatgaca | actctccttc | ctttatccaa | attcgctcag | ttgccaagaa | gcatcctaaa | 1140 |
| acttgggtac | attacattgc | tgctgaagag | gaggactggg | actatgctcc | cttagtcctc | 1200 |
| gcccccgatg | acagaagtta | taaagtcaa | tatttgaaca | atggccctca | gcggattggt | 1260 |
| aggaagtaca | aaaagtccg | atttatggca | tacacagatg | aaacctttaa | gactcgtgaa | 1320 |
| gctattcagc | atgaatcagg | aatcttggga | cctttacttt | atggggaagt | tggagacaca | 1380 |
| ctgttgatta | tatttaagaa | tcaagcaagc | agaccatata | acatctaccc | tcacggaatc | 1440 |
| actgatgtcc | gtccttttgta | ttcaaggaga | ttaccaaaag | gtgtaaaaca | tttgaaggat | 1500 |
| tttccaattc | tgccaggaga | aatattcaaa | tataaatgga | cagtgactgt | agaagatggg | 1560 |
| ccaactaaat | cagatcctcg | gtgcctgacc | cgctattact | ctagtttcgt | taatatggag | 1620 |
| agagatctag | cttcaggact | cattggccct | ctcctcatct | gctacaaaga | atctctggat | 1680 |
| caattcggaa | acgagataat | gtcagacaag | aggaatgtca | tcctgttttc | tgtatttgat | 1740 |
| gagaaccgaa | gctggtacct | cacagagaat | atacaacgct | ttctccccaa | tccagctgga | 1800 |
| gtgcagcttg | aggatccaga | gttccaagcc | tccaacatca | tgcacagcat | caatggctat | 1860 |
| gttttgata | gtttgcagtt | gtcagtttgt | ttgcatgagg | tggcatactg | gtacattcta | 1920 |
| agcattggag | cacagactga | cttcctttct | gtcttcttct | ctggatatac | cttcaaacac | 1980 |
| aaaatggtct | atgaagacac | actcacccta | ttcccattct | caggagaaac | tgtcttcatg | 2040 |
| tcgatgaaa | acccaggtct | atggattctg | gggtgccaca | actcagactt | tcggaacaga | 2100 |
| ggcatgaccg | ccttactgaa | ggtttctagt | tgtgacaaga | acactggtga | ttattacgag | 2160 |

```
gacagttatg aagatatttc agcatacttg ctgagtaaaa acaatgccat tgaaccaaga    2220
agcttctccc agaattcaag cacccctagc actaggcaaa agcaatttaa tgccaccaca    2280
attccagaaa atgacataga gaagactgac ccttggtttg cacacagaac acctatgcct    2340
aaaatacaaa atgtctcctc tagtgatttg ttgatgctct tgcgacagag tcctactcca    2400
catgggctat ccttatctga tctccaagaa gccaaatatg agacttttc tgatgatcca     2460
tcacctggag caatagacag taataacagc ctgtctgaaa tgacacactt caggccacag    2520
ctccatcaca gtggggacat ggtatttacc cctgagtcag gcctccaatt aagattaaat    2580
gagaaactgg ggacaactgc agcaacagag ttgaagaaac ttgatttcaa agtttctagt    2640
acatcaaata atctgatttc aacaattcca tcagacaatt tggcagcagg tactgataat    2700
acaagttcct taggaccccc aagtatgcca gttcattatg atagtcaatt agataccact    2760
ctatttggca aaaagtcatc tccccttact gagtctggtg gacctctgag cttgagtgaa    2820
gaaaataatg attcaaagtt gttagaatca ggtttaatga atagccaaga aagttcatgg    2880
ggaaaaaatg tatcgtcaac agagagtggt aggttattta agggaaaaag agctcatgga    2940
cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaa ttcaggaaga aatagaaaag     3600
aaggaaacat taatccaaga gaatgtagtt ttgcctcaga tacatacagt gactggcact    3660
aagaatttca tgaagaacct tttcttactg agcactaggc aaaatgtaga aggttcatat    3720
gacgggggcat atgctccagt acttcaagat tttaggtcat taaatgattc aacaaataga    3780
acaaagaaac acacagctca tttctcaaaa aaggggagg aagaaaactt ggaaggcttg     3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gacccccgagc accctcacac agatagacta caatgagaag   4080
gagaaagggg ccattactca gtctccctta tcagattgcc ttacgaggag tcatagcatc    4140
cctcaagcaa atagatctcc attacccatt gcaaaggtat catcatttcc atctattaga    4200
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320
aataaccttt cttagccat tctaaccttg gagatgactg gtgatcaaag agaggttggc     4380
tccctgggga caagtgccac aaaattcagtc acatacaaga aagttgagaa cactgttctc    4440
ccgaaaccag acttgcccaa aacatctggc aaagttgaat tgcttccaaa agttcacatt    4500
```

```
tatcagaagg acctattccc tacggaaact agcaatgggt ctcctggcca tctggatctc    4560
gtggaaggga gccttcttca gggaacagag ggagcgatta agtggaatga agcaaacaga    4620
cctggaaaag ttccctttct gagagtagca acagaaagct ctgcaaagac tccctccaag    4680
ctattggatc ctcttgcttg ggataaccac tatggtactc agataccaaa agaagagtgg    4740
aaatcccaag agaagtcacc agaaaaaaca gcttttaaga aaaggatac cattttgtcc     4800 ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga aacgccatca acgggaaata actcgtacta ctcttcagtc agatcaagag    4980
gaaattgact atgatgatac catatcagtt gaaatgaaga aggaagattt tgacatttat    5040
gatgaggatg aaaatcagag cccccgcagc tttcaaaaga aaacacgaca ctattttatt    5100
gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagccctt ataccgtgga gaactaaatg aacatttggg actcctgggg    5280
ccatatataa gagcagaagt tgaagataat atcatggtaa cttttcagaaa tcaggcctct   5340 cgtccctatt ccttctattc tagccttatt tcttatgagg aagatcagag gcaaggagca    5400
gaacctagaa aaaactttgt caagcctaat gaaaccaaaa cttacttttg gaaagtgcaa    5460
catcatatgg cacccactaa agatgagttt gactgcaaag cctgggctta tttctctgat    5520
gttgacctgg aaaagatgt gcactcaggc ctgattggac cccttctggt ctgccacact    5580
aacacactga accctgctca tgggagacaa gtgacagtac aggaatttgc tctgttttc    5640 accatctttg atgagaccaa agctggtac ttcactgaaa atatggaaag aaactgcagg    5700
gctccctgca atatccagat ggaagatccc acttttaaag agaattatcg cttccatgca    5760
atcaatgggc tacataatgg gtacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaaagaggag tataaaatgg cactgtacaa tctctatcca    5940
ggtgtttttg agacagtgga aatgttacca tccaaagctg gaattggcg ggtgaatgc     6000 cttattggcg agcatctaca tgctgggatg agcacacttt ttctggtgta cagcaataag    6060
tgtcagactc ccctgggaat ggcttctgga cacattagag attttcagat tacagcttca    6120
ggacaatatg gacagtgggc cccaaagctg gccagacttc attattccgg atcaatcaat    6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg gataaaaca caatatttt     6420 aaccctccaa ttattgctcg atacatccgt ttgcacccaa tcattatag cattcgcagc     6480 actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840
aaggtttttc agggaaatca agactccttc acacctgtgg tgaactctct agacccaccg    6900
```

```
ttactgactc gctaccttcg aattcacccc cagagttggg tgcaccagat tgccctgagg    6960
atggaggttc tgggctgcga ggcacaggac ctctac                              6996
```

<210> SEQ ID NO 45
<211> LENGTH: 1438
<212> TYPE: PRT
<213> ORGANISM: Artificial Sequence
<220> FEATURE:
<223> OTHER INFORMATION: Variant peptide

<400> SEQUENCE: 45

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
```

```
              340                 345                 350
Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
        370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Val Arg Phe Met Ala Tyr Thr
                420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Leu Asp
545                 550                 555                 560

Gln Phe Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
        740                 745                 750

Gln Arg Glu Ile Thr Arg Thr Thr Leu Gln Ser Asp Gln Glu Glu Ile
        755                 760                 765
```

```
Asp Tyr Asp Asp Thr Ile Ser Val Glu Met Lys Lys Glu Asp Phe Asp
        770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170
```

```
Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
    1340                1345                1350

Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 46
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 46
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca cctttttcaac    180 atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatcttcct     480
```

```
catgtggacc tggtaaaaga cttgaattca ggcctcattg gagccctact agtatgtaga    540
gaagggagtc tggccaagga aaagacacag accttgcaca aatttatact acttttgct    600
gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg gacagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaaagtccg atttatggca tacacagatg aaacctttaa gactcgtgaa   1320
gctattcagc atgaatcagg aatcttggga cctttacttt atggggaagt tggagacaca   1380
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctctggat   1680
caattcggaa acgagataat gtcagacaag aggaatgtca tcctgttttc tgtatttgat   1740
gagaaccgaa gctggtacct cacagagaat atacaacgct ttctcccaa tccagctgga   1800
gtgcagcttg aggatccaga gttccaagcc tccaacatca tgcacagcat caatggctat   1860
gtttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg ggtgccaca actcagactt tcggaacaga   2100
ggcatgaccg ccttactgaa ggtttctagt tgtgacaaga cactggtga ttattacgag   2160
gacagttatg aagatatttc agcatacttg ctgagtaaaa acaatgccat tgaaccaaga   2220
agcttctccc agaacccacc agtcttgaaa cgccatcaac gggaaataac tcgtactact   2280
cttcagtcag atcaagagga aattgactat gatgatacca tatcagttga aatgaagaag   2340
gaagattttg acatttatga tgaggatgaa aatcagagcc cccgcagctt tcaaaagaaa   2400
acacgacact attttattgc tgcagtggag aggctctggg attatgggat gagtagctcc   2460
ccacatgttc taagaaacag ggctcagagt ggcagtgtcc ctcagttcaa gaaagttgtt   2520
ttccaggaat ttactgatgg ctcctttact cagcccttat accgtggaga actaaatgaa   2580
catttgggac tcctggggcc atatataaga gcagaagttg aagataatat catggtaact   2640
ttcagaaatc aggcctctcg tccctattcc ttctattcta gccttatttc ttatgaggaa   2700
gatcagaggc aaggagcaga acctagaaaa aactttgtca agcctaatga aaccaaaact   2760
tactttttgga aagtgcaaca tcatatggca cccactaaag atgagtttga ctgcaaagcc   2820
```

```
tgggcttatt tctctgatgt tgacctggaa aaagatgtgc actcaggcct gattggaccc    2880
cttctggtct gccacactaa cacactgaac cctgctcatg ggagacaagt gacagtacag    2940
gaatttgctc tgtttttcac catctttgat gagaccaaaa gctggtactt cactgaaaat    3000
atggaaagaa actgcagggc tccctgcaat atccagatgg aagatcccac ttttaaagag    3060
aattatcgct tccatgcaat caatggctac ataatggata cactacctgg cttagtaatg    3120
gctcaggatc aaaggattcg atggtatctg ctcagcatgg gcagcaatga aacatccat    3180 tctattcatt tcagtggaca tgtgttcact gtacgaaaaa aagaggagta taaaatggca    3240
ctgtacaatc tctatccagg tgtttttgag acagtgaaaa tgttaccatc aaagctgga    3300 atttggcggg tggaatgcct tattggcgag catctacatg ctgggatgag cacttttt    3360 ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct tttcttggat caaggtggat    3540
ctgttggcac caatgattat tcacggcatc aagacccagg gtgcccgtca gaagttctcc    3600
agcctctaca tctctcagtt tatcatcatg tatagtcttg atgggaagaa gtggcagact    3660
tatcgaggaa attccactgg aaccttaatg gtcttctttg caatgtggga ttcatctggg    3720
ataaaacaca atattttaa ccctccaatt attgctcgat acatccgttt gcacccaact    3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggga taaaatctct gcttaccagc    4080
atgtatgtga aggagttcct catctccagc agtcaagatg gccatcagtg gactctcttt    4140
tttcagaatg gcaaagtaaa ggttttttcag ggaaatcaag actccttcac acctgtggtg    4200
aactctctag acccaccgtt actgactcgc taccttcgaa ttcaccccca gagttgggtg    4260
caccagattg ccctgaggat ggaggttctg ggctgcgagg cacaggacct ctac         4314
```

<210> SEQ ID NO 47
<211> LENGTH: 1438
<212> TYPE: PRT
<213> ORGANISM: Artificial Sequence
<220> FEATURE:
<223> OTHER INFORMATION: Variant peptide

<400> SEQUENCE: 47

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
```

```
            100                 105                 110
Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
            130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                    165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                    245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                    325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
        370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                    405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                    485                 490                 495

His Leu Lys Asp Phe Pro Ile Leu Pro Gly Glu Ile Phe Lys Tyr Lys
                500                 505                 510

Trp Thr Val Thr Val Glu Val Gly Pro Thr Lys Ser Asp Pro Arg Cys
            515                 520                 525
```

```
Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560

Gln Phe Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Val Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
                740                 745                 750

Gln Arg Glu Ile Thr Arg Thr Thr Leu Gln Ser Asp Gln Glu Glu Ile
            755                 760                 765

Asp Tyr Asp Asp Thr Ile Ser Val Glu Met Lys Lys Glu Asp Phe Asp
        770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
                820                 825                 830

Val Pro Gln Phe Lys Lys Val Val Phe Gln Glu Phe Thr Asp Gly Ser
            835                 840                 845

Phe Thr Gln Pro Leu Tyr Arg Gly Glu Leu Asn Glu His Leu Gly Leu
        850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                885                 890                 895

Ser Tyr Glu Glu Asp Gln Arg Gln Gly Ala Glu Pro Arg Lys Asn Phe
                900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
        930                 935                 940
```

```
Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
            965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

Ala Gln Ile Thr Ala Ser Ser Tyr Phe Thr Asn Met Phe Ala Thr
    1295                1300                1305

Trp Ser Pro Ser Lys Ala Arg Leu His Leu Gln Gly Arg Ser Asn
    1310                1315                1320

Ala Trp Arg Pro Gln Val Asn Asn Pro Lys Glu Trp Leu Gln Val
    1325                1330                1335

Asp Phe Gln Lys Thr Met Lys Val Thr Gly Val Thr Thr Gln Gly
```

```
Val Lys Ser Leu Leu Thr Ser Met Tyr Val Lys Glu Phe Leu Ile
    1355                1360                1365

Ser Ser Ser Gln Asp Gly His Gln Trp Thr Leu Phe Phe Gln Asn
    1370                1375                1380

Gly Lys Val Lys Val Phe Gln Gly Asn Gln Asp Ser Phe Thr Pro
    1385                1390                1395

Val Val Asn Ser Leu Asp Pro Pro Leu Leu Thr Arg Tyr Leu Arg
    1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 48
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 48
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg agccctact agtatgtaga     540
gaagggagtc tggccaagga aaagacacag accttgcaca aatttatact acttttgct     600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctaccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca acactcttg     900
atggaccttg acagtttct actgttttgt catatctctt cccaccaaca tgatggcatg     960
gaagcttatg tcaaagtaga cagctgtcca gaggaacccc aactacgaat gaaaaataat    1020
gaagaagcgg aagactatga tgatgatctt actgattctg aaatggatgt ggtcaggttt    1080
gatgatgaca actctccttc ctttatccaa attcgctcag ttgccaagaa gcatcctaaa    1140
acttgggtac attacattgc tgctgaagag gaggactggg actatgctcc cttagtcctc    1200
gcccccgatg acagaagtta taaagtcaa tatttgaaca atggccctca gcggattggt    1260
aggaagtaca aaaagtccg atttatggca tacacagatg aaacctttaa gacgcgtgaa    1320
gctattcagc atgaatcagg aatcttggga cctttacttt atgggaagt tggagacaca    1380
ctgttgatta tatttaagaa tcaagcaagc agaccatata cactctaccc tcacggaatc    1440
actgatgtcc gtccttgta ttcaaggaga ttaccaaaag gtgtaaaaca tttgaaggat    1500
```

-continued

```
tttccaattc tgccaggaga aatattcaaa tataaatgga cagtgactgt agaagttggg    1560
ccaactaaat cagatccgcg gtgcctgacc cgctattact ctagtttcgt taatatggag    1620
agagatctag cttcaggact cattggccct ctcctcatct gctacaaaga atctctggat    1680
caattcggaa acgagataat gtcagacaag aggaatgtca tcctgttttc tgtatttgat    1740
gagaaccgaa gctggtacct cacagagaat atacaacgct ttctccccaa tccagctgga    1800
gtgcagcttg aggatccaga gttccaagcc tccaacatca tgcacagcat caatggctat    1860
gttttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgtagacac actcacccta ttcccattct caggagaaac tgtcttcatg    2040
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttacg aagatatttc agcatacttg ctgagtaaaa acaatgccat tgaacctagg    2220
agcttctctc agaatccacc agtcttgaaa cgccatcaac gggaaataac tcgtacgact    2280
cttcagtcag atcaagagga aattgactat gatgatacca tatcagttga aatgaagaag    2340
gaagattttg acatttatga tgaggatgaa aatcagagcc cccgcagctt tcaaaagaaa    2400
acacgacact attttattgc tgcagtggag aggctctggg attatgggat gagtagctcc    2460
ccacatgttc taagaaacag ggctcagagt ggcagtgtcc ctcagttcaa gaaagttgtt    2520
ttccaggaat ttactgatgg ctcctttact cagcccttat accgtggaga actaaatgaa    2580
catttgggac tcctggggcc atatataaga gcagaagttg aagataatat catggtaact    2640
ttcagaaatc aggcctctcg tccctattcc ttctattcta gccttatttc ttatgaggaa    2700
gatcagaggc aaggagcaga acctagaaaa actttgtca agcctaatga aaccaaaact    2760
tactttggga aagtgcaaca tcatatggca cccactaaag atgagtttga ctgcaaagcc    2820
tgggcttatt tctctgatgt tgacctggaa aaagatgtgc actcaggcct gattggaccc    2880
cttctggtct gccacactaa cacactgaac cctgctcatg ggagacaagt gacagtacag    2940
gaatttgctc tgttttcac catctttgat gagaccaaaa gctggtactt cactgaaaat    3000
atggaaagaa actgcagggc tccctgcaat atccagatgg aagatccac ttttaaagag    3060
aattatcgct tccatgcaat caatggctac ataatggata cactacctgg cttagtaatg    3120
gctcaggatc aaaggattcg atggtatctg ctcagcatgg gcagcaatga aacatccat     3180
tctattcatt tcagtggaca tgtgttcact gtacgaaaaa aagaggagta taaaatggca    3240
ctgtacaatc tctatccagg tgttttttgag acagtggaaa tgttaccatc caaagctgga    3300
atttggcggg tggaatgcct tattggcgag catctacatg ctgggatgag cacactttt    3360
ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct tttcttggat caaggtggat    3540
ctgttggcac caatgattat tcacggcatc aagacccagg gtgcccgtca gaagttctcc    3600
agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atattttaa ccctccaatt attgctcgat acatccgttt gcacccaact    3780
cattatagca ttcgcagcac tcttcgcatg gagttgatgg gctgtgattt aaatagttgc    3840
```

```
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggag taaaatctct gcttaccagc    4080
atgtatgtga aggagttcct catctccagc agtcaagatg ccatcagtg gactctcttt     4140 tttcagaatg gcaaagtaaa ggttttcag ggaaatcaag actccttcac acctgtggtg     4200
aactctctag acccaccgtt actgactcgc taccttcgaa ttcaccccca gagttgggtg    4260
caccagattg ccctgaggat ggaggttctg ggctgcgagg cacaggacct ctac           4314
```

<210> SEQ ID NO 49
<211> LENGTH: 2332
<212> TYPE: PRT
<213> ORGANISM: Artificial Sequence
<220> FEATURE:
<223> OTHER INFORMATION: Variant peptide

<400> SEQUENCE: 49

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285
```

-continued

```
Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Pro Arg Ser Phe Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Leu Asp
545                 550                 555                 560

Gln Trp Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700
```

```
Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
        770                 775                 780

Val Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
            930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
```

-continued

```
            1115                1120                1125

Leu Val Ser Leu Gly Pro Glu Lys Ser Val Gly Gln Asn Phe
    1130                1135                1140

Leu Ser Glu Lys Asn Lys Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515
```

```
Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905
```

```
Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
```

```
                2300            2305               2310
Val His Gln Ile Ala Leu Arg Met Glu Val Leu Gly Cys Glu Ala
        2315                2320             2325
Gln Asp Leu Tyr
        2330

<210> SEQ ID NO 50
<211> LENGTH: 6996
<212> TYPE: DNA
<213> ORGANISM: Artificial Sequence
<220> FEATURE:
<223> OTHER INFORMATION: Variant nucleotide

<400> SEQUENCE: 50
gccaccagaa gatactacct gggtgcagtg gaactgtcat gggactatat gcaaagtgat      60
ctcggtgagc tgcctgtgga cgcaagattt cctcctagag tgccaaaatc tttttccattc   120 aacacctcag tcgtgtacaa aaagactctg tttgtagaat tcacggttca ccttttcaac    180
atcgctaagc caaggccacc ctggatgggt ctgctaggtc ctaccatcca ggctgaggtt    240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg agccctact agtatgtaga    540 gaagggagtc tggccaagga aaagacacag accttgcaca aatttatact acttttttgct  600 gtatttgatg aagggaaaag ttggcactca gaaacaaaga actccttgat gcaggatagg   660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg acagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa ccccgctcat cgccaagaa gcatcctaaa    1140 acttgggtac attacattgc tgctgaagag gaggactggg actatgctcc cttagtcctc    1200
gcccccgatg acagaagtta taaagtcaa tatttgaaca atggccctca gcggattggt    1260
aggaagtaca aaaagtccg atttatggca tacacagatg aaaccttaa gactcgtgaa     1320 gctattcagc atgaatcagg aatcttggga cctttacttt atggggaagt tggagacaca   1380
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga atattcaaa tataaatgga cagtgactgt agaagatggg    1560
ccaactaaat cagatcctcg gtgcctgacc cgctattact ctagtttcgt taatatggag   1620
agagatctag cttcaggact cattggccct ctcctcatct gctacaaaga atctctggat   1680
caatggggaa acgagataat gtcagacaag aggaatgtca tcctgttttc tgtatttgat   1740
gagaaccgaa gctggtacct cacagagaat atacaacgct ttctccccaa tccagctgga   1800
gtgcagcttg aggatccaga gttccaagcc tccaacatca tgcacagcat caatggctat   1860
```

```
gtttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcaccota ttcccattct caggagaaac tgtcttcatg    2040
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
agcttctccc agaattcaag acaccctagc actaggcaaa agcaatttaa tgccaccaca    2280
attccagaaa atgacataga gaagactgac ccttggtttg cacacagaac acctatgcct    2340
aaaatacaaa atgtctcctc tagtgatttg ttgatgctct gcgacagag tcctactcca     2400 catgggctat ccttatctga tctccaagaa gccaaatatg agacttttc tgatgatcca     2460 tcacctggag caatagacag taataacagc ctgtctgaaa tgacacactt caggccacag    2520
ctccatcaca gtggggacat ggtatttacc cctgagtcag gcctccaatt aagattaaat    2580
gagaaactgg gacaactgc agcaacagag ttgaagaaac ttgatttcaa agtttctagt     2640
acatcaaata atctgatttc aacaattcca tcagacaatt tggcagcagg tactgataat    2700
acaagttcct taggacccc aagtatgcca gttcattatg atagtcaatt agataccact     2760
ctatttggca aaaagtcatc tcccttact gagtctggtg gacctctgag cttgagtgaa     2820
gaaaataatg attcaaagtt gttagaatca ggtttaatga atagccaaga aagttcatgg    2880
ggaaaaaatg tatcgtcaac agagagtggt aggttattta aagggaaaag agctcatgga    2940
cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagttttaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt taagatgcta    3300
ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca agagatggt ttttccaagc agcagaaacc tatttcttac taacttggat     3540
aatttacatg aaaataatac acacaatcaa gaaaaaaaaa ttcaggaaga atagaaaag    3600 aaggaaacat taatccaaga gaatgtagtt ttgcctcaga tacatacagt gactggcact    3660
aagaatttca tgaagaacct tttcttactg agcactaggc aaaatgtaga aggttcatat    3720
gacggggcat atgctccagt acttcaagat tttaggtcat taaatgattc aacaaataga    3780
acaaagaaac acacagctca tttctcaaaa aaggggagg aagaaaactt ggaaggcttg     3840
ggaaatcaaa ccaagcaaat tgtagagaaa tatgcatgca ccacaaggat atctcctaat    3900
acaagccagc agaattttgt cacgcaacgt agtaagagag ctttgaaaca attcagactc    3960
ccactagaag aaacagaact tgaaaaaagg ataattgtgg atgacacctc aacccagtgg    4020
tccaaaaaca tgaaacattt gaccccgagc accctcacac agatagacta caatgagaag    4080
gagaaagggg ccattactca gtctcccta tcagattgcc ttacgaggag tcatagcatc     4140
cctcaagcaa atagatctcc attacccatt gcaaaggtat catcatttcc atctattaga    4200
```

```
cctatatatc tgaccagggt cctattccaa gacaactctt ctcatcttcc agcagcatct    4260
tatagaaaga aagattctgg ggtccaagaa agcagtcatt tcttacaagg agccaaaaaa    4320
aataaccttt ctttagccat tctaaccttg gagatgactg gtgatcaaag agaggttggc    4380
tccctgggga caagtgccac aaattcagtc acatacaaga aagttgagaa cactgttctc    4440
ccgaaaccag acttgcccaa aacatctggc aaagttgaat tgcttccaaa agttcacatt    4500
tatcagaagg acctattccc tacggaaact agcaatgggc tcctggccca tctggatctc    4560
gtggaaggga gccttcttca gggaacagag ggagcgatta agtggaatga agcaaacaga    4620
cctggaaaaa ttcccttct gagagtagca acagaaagct ctgcaaagac tccctccaag    4680
ctattggatc ctcttgcttg ggataaccac tatggtactc agataccaaa agaagagtgg    4740
aaatcccaag agaagtcacc agaaaaaaca gcttttaaga aaaaggatac cattttgtcc    4800
ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga aacgccatca acgggaaata actcgtacta ctcttcagtc agatcaagag    4980
gaaattgact atgatgatac catatcagtt gaaatgaaga aggaagattt tgacatttat    5040
gatgaggatg aaaatcagag cccccgcagc tttcaaaaga aaacacgaca ctatttatt    5100 gctgcagtgg agaggctctg ggattatggg atgagtagct ccccacatgt tctaagaaac    5160
agggctcaga gtggcagtgt ccctcagttc aagaaagttg ttttccagga atttactgat    5220 ggctcctta ctcagccctt ataccgtgga gaactaaatg aacatttggg actcctgggg    5280
ccatatataa gagcagaagt tgaagataat atcatggtaa ctttcagaaa tcaggcctct    5340
cgtccctatt ccttctattc tagccttatt tcttatgagg aagatcagag gcaaggagca    5400
gaacctagaa aaaactttgt caagcctaat gaaaccaaaa cttactttg gaaagtgcaa    5460 catcatatgg cacccactaa agatgagttt gactgcaaag cctgggctta tttctctgat    5520
gttgacctgg aaaagatgt gcactcaggc ctgattggac cccttctggt ctgccacact    5580
aacacactga accctgctca tgggagacaa gtgacagtac aggaatttgc tctgttttc    5640 accatctttg atgagaccaa aagctggtac ttcactgaaa atatggaaag aaactgcagg    5700
gctccctgca atatccagat ggaagatccc acttttaaag agaattatcg cttccatgca    5760
atcaatggct acataatgga tacactacct ggcttagtaa tggctcagga tcaaaggatt    5820
cgatggtatc tgctcagcat gggcagcaat gaaaacatcc attctattca tttcagtgga    5880
catgtgttca ctgtacgaaa aaaagaggag tataaaatgg cactgtacaa tctctatcca    5940 ggtgttttg agacagtgga aatgttacca tccaaagctg gaatttggcg ggtggaatgc    6000
cttattggcg agcatctaca tgctgggatg agcacctttt ttctggtgta cagcaataag    6060
tgtcagactc ccctgggaat ggcttctgga cacattagag attttcagat tacagcttca    6120
ggacaatatg gacagtgggc cccaaagctg gccagacttc attattccgg atcaatcaat    6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg ggataaaaca caatatttt    6420 aacccctccaa ttattgctcg atacatccgt ttgcacccaa tcattatag cattcgcagc    6480 actcttcgca tggagttgat gggctgtgat ttaaatagtt gcagcatgcc attgggaatg    6540
gagagtaaag caatatcaga tgcacagatt actgcttcat cctactttac caatatgttt    6600
```

-continued

```
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840 aaggttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctac                              6996
```

<210> SEQ ID NO 51
<211> LENGTH: 1438
<212> TYPE: PRT
<213> ORGANISM: Artificial Sequence
<220> FEATURE:
<223> OTHER INFORMATION: Variant peptide

<400> SEQUENCE: 51

```
Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285
```

```
Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
            355                 360                 365

Ile Gln Pro Arg Ser Phe Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Leu Asp
545                 550                 555                 560

Gln Trp Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
```

```
            705                 710                 715                 720
        Asp Ser Tyr Glu Asp Ile Ser Ala Tyr Leu Leu Ser Lys Asn Asn Ala
                        725                 730                 735
        Ile Glu Pro Arg Ser Phe Ser Gln Asn Pro Val Leu Lys Arg His
                        740                 745                 750
        Gln Arg Glu Ile Thr Arg Thr Thr Leu Gln Ser Asp Gln Glu Ile
                        755                 760                 765
        Asp Tyr Asp Asp Thr Ile Ser Val Glu Met Lys Lys Glu Asp Phe Asp
                        770                 775                 780
        Ile Tyr Asp Glu Asp Glu Asn Gln Ser Pro Arg Ser Phe Gln Lys Lys
        785                 790                 795                 800
        Thr Arg His Tyr Phe Ile Ala Ala Val Glu Arg Leu Trp Asp Tyr Gly
                        805                 810                 815
        Met Ser Ser Ser Pro His Val Leu Arg Asn Arg Ala Gln Ser Gly Ser
                        820                 825                 830
        Val Pro Gln Phe Lys Lys Val Val Phe Gln Glu Phe Thr Asp Gly Ser
                        835                 840                 845
        Phe Thr Gln Pro Leu Tyr Arg Gly Glu Leu Asn Glu His Leu Gly Leu
                        850                 855                 860
        Leu Gly Pro Tyr Ile Arg Ala Glu Val Glu Asp Asn Ile Met Val Thr
        865                 870                 875                 880
        Phe Arg Asn Gln Ala Ser Arg Pro Tyr Ser Phe Tyr Ser Ser Leu Ile
                        885                 890                 895
        Ser Tyr Glu Glu Asp Gln Arg Gln Gly Ala Glu Pro Arg Lys Asn Phe
                        900                 905                 910
        Val Lys Pro Asn Glu Thr Lys Thr Tyr Phe Trp Lys Val Gln His His
                        915                 920                 925
        Met Ala Pro Thr Lys Asp Glu Phe Asp Cys Lys Ala Trp Ala Tyr Phe
                        930                 935                 940
        Ser Asp Val Asp Leu Glu Lys Asp Val His Ser Gly Leu Ile Gly Pro
        945                 950                 955                 960
        Leu Leu Val Cys His Thr Asn Thr Leu Asn Pro Ala His Gly Arg Gln
                        965                 970                 975
        Val Thr Val Gln Glu Phe Ala Leu Phe Phe Thr Ile Phe Asp Glu Thr
                        980                 985                 990
        Lys Ser Trp Tyr Phe Thr Glu Asn Met Glu Arg Asn Cys Arg Ala Pro
                        995                 1000                1005
        Cys Asn Ile Gln Met Glu Asp Pro Thr Phe Lys Glu Asn Tyr Arg
                        1010                1015                1020
        Phe His Ala Ile Asn Gly Tyr Ile Met Asp Thr Leu Pro Gly Leu
                        1025                1030                1035
        Val Met Ala Gln Asp Gln Arg Ile Arg Trp Tyr Leu Leu Ser Met
                        1040                1045                1050
        Gly Ser Asn Glu Asn Ile His Ser Ile His Phe Ser Gly His Val
                        1055                1060                1065
        Phe Thr Val Arg Lys Lys Glu Glu Tyr Lys Met Ala Leu Tyr Asn
                        1070                1075                1080
        Leu Tyr Pro Gly Val Phe Glu Thr Val Glu Met Leu Pro Ser Lys
                        1085                1090                1095
        Ala Gly Ile Trp Arg Val Glu Cys Leu Ile Gly Glu His Leu His
                        1100                1105                1110
        Ala Gly Met Ser Thr Leu Phe Leu Val Tyr Ser Asn Lys Cys Gln
                        1115                1120                1125
```

```
Thr Pro Leu Gly Met Ala Ser Gly His Ile Arg Asp Phe Gln Ile
    1130            1135                1140

Thr Ala Ser Gly Gln Tyr Gly Gln Trp Ala Pro Lys Leu Ala Arg
    1145            1150                1155

Leu His Tyr Ser Gly Ser Ile Asn Ala Trp Ser Thr Lys Glu Pro
    1160            1165                1170

Phe Ser Trp Ile Lys Val Asp Leu Leu Ala Pro Met Ile Ile His
    1175            1180                1185

Gly Ile Lys Thr Gln Gly Ala Arg Gln Lys Phe Ser Ser Leu Tyr
    1190            1195                1200

Ile Ser Gln Phe Ile Ile Met Tyr Ser Leu Asp Gly Lys Lys Trp
    1205            1210                1215

Gln Thr Tyr Arg Gly Asn Ser Thr Gly Thr Leu Met Val Phe Phe
    1220            1225                1230

Gly Asn Val Asp Ser Ser Gly Ile Lys His Asn Ile Phe Asn Pro
    1235            1240                1245

Pro Ile Ile Ala Arg Tyr Ile Arg Leu His Pro Thr His Tyr Ser
    1250            1255                1260

Ile Arg Ser Thr Leu Arg Met Glu Leu Met Gly Cys Asp Leu Asn
    1265            1270                1275

Ser Cys Ser Met Pro Leu Gly Met Glu Ser Lys Ala Ile Ser Asp
    1280            1285                1290

Ala Gln Ile Thr Ala Ser Ser Tyr Phe Thr Asn Met Phe Ala Thr
    1295            1300                1305

Trp Ser Pro Ser Lys Ala Arg Leu His Leu Gln Gly Arg Ser Asn
    1310            1315                1320

Ala Trp Arg Pro Gln Val Asn Asn Pro Lys Glu Trp Leu Gln Val
    1325            1330                1335

Asp Phe Gln Lys Thr Met Lys Val Thr Gly Val Thr Thr Gln Gly
    1340            1345                1350

Val Lys Ser Leu Leu Thr Ser Met Tyr Val Lys Glu Phe Leu Ile
    1355            1360                1365

Ser Ser Ser Gln Asp Gly His Gln Trp Thr Leu Phe Phe Gln Asn
    1370            1375                1380

Gly Lys Val Lys Val Phe Gln Gly Asn Gln Asp Ser Phe Thr Pro
    1385            1390                1395

Val Val Asn Ser Leu Asp Pro Pro Leu Leu Thr Arg Tyr Leu Arg
    1400            1405                1410

Ile His Pro Gln Ser Trp Val His Gln Ile Ala Leu Arg Met Glu
    1415            1420                1425

Val Leu Gly Cys Glu Ala Gln Asp Leu Tyr
    1430            1435

<210> SEQ ID NO 52
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 52
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
```

```
atcgctaagc caaggccacc ctggatgggt ctgctaggtc ctaccatcca ggctgaggtt    240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttgct    600 gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctgccag gtctgattgg atgccacagg aaatcagtct attggcatgt gattggaatg    780
ggcaccactc ctgaagtgca ctcaatattc ctcgaaggtc acacatttct tgtgaggaac    840
catcgccagg cgtccttgga aatctcgcca ataactttcc ttactgctca aacactcttg    900
atggaccttg gacagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa ccccgctcat cgccaagaa gcatcctaaa    1140 acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaagtccg atttatggca tacacagatg aaacctttaa gactcgtgaa    1320
gctattcagc atgaatcagg aatcttggga ccttttacttt atggggaagt tggagacaca   1380
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctctggat   1680
caatggggaa acgagataat gtcagacaag aggaatgtca tcctgttttc tgtatttgat   1740
gagaaccgaa gctggtacct cacagagaat atacaacgct tctcccccaa tccagctgga   1800
gtgcagcttg aggatccaga gttccaagcc tccaacatca tgcacagcat caatggctat   1860 gttttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcacccta ttcccattct caggagaaac tgtcttcatg   2040
tcgatggaaa acccaggtct atggattctg ggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat tgaaccaaga   2220
agcttctccc agaacccacc agtcttgaaa cgccatcaac gggaaataac tcgtactact   2280
cttcagtcag atcaagagga aattgactat gatgatacca tatcagttga aatgaagaag   2340
gaagattttg acatttatga tgaggatgaa aatcagagcc cccgcagctt tcaaaagaaa   2400
acacgacact attttattgc tgcagtggag aggctctggg attatgggat gagtagctcc   2460
ccacatgttc taagaaacag ggctcagagt ggcagtgtcc ctcagttcaa gaaagttgtt   2520
```

```
ttccaggaat tactgatgg ctcctttact cagcccttat accgtggaga actaaatgaa   2580
catttgggac tcctgggcc atatataaga gcagaagttg aagataatat catggtaact   2640
ttcagaaatc aggcctctcg tccctattcc ttctattcta gccttatttc ttatgaggaa   2700
gatcagaggc aaggagcaga acctagaaaa aactttgtca agcctaatga aaccaaaact   2760
tacttttgga aagtgcaaca tcatatggca cccactaaag atgagtttga ctgcaaagcc   2820
tgggcttatt tctctgatgt tgacctggaa aaagatgtgc actcaggcct gattggaccc   2880
cttctggtct gccacactaa cacactgaac cctgctcatg ggagacaagt gacagtacag   2940
gaatttgctc tgttttttcac catctttgat gagaccaaaa gctggtactt cactgaaaat   3000
atggaaagaa actgcagggc tccctgcaat atccagatgg aagatcccac ttttaaagag   3060
aattatcgct tccatgcaat caatggctac ataatggata cactacctgg cttagtaatg   3120
gctcaggatc aaaggattcg atggtatctg ctcagcatgg gcagcaatga aaacatccat   3180
tctattcatt tcagtggaca tgtgttcact gtacgaaaaa aagaggagta taaaatggca   3240
ctgtacaatc tctatccagg tgttttttgag acagtggaaa tgttaccatc caaagctgga   3300
atttggcggg tggaatgcct tattggcgag catctacatg ctgggatgag cacactttttt  3360
ctggtgtaca gcaataagtg tcagactccc ctgggaatgg cttctggaca cattagagat   3420
tttcagatta cagcttcagg acaatatgga cagtgggccc caaagctggc cagacttcat   3480
tattccggat caatcaatgc ctggagcacc aaggagccct ttcttggat caaggtggat   3540
ctgttggcac caatgattat tcacggcatc aagacccagg gtgcccgtca gaagttctcc   3600
agcctctaca tctctcagtt tatcatcatg tatagtcttg atgggaagaa gtggcagact   3660
tatcgaggaa attccactgg aaccttaatg gtcttctttg gcaatgtgga ttcatctggg   3720
ataaaacaca atattttttaa ccctccaatt atggctcgat acatccgttt gcacccaact   3780
cattatagca ttcgcagcac tcttcgcatg gagttgatgg gctgtgattt aaatagttgc   3840
agcatgccat tgggaatgga gagtaaagca atatcagatg cacagattac tgcttcatcc   3900
tactttacca atatgtttgc cacctggtct ccttcaaaag ctcgacttca cctccaaggg   3960
aggagtaatg cctggagacc tcaggtgaat aatccaaaag agtggctgca agtggacttc   4020
cagaagacaa tgaaagtcac aggagtaact actcagggag taaaatctct gcttaccagc   4080
atgtatgtga aggagttcct catctccagc agtcaagatg ccatcagtg gactctctt    4140
tttcagaatg gcaaagtaaa ggttttttcag ggaaatcaag actccttcac acctgtggtg   4200
aactctctag acccaccgtt actgactcgc taccttcgaa ttcaccccca gagttgggtg   4260
caccagattg ccctgaggat ggaggttctg ggctgcgagg cacaggacct ctac          4314
```

```
<210> SEQ ID NO 53
<211> LENGTH: 1438
<212> TYPE: PRT
<213> ORGANISM: Artificial Sequence
<220> FEATURE:
<223> OTHER INFORMATION: Variant peptide

<400> SEQUENCE: 53

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45
```

Thr Leu Phe Val Glu Phe Thr Asp His Leu Phe Asn Ile Ala Lys Pro
 50                     55                      60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Pro Arg Ser Phe Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile

```
            465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Val Gly Pro Thr Lys Ser Asp Pro Arg Cys
                515                 520                 525
Leu Thr Arg Tyr Tyr Ser Ser Phe Val Asn Met Glu Arg Asp Leu Ala
            530                 535                 540
Ser Gly Leu Ile Gly Pro Leu Leu Ile Cys Tyr Lys Glu Ser Leu Asp
545                 550                 555                 560
Gln Trp Gly Asn Glu Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
            610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Val Asp Thr Leu Thr Leu Phe Pro
                660                 665                 670
Phe Ser Gly Glu Thr Val Phe Met Ser Met Glu Asn Pro Gly Leu Trp
                675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Pro Pro Val Leu Lys Arg His
                740                 745                 750
Gln Arg Glu Ile Thr Arg Thr Thr Leu Gln Ser Asp Gln Glu Glu Ile
            755                 760                 765
Asp Tyr Asp Asp Thr Ile Ser Val Glu Met Lys Lys Glu Asp Phe Asp
            770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Ser Pro His Val Leu Arg Asn Arg Ala Gln Ser Gly Ser
            820                 825                 830
Val Pro Gln Phe Lys Lys Val Val Phe Gln Glu Phe Thr Asp Gly Ser
            835                 840                 845
Phe Thr Gln Pro Leu Tyr Arg Gly Glu Leu Asn Glu His Leu Gly Leu
            850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
```

-continued

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
        915                 920                 925

Met Ala Pro Thr Lys Asp Glu Phe Asp Cys Lys Ala Trp Ala Tyr Phe
    930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
        995                 1000                1005

Cys Asn Ile Gln Met Glu Asp Pro Thr Phe Lys Glu Asn Tyr Arg
    1010                1015                1020

Phe His Ala Ile Asn Gly Tyr Ile Met Asp Thr Leu Pro Gly Leu
    1025                1030                1035

Val Met Ala Gln Asp Gln Arg Ile Arg Trp Tyr Leu Leu Ser Met
    1040                1045                1050

Gly Ser Asn Glu Asn Ile His Ser Ile His Phe Ser Gly His Val
    1055                1060                1065

Phe Thr Val Arg Lys Lys Glu Glu Tyr Lys Met Ala Leu Tyr Asn
    1070                1075                1080

Leu Tyr Pro Gly Val Phe Glu Thr Val Glu Met Leu Pro Ser Lys
    1085                1090                1095

Ala Gly Ile Trp Arg Val Glu Cys Leu Ile Gly Glu His Leu His
    1100                1105                1110

Ala Gly Met Ser Thr Leu Phe Leu Val Tyr Ser Asn Lys Cys Gln
    1115                1120                1125

Thr Pro Leu Gly Met Ala Ser Gly His Ile Arg Asp Phe Gln Ile
    1130                1135                1140

Thr Ala Ser Gly Gln Tyr Gly Gln Trp Ala Pro Lys Leu Ala Arg
    1145                1150                1155

Leu His Tyr Ser Gly Ser Ile Asn Ala Trp Ser Thr Lys Glu Pro
    1160                1165                1170

Phe Ser Trp Ile Lys Val Asp Leu Leu Ala Pro Met Ile Ile His
    1175                1180                1185

Gly Ile Lys Thr Gln Gly Ala Arg Gln Lys Phe Ser Ser Leu Tyr
    1190                1195                1200

Ile Ser Gln Phe Ile Ile Met Tyr Ser Leu Asp Gly Lys Lys Trp
    1205                1210                1215

Gln Thr Tyr Arg Gly Asn Ser Thr Gly Thr Leu Met Val Phe Phe
    1220                1225                1230

Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser
    1250                1255                1260

Ile Arg Ser Thr Leu Arg Met Glu Leu Met Gly Cys Asp Leu Asn
    1265                1270                1275

Ser Cys Ser Met Pro Leu Gly Met Glu Ser Lys Ala Ile Ser Asp
    1280                1285                1290

| Ala | Gln | Ile | Thr | Ala | Ser | Ser | Tyr | Phe | Thr | Asn | Met | Phe | Ala | Thr |
| | 1295 | | | | 1300 | | | | | 1305 | | | | |

Trp Ser Pro Ser Lys Ala Arg Leu His Leu Gln Gly Arg Ser Asn
    1310            1315                1320

Ala Trp Arg Pro Gln Val Asn Asn Pro Lys Glu Trp Leu Gln Val
    1325            1330                1335

Asp Phe Gln Lys Thr Met Lys Val Thr Gly Val Thr Thr Gln Gly
    1340            1345                1350

Val Lys Ser Leu Leu Thr Ser Met Tyr Val Lys Glu Phe Leu Ile
    1355            1360                1365

Ser Ser Ser Gln Asp Gly His Gln Trp Thr Leu Phe Phe Gln Asn
    1370            1375                1380

Gly Lys Val Lys Val Phe Gln Gly Asn Gln Asp Ser Phe Thr Pro
    1385            1390                1395

Val Val Asn Ser Leu Asp Pro Pro Leu Leu Thr Arg Tyr Leu Arg
    1400            1405                1410

Ile His Pro Gln Ser Trp Val His Gln Ile Ala Leu Arg Met Glu
    1415            1420                1425

Val Leu Gly Cys Glu Ala Gln Asp Leu Tyr
    1430            1435

<210> SEQ ID NO 54
<211> LENGTH: 4314
<212> TYPE: DNA
<213> ORGANISM: Artificial Sequence
<220> FEATURE:
<223> OTHER INFORMATION: Variant nucleotide

<400> SEQUENCE: 54

```
gccaccagaa gatactacct gggtgcagtg gaactgtcat gggactatat gcaaagtgat     60
ctcggtgagc tgcctgtgga cgcaagattt cctcctagag tgccaaaatc ttttccattc    120
aacacctcag tcgtgtacaa aaagactctg tttgtagaat tcacggatca ccttttcaac    180
atcgctaagc caaggccacc ctggatgggt ctgctaggtc ctaccatcca ggctgaggtt    240
tatgatacag tggtcattac acttaagaac atggcttccc atcctgtcag tcttcatgct    300
gttggtgtat cctactggaa agcttctgag ggagctgaat atgatgatca gaccagtcaa    360
agggagaaag aagatgataa agtcttccct ggtggaagcc atacatatgt ctggcaggtc    420
ctgaaagaga atggtccaat ggcctctgac ccactgtgcc ttacctactc atatctttct    480
catgtggacc tggtaaaaga cttgaattca ggcctcattg gagccctact agtatgtaga    540
gaagggagtc tggccaagga aaagacacag accttgcaca aatttatact acttttgct    600
gtatttgatg aagggaaaag ttggcactca gaaacaaaga actccttgat gcaggatagg    660
gatgctgcat ctgctcgggc ctggcctaaa atgcacacag tcaatggtta tgtaaacagg    720
tctctaccag gtctgattgg atgccacagg aaatcagtct attggcatgt gattggaatg    780
ggcaccactc ctgaagtgca ctcaatattc ctcgaaggtc acacatttct gtgaggaac    840
catcgccagg cgtccttgga aatctcgcca ataactttcc ttactgctca aacactcttg    900
atggaccttg acagtttct actgttttgt catatctctt cccaccaaca tgatggcatg    960
gaagcttatg tcaaagtaga cagctgtcca gaggaaccc aactacgaat gaaaataat    1020
gaagaagcgg aagactatga tgatgatctt actgattctg aaatggatgt ggtcaggttt    1080
gatgatgaca actctcctcc ctttatccaa ccccgctcat cgccaagaa gcatcctaaa    1140
acttgggtac attacattgc tgctgaagag gaggactggg actatgctcc cttagtcctc    1200
```

-continued

```
gcccccgatg acagaagtta taaaagtcaa tatttgaaca atggccctca gcggattggt    1260
aggaagtaca aaaaagtccg atttatggca tacacagatg aaacctttaa gacgcgtgaa    1320
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagttggg    1560
ccaactaaat cagatccgcg gtgcctgacc cgctattact ctagtttcgt taatatggag    1620
agagatctag cttcaggact cattggccct ctcctcatct gctacaaaga atctctggat    1680
caatggggaa acgagataat gtcagacaag aggaatgtca tcctgttttc tgtatttgat    1740
gagaaccgaa gctggtacct cacagagaat atacaacgct ttctcccaa tccagctgga    1800 gtgcagcttg aggatccaga gttccaagcc tccaacatca tgcacagcat caatggctat    1860 gttttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgtagacac actcacccta ttcccattct caggagaaac tgtcttcatg    2040
tcgatggaaa acccaggtct atggattctg ggtgccaca actcagactt tcggaacaga    2100
ggcatgaccg ccttactgaa ggtttctagt tgtgacaaga acactggtga ttattacgag    2160
gacagttacg aagatatttc agcatacttg ctgagtaaaa acaatgccat tgaacctagg    2220
agcttctctc agaatccacc agtcttgaaa cgccatcaac gggaaataac tcgtacgact    2280
cttcagtcag atcaagagga aattgactat gatgatacca tatcagttga aatgaagaag    2340
gaagattttg acatttatga tgaggatgaa aatcagagcc cccgcagctt tcaaaagaaa    2400
acacgacact attttattgc tgcagtggag aggctctggg attatgggat gagtagctcc    2460
ccacatgttc taagaaacag ggctcagagt ggcagtgtcc ctcagttcaa gaaagttgtt    2520
ttccaggaat ttactgatgg ctcctttact cagcccttat accgtggaga actaaatgaa    2580
catttgggac tcctgggcc atatataaga gcagaagttg aagataatat catggtaact    2640
ttcagaaatc aggcctctcg tccctattcc ttctattcta gccttatttc ttatgaggaa    2700
gatcagaggc aaggagcaga acctagaaaa aactttgtca agcctaatga aaccaaaact    2760 tactttttgga aagtgcaaca tcatatggca cccactaaag atgagtttga ctgcaaagcc    2820
tgggcttatt tctctgatgt tgacctggaa aaagatgtgc actcaggcct gattggaccc    2880
cttctggtct gccacactaa cacactgaac cctgctcatg ggacaagt gacagtacag    2940 gaatttgctc tgttttttcac catctttgat gagaccaaaa gctggtactt cactgaaaat    3000
atggaaagaa actgcagggc tccctgcaat atccagatgg aagatccac ttttaaagag    3060 aattatcgct tccatgcaat caatggctac ataatggata cactacctgg cttagtaatg    3120
gctcaggatc aaaggattcg atggtatctg ctcagcatgg gcagcaatga aacatccat    3180 tctattcatt tcagtggaca tgtgttcact gtacgaaaaa aagaggagta taaatggca    3240 ctgtacaatc tctatccagg tgttttttgag acagtggaaa tgttaccatc caaagctgga    3300
atttggcggg tggaatgcct tattggcgag catctacatg ctgggatgag cacacttttt    3360
ctggtgtaca gcaataagtg tcagactccc ctgggaatgg cttctggaca cattagagat    3420
tttcagatta cagcttcagg acaatatgga cagtgggccc caaagctggc cagacttcat    3480
tattccggat caatcaatgc ctggagcacc aaggagccct tttcttggat caaggtggat    3540
```

-continued

```
ctgttggcac caatgattat tcacggcatc aagacccagg gtgcccgtca gaagttctcc    3600
agcctctaca tctctcagtt tatcatcatg tatagtcttg atgggaagaa gtggcagact    3660
tatcgaggaa attccactgg aaccttaatg gtcttctttg gcaatgtgga ttcatctggg    3720
ataaaacaca atattttaa ccctccaatt attgctcgat acatccgttt gcacccaact     3780
cattatagca ttcgcagcac tcttcgcatg gagttgatgg gctgtgattt aaatagttgc    3840
agcatgccat tgggaatgga gagtaaagca atatcagatg cacagattac tgcttcatcc    3900
tactttacca atatgtttgc cacctggtct ccttcaaaag ctcgacttca cctccaaggg    3960
aggagtaatg cctggagacc tcaggtgaat aatccaaaag agtggctgca agtggacttc    4020
cagaagacaa tgaaagtcac aggagtaact actcagggag taaaatctct gcttaccagc    4080
atgtatgtga aggagttcct catctccagc agtcaagatg ccatcagtg gactctcttt     4140
tttcagaatg gcaaagtaaa ggttttcag ggaaatcaag actccttcac acctgtggtg     4200
aactctctag acccaccgtt actgactcgc taccttcgaa ttcaccccca gagttgggtg    4260
caccagattg ccctgaggat ggaggttctg ggctgcgagg cacaggacct ctac          4314
```

<210> SEQ ID NO 55
<211> LENGTH: 1438
<212> TYPE: PRT
<213> ORGANISM: Artificial Sequence
<220> FEATURE:
<223> OTHER INFORMATION: Variant peptide

<400> SEQUENCE: 55

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
```

```
                225                 230                 235                 240
Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
                275                 280                 285

Ser Pro Ile Thr Phe Leu Thr Ala Gln Thr Leu Leu Met Asp Leu Gly
                290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Ile
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asn Ser Pro Ser Phe
                355                 360                 365

Ile Gln Pro Arg Ser Phe Ala Lys Lys His Pro Lys Thr Trp Val His
                370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
                450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Val Gly Pro Thr Lys Ser Asp Pro Arg Cys
                515                 520                 525

Leu Thr Arg Tyr Tyr Ser Ser Phe Val Asn Met Glu Arg Asp Leu Ala
                530                 535                 540

Ser Gly Leu Ile Gly Pro Leu Leu Ile Cys Tyr Lys Glu Ser Leu Asp
545                 550                 555                 560

Gln Trp Gly Asn Glu Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
                610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655
```

-continued

```
Thr Phe Lys His Lys Met Val Tyr Val Asp Thr Leu Thr Leu Phe Pro
            660             665             670

Phe Ser Gly Glu Thr Val Phe Met Ser Met Glu Asn Pro Gly Leu Trp
        675             680             685

Ile Leu Gly Cys His Asn Ser Asp Phe Arg Asn Arg Gly Met Thr Ala
    690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
            725             730             735

Ile Glu Pro Arg Ser Phe Ser Gln Asn Pro Val Leu Lys Arg His
            740             745             750

Gln Arg Glu Ile Thr Arg Thr Thr Leu Gln Ser Asp Gln Glu Glu Ile
        755             760             765

Asp Tyr Asp Asp Thr Ile Ser Val Glu Met Lys Lys Glu Asp Phe Asp
        770             775             780

Ile Tyr Asp Glu Asp Glu Asn Gln Ser Pro Arg Ser Phe Gln Lys Lys
785             790             795             800

Thr Arg His Tyr Phe Ile Ala Ala Val Glu Arg Leu Trp Asp Tyr Gly
            805             810             815

Met Ser Ser Ser Pro His Val Leu Arg Asn Arg Ala Gln Ser Gly Ser
            820             825             830

Val Pro Gln Phe Lys Lys Val Val Phe Gln Glu Phe Thr Asp Gly Ser
            835             840             845

Phe Thr Gln Pro Leu Tyr Arg Gly Glu Leu Asn Glu His Leu Gly Leu
            850             855             860

Leu Gly Pro Tyr Ile Arg Ala Glu Val Glu Asp Asn Ile Met Val Thr
865             870             875             880

Phe Arg Asn Gln Ala Ser Arg Pro Tyr Ser Phe Tyr Ser Ser Leu Ile
            885             890             895

Ser Tyr Glu Glu Asp Gln Arg Gln Gly Ala Glu Pro Arg Lys Asn Phe
            900             905             910

Val Lys Pro Asn Glu Thr Lys Thr Tyr Phe Trp Lys Val Gln His His
            915             920             925

Met Ala Pro Thr Lys Asp Glu Phe Asp Cys Lys Ala Trp Ala Tyr Phe
            930             935             940

Ser Asp Val Asp Leu Glu Lys Asp Val His Ser Gly Leu Ile Gly Pro
945             950             955             960

Leu Leu Val Cys His Thr Asn Thr Leu Asn Pro Ala His Gly Arg Gln
            965             970             975

Val Thr Val Gln Glu Phe Ala Leu Phe Phe Thr Ile Phe Asp Glu Thr
            980             985             990

Lys Ser Trp Tyr Phe Thr Glu Asn Met Glu Arg Asn Cys Arg Ala Pro
        995             1000            1005

Cys Asn Ile Gln Met Glu Asp Pro Thr Phe Lys Glu Asn Tyr Arg
    1010            1015            1020

Phe His Ala Ile Asn Gly Tyr Ile Met Asp Thr Leu Pro Gly Leu
    1025            1030            1035

Val Met Ala Gln Asp Gln Arg Ile Arg Trp Tyr Leu Leu Ser Met
    1040            1045            1050

Gly Ser Asn Glu Asn Ile His Ser Ile His Phe Ser Gly His Val
    1055            1060            1065
```

-continued

Phe Thr Val Arg Lys Lys Glu Glu Tyr Lys Met Ala Leu Tyr Asn
1070                1075                1080

Leu Tyr Pro Gly Val Phe Glu Thr Val Glu Met Leu Pro Ser Lys
1085                1090                1095

Ala Gly Ile Trp Arg Val Glu Cys Leu Ile Gly Glu His Leu His
1100                1105                1110

Ala Gly Met Ser Thr Leu Phe Leu Val Tyr Ser Asn Lys Cys Gln
1115                1120                1125

Thr Pro Leu Gly Met Ala Ser Gly His Ile Arg Asp Phe Gln Ile
1130                1135                1140

Thr Ala Ser Gly Gln Tyr Gly Gln Trp Ala Pro Lys Leu Ala Arg
1145                1150                1155

Leu His Tyr Ser Gly Ser Ile Asn Ala Trp Ser Thr Lys Glu Pro
1160                1165                1170

Phe Ser Trp Ile Lys Val Asp Leu Leu Ala Pro Met Ile Ile His
1175                1180                1185

Gly Ile Lys Thr Gln Gly Ala Arg Gln Lys Phe Ser Ser Leu Tyr
1190                1195                1200

Ile Ser Gln Phe Ile Ile Met Tyr Ser Leu Asp Gly Lys Lys Trp
1205                1210                1215

Gln Thr Tyr Arg Gly Asn Ser Thr Gly Thr Leu Met Val Phe Phe
1220                1225                1230

Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser
1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
1280                1285                1290

Ala Gln Ile Thr Ala Ser Ser Tyr Phe Thr Asn Met Phe Ala Thr
1295                1300                1305

Trp Ser Pro Ser Lys Ala Arg Leu His Leu Gln Gly Arg Ser Asn
1310                1315                1320

Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
1400                1405                1410

Ile His Pro Gln Ser Trp Val His Gln Ile Ala Leu Arg Met Glu
1415                1420                1425

Val Leu Gly Cys Glu Ala Gln Asp Leu Tyr
1430                1435

<210> SEQ ID NO 56
<211> LENGTH: 4314
<212> TYPE: DNA

<213> ORGANISM: Artificial Sequence
<220> FEATURE:
<223> OTHER INFORMATION: Variant nucleotide

<400> SEQUENCE: 56

```
gccaccagaa gatactacct gggtgcagtg gaactgtcat gggactatat gcaaagtgat      60
ctcggtgagc tgcctgtgga cgcaagattt cctcctagag tgccaaaatc tttccattc     120
aacacctcag tcgtgtacaa aaagactctg tttgtagaat tcacggatca cctttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg agccctact agtatgtaga      540
gaagggagtc tggccaagga aaagacacag accttgcaca aatttatact acttttgct      600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctaccag gtctgattgg atgccacagg aaatcagtct attggcatgt gattggaatg     780
ggcaccactc ctgaagtgca ctcaatattc ctcgaaggtc acacatttct gtgaggaac      840
catcgccagg cgtccttgga aatctcgcca ataactttcc ttactgctca aacactcttg     900
atggaccttg acagtttct actgttttgt catatctctt cccaccaaca tgatggcatg      960
gaagcttatg tcaaagtaga cagctgtcca gaggaacccc aattgatcat gaaaaataat     1020
gaagaagcgg aagactatga tgatgatctt actgattctg aaatggatgt ggtcaggttt     1080
gatgatgaca actctccttc ctttatccaa ccccgctcat tcgccaagaa gcatcctaaa     1140
acttgggtac attacattgc tgctgaagag gaggactggg actatgctcc cttagtcctc     1200
gcccccgatg acagaagtta taaaagtcaa tatttgaaca atggccctca gcggattggt     1260
aggaagtaca aaaagtccg atttatggca tacacagatg aaacctttaa gacgcgtgaa      1320
gctattcagc atgaatcagg aatcttggga ccttttacttt atggggaagt tggagacaca     1380
ctgttgatta tatttaagaa tcaagcaagc agaccatata acatctaccc tcacggaatc     1440
actgatgtcc gtcctttgta ttcaaggaga ttaccaaaag gtgtaaaaca tttgaaggat     1500
tttccaattc tgccaggaga aatattcaaa tataaatgga cagtgactgt agaagttggg     1560
ccaactaaat cagatccgcg gtgcctgacc cgctattact ctagtttcgt taatatggag     1620
agagatctag cttcaggact cattggccct ctcctcatct gctacaaaga atctctggat     1680
caatggggaa acgagataat gtcagacaag aggaatgtca tcctgttttc tgtatttgat     1740
gagaaccgaa gctggtacct cacagagaat atacaacgct ttctccccaa tccagctgga     1800
gtgcagcttg aggatccaga gttccaagcc tccaacatca tgcacagcat caatggctat     1860
gttttgata gtttgcagtt gtcagtttgt ttgcatgagg tggcatactg gtacattcta     1920
agcattggag cacagactga cttccttct gtcttcttct ctggatatac cttcaaacac     1980
aaaatggtct atgtagacac actcacccta ttcccattct caggagaaac tgtcttcatg     2040
tcgatggaaa acccaggtct atggattctg gggtgccaca actcagactt tcggaacaga     2100
ggcatgaccg ccttactgaa ggtttctagt tgtgacaaga acactggtga ttattacgag     2160
gacagttacg aagatatttc agcatacttg ctgagtaaaa acaatgccat tgaacctagg     2220
```

```
agcttctctc agaatccacc agtcttgaaa cgccatcaac gggaaataac tcgtacgact   2280
cttcagtcag atcaagagga aattgactat gatgatacca tatcagttga aatgaagaag   2340
gaagattttg acatttatga tgaggatgaa aatcagagcc cccgcagctt tcaaaagaaa   2400
acacgacact attttattgc tgcagtggag aggctctggg attatgggat gagtagctcc   2460
ccacatgttc taagaaacag ggctcagagt ggcagtgtcc ctcagttcaa gaaagttgtt   2520
ttccaggaat ttactgatgg ctcctttact cagcccttat accgtggaga actaaatgaa   2580
catttgggac tcctggggcc atatataaga gcagaagttg aagataatat catggtaact   2640
ttcagaaatc aggcctctcg tccctattcc ttctattcta gccttatttc ttatgaggaa   2700
gatcagaggc aaggagcaga acctagaaaa aactttgtca agcctaatga aaccaaaact   2760
tactttggga agtgcaaca tcatatggca cccactaaag atgagtttga ctgcaaagcc   2820
tgggcttatt tctctgatgt tgacctggaa aaagatgtgc actcaggcct gattggaccc   2880
cttctggtct gccacactaa cacactgaac cctgctcatg ggagacaagt gacagtacag   2940
gaatttgctc tgttttcac catctttgat gagaccaaaa gctggtactt cactgaaaat   3000
atggaaagaa actgcagggc tccctgcaat atccagatgg aagatcccac ttttaaagag   3060
aattatcgct tccatgcaat caatggctac ataatggata cactacctgg cttagtaatg   3120
gctcaggatc aaaggattcg atggtatctg ctcagcatgg gcagcaatga aacatccat   3180 tctattcatt tcagtggaca tgtgttcact gtacgaaaaa aagaggagta taaaatggca   3240
ctgtacaatc tctatccagg tgtttttgag acagtgaaaa tgttaccatc caaagctgga   3300
atttggcggg tggaatgcct tattggcgag catctacatg ctgggatgag cacactttt   3360 ctggtgtaca gcaataagtg tcagactccc ctgggaatgg cttctggaca cattagagat   3420
tttcagatta cagcttcagg acaatatgga cagtgggccc caaagctggc cagacttcat   3480
tattccggat caatcaatgc ctggagcacc aaggagccct tttcttggat caaggtggat   3540
ctgttggcac caatgattat tcacggcatc aagacccagg gtgcccgtca agttctcc    3600 agcctctaca tctctcagtt tatcatcatg tatagtcttg atgggaagaa gtggcagact   3660
tatcgaggaa attccactgg aaccttaatg gtcttctttg gcaatgtgga ttcatctggg   3720
ataaaacaca atatttttaa ccctccaatt attgctcgat acatccgttt gcacccaact   3780
cattatagca ttcgcagcac tcttcgcatg gagttgatgg gctgtgattt aaatagttgc   3840
agcatgccat tgggaatgga gagtaaagca atatcagatg cacagattac tgcttcatcc   3900
tactttacca atatgtttgc cacctggtct ccttcaaaag ctcgacttca cctccaaggg   3960
aggagtaatg cctggagacc tcaggtgaat aatccaaaag agtggctgca agtggacttc   4020
cagaagacaa tgaaagtcac aggagtaact actcagggag taaatctct gcttaccagc   4080 atgtatgtga aggagttcct catctccagc agtcaagatg ccatcagtg gactctcttt   4140 tttcagaatg gcaaagtaaa ggttttcag ggaaatcaag actccttcac acctgtggtg   4200
aactctctag acccaccgtt actgactcgc taccttcgaa ttcacccca gagttgggtg   4260 caccagattg ccctgaggat ggaggttctg ggctgcgagg cacaggacct ctac         4314
```